US011389541B2

(12) United States Patent
Adams et al.

(10) Patent No.: US 11,389,541 B2
(45) Date of Patent: Jul. 19, 2022

(54) SUSTAINED DELIVERY OF ANGIOPOETIN-LIKE 3 POLYPEPTIDES

(71) Applicant: NOVARTIS AG, Basel (CH)

(72) Inventors: Christopher M. Adams, Arlington, MA (US); Myriam April, Cambridge, MA (US); Tanzina Fazal, Burlington, MA (US); Cornelia Jutta Forster, Pelham, NH (US); Nicole Gerwin, Basel (CH); Edward Charles Hall, Boston, MA (US); Jean-Baptiste Georges Armand Langlois, Schlierbach (FR); Cameron Chuck-munn Lee, Cambridge, MA (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 16/591,053

(22) Filed: Oct. 2, 2019

(65) Prior Publication Data

US 2020/0108153 A1 Apr. 9, 2020

Related U.S. Application Data

(60) Provisional application No. 62/740,609, filed on Oct. 3, 2018.

(51) Int. Cl.

| | | |
|---|---|---|
| *A61K 47/65* | (2017.01) | |
| *A61K 47/54* | (2017.01) | |
| *A61K 47/69* | (2017.01) | |
| *A61P 19/02* | (2006.01) | |
| *A61K 47/10* | (2017.01) | |
| *A61K 47/18* | (2017.01) | |
| *A61K 47/26* | (2006.01) | |
| *C07K 14/515* | (2006.01) | |

(52) U.S. Cl.
CPC .............. *A61K 47/65* (2017.08); *A61K 47/10* (2013.01); *A61K 47/18* (2013.01); *A61K 47/26* (2013.01); *A61K 47/555* (2017.08); *A61K 47/6903* (2017.08); *A61P 19/02* (2018.01); *C07K 14/515* (2013.01)

(58) Field of Classification Search
CPC .................. A61K 47/65; A61K 47/555; A61K 47/6903; A61K 47/10; A61K 47/18; A61K 47/26; A61K 47/61; A61P 19/02; C07K 14/515
See application file for complete search history.

(56) References Cited

U.S. PATENT DOCUMENTS

| | | | |
|---|---|---|---|
| 5,015,573 A | 5/1991 | Yarranton et al. | |
| 5,051,407 A | 9/1991 | Boshagen et al. | |
| 5,288,931 A | 2/1994 | Chang et al. | |
| 5,567,440 A | 10/1996 | Hubbell et al. | |
| 5,770,229 A | 6/1998 | Tanihara et al. | |
| 6,030,831 A | 2/2000 | Godowski et al. | |
| 6,348,351 B1 | 2/2002 | Fong et al. | |
| 7,112,660 B1 | 9/2006 | Domingues et al. | |
| 7,186,413 B2 | 3/2007 | Bouhadir et al. | |
| 7,267,819 B2 | 9/2007 | Ferrara et al. | |
| 7,807,464 B2 | 10/2010 | Zhang et al. | |
| 8,512,752 B2 | 8/2013 | Crescenzi et al. | |
| 8,791,136 B2 | 7/2014 | Goff et al. | |
| 8,809,370 B2 | 8/2014 | Goff et al. | |
| 8,980,921 B2 | 3/2015 | Goff et al. | |
| 8,987,303 B2 | 3/2015 | Goff et al. | |
| 9,266,856 B2 | 2/2016 | Goff et al. | |
| 9,301,971 B2 | 4/2016 | Johnson et al. | |
| 9,301,972 B2 | 4/2016 | Miyamoto | |
| 9,562,022 B2 | 2/2017 | Garvey et al. | |
| 9,649,359 B2 | 5/2017 | Johnson et al. | |
| 9,745,358 B2 | 8/2017 | Johnson et al. | |
| 9,868,771 B2 | 1/2018 | Johnson et al. | |
| 10,239,927 B2 | 3/2019 | Johnson et al. | |
| 10,328,126 B2 | 6/2019 | Johnson et al. | |
| 10,533,042 B2 | 1/2020 | Johnson et al. | |
| 10,751,417 B2 * | 8/2020 | Adams | A61P 27/02 |
| 11,111,283 B2 | 9/2021 | Johnson et al. | |
| 11,179,442 B2 | 11/2021 | Johnson et al. | |
| 2003/0045474 A1 | 3/2003 | Sailer et al. | |
| 2003/0068627 A1 | 4/2003 | Rosen et al. | |
| 2003/0120056 A1 | 6/2003 | Goddard et al. | |
| 2003/0215451 A1 | 11/2003 | Ferrara et al. | |
| 2004/0116649 A1 | 6/2004 | Kozlowski | |

(Continued)

FOREIGN PATENT DOCUMENTS

| | | |
|---|---|---|
| CN | 104292454 A | 1/2015 |
| EP | 3 100 723 A1 | 6/2010 |

(Continued)

OTHER PUBLICATIONS

Agrebi, Asma et al.: "Cyclization Cascade of Hydrazono Ugi Adducts towards Pyrazoles", European Journal of Organic Chemistry, (2013), pp. 5805-5808.

An, Seong Soo A. et al.: "Retention of the Cis Proline Conformation in Tripeptide Fragments of Bovine Pancreatic Ribonuclease A Containing a Non-natural Proline Analogue, 5,5-Dimethylproline", Journal of the American Chemical Society, (1999), vol. 121, pp. 11558-11566.

Gulevich, Anton V. et al.: "The Ugi reaction with CF3-carbonyl compounds: effective synthesis of alpha-trifluoromethyl amino acid derivatives", Tetraheron, (2008), vol. 64, pp. 11706-11712.

Halab, Liliane et al.: Effect of Sequence on Peptide Geometry in 5-tert-Butylprolyl Type VI Beta-Turn Mimics, Journal of the American Chemical Society, (2002). vol. 124, No. 11, pp. 2474-2484.

(Continued)

*Primary Examiner* — Sudhakar Katakam

(74) *Attorney, Agent, or Firm* — Seth E. Cockrum

(57) ABSTRACT

Described herein are drug delivery systems for delivering biologically active agents comprising primary or secondary amines, or a ring nitrogen atom of an azaheteroaryl ring, pharmaceutically acceptable salts thereof, drug delivery reagents related thereto, pharmaceutical compositions comprising the drug delivery systems, and the use of the drug delivery systems as sustained release therapeutics.

18 Claims, 7 Drawing Sheets

Specification includes a Sequence Listing.

(56) References Cited

U.S. PATENT DOCUMENTS

| | | |
|---|---|---|
| 2005/0054563 A1 | 3/2005 | Desnoyer et al. |
| 2006/0002890 A1 | 1/2006 | Hersel et al. |
| 2007/0020757 A1 | 1/2007 | Zhang et al. |
| 2007/0122881 A1 | 5/2007 | Surber |
| 2007/0134250 A1 | 6/2007 | Ferrara et al. |
| 2009/0098117 A1 | 4/2009 | Ferrara et al. |
| 2010/0291171 A1 | 11/2010 | Crescenzi et al. |
| 2011/0097330 A1 | 4/2011 | Horner et al. |
| 2011/0230497 A1 | 9/2011 | Peterson et al. |
| 2012/0177644 A1 | 7/2012 | Schultz et al. |
| 2014/0120069 A1 | 5/2014 | Huerta-Angeles et al. |
| 2014/0154743 A1 | 6/2014 | Levy et al. |
| 2014/0256643 A1 | 9/2014 | Johnson et al. |
| 2014/0256831 A1 | 9/2014 | Ito et al. |
| 2015/0267196 A1 | 9/2015 | Alsberg et al. |
| 2016/0008433 A1 | 1/2016 | Johnson et al. |
| 2016/0229838 A1 | 8/2016 | Goff et al. |
| 2016/0289219 A1 | 10/2016 | Song et al. |
| 2017/0037018 A1 | 2/2017 | Garvey et al. |

FOREIGN PATENT DOCUMENTS

| | | |
|---|---|---|
| EP | 2 325 730 | 5/2011 |
| EP | 2 678 326 | 1/2014 |
| EP | 2 442 644 B1 | 8/2016 |
| EP | 2 061 816 B1 | 2/2017 |
| GB | 2 427 360 A | 12/2006 |
| JP | 2013-116858 A | 6/2013 |
| JP | 2016-172783 A | 9/2016 |
| WO | 1998/09987 A1 | 3/1998 |
| WO | 99/55869 A1 | 11/1999 |
| WO | 99/58660 A1 | 11/1999 |
| WO | 99/67382 A2 | 12/1999 |
| WO | 00/053757 A2 | 9/2000 |
| WO | 01/005972 A1 | 1/2001 |
| WO | 2002/059095 A1 | 8/2002 |
| WO | 02/083851 A2 | 10/2002 |
| WO | 03/044172 A2 | 5/2003 |
| WO | 2005/028502 A1 | 3/2005 |
| WO | 2005/099768 A2 | 10/2005 |
| WO | 2006127809 A2 | 11/2006 |
| WO | 2007/003054 A1 | 1/2007 |
| WO | 2007/027493 A2 | 3/2007 |
| WO | 2008073300 A2 | 6/2008 |
| WO | 2008/097676 A1 | 8/2008 |
| WO | 2008/116107 A2 | 9/2008 |
| WO | 2008/119741 A1 | 10/2008 |
| WO | 2008137641 A2 | 11/2008 |
| WO | 2008/148839 A2 | 12/2008 |
| WO | 2009/095479 A2 | 8/2009 |
| WO | 2010/053861 A2 | 5/2010 |
| WO | 2010069532 A1 | 6/2010 |
| WO | 2010/095049 A1 | 8/2010 |
| WO | 2010/099818 A1 | 9/2010 |
| WO | 2010/102663 A1 | 9/2010 |
| WO | 2010/147653 A1 | 12/2010 |
| WO | 2011/000945 A2 | 1/2011 |
| WO | 2011008773 A2 | 1/2011 |
| WO | 2011/012715 A1 | 2/2011 |
| WO | 2011/012718 A1 | 2/2011 |
| WO | 2011/012719 A1 | 2/2011 |
| WO | 2011/012721 A1 | 2/2011 |
| WO | 2011/012722 A1 | 2/2011 |
| WO | 2011/012723 A1 | 2/2011 |
| WO | 2011/042450 A1 | 4/2011 |
| WO | 2011/042453 A1 | 4/2011 |
| WO | 2011/051406 A1 | 5/2011 |
| WO | 2011/089214 A1 | 7/2011 |
| WO | 2011/089215 A1 | 7/2011 |
| WO | 2011/089216 A1 | 7/2011 |
| WO | 2011/136645 A1 | 11/2011 |
| WO | 2011/140392 A1 | 11/2011 |
| WO | 2012/016217 A1 | 2/2012 |
| WO | 2012/116250 A1 | 8/2012 |
| WO | 2012129562 A2 | 9/2012 |
| WO | 2012/146218 A1 | 11/2012 |
| WO | 2012/173952 A1 | 12/2012 |
| WO | 2013/024051 A1 | 2/2013 |
| WO | 2013/036748 A1 | 3/2013 |
| WO | 2013/036847 A1 | 3/2013 |
| WO | 2013/053856 A1 | 4/2013 |
| WO | 2013/078562 A2 | 6/2013 |
| WO | 2013/078564 A2 | 6/2013 |
| WO | 2013/171485 A1 | 11/2013 |
| WO | 2014004465 A1 | 1/2014 |
| WO | 2014/056915 A1 | 4/2014 |
| WO | 2014/056923 A1 | 4/2014 |
| WO | 2014/056926 A1 | 4/2014 |
| WO | 2014/116717 A1 | 7/2014 |
| WO | 2014/138687 A1 | 9/2014 |
| WO | 2014150937 A1 | 9/2014 |
| WO | 2014/173759 A1 | 10/2014 |
| WO | 2014/173762 A1 | 10/2014 |
| WO | 2014/181287 A1 | 11/2014 |
| WO | 2015/020206 A1 | 2/2015 |
| WO | 2015/052154 A1 | 4/2015 |
| WO | 2015/061503 A1 | 4/2015 |
| WO | 2015/067791 A1 | 5/2015 |
| WO | 2015/130878 A1 | 9/2015 |
| WO | 2016/020373 A1 | 2/2016 |
| WO | 2016/025752 A1 | 2/2016 |
| WO | 2016073915 A1 | 5/2016 |
| WO | 2016/110577 A1 | 7/2016 |
| WO | 2016/149501 A2 | 9/2016 |
| WO | 2016/196124 A2 | 12/2016 |
| WO | 2017/086794 A1 | 5/2017 |
| WO | 2017/161174 A1 | 9/2017 |
| WO | 2018/011266 A1 | 1/2018 |
| WO | 2018/193408 A1 | 10/2018 |

OTHER PUBLICATIONS

Machinaga, Nobuo et al.: "A Controlled Release System for Long-Acting Intravitreal Delivery of Small Molecules", TVST, (2018), vol. 7, No. 4, Article 21, pp. 1-8.

Szymanski, Wiktor et al.: "Studies on the application of the Passerini reaction and enzymatic procedures to the syntheses of tripeptide mimetics", Tetrahedron, (2007), vol. 63, pp. 7647-7653.

Tanihara, Masao et al.: "A Novel Microbial Infection-Responsive Drug Release System", Journal of Pharmaceutical Sciences, May 1999, vol. 88, No. 5, pp. 510-514.

Van Lierop, Bianca J. et al.: "5,5-Dimethylproline dipeptides: an acid-stable class of pseudoproline", Tetrahedron, (2010), vol. 66, pp. 5357-5366.

Weissleder, Ralph et al.: "Quantitation of Slow Drug Release from an Implantable and Degradable Gentamicin Conjugate by In Vivo Magnetic Resonance Imaging", Antimicrobial Agents And Chemotherapy, Apr. 1995, vol. 39, No. 4, p. 839-845.

CAS Registry No. 2039789-95-0, Chemical or Trade Name: 1-Piperidineacetamide, 2-aminomethyl)-N,4-dimethyl-N-phenyl-, hydrochloride (1:1) (CA Index Name), Entry Date: Nov. 28, 2016.

CAS Registry No. 1975813-13-8, Chemical or Trade Name: 1-Piperidineacetamide, 2-(aminomethyl)-4-ethyl-N-methyl-N-phenyl (CA Index Name), Entry Date: Aug. 19, 2016.

CAS Reigstry No. 2038444-00-5, Chemical or Trade Name: 1-Piperidineacetamide, 2-(aminomethyl)-N-ethyl-4-methoxy-N-phenyl- (CA Index Name), Entry Date: Nov. 27, 2016.

CAS Registry No. 2038268-41-4, Chemical or Trade Name: 1-Piperidineacetamide, 2-(aminomethyl)-4-methyl-N-(1-methylethyl)-N-phenyl-, hydrochloride (1:1) (CA Index Name), Entry Date: Nov. 27, 2016.

CAS Registry No. 2038617-65-9, Chemical or Trade Name: 1-Piperidineacetamide, 2-(aminomethyl)-4-methoxy-N-methyl-N-phenyl-, hydrochloride (1:1) (CA Index Name), Entry Date: Nov. 27, 2016.

CAS Registry No. 1967996-72-0, Chemical or Trade Name: 1-Piperidineacetamide, 2-(aminomethyl)-N,4-dimethyl-N-phenyl- (CA Index Name), Entry Date: Aug. 7, 2016.

CAS Registry No. 1941073-29-5, Chemical or Trade Name: 1-Piperidineacetamide, 2-(aminomethyl)-N-ethyl-4-methyl-N-phenyl-,hydrochloride (1:1) (CA Index Name), Entry Date: Jun. 28, 2016.

(56) References Cited

OTHER PUBLICATIONS

CAS Registry No. 1940483-27-1, Chemical or Trade Name: 1-Piperidineacetamide, 2-(aminomethyl)-N-cyclohexyl-4-methoxy-N-methyl-, hydrochloride (1:1) (CA Index Name), Entry Date: Jun. 28, 2016.
CAS Registry No. 1538942-79-8, Chemical or Trade Name: 4-Piperidineacetic acid, 1-[2-[(5-bromo-2-pyridinyl) amino]-2-oxoethyl]- (CA Index Name), Entry Date: Feb. 7, 2014.
CAS Registry No. 1455956-36-1, Chemical or Trade Name: 1-Piperazineacetamide, N-(3,5-dichloro-2-pyridinyl)-4-(2-hydroxyethyl)- (CA Index Name), Entry Date: Oct. 6, 2013.
CAS Registry No. 1424558-83-7, Chemical or Trade Name: 1-Piperazineacetamide, N-(5-chloro-2-pyridinyl)-3-ethyl-4-(2-hydroxypropyl)- (CA Index Name), Entry Date: Mar. 17, 2013.
CAS Registry No. 1411210-79-1, Chemical or Trade Name: 1-Piperidineacetamide, 4-(1-aminoethyl)-N-(5-bromo-2-pyridinyl)- (CA Index Name), Entry Date: Dec. 5, 2012.
CAS Registry No. 1410985-45-3, Chemical or Trade Name: 1-Piperidineacetamide, 4-(2-aminoethyl)-N-(5-bromo-2-pyridinyl)- (CA Index Name), Entry Date: Dec. 4, 2012.
CAS Registry No. 1409425-24-6, Chemical or Trade Name: 1-Piperidineacetamide, N-(5-bromo-2-pyridinyl)-4-[2-methylamino)ethyl]- (CA Index Name), Entry Date: Dec. 2, 2012.
CAS Registry No. 1406904-63-9, Chemical or Trade Name: 1-Piperidineacetamide, 4-(2-aminoethyl)-N-(3,5-dichloro-2-pyridinyl)- (CA Index Name), Entry Date: Nov. 26, 2012.
CAS Registry No. 1405365-95-8, Chemical or Trade Name: 1-Piperidineacetamide, 4-(1-aminoethyl)-N-(3,5-dichloro-2-pyridinyl)- (CA Index Name), Entry Date: Nov. 23, 2012.
CAS Registry No. 1356718-30-3, Chemical or Trade Name: 1-Piperazineacetamide, N-(5-chloro-2-pyridinyl)-4-(2-methoxyethyl)-3-methyl- (CA Index Name), Entry Date: Feb. 14, 2012.
CAS Registry No. 1333940-16-1, Chemical or Trade Name: 1-Piperazineacetamide, N-(5-chloro-2-pyridinyl)-3-ethyl-4-(2-methoxyethyl)- (CA Index Name), Entry Date: Sep. 29, 2011.
CAS Registry No. 1330932-38-1, Chemical or Trade Name: 1-Piperazineacetamide, 4-acetyl-N-(5-chloro-2-pyridinyl)-(CA Index Name), Entry Date: Sep. 11, 2011.
CAS Registry No. 1330451-85-8, Chemical or Trade Name: 1-Piperazineacetamide, N-(5-bromo-2-pyridinyl)-4-(2-methyl-1-oxopropyl)- (CA Index Name), Entry Date: Sep. 9, 2011.
CAS Registry No. 1316934-54-9, Chemical or Trade Name: 1,4-Piperazinediacetamide, N1-(5-bromo-2-pyridinyl)-N4-2-methoxyethyl)- (CA Index Name), Entry Date: Aug. 14, 2011.
CAS Registry No. 1061959-09-8, Chemical or Trade Name: 1-Piperazineacetamide, N-(5-chloro-2-pyridinyl)-4-(2-methyl-1-oxopropyl)- (CA Index Name), Entry Date: Oct. 16, 2008.
CAS Registry No. 1155165-04-0, Chemical or Trade Name: 1-Piperazineacetic acid, 4-[2-[(5-bromo-2-pyridinyl)amino]-2-oxoethyl]- (CA Index Name), Entry Date: Jun. 10, 2009.
CAS Registry No. 931639-05-3, Chemical or Trade Name: 1-Piperazineacetamide, 4-acetyl-N-[3-chloro-5-(trifluoromethyl)-2-pyridinyl]- (CA Index Name), Entry Date: Apr. 22, 2007.
CAS Registry No. 1031090-72-8, Chemical or Trade Name: 1-Piperazineacetamide, N-(5-chloro-2-pyridinyl)-4-(2,2,2-trifluoroethyl)- (CA Index Name), Entry Date: Jun. 27, 2008.
CAS Registry No. 896220-97-6, Chemical or Trade Name: 1-Piperazineacetamide, N-(5-bromo-2-pyridinyl)-4-ethyl-(CA Index Name), Entry Date: Jul. 27, 2006.
CAS Registry No. 895350-14-8, Chemical or Trade Name: 1-Piperazineacetamide, N-(5-bromo-2-pyridinyl)-4-(2-hydroxyethyl)- (CA Index Name), Entry Date: Jul. 23, 2006.
CAS Registry No. 895350-02-4, Chemical or Trade Name: 1-Piperazineacetamide, N-(5-chloro-2-pyridinyl)-4-(2-hydroxyethyl)- (CA Index Name), Entry Date: Jul. 23, 2006.
CAS Registry No. 890273-72-0, Chemical or Trade Name: 1-Piperazineacetamide, N-(5-chloro-2-pyridinyl)-4-propyl-(CA Index Name), Entry Date: Jul. 2, 2006.
CAS Registry No. 890273-49-1, Chemical or Trade Name: 1-Piperazineacetamide, N-(5-bromo-2-pyridinyl)-4-propyl-(CA Index Name), Entry Date: Jul. 2, 2006.
CAS Registry No. 517902-58-8, Chemical or Trade Name: 1-Piperazineacetamide, N-(5-chloro-2-pyridinyl)-4-ethyl-(CA Index Name), Entry Date: May 19, 2003.
Dommerholt, Jan et al.: "Readily Accessible Bicyclononynes for Bioorthogonal Labeling and Three-Dimensional Imaging of Living Cells", Angew. Chem. Int. Ed., (2010), vol. 49, No. 49, pp. 9422-9425.
Puthenveetil, Sujiet et al.: "Development of Solid-Phase Site-Specific Conjugation and Its Application toward Generation of Dual Labeled Antibody and Fab Drug Conjugates", Bioconjugate Chemistry, (2016), vol. 27, No. 4, pp. 1030-1039.
Alaoui-Ismaili, et al., "Design of second generation therapeutic recombinant bone morphogenetic proteins," Cytokine & Growth Factor Reviews, 20 (2009) 501-507.
Bernier, et al., "Pharmacological chaperone action on G-protein-coupled receptors," Current Opinion in Pharmacology, 2004, 4:528-533.
Bhattacharya, et al., "Impact of genetic variation on three dimensional structure and function of proteins," PLoS One, 12(3): e0171355 (2017).
Camenish, et al., "ANGPTL3 Stimulates Endothelial Cell Adhesion and Migration via Integrin avb3 and Induces Blood Vessel Formation in Vivo", JBC, May 10, 2002, vol. 277, No. 19, pp. 17281-17290.
Chen, et al., "Angiopoietin-like protein 3 cDNA from goat", GenBank Direct Submission ACT67418, Jun. 21, 2009, http://www.ncbi.nlm.nih.gov/protein/ACT67418.1.
Civinini et al., "Growth factors in the treatment of early osteoarthritis," Clin. Cases Miner. Bone Metab., 10:26-29, 2013.
Conklin, et al., "Angiopoietin-Related Protein 3 (Homo sapiens)", GenBank Direct Submission Accession: AAD34156, Jan. 28, 2000 (retrieved on Jun. 16, 2011), retrieved from the internet http://www.ncbi.nlm.nih.gov/protein/AAD34156, p. 1.
Conklin, et al., "Identification of a Mammalian Angiopoietin-Related Protein Expressed Specifically in Liver", Genomics, Dec. 1999, vol. 62, No. 3, pp. 477-482.
Conklin, et al., "Angiopoietin-Related Protein 3 Precursor (Angiopoietin-Like 3)", Uniprot Direct Submission Accession O9R182 (online). Jun. 15, 2002 (retrieved on Jun. 16, 2011), http://uniprot.org/uniprot/Q9R182.bd?version=9, p. 1.
Database Accession No. XP_001501115.1; Jun. 25, 2007; Predicted: similar to angiopoietin-related protein 3 [Equus caballus]; http://www.ncbi.nlm.mh.gov/protein/149709517'?sat=12&satkey=5358126.
Database Accession NP_01073814.1; Feb. 24, 2008; "angiopoietin-like 3 [Bos taurus]" http://www.ncbi.nlm.nih.gov/protein/122692391?sat=13&satkey=1115-8563.
Database Accession NP_038941.1, Dec. 30, 2007; angiopoietin-like 3 [Mus musculus]; http://www.ncbi.nlm.nih.gov/protein/33469117?sat=12%satkey =1625442.
Fenton, et al., "Rheostat positions: A new classification of protein positions relevant to pharmacogenomics," Medicinal Chemistry Research (2020) 29:1133-1146.
Figure 1, available at http://www.orthop.washington.edu/orthodev/drupal/sites/default/files/Port- als/21/LiveContent/7659/lmages/figure1.gif, last accessed Jan. 31, 2019.
Fortier et al., "The Role of Growth Factors in Cartilage Repair," Clin. Orthop. Relat. Res. 469:2706-2715,2011.
Geiger et al., "Cartilage-penetrating nanocarriers improve delivery and efficacy of growth factor treatment of osteoarthrtis," Sci. Transl. Med 10:1-12,2018.
Gerwin et al., "The OARSI histopathology initiative-recommendations for histological assessments of osteoarthritis in the rat", Osteoarthritis and Cartilage, 2010, vol. 18, pp. 524-534.
Guo, et al., "Protein tolerance to random amino acid change," PNAS, Jun. 22, 2004, vol. 1010, No. 25, 9205-9210.
Hato et al., "The Role of Angiopoietin-Like Proteins in Angiogenesis and Metabolism", Trends in Cardiovascular Medicine, Jan. 16, 2008, vol. 18, No. 1.

(56) References Cited

OTHER PUBLICATIONS

Mananatomy, "Cartilage and Its Types: Human Anatomy," https://www.mananatomy.com/basic-anatomy/cartliage-types, accessed Jul. 6, 2018.
Khan et al., "One Flew Over the Progenitor's Nest: Migratory Cells Find a Home in Osteoarthritic Cartilage", Cell Stem Dell, Apr. 2009, vol. 4, pp. 282-284.
Koyama et al., "ANGPTL, 3 is a novel biomarker as it activates ERK/MAPK pathway in oral cancer", Cancer Medicine, vol. 4(5), pp. 759-769, 2015.
McGregor D. P., Discovering and improving novel peptide therapeutics. Curr.Opin. Pharmacol., Jul. 16, 2008, vol. 8, No. 5, pp. 616-619.
Moore, et al., "Fibroblast growth factor-18 stimulates chondrogenesis and cartilage repair in a rat model of injury-nduced osteoarthritis", Osteoarthritis and Cartilage, 2005, pp. 623-631.
Oike, et al;, "Angiopoietin-Related/Angiopoietin-Like Proteins Refulate Angiogenesis", International Journal of Hematology, 2004, vol. 80, pp. 21-28.
O'Shea, et al. "Synthesis of Trypsin-Resistant Variants of the Listeria-Active Bacteriocin Salivaricin P", Applied and Environmental Microbiology, Aug. 2010, vol. 76, No. 16, pp. 5356-5362.
Phinney, et al., "Biochemical Heterogeneity of Mesenchymal Stem Cell Populations", Cell Cycle, Dec. 1, 2007, vol. 6, No. 23, pp. 2884-2889. Landes Bioscience.
Qvist, et al., "The disease modifying osteosrthritis drug (DMOAD): Is it in the horizon?", Pharmacological Research, 2008, vol. 58, pp. 1-7.
Schminke, et al., "Cartilage Repair in Vivo: The Role of Migratory Progenitor Cells", Curr. Rheumatol. Rep., 2014, col. 16, No. 461, pp. 1-8.
Shan et al., "The angiopoietin-like proteins ANGPTL3 and ANGPTL4 inhibit lipoprotein lipase activity through distinct mechanisms" The Journal of Biological Chemistry, vol. 284 (3), pp. 1419-1424, 2009.
Siepen, et al., "Prediction of Missed Cleavage Sites in Tryptic Peptides Aids Protein Identification in Protemics", Journal of Proteome Research, 2007, vol. 6, pp. 399-408.
Sokoloff, "Joint Disease," https://www.britannica.com/science/joint-disease, accessed May 17, 2017.
Tokuriki, et al., "Stability effects of mutations and protein evolvability," Curren Opinion in Structural Biology, 2009, 19:596-604.
Ulloa-Aguirre, et al., "Pharmacologic Rescue of Conformationally-Defective Proteins: Implications for the Treatment of Human Disease," Traffic, 2004, 5:821-837.
Valenzuela, et al., "Angiopoietins 3 and 4: Diverging gene counterparts in mice and humans", Proceedings of the National Academy of Sciences of the United States of America, 1999, vol. 96, No. 5, pp. 1904-1909.
Wilder, et al., "Integrin alpha V beta 3 as a target for treatment of rheumatoid arthritis acid related rheumatic diseases", Ann Rheum Dis, Nov. 2002, vol. 61, No. 2, pp. 96-99.
Yau et al., "A Highly Conserved Motif within the NH2-terminal Coiled-coil Domain of Angiopoietin-like Protein 4 Confers ts Inhibitory Effects on Lipoprotein Lipase by Disrupting the Enzyme Dimerization," J. Biol. Chem., 2009, vol. 284 (18):11942-52.
Zheng, et al., "Angiopoietin-Like 3 Deficient Bone Marrow has Decreased Ability to Support Hemaotpoietic Stem Dells", Blood, Nov. 16, 2008, vol. 112, No. 11, p. 490.
PubChem, title: Alexa Fluor 555, product information in Pubchem, downloaded from https://pubchem.ncbi.nlm.nih.gov/compound/ Alexa-Fluor-555 on May 19, 2020. (Year: 2020).
Dugel et al., "Hawk and Harrier: Phase 3, Multicenter, Randomized, Double-Masked Trials of Brolucizumab for Neovascular Age-Related Macular Degeneration," Ophthalmology. 127(1):72-84 (2020), epublished Apr. 12, 2019.

\* cited by examiner

Functionalized hyaluronic acid
Soluble polymer

SUSTAINED DELIVERY OF ANGIOPOETIN-LIKE 3 POLYPEPTIDES

The present application claims the benefit of U.S. Provisional Application Ser. No. 62/740,609, filed on Oct. 3, 2018, which is hereby incorporated by reference in its entirety.

TECHNICAL FIELD

Described herein are drug delivery systems for delivering biologically active agents comprising primary or secondary amines, or a ring nitrogen atom of an azaheteroaryl ring, pharmaceutically acceptable salts thereof, drug delivery reagents related thereto, pharmaceutical compositions comprising the drug delivery systems, and the use of the drug delivery systems as sustained release therapeutics.

REFERENCE TO SEQUENCE LISTING

This application is filed with a Computer Readable Form of a Sequence Listing in accordance with 37 C.F.R. § 1.821(c). The text file submitted, "PAT058317-US-NP_SL.txt" was created on Dec. 6, 2019, has a file size of 102,696 bytes, and is hereby incorporated by reference in its entirety.

BACKGROUND

Modulation of the physicochemical or pharmacokinetic properties of a drug in vivo may be affected by conjugation of the drug with a carrier. In particular, conjugation of a drug with a carrier is frequently used as a means to increase the therapeutic duration of action, reduce the maximum concentration of the drug after administration or localize delivery of the drug to a desired tissue or compartment or a combination of these purposes. Typically, carriers in drug delivery systems are either (a) used in a non-covalent fashion with the drug physicochemically formulated into a solvent-carrier mixture or (b) linked by covalent attachment of a carrier reagent to a functional group present in the drug.

Non-covalent approaches require a highly efficient drug encapsulation to prevent uncontrolled burst release of the drug that may occur either at initial administration of the carrier-drug system or during degradation of the carrier after administration to a subject. Restraining the diffusion of an unbound, water-soluble drug molecule requires strong van der Waals contacts, frequently mediated through hydrophobic moieties, hydrogen-bonding, or electrostatic binding mediated through charged moieties. Many conformationally sensitive drugs, such as proteins, peptides, or antibodies are rendered dysfunctional during the encapsulation process and/or during subsequent storage of the encapsulated drug.

Alternatively, a drug may be covalently conjugated to a carrier via a stable linker or via a reversible linker moiety from which the drug is released. If the drug is stably connected to the carrier, such a conjugate needs to exhibit sufficient residual activity to have a pharmaceutical effect and the conjugate is constantly in an active form.

If the drug is conjugated to the carrier through a cleavable linker, such conjugates are typically referred to as carrier-linked drugs. This approach can be applied to various classes and sizes of biologically active molecules, from low molecular weight organic molecules, natural products, antibodies and analogs thereof, proteins, peptides, and the like. An important consideration for carrier-linked drugs is the mechanism for releasing the drug from the carrier. The release mechanism may be enzymatic, pH-dependent, or via autonomous hydrolysis. Typically, the drug release is not easily controllable and difficult to sustain over long time periods.

There continues to be a need for new drug delivery systems suitable for the sustained release of biologically active moieties in therapeutic applications. Described herein are drug delivery systems that provide sustained release of biologically active moieties for therapeutically relevant applications.

SUMMARY

One embodiment described herein is a drug delivery system or pharmaceutically acceptable salt thereof comprising D-R, that is represented by Formula (I), where D comprises an ANGPTL3 polypeptide comprising at least one primary amine; and R is a linker suitable for release of D:

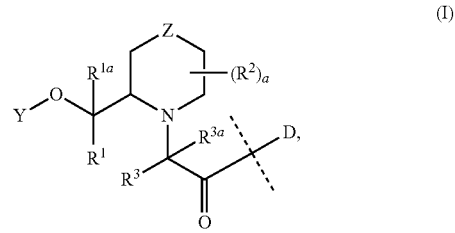

(I)

where the dashed line indicates attachment to the primary amine; $R^1$ is hydrogen or $C_1$-$C_4$alkyl; $R^{1a}$ is hydrogen or $C_1$-$C_4$alkyl, or $CR^1R^{1a}$, taken in combination form a $C_3$-$C_6$cycloalk-1,1-diyl; $R^2$ is independently selected at each occurrence from $C_1$-$C_4$alkyl or oxo, or two $R^2$ groups taken in combination with the carbon atom(s) to which they are attached form a fused $C_3$-$C_6$ cycloalkyl or spiro $C_3$-$C_6$cycloalk-1,1-diyl group; a is 0, 1, 2, 3 or 4; $R^3$ is hydrogen or $C_1$-$C_4$alkyl; $R^{3a}$ is hydrogen, $C_1$-$C_4$alkyl, or $CR^3R^{3a}$, taken in combination form a $C_3$-$C_6$cycloalk-1,1-diyl; Y is $C(O)R^4$, $C(O)OR^4$, $C(O)NHR^4$, $C(O)NR^5R^6$, $SiR^5R^6R^7$, or $CR^{12}R^{12a}OR^{13}$; $R^{12}$ is hydrogen or $C_1$-$C_4$alkyl; $R^{12a}$ is hydrogen or $C_1$-$C_4$alkyl, or $CR^{12}R^{12a}$, taken in combination form a $C_3$-$C_6$cycloalk-1,1-diyl; $R^{13}$ is $C_1$-$C_4$alkyl; or $R^{12}$ and $R^{13}$, taken in combination with $C(R^{12a})$ and O form a 5, 6, or 7-member cyclic ether; $R^4$ is $C_1$-$C_8$alkyl or $C_3$-$C_7$cycloalkyl, wherein cycloalkyl is optionally substituted with 0, 1, or 2 independently selected $C_1$-$C_4$alkyl groups and wherein alkyl is optionally substituted by $C_1$-$C_4$alkoxy; $R^5$ and $R^6$ are each independently selected from $C_1$-$C_4$alkyl and $C_3$-$C_6$cycloalkyl; $R^7$ is $C_1$-$C_8$alkyl, $C_3$-$C_7$cycloalkyl, $C_1$-$C_8$alkoxy, $C_3$-$C_7$cycloalkyloxy, heterocycloalkyloxy, or —(OCHR$^3$CH$_2$)$_b$O—$C_1$-$C_4$alkyl, wherein the heterocycloalkyloxy is a 4 to 7 member saturated heterocyclic ring having one ring heteroatom selected from N, O, and S and optionally substituted with 0, 1, or 2 independently selected $C_1$-$C_4$alkyl groups; b is an integer of from 1 to 10; Z is CH-L-A, CH-A, N-L-A, or N-A; L is an optionally substituted bivalent linker; A is hydrogen, $C_1$-$C_8$alkyl, $C(O)C_1$-$C_8$alkyl, $C(O)N(H)C_1$-$C_8$alkyl, $C(O)OC_1$-$C_8$alkyl, $R^{10}$, or $R^{11}$, wherein the alkyl group is optionally substituted with 0 or 1 $R^{10}$; $R^{10}$ is a reactive functional group suitable for coupling Formula (I) to a carrier; and $R^{11}$ is a carrier. In one aspect, D comprises an ANGPTL3 polypeptide having at least 95% identity to any one of SEQ ID NO: 1 or 3-45. In another aspect, D comprises any one of SEQ ID NO: 1 or 3-45. In another aspect, D comprises an ANGPTL3 polypeptide having a K423Q substitution or a K423 deletion. In another aspect, D comprises an ANGPTL3 polypeptide comprising amino acid residues 201-460; 207-460; 225-455; 225-455; 225-460; 225-460; 226-455; 226-455; 226-460; 226-460; 228-455; 228-455; 228-460; 228-460; 233-455; 233-455; 233-460; 233-460; 241-455; 241-455; 241-460; 241-460; 242-455; 242-455; 242-460; or 242-460, each in reference to SEQ ID NO:1. In another aspect, D comprises an ANGPTL3 polypeptide comprising at least 95% identity to amino acid residues 242-460 in reference to SEQ ID NO:1 and a K423Q substitution. In another aspect, D comprises an ANGPTL3 polypeptide comprising amino acid residues 242-460 in reference to SEQ ID NO: 1 and a K423Q substitution, D1, (SEQ ID NO: 19). In another aspect, $R^1$ is hydrogen or methyl, $R^{1a}$ is hydrogen or methyl, or $CR^1R^{1a}$, taken in combination form a cyclopropan-1,1-diyl group. In another aspect, the variable a is 0. In another aspect, $R^3$ and $R^{3a}$ are each hydrogen. In another aspect, Y is $C(O)R^4$ and $R^4$ is $C_1$-$C_6$alkyl, $C_3$-$C_6$cycloalkyl or $C_1$-$C_2$alkoxyC$_1$-C$_2$alkyl. In another aspect, $R^4$ is methyl, ethyl, propyl, isopropyl, 1-methyl-cyclopropyl, or methoxymethyl. In another aspect, Y is $SiR^5R^6R^7$; $R^5$ and $R^6$ are each methyl, ethyl, propyl or isopropyl; and $R^7$ is $C_1$-$C_4$ alkyl, ethoxy, propoxy, isopropoxy, butoxy, iso-butoxy, sec-butoxy, 2-ethoxyethoxy, 2-isopropoxy-ethoxy, tetrahydropyranyloxy, or —(OCHR$^3$CH$_2$)$_b$O—C$_1$-C$_4$alkyl where b is 2, 3, or 4. In another aspect, Z is CH-L-A, CH-A, N-L-A, or N-A; L is an optionally substituted bivalent linker Q-[Sp-Q]$_h$-Q; Q is independently selected at each occurrence from a bond, O, C(O), N(H), N(C$_1$-C$_4$alkyl), C(O)NH, C(O)N(C$_1$-C$_4$alkyl), N(H)C(O), N(C$_1$-C$_4$alkyl)C(O), N(H)C(O)O, N(C$_1$-C$_4$alkyl)C(O)O, OC(O)N(H), OC(O)N(C$_1$-C$_4$alkyl), N(H)C(O)N(H), N(C$_1$-C$_4$alkyl)C(O)N(H), N(H)C(O)N(C$_1$-C$_4$alkyl), N(C$_1$-C$_4$alkyl)C(O)N(C$_1$-C$_4$alkyl), C(O)O, OC(O), OC(O)O, S, S(O)$_2$, N(H)S(O)$_2$, N(C$_1$-C$_4$alkyl)S(O)$_2$, S(O)$_2$N(H), S(O)$_2$N(C$_1$-C$_4$alkyl), C$_1$-C$_2$alkyl-C(O)N(H), N(H)C(O)C$_1$-C$_2$alkyl, C$_1$-C$_2$alkyl-C(O)O, OC(O)C$_1$-C$_2$alkyl, 1,2,3-triazole, OP(O)$_2$, P(O)$_2$O, C$_1$-C$_4$alkyl-P(O)$_2$—O, or O—P(O)$_2$—C$_{1-4}$alkyl; Sp is independently selected at each occurrence from an optionally substituted C$_1$-C$_{20}$alkyl, C$_2$-C$_{20}$alkenyl, C$_2$-C$_{20}$alkynyl, [W—O]$_g$, C$_1$-C$_8$alkyl-[O—W]$_g$, [O—W]$_g$—O—C$_1$-C$_8$alkyl, C$_1$-C$_8$Calkyl-[O—W]$_g$—O—C$_1$-C$_8$alkyl, or oligopeptide; h is an integer of between 1 and 20; g is a weighted average number of between about 2 and about 50; W is C$_2$-C$_4$alkyl-1,2-diyl in which a hydrogen, methyl, or ethyl side chain may be present on either backbone carbon atom; A is hydrogen, C$_1$-C$_8$alkyl, C(O)C$_1$-C$_8$alkyl, C(O)OC$_1$-C$_8$alkyl, C(O)N(H)C$_1$-C$_8$alkyl, $R^{10}$, or $R^{11}$ wherein the alkyl group is optionally substituted with 0 or 1 $R^{10}$; $R^{10}$ is a reactive functional group suitable for coupling Formula (I) to a carrier; and $R^{11}$ is a carrier. In another aspect, Z is CHR$^8$ or NR$^9$; $R^8$ and $R^9$ are each independently selected from hydrogen, C$_1$-C$_8$ alkyl, C(O)—(CH$_2$)$_n$-Q-A, C(O)C$_1$-C$_8$ alkyl, or —C(O)(CH$_2$)$_q$[O—W]$_g$(NHC(O))$_m$(CH$_2$)$_q$[O—W]$_p$-Q-A, wherein the alkyl group is optionally substituted with 0 or 1 Q-A; q is independently at each occurrence 1, 2, or 3; g and p each independently have a weighted average length of between about 2 and about 50; m is 1 or 0; W is C$_2$-C$_4$alkyl-1,2-diyl in which a hydrogen, methyl, or ethyl side chain may be present on either backbone carbon atom; Q is a bond, O, N(H) or N(C$_1$-C$_4$alkyl); A is hydrogen, C$_1$-C$_8$alkyl, C(O)C$_1$-C$_8$alkyl, C(O)N(H)C$_1$-C$_8$alkyl, C(O)OC$_1$-C$_8$alkyl, $R^{10}$, or $R^{11}$, wherein the alkyl group is optionally substituted with 0 or 1 $R^{10}$; $R^{10}$ is a reactive functional group suitable for coupling Formula (I) to a carrier; and R is a carrier. In another aspect, Z is NR$^9$; $R^9$ is C(O)—(CH$_2$)$_n$-Q-A or —C(O)(CH$_2$)$_q$[O—W]$_g$(NHC(O))$_m$(CH$_2$)$_q$[O—W]$_p$-Q-A; n is an integer of 1 to 8; and A is $R^{10}$ or $R^{11}$. In another aspect, $R^{10}$ is azidyl, alkynyl, substituted or unsubstituted C$_7$-C$_{12}$ cycloalkynyl, substituted or unsubstituted C$_7$-C$_{12}$ heterocycloalkynyl, substituted or unsubstituted C$_7$-C$_{12}$ cycloalkenyl, norbornyl, substituted or unsubstituted vinyl carboxyl, substituted or unsubstituted vinyl sulfonyl, substituted or unsubstituted C$_2$-C$_8$ alkenyl, amino, thiol, substituted or unsubstituted C$_1$-C$_8$ carboxyl, substituted or unsubstituted C$_1$-C$_8$ carbonyl, —O—NH$_2$, hydrazidyl, maleimide, alpha-halo carbonyl, furan, substituted or unsubstituted tetrazinyl, lysine, glutamine, cyclodextrin, or adamantanyl. In another aspect, $R^{10}$ comprises a reactive functional group suitable for coupling the drug delivery system or pharmaceutically acceptable salt of Formula (I) to a carrier. In another aspect, $R^{11}$ is biodegradable. In another aspect, $R^{11}$ comprises a polymer or cross-linked polymer. In another aspect, $R^{11}$ comprises a hydrogel comprising one or more cross-linked polymers. In another aspect, $R^{11}$ comprises a polymer, cross-linked polymer, or hydrogel comprising one or more of hyaluronic acid, polyethylene glycol, polypropylene glycol, polyethylene oxide, polypropylene oxide, polyglutamate, polylysine, polysialic acid, polyvinyl alcohol, polyacrylate, polymethacrylate, polyacrylamide, polymethacrylamide, polyvinyl pyrrolidone, polyoxazoline, polyiminocarbonate, polyamino acid, hydrophilic polyester, polyamide, polyurethane, polyurea, dextran, agarose, xylan, mannan, carrageenan, alginate, gelatin, collagen, albumin, cellulose, methylcellulose, ethylcellulose, hydroxypropylmethylcellulose, hydroxyethyl starch, chitosan, nucleic acids, derivatives thereof, co-polymers thereof, or combinations thereof. In another aspect, $R^{11}$ comprises hyaluronic acid, polyethylene glycol, a cross-linked hydrogel of hyaluronic acid, a cross-linked hydrogel of polyethylene glycol, or combinations thereof. In another aspect, $R^{11}$ comprises hyaluronic acid or polyethylene glycol. In another aspect, $R^{11}$ comprises a hydrogel comprising cross-linked hyaluronic acid or cross-linked polyethylene glycol. In another aspect, the hyaluronic acid or polyethylene glycol are functionalized with at least one functional group comprising azidyl, alkynyl, substituted or unsubstituted C$_7$-C$_{12}$ cycloalkynyl, substituted or unsubstituted C$_7$-C$_{12}$ heterocycloalkynyl, C$_7$-C$_{12}$ cycloalkenyl, norbornyl, vinyl carboxyl, vinyl sulfonyl, C$_2$-C$_8$ alkenyl, amino, thiol, C$_1$-C$_8$ carboxyl, C$_1$-C$_8$ carbonyl, —O—NH$_2$, carbohydrazide, maleimide, alpha-halo carbonyl, furan, substituted or unsubstituted tetrazinyl, lysine, glutamine, cyclodextrin, adamantanyl, or combinations thereof. In another aspect, $R^{11}$ comprises a hydrogel comprising cross-linked hyaluronic acid, wherein the hyaluronic acid comprises at least one side chain selected from —NH(W1) (O(W1))$_d$—V, wherein W1 is C$_2$-C$_4$alkyl-1,2-diyl in which a hydrogen, methyl, or ethyl side chain may be present on either backbone carbon atom; d is a number average of 0 to 500; and V is a suitable functional group comprising azidyl, alkynyl, substituted or unsubstituted C$_7$-C$_{12}$ cycloalkynyl, substituted or unsubstituted C$_7$-C$_{12}$ heterocycloalkynyl, C$_7$-C$_{12}$ cycloalkenyl, norbornyl, vinyl carboxyl, vinyl sulfonyl, C$_2$-C$_8$ alkenyl, amino, thiol, C$_1$-C$_8$ carboxyl, C$_1$-C$_8$ carbonyl, —O—NH$_2$, carbohydrazide, maleimide, alpha-halo carbonyl, furan, substituted or unsubstituted tetrazinyl, lysine, glutamine, cyclodextrin, or adamantanyl. In another aspect, V is azide.

Another embodiment described herein is a process for making a cross-linked carrier formulation, the process comprising: (a) functionalizing a carrier molecule, R$^{11}$; (b) preparing a reactive cross-linker; and (c) reacting the functionalized carrier molecule with the reactive cross-linker to form a cross-linked carrier by incubation for about 0.5 hours to about 48 hours at a temperature of about 4° C. to about 60° C. In one aspect, the carrier molecule comprises hyaluronic acid or polyethylene glycol. In another aspect, the carrier molecule is functionalized with azide, sulfhydryl, amine, aminoxy (O—NH$_2$), or aldehyde moieties to provide reactive functional groups for cross-linking. In another aspect, the preparation of the reactive crosslinker comprises reacting a polyethylene glycol with 1-((tert-butoxycarbonyl) amino)cyclopropane-1-carboxylic acid, 3-((tert-butoxycarbonyl)amino)propanoic acid, 1-(tert-butoxycarbonyl)piperidine-4-carboxylic acid, 2-(1-(((tert-butoxycarbonyl)amino) methyl)cyclopropyl)acetic acid, 2-methyl-3-((tert-butoxycarbonyl)amino)propanoic acid, or 7-((tert-butoxycarbonyl)amino)heptanoic acid and deprotecting the functionalized polyethylene glycol ester. In another aspect, the preparation of the reactive crosslinker further comprises introduction at least two bicyclo[6.1.0]non-4-yn-9-yl) methyl groups after deprotection of the functionalized polyethylene glycol ester. Another aspect comprises a cross-linked hydrogel obtainable using the methods described herein. In another aspect, the carrier molecule is functionalized with azide.

Another embodiment described herein is a process for preparing a drug adduct, comprising a traceless linker, R, coupled to an ANGPTL3 polypeptide comprising at least one primary amine, D, the process comprising: (a) providing an ANGPTL3 polypeptide comprising at least one primary amine, D; (b) reacting the biologically active agent with a traceless linker, R, that has an activated carbonyl functional group; and (c) purifying the drug adduct from the reagents. One aspect is a drug adduct obtainable using the process described herein.

Another embodiment described herein is a process for making a drug delivery system, the process comprising: (a) preparing a carrier molecule, R$^{11}$, wherein R$^{11}$ is a cross-linked hydrogel; optionally, step (a) may further comprise purifying the cross-linked hydrogel carrier molecule R$^{11}$; (b) separately conjugating the traceless linker, R, to an ANGPTL3 polypeptide comprising at least one primary amine, D, thereby forming the traceless linker-D adduct; step (b) may optionally further comprise purification of the traceless linker-D adduct, (c) conjugating the carrier molecule, R$^{11}$, with the traceless linker-D adduct; and (d) purifying the drug delivery system from the reagents. One aspect is a drug delivery system made using the method described herein.

Another embodiment described herein is a method for treating macular degeneration comprising administering to a subject in need thereof a drug delivery system or pharmaceutically acceptable salt thereof comprising a conjugate D-R, that is represented by Formula (I), where D comprises an ANGPTL3 polypeptide comprising at least one primary amine; R is a linker suitable for release of D:

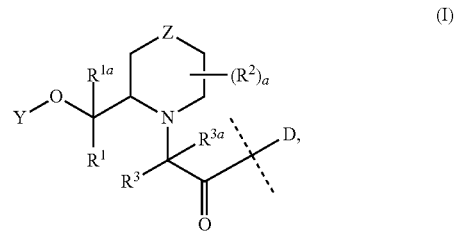

(I)

where the dashed line indicates attachment to the primary amine; R$^1$ is hydrogen or C$_1$-C$_4$alkyl; R$^{1a}$ is hydrogen or C$_1$-C$_4$alkyl, or CR$^1$R$^{1a}$, taken in combination form a C$_3$-C$_6$cycloalk-1,1-diyl; R$^2$ is independently selected at each occurrence from C$_1$-C$_4$alkyl or oxo, or two R$^2$ groups taken in combination form a fused C$_3$-C$_6$ cycloalkyl or spiro C$_3$-C$_6$cycloalk-1,1-diyl group; a is 0, 1, 2, 3 or 4; R$^3$ is hydrogen or C$_1$-C$_4$alkyl; R$^{3a}$ is hydrogen, C$_1$-C$_4$alkyl, or CR$^3$R$^{3a}$, taken in combination form a C$_3$-C$_6$cycloalk-1,1-diyl; Y is C(O)R$^4$, C(O)OR$^4$, C(O)NHR$^4$, C(O)NR$^5$R$^6$, SiR$^5$R$^6$R$^7$, or CR$^{12}$R$^{12a}$OR$^{13}$; R$^{12}$ is hydrogen or C$_1$-C$_4$alkyl; R$^{12a}$ is hydrogen or C$_1$-C$_4$alkyl, or CR$^{12}$R$^{12a}$, taken in combination form a C$_3$-C$_6$cycloalk-1,1-diyl; R$^{13}$ is C$_1$-C$_4$alkyl; or CHR$^{12}$OR$^{13}$, taken in combination form a 5, 6, or 7-member cyclic ether; R$^4$ is C$_1$-C$_8$alkyl or C$_3$-C$_7$cycloalkyl, wherein cycloalkyl is optionally substituted with 0, 1, or 2 independently selected C$_1$-C$_4$alkyl groups and wherein alkyl is optionally substituted by hydroxy, amino, C$_1$-C$_4$alkoxy or mono- and di-C$_1$-C$_4$alkylamino; R$^5$ and R$^6$ are each independently selected from C$_1$-C$_4$alkyl and C$_3$-C$_6$cycloalkyl; R$^7$ is C$_1$-C$_8$alkyl, C$_3$-C$_7$cycloalkyl, C$_1$-C$_8$alkoxy, C$_3$-C$_7$cycloalkyloxy, heterocycloalkyloxy, or —(OCHR$^3$CH$_2$)$_b$O—C$_1$-C$_4$alkyl, wherein the heterocycloalkyloxy is a 4 to 7 member saturated heterocyclic ring having one ring heteroatom selected from N, O, and S and optionally substituted with 0, 1, or 2 independently selected C$_1$-C$_4$alkyl groups; b is an integer of from 1 to 10; Z is CHR$^8$ or NR$^9$; R$^8$ and R$^9$ are each independently selected from hydrogen, C$_1$-C$_8$ alkyl, C(O)C$_1$-C$_8$ alkyl, or —C(O)(CH$_2$)$_q$[O—W]$_g$(NHC(O))$_m$(CH$_2$)$_q$[O—W]$_p$-Q-A, wherein the alkyl group is optionally substituted with 0 or 1 Q-A; q is independently at each occurrence 1, 2, or 3; g and p each independently have a weighted average length of between about 2 and about 50; m is 1 or 0; W is C$_2$-C$_4$alkyl-1,2-diyl in which the hydrogen, methyl, or ethyl side chain may be present on either backbone carbon atom; Q is a bond, O, N(H) or N(C$_1$-C$_4$alkyl); A is hydrogen, C$_1$-C$_8$alkyl, C(O)C$_1$-C$_8$alkyl, C(O)N(H)C$_1$-C$_8$alkyl, C(O)OC$_1$-C$_8$alkyl, R$^{10}$, or R$^{11}$, wherein the alkyl group is optionally substituted with 0 or 1 $R^{10}$; $R^{10}$ is a reactive functional group suitable for coupling Formula (I) to a carrier; and $R^{11}$ is a carrier.

Another embodiment described herein is a method for treating musculoskeletal disorders comprising administering to a subject in need thereof a drug delivery system or pharmaceutically acceptable salt thereof comprising a conjugate D-R, that is represented by Formula (I), where D an ANGPTL3 polypeptide comprising at least one primary amine; R is a linker suitable for release of D:

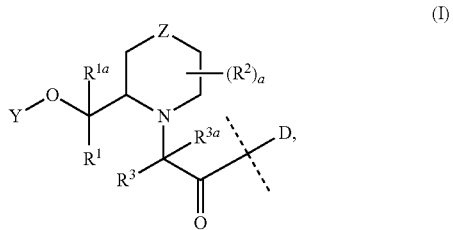

(I)

where the dashed line indicates attachment to the primary amine, secondary amine, or ring nitrogen atom of an aza-heteroaryl ring; $R^1$ is hydrogen or $C_1$-$C_4$alkyl; $R^{1a}$ is hydrogen or $C_1$-$C_4$alkyl, or $CR^1R^{1a}$, taken in combination form a $C_3$-$C_6$cycloalk-1,1-diyl; $R^2$ is independently selected at each occurrence from $C_1$-$C_4$alkyl or oxo, or two $R^2$ groups taken in combination form a fused $C_3$-$C_6$ cycloalkyl or spiro $C_3$-$C_6$cycloalk-1,1-diyl group; a is 0, 1, 2, 3 or 4; $R^3$ is hydrogen or $C_1$-$C_4$alkyl; $R^{3a}$ is hydrogen, $C_1$-$C_4$alkyl, or $CR^3R^{3a}$, taken in combination form a $C_3$-$C_6$cycloalk-1,1-diyl; Y is $C(O)R^4$, $C(O)OR^4$, $C(O)NHR^4$, $C(O)NR^5R^6$, $SiR^5R^6R^7$, or $CR^{12}R^{12a}OR^{13}$; $R^{12}$ is hydrogen or $C_1$-$C_4$alkyl; $R^{12a}$ is hydrogen or $C_1$-$C_4$alkyl, or $CR^{12}R^{12a}$, taken in combination form a $C_3$-$C_6$cycloalk-1,1-diyl; $R^{13}$ is $C_1$-$C_4$alkyl; or $CHR^{12}OR^{13}$, taken in combination form a 5, 6, or 7-member cyclic ether; $R^4$ is $C_1$-$C_8$alkyl or $C_3$-$C_7$cycloalkyl, wherein cycloalkyl is optionally substituted with 0, 1, or 2 independently selected $C_1$-$C_4$alkyl groups and wherein alkyl is optionally substituted by hydroxy, amino, $C_1$-$C_4$alkoxy or mono- and di-$C_1$-$C_4$alkylamino; $R^5$ and $R^6$ are each independently selected from $C_1$-$C_4$alkyl and $C_3$-$C_6$cycloalkyl; $R^7$ is $C_1$-$C_8$alkyl, $C_3$-$C_7$cycloalkyl, $C_1$-$C_8$alkoxy, $C_3$-$C_7$cycloalkyloxy, heterocycloalkyloxy, or —$(OCHR^3CH_2)_bO$—$C_1$-$C_4$alkyl, wherein the heterocycloalkyloxy is a 4 to 7 member saturated heterocyclic ring having one ring heteroatom selected from N, O, and S and optionally substituted with 0, 1, or 2 independently selected $C_1$-$C_4$alkyl groups; b is an integer of from 1 to 10; Z is $CHR^8$ or $NR^9$; $R^8$ and $R^9$ are each independently selected from hydrogen, $C_1$-$C_8$ alkyl, $C(O)C_1$-$C_8$ alkyl, or —$C(O)(CH_2)_q[O$—$W]_g(NHC(O))_m(CH_2)_q[O$—$W]_p$-Q-A, wherein the alkyl group is optionally substituted with 0 or 1 Q-A; q is independently at each occurrence 1, 2, or 3; g and p each independently have a weighted average length of between about 2 and about 50; m is 1 or 0; W is $C_2$-$C_4$alkyl-1,2-diyl in which the hydrogen, methyl, or ethyl side chain may be present on either backbone carbon atom; Q is a bond, O, N(H) or $N(C_1$-$C_4$alkyl); A is hydrogen, $C_1$-$C_8$alkyl, $C(O)C_1$-$C_8$alkyl, $C(O)N(H)C_1$-$C_8$alkyl, $C(O)OC_1$-$C_8$alkyl, $R^{10}$, or $R^{11}$, wherein the alkyl group is optionally substituted with 0 or 1 $R^{10}$; $R^{10}$ is a reactive functional group suitable for coupling Formula (I) to a carrier; and $R^{11}$ is a carrier.

Another embodiment described herein is a method for treating a disease or disorder comprising administering to a subject in need thereof a drug delivery system or pharmaceutically acceptable salt thereof comprising a conjugate D-R, that is represented by Formula (I), where D comprises an ANGPTL3 polypeptide comprising at least one primary amine; R is a linker suitable for release of D:

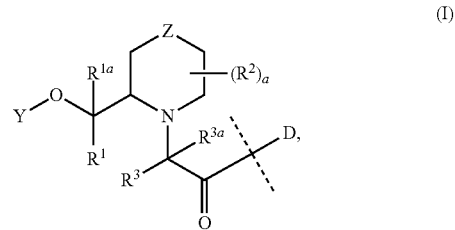

(I)

where the dashed line indicates attachment to the primary amine; $R^1$ is hydrogen or $C_1$-$C_4$alkyl; $R^{1a}$ is hydrogen or $C_1$-$C_4$alkyl, or $CR^1R^{1a}$, taken in combination form a $C_3$-$C_6$cycloalk-1,1-diyl; $R^2$ is independently selected at each occurrence from $C_1$-$C_4$alkyl or oxo, or two $R^2$ groups taken in combination form a fused $C_3$-$C_6$ cycloalkyl or spiro $C_3$-$C_6$cycloalk-1,1-diyl group; a is 0, 1, 2, 3 or 4; $R^3$ is hydrogen or $C_1$-$C_4$alkyl; $R^{3a}$ is hydrogen, $C_1$-$C_4$alkyl, or $CR^3R^{3a}$, taken in combination form a $C_3$-$C_6$cycloalk-1,1-diyl; Y is $C(O)R^4$, $C(O)OR^4$, $C(O)NHR^4$, $C(O)NR^5R^6$, $SiR^5R^6R^7$, or $CR^{12}R^{12a}OR^{13}$; $R^{12}$ is hydrogen or $C_1$-$C_4$alkyl; $R^{12a}$ is hydrogen or $C_1$-$C_4$alkyl, or $CR^{12}R^{12a}$, taken in combination form a $C_3$-$C_6$cycloalk-1,1-diyl; $R^{13}$ is $C_1$-$C_4$alkyl; or $CHR^{12}OR^{13}$, taken in combination form a 5, 6, or 7-member cyclic ether; $R^4$ is $C_1$-$C_8$alkyl or $C_3$-$C_7$cycloalkyl, wherein cycloalkyl is optionally substituted with 0, 1, or 2 independently selected $C_1$-$C_4$alkyl groups and wherein alkyl is optionally substituted by hydroxy, amino, $C_1$-$C_4$alkoxy or mono- and di-$C_1$-$C_4$alkylamino; $R^5$ and $R^6$ are each independently selected from $C_1$-$C_4$alkyl and $C_3$-$C_6$cycloalkyl; $R^7$ is $C_1$-$C_8$alkyl, $C_3$-$C_7$cycloalkyl, $C_1$-$C_8$alkoxy, $C_3$-$C_7$cycloalkyloxy, heterocycloalkyloxy, or —$(OCHR^3CH_2)_bO$—$C_1$-$C_4$alkyl, wherein the heterocycloalkyloxy is a 4 to 7 member saturated heterocyclic ring having one ring heteroatom selected from N, O, and S and optionally substituted with 0, 1, or 2 independently selected $C_1$-$C_4$alkyl groups; b is an integer of from 1 to 10; Z is $CHR^8$ or $NR^9$; $R^8$ and $R^9$ are each independently selected from hydrogen, $C_1$-$C_8$ alkyl, $C(O)C_1$-$C_8$ alkyl, or —$C(O)(CH_2)_q[O$—$W]_g(NHC(O))_m(CH_2)_q[O$—$W]_p$-Q-A, wherein the alkyl group is optionally substituted with 0 or 1 Q-A; q is independently at each occurrence 1, 2, or 3; g and p each independently have a weighted average length of between about 2 and about 50; m is 1 or 0; W is $C_2$-$C_4$alkyl-1,2-diyl in which the hydrogen, methyl, or ethyl side chain may be present on either backbone carbon atom; Q is a bond, O, N(H) or $N(C_1$-$C_4$alkyl); A is hydrogen, $C_1$-$C_8$alkyl, $C(O)C_1$-$C_8$alkyl, $C(O)N(H)C_1$-$C_8$alkyl, $C(O)OC_1$-$C_8$alkyl, $R^{10}$, or $R^{11}$, wherein the alkyl group is optionally substituted with 0 or 1 $R^{10}$; $R^{10}$ is a reactive functional group suitable for coupling Formula (I) to a carrier; and $R^{11}$ is a carrier.

Another embodiment described herein is a means for extending half-life of an ANGPTL3 polypeptide comprising at least one primary amine, D, the means comprising attaching D to R, that is represented by Formula (I), where R is a linker suitable for release of D:

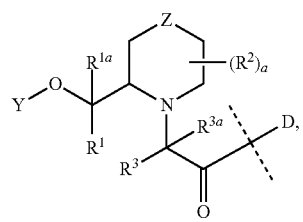
(I)

where the dashed line indicates attachment to the primary amine; $R^1$ is hydrogen or $C_1$-$C_4$alkyl; $R^{1a}$ is hydrogen or $C_1$-$C_4$alkyl, or $CR^1R^{1a}$, taken in combination form a $C_3$-$C_6$cycloalk-1,1-diyl; $R^2$ is independently selected at each occurrence from $C_1$-$C_4$alkyl or oxo, or two $R^2$ groups taken in combination form a fused $C_3$-$C_6$ cycloalkyl or spiro $C_3$-$C_6$cycloalk-1,1-diyl group; a is 0, 1, 2, 3 or 4; $R^3$ is hydrogen or $C_1$-$C_4$alkyl; $R^{3a}$ is hydrogen, $C_1$-$C_4$alkyl, or $CR^3R^{3a}$, taken in combination form a $C_3$-$C_6$cycloalk-1,1-diyl; Y is $C(O)R^4$, $C(O)OR^4$, $C(O)NHR^4$, $C(O)NR^5R^6$, $SiR^5R^6R^7$, or $CR^{12}R^{12a}OR^{13}$; $R^{12}$ is hydrogen or $C_1$-$C_4$alkyl; $R^{12a}$ is hydrogen or $C_1$-$C_4$alkyl, or $CR^{12}R^{12a}$, taken in combination form a $C_3$-$C_6$cycloalk-1,1-diyl; $R^{13}$ is $C_1$-$C_4$alkyl; or $CHR^{12}OR^{13}$, taken in combination form a 5, 6, or 7-member cyclic ether; $R^4$ is $C_1$-$C_8$alkyl or $C_3$-$C_7$cycloalkyl, wherein cycloalkyl is optionally substituted with 0, 1, or 2 independently selected $C_1$-$C_4$alkyl groups and wherein alkyl is optionally substituted by hydroxy, amino, $C_1$-$C_4$alkoxy or mono- and di-$C_1$-$C_4$alkylamino; $R^5$ and $R^6$ are each independently selected from $C_1$-$C_4$alkyl and $C_3$-$C_6$cycloalkyl; $R^7$ is $C_1$-$C_8$alkyl, $C_3$-$C_7$cycloalkyl, $C_1$-$C_8$alkoxy, $C_3$-$C_7$cycloalkyloxy, heterocycloalkyloxy, or —(OCHR$^3$CH$_2$)$_b$O—$C_1$-$C_4$alkyl, wherein the heterocycloalkyloxy is a 4 to 7 member saturated heterocyclic ring having one ring heteroatom selected from N, O, and S and optionally substituted with 0, 1, or 2 independently selected $C_1$-$C_4$alkyl groups; b is an integer of from 1 to 10; Z is $CHR^8$ or $NR^9$; $R^8$ and $R^9$ are each independently selected from hydrogen, $C_1$-$C_8$ alkyl, $C(O)C_1$-$C_8$ alkyl, or —C(O)(CH$_2$)$_q$[O—W]$_g$(NHC(O))$_m$(CH$_2$)$_q$[O—W]$_p$-Q-A, wherein the alkyl group is optionally substituted with 0 or 1 Q-A; q is independently at each occurrence 1, 2, or 3; g and p each independently have a weighted average length of between about 2 and about 50; m is 1 or 0; W is $C_2$-$C_4$alkyl-1,2-diyl in which the hydrogen, methyl, or ethyl side chain may be present on either backbone carbon atom; Q is a bond, O, N(H) or N($C_1$-$C_4$alkyl); A is hydrogen, $C_1$-$C_8$alkyl, $C(O)C_1$-$C_8$alkyl, $C(O)N(H)C_1$-$C_8$alkyl, $C(O)OC_1$-$C_8$alkyl, $R^{10}$, or $R^{11}$, wherein the alkyl group is optionally substituted with 0 or 1 $R^{10}$; $R^{10}$ is a reactive functional group suitable for coupling Formula (I) to a carrier; and $R^{11}$ is a carrier. In one aspect, D comprises an ANGPTL3 polypeptide having at least 95% identity to any one of SEQ ID NO: 1 or 3-45.

Another embodiment described herein is a drug delivery system comprising Formula (III):

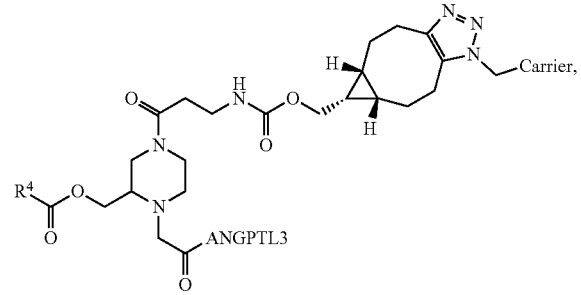
(III)

wherein ANGPTL3 comprises an ANGPTL3 polypeptide having at least 95% identity to any one of SEQ ID NO: 1 or 3-45, or combinations thereof.

Another embodiment described herein is a drug delivery system comprising Formula (IV):

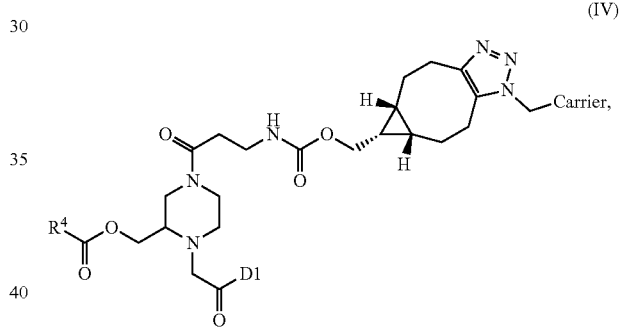
(IV)

wherein D1 comprises an ANGPTL3 polypeptide comprising amino acid residues 242-460 in reference to SEQ ID NO:1 and a K423Q substitution (SEQ ID NO:19).

Another embodiment described herein is a drug delivery system comprising D-R—$R^1$, wherein R comprises a traceless linker, coupled to a biologically-active agent, D; D comprises an ANGPTL3 polypeptide comprising at least one primary amine; and $R^{11}$ comprises a plurality of hyaluronic acid polymers each of which comprises a random series of unfunctionalized D-glucuronic acid monomers, one or more D-glucuronic acid monomers functionalized with a cross-linker, or one or more D-glucuronic acid monomers functionalized with a drug adduct, D-R. In one aspect, D comprises an ANGPTL3 polypeptide having at least 95% identity to any one of SEQ ID NO: 1 or 3-45.

Another embodiment described herein is a drug delivery system or pharmaceutically acceptable salt thereof comprising D-R, that is represented by Formula (XXIV), where D is an ANGPTL3 polypeptide comprising at least one primary amine; and R is a linker suitable for release D:

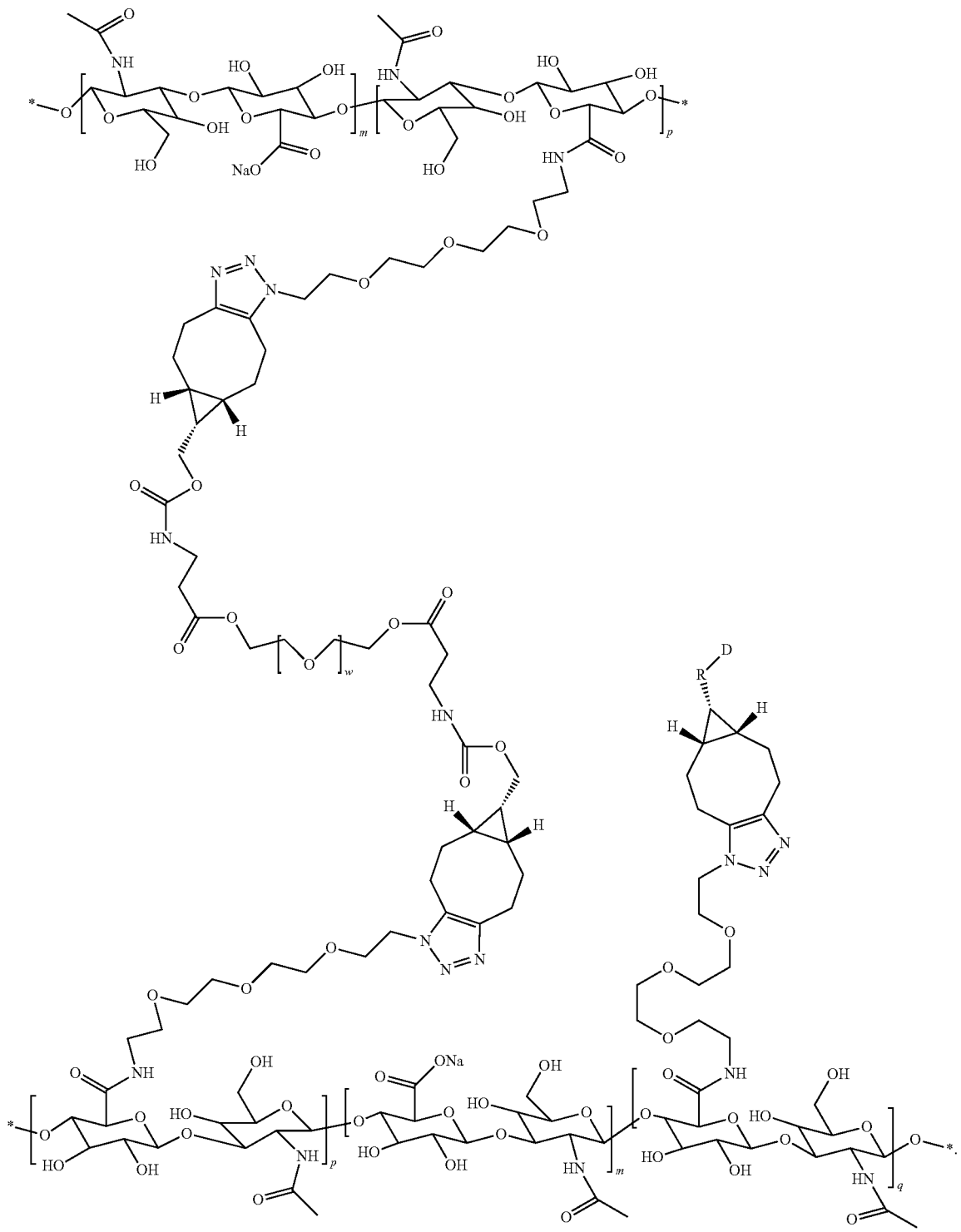
(XXIV)

Another embodiment described herein is a drug delivery system or pharmaceutically acceptable salt thereof comprising D-R, that is represented by Formula (XXV), where D comprises an ANGPTL3 polypeptide comprising at least one primary amine; and R is a linker suitable for release of D:
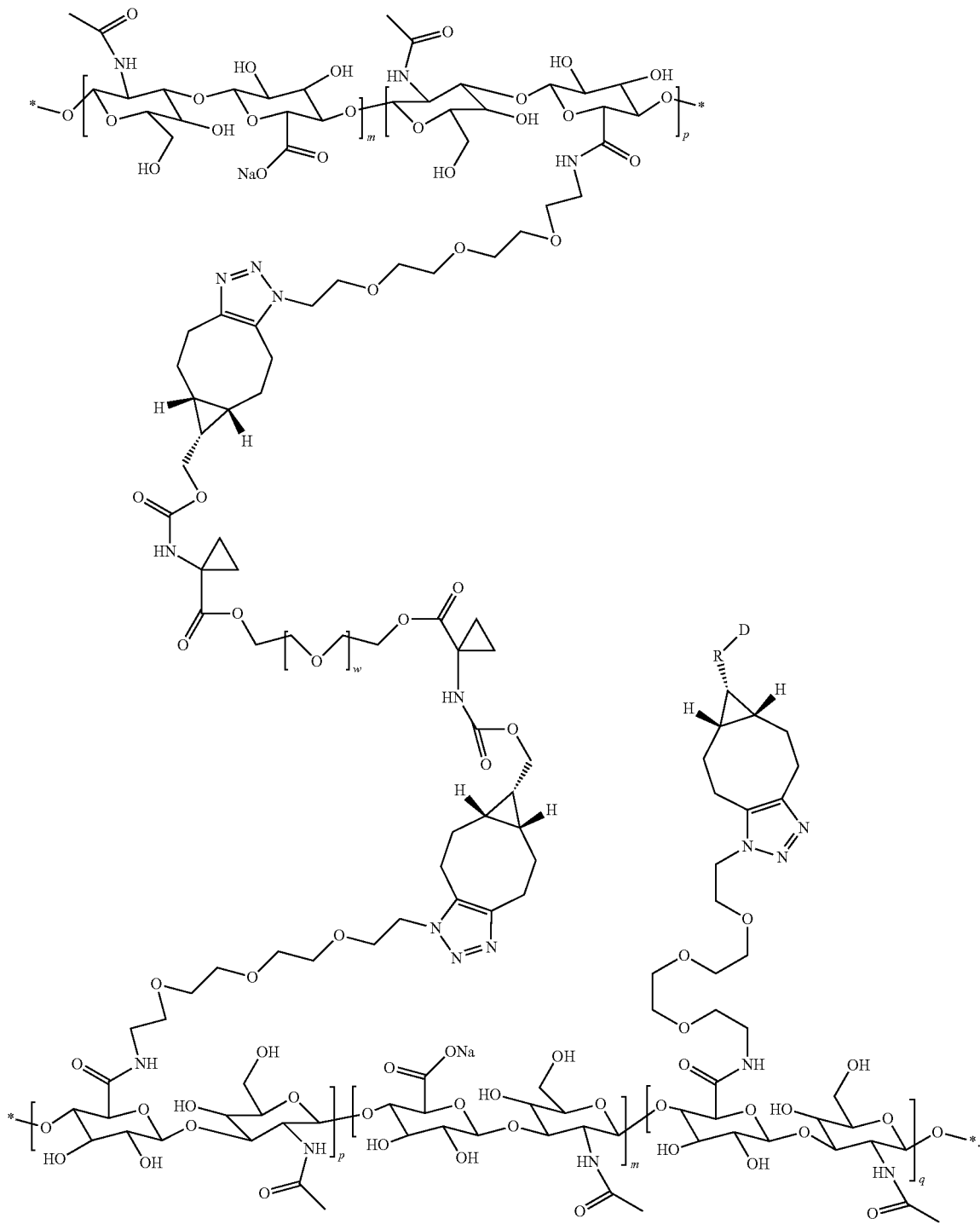
(XXV)

Another embodiment described herein is a drug delivery system or pharmaceutically acceptable salt thereof comprising D-R, that is represented by Formula (XXVI), where D comprises an ANGPTL3 polypeptide comprising at least one primary amine; and R is a linker suitable for release of D:
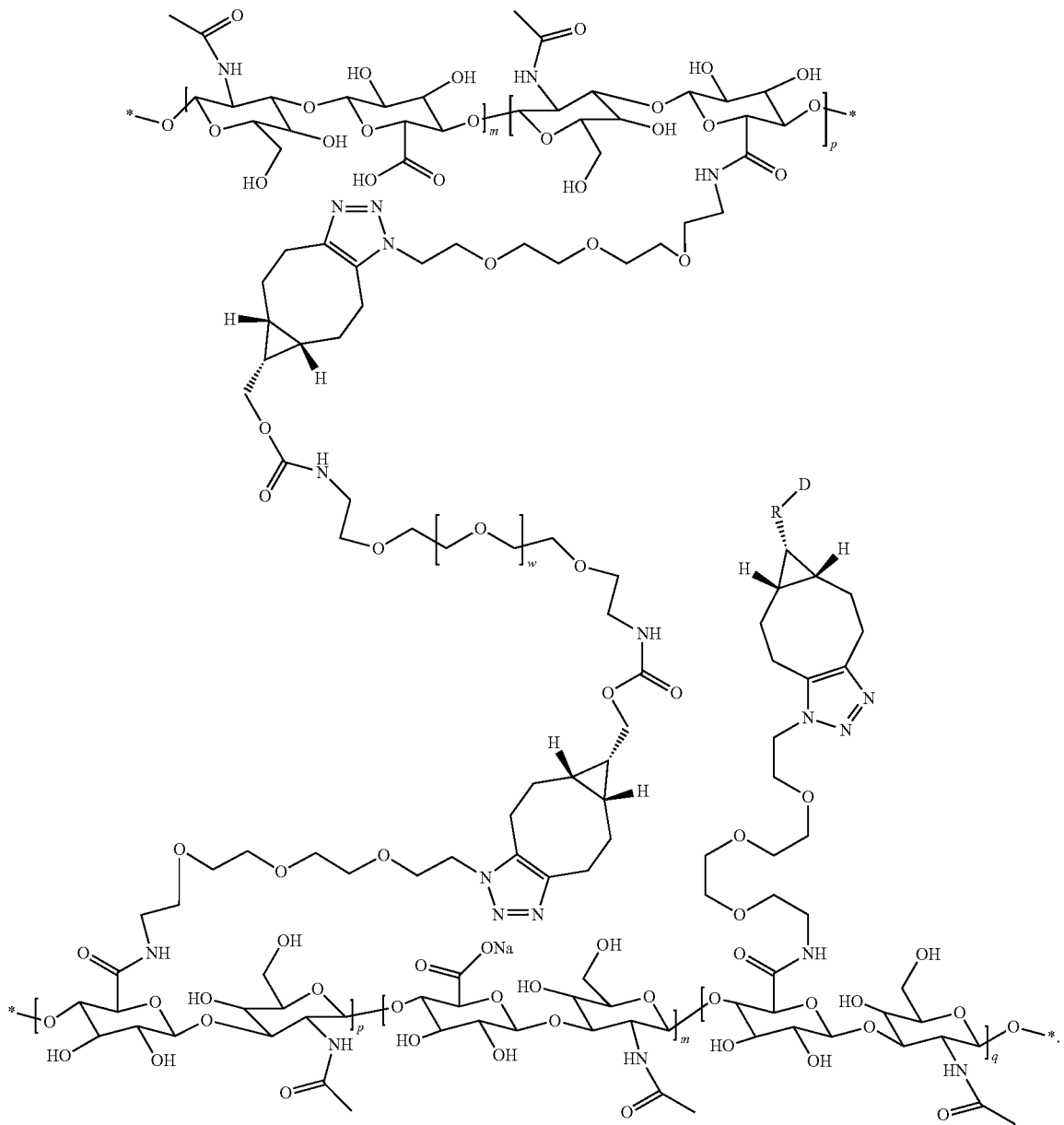
(XXVI)

Another embodiment described herein is a drug delivery system or pharmaceutically acceptable salt thereof comprising D-R, that is represented by Formula (XXVII), where D comprises an ANGPTL3 polypeptide comprising at least one primary amine; and R is a linker suitable for release of D:
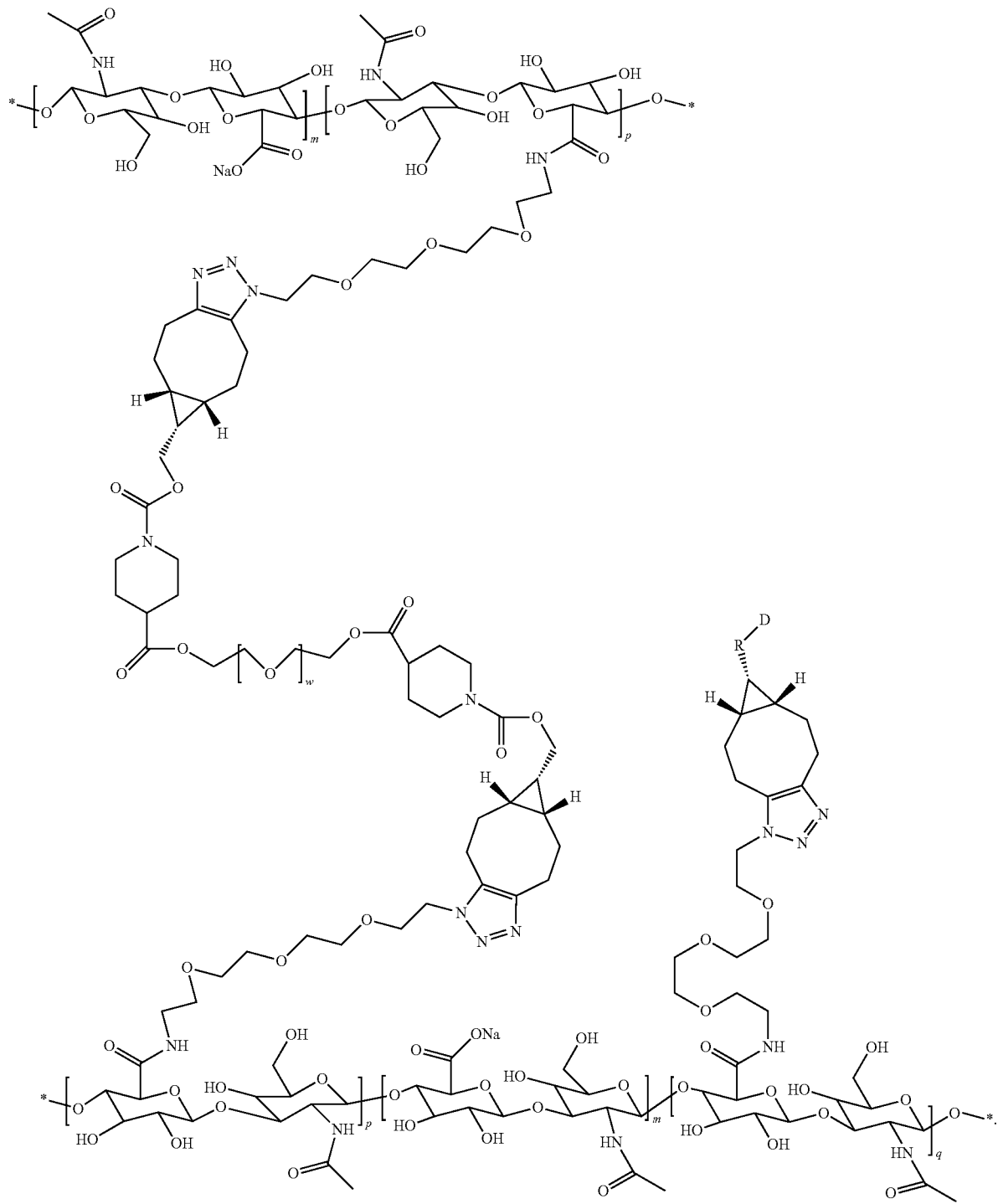

Another embodiment described herein is a drug delivery system or pharmaceutically acceptable salt thereof comprising D-R, that is represented by Formula (XXVIII), where D comprises an ANGPTL3 polypeptide comprising at least one primary amine; and R is a linker suitable for release of D:
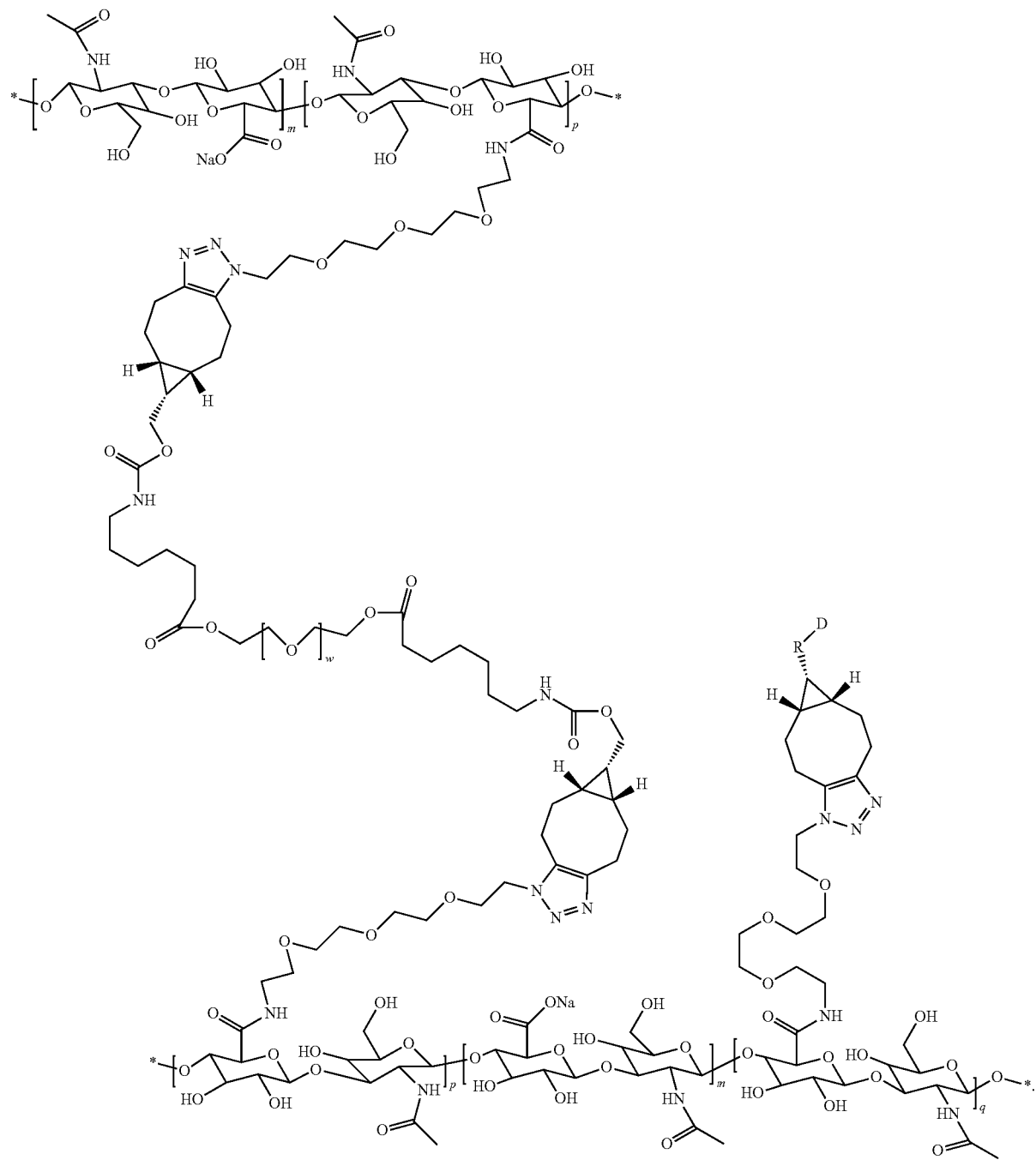
(XXVIII)

Another embodiment described herein is a drug delivery system or pharmaceutically acceptable salt thereof comprising D-R, that is represented by Formula (XXIX), where D comprises an ANGPTL3 polypeptide comprising at least one primary amine; and R is a linker suitable for release of D:
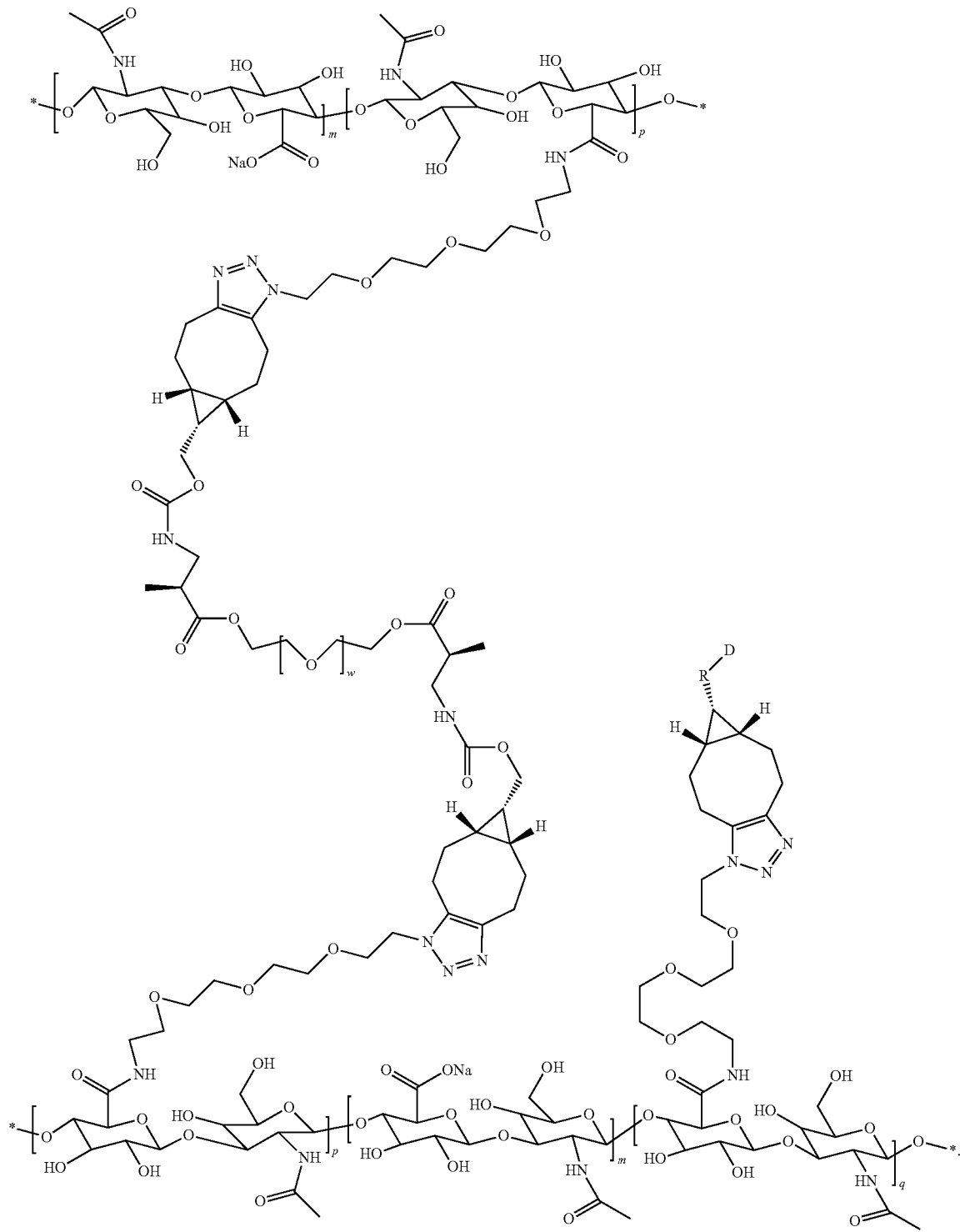
(XXIX)

Another embodiment described herein is a drug delivery system or pharmaceutically acceptable salt thereof that is represented by Formula (XXX), where D comprises an ANGPTL3 polypeptide comprising at least one primary amine; and $R^4$ is methyl, ethyl, propyl, isopropyl, 1-methyl-cyclopropyl, or methoxymethyl:

Another embodiment described herein is a drug delivery system or pharmaceutically acceptable salt thereof comprising D-R, that is represented by Formula (XXXI), where D comprises an ANGPTL3 polypeptide comprising at least one primary amine; and R is a linker suitable for release of D:

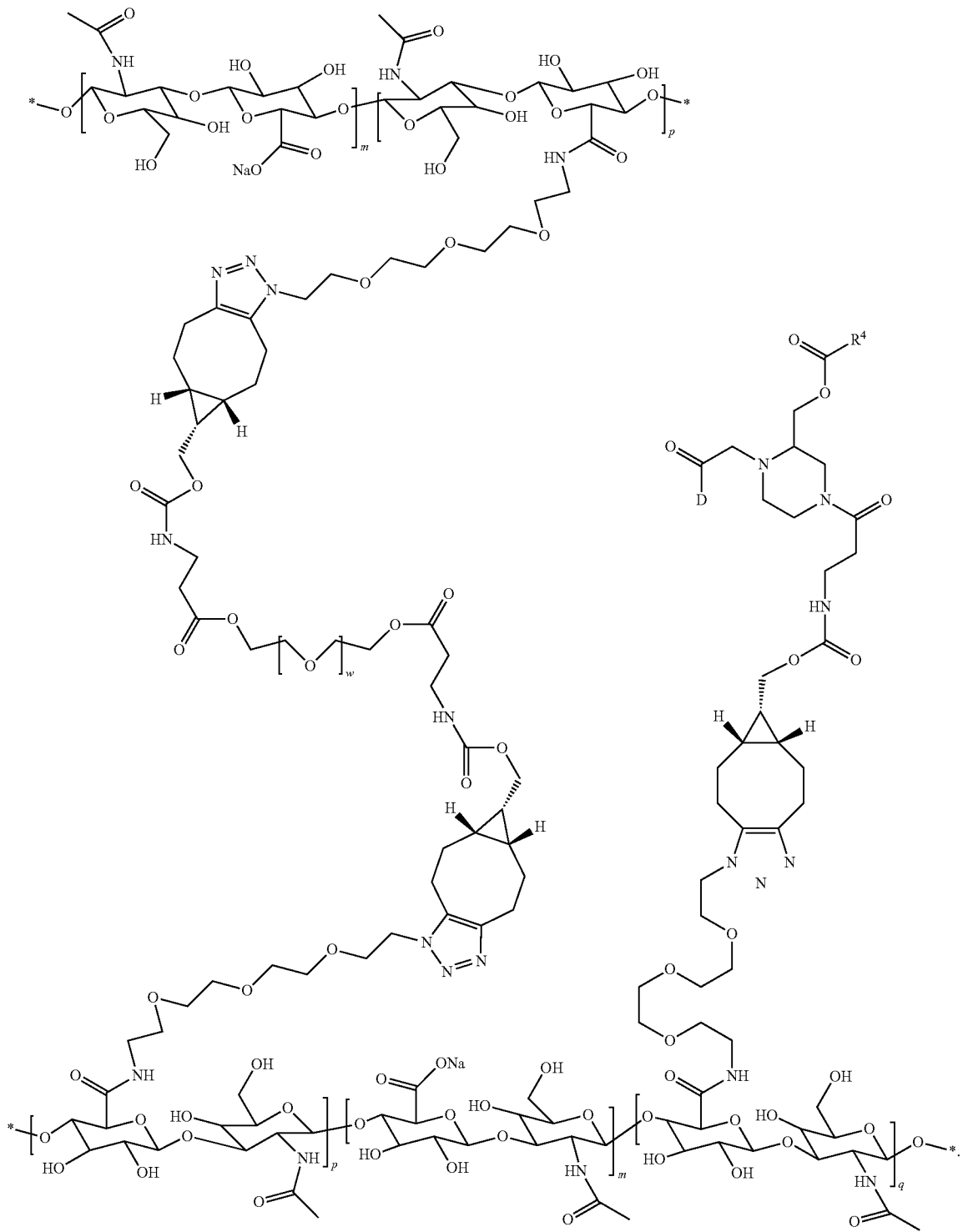

(XXX)

(XXXI)

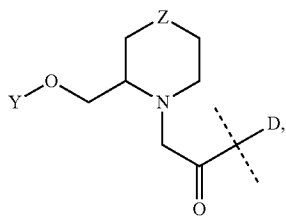

where the dashed line indicates attachment to the primary amine; Y is $C(O)R^4$; $R^4$ is $C_1$-$C_8$alkyl or $C_3$-$C_7$cycloalkyl, wherein cycloalkyl is optionally substituted with 0, 1, or 2 independently selected $C_1$-$C_4$alkyl groups and wherein alkyl is optionally substituted by $C_1$-$C_4$alkoxy; Z is N-L-A; L is $C(O)CH_2CH_2NH$; A is $R^{11}$; $R^{11}$ is a hydrogel derived from a cross-linked hyaluronic acid, wherein the hyaluronic acid comprises at least one amide-linked side chain of N(H)$(CH_2CH_2O)_3CH_2CH_2N_3$, and wherein the cross-linker used to form the hydrogel comprises PEG(2000)-bis-[3-(((((1R,8S,9s)-bicyclo[6.1.0]non-4-yn-9-yl)methoxy)carbonyl)amino)propanoate].

Another embodiment described herein is a drug delivery system or pharmaceutically acceptable salt thereof that is represented by Formula (XXXII), where D comprises an ANGPTL3 polypeptide comprising at least one primary amine; and $R^4$ is methyl, ethyl, propyl, isopropyl, 1-methylcyclopropyl, or methoxymethyl:

(XXXII)

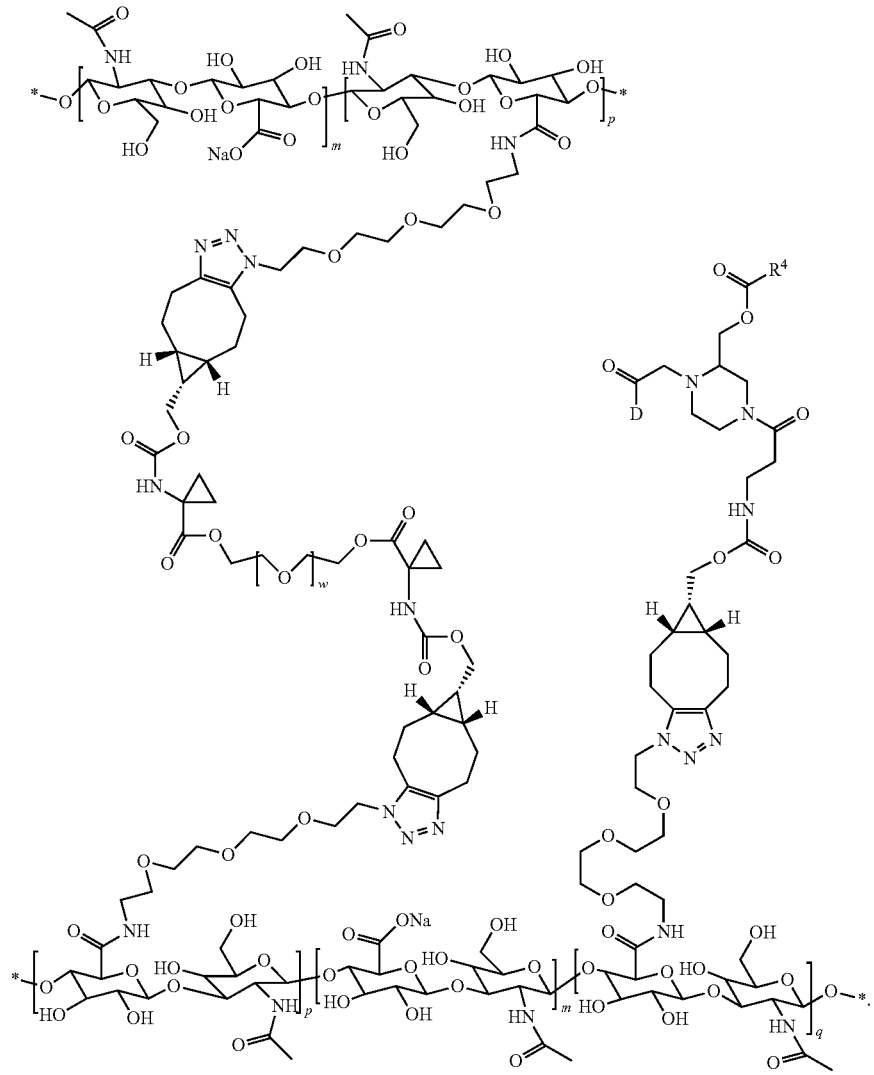

Another embodiment described herein is a drug delivery system or pharmaceutically acceptable salt thereof comprising D-R, that is represented by Formula XXXIII, where D comprises an ANGPTL3 polypeptide comprising at least one primary amine; and R is a linker suitable for release of D:

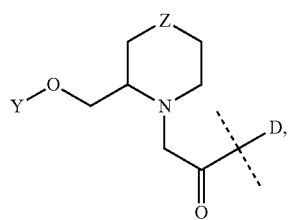

(XXXIII)

where the dashed line indicates attachment to the primary amine; Y is $C(O)R^4$; $R^4$ is $C_1$-$C_8$alkyl or $C_3$-$C_7$cycloalkyl, wherein cycloalkyl is optionally substituted with 0, 1, or 2 independently selected $C_1$-$C_4$alkyl groups and wherein alkyl is optionally substituted by $C_1$-$C_4$alkoxy; Z is N-L-A; L is $C(O)CH_2CH_2NH$; A is $R^{11}$; $R^{11}$ is a hydrogel derived from a cross-linked hyaluronic acid, wherein the hyaluronic acid comprises at least one amide-linked side chain of $N(H)(CH_2CH_2O)_3CH_2CH_2N_3$, and wherein the cross-linker used to form the hydrogel comprises PEG(2000)-bis-[1-((((1'R, 8'S,9's)-bicyclo[6.1.0]non-4'-yn-9'-yl)methoxy)carbonyl)amino-cyclopropane-1-carboxylic acid ester].

Another embodiment described herein is a drug delivery system or pharmaceutically acceptable salt thereof that is represented by Formula (XXXIV), where D comprises an ANGPTL3 polypeptide comprising at least one primary amine; and $R^4$ is methyl, ethyl, propyl, isopropyl, 1-methylcyclopropyl, or methoxymethyl:

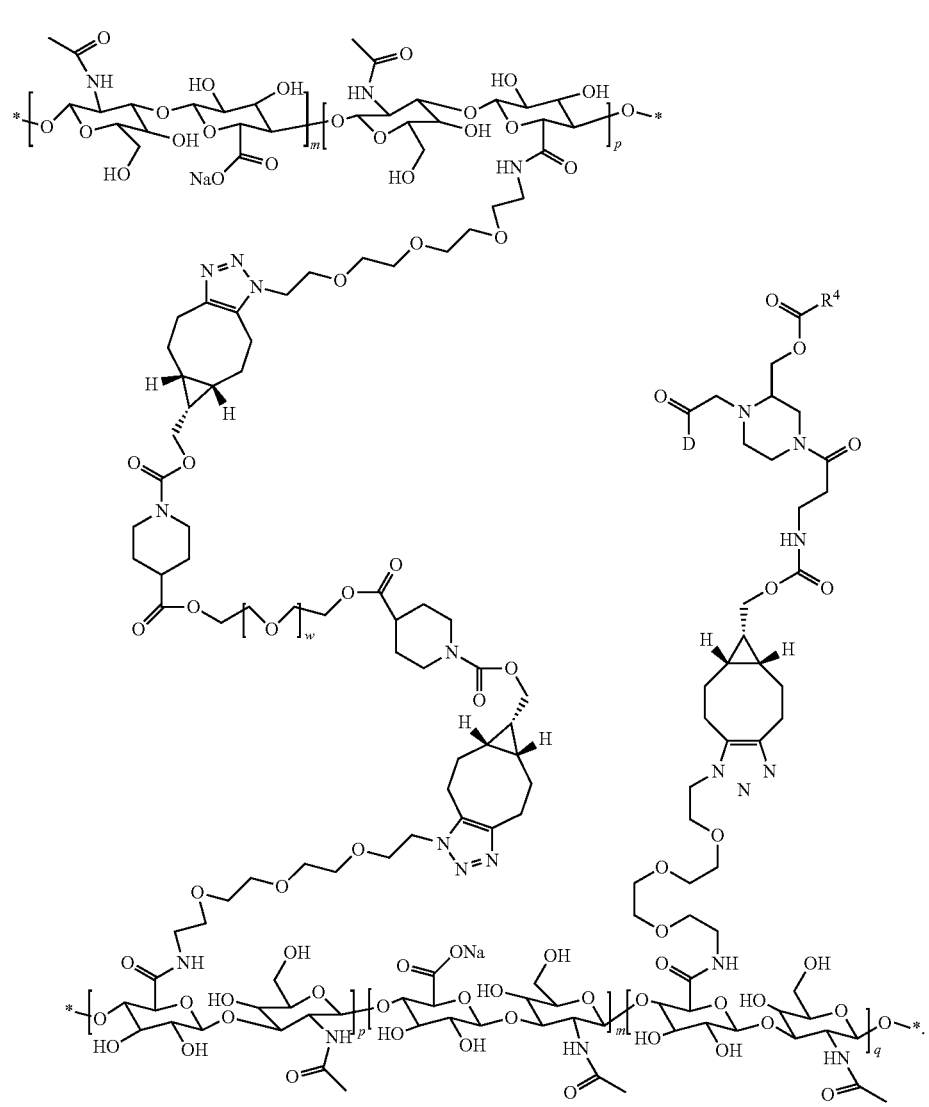

(XXXIV)

Another embodiment described herein is a drug delivery system or pharmaceutically acceptable salt thereof comprising D-R, that is represented by Formula XXXV, where D comprises an ANGPTL3 polypeptide comprising at least one primary amine; and R is a linker suitable for release of D:

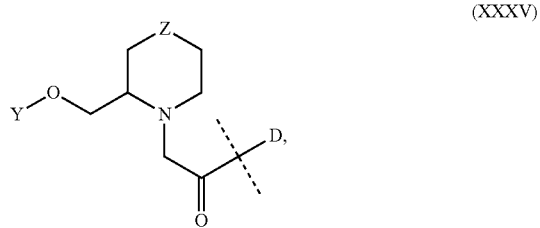

(XXXV)

where the dashed line indicates attachment to the primary amine; Y is $C(O)R^4$; $R^4$ is $C_1$-$C_8$alkyl or $C_3$-$C_7$cycloalkyl, wherein cycloalkyl is optionally substituted with 0, 1, or 2 independently selected $C_1$-$C_4$alkyl groups and wherein alkyl is optionally substituted by $C_1$-$C_4$alkoxy; Z is N-L-A; L is $C(O)CH_2CH_2NH$; A is $R^{11}$; $R^{11}$ is a hydrogel derived from a cross-linked hyaluronic acid, wherein the hyaluronic acid comprises at least one amide-linked side chain of $N(H)(CH_2CH_2O)_3CH_2CH_2N_3$, and wherein the cross-linker used to form the hydrogel comprises PEG(2000)-bis-[1-((((1'R,8'S,9's)-bicyclo[6.1.0]non-4'-yn-9'-yl)methoxy)carbonyl)piperidine-4-carboxylic acid ester].

Another embodiment described herein is a drug delivery system or pharmaceutically acceptable salt thereof that is represented by Formula (XXXVI), where Drug, D, comprises an ANGPTL3 polypeptide comprising at least one primary amine; and $R^4$ is methyl, ethyl, propyl, isopropyl, 1-methyl-cyclopropyl, or methoxymethyl:

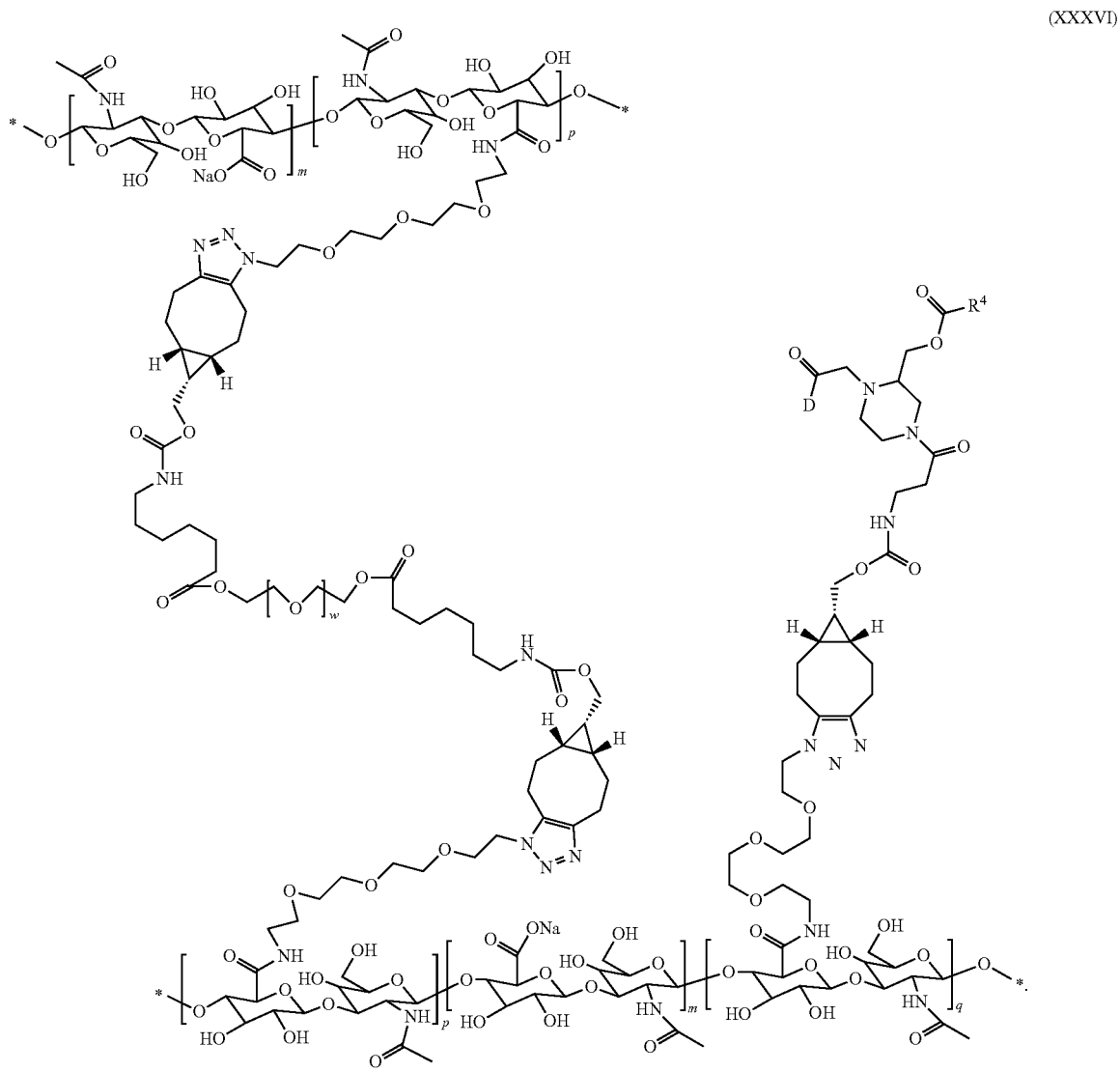

(XXXVI)

Another embodiment described herein is a drug delivery system or pharmaceutically acceptable salt thereof comprising D-R, that is represented by Formula XXXVII, where D comprises an ANGPTL3 polypeptide comprising at least one primary amine; and R is a linker suitable for release of D:

(XXXVII)

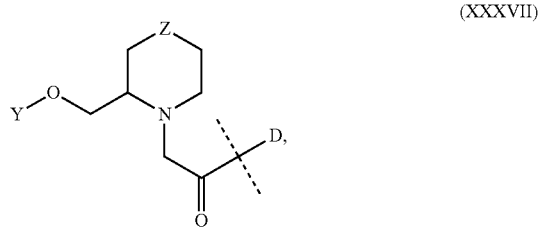

where the dashed line indicates attachment to the primary amine; Y is $C(O)R^4$; $R^4$ is $C_1$-$C_8$alkyl or $C_3$-$C_7$cycloalkyl, wherein cycloalkyl is optionally substituted with 0, 1, or 2 independently selected $C_1$-$C_4$alkyl groups and wherein alkyl is optionally substituted by $C_1$-$C_4$alkoxy; Z is N-L-A; L is $C(O)CH_2CH_2NH$; A is $R^{11}$; $R^{11}$ is a hydrogel derived from a cross-linked hyaluronic acid, wherein the hyaluronic acid comprises at least one amide-linked side chain of $N(H)(CH_2CH_2O)_3CH_2CH_2N_3$, and wherein the cross-linker used to form the hydrogel comprises PEG(2000)-bis-[7-(((((1'R,8'S,9's)-bicyclo[6.1.0]non-4'-yn-9'-yl)methoxy)carbonyl)amino)heptanoate].

Another embodiment described herein is a drug delivery system or pharmaceutically acceptable salt thereof that is represented by Formula (XXXVIII), where Drug, D, comprises an ANGPTL3 polypeptide comprising at least one primary amine; and $R^4$ is methyl, ethyl, propyl, isopropyl, 1-methyl-cyclopropyl, or methoxymethyl:

(XXXVIII)

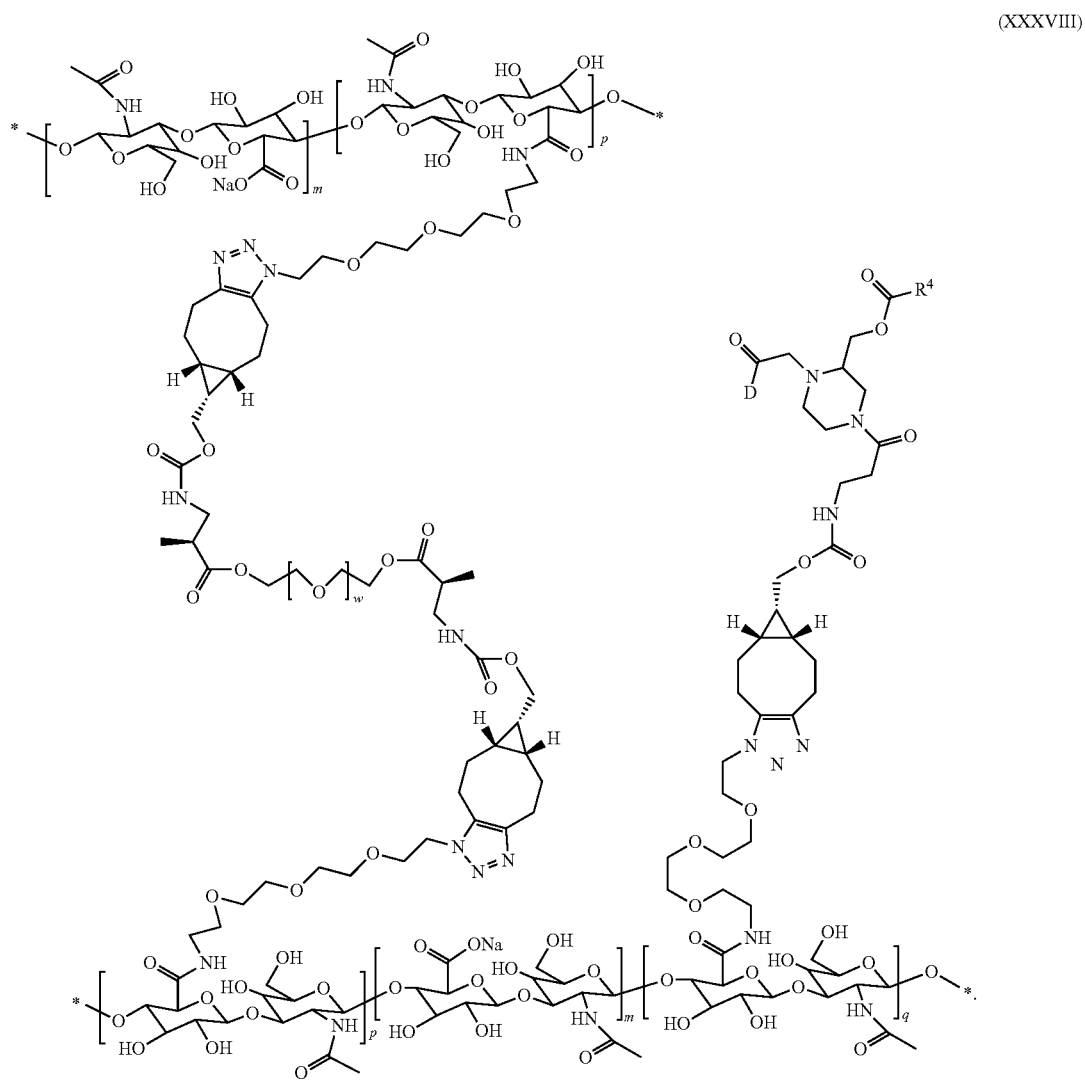

Another embodiment described herein is a drug delivery system or pharmaceutically acceptable salt thereof comprising D-R, that is represented by Formula (XXXIX), where D comprises an ANGPTL3 polypeptide comprising at least one primary amine; and R is a linker suitable for release of D:

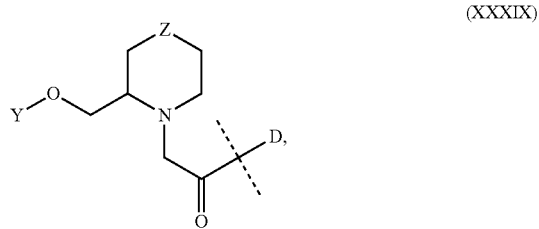

(XXXIX)

where the dashed line indicates attachment to the primary amine, secondary amine, or ring nitrogen atom of an azaheteroaryl ring; Y is $C(O)R^4$; $R^4$ is $C_1$-$C_8$alkyl or $C_3$-$C_7$cycloalkyl, wherein cycloalkyl is optionally substituted with 0, 1, or 2 independently selected $C_1$-$C_4$alkyl groups and wherein alkyl is optionally substituted by $C_1$-$C_4$alkoxy; Z is N-L-A; L is $C(O)CH_2CH_2NH$; A is $R^{11}$; $R^{11}$ is a hydrogel derived from a cross-linked hyaluronic acid, wherein the hyaluronic acid comprises at least one amide-linked side chain of $N(H)(CH_2CH_2O)_3CH_2CH_2N_3$, and wherein the cross-linker used to form the hydrogel comprises PEG(2000)-bis-[2-methyl-3-(((((1'R,8'S,9's)-bicyclo[6.1.0]non-4'-yn-9'-yl)methoxy)carbonyl)amino)propanoate]. In one aspect, D is D1 (SEQ ID NO: 19) and $R^4$ is —$CH_3$, —$CH_2CH_3$, —$CH(CH_3)CH_3$, or methylcyclopropyl. In another aspect, D is D1 (SEQ ID NO:19) and $R^4$ is —$CH_3$. In another aspect, the D-R adduct comprises:

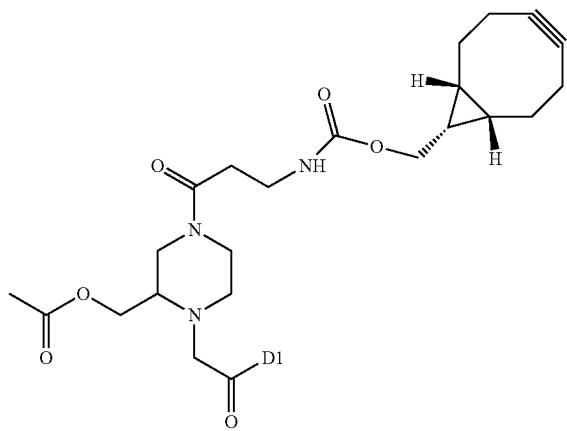

BRIEF DESCRIPTION OF THE DRAWINGS

In FIG. 2 and throughout the specification, polymeric molecules, such as hyaluronic acid, are represented as $[P]_n$, where P represents the monomeric repeating unit and n represents an average number of repeating unit of the monomer. The number of repeating units is a random distribution for any given polymer population. In addition, the relative connectivity of the independent molecules for hydrogels or drug delivery systems described herein is random within a population. Structural depictions of hydrogels or drug delivery systems represent a single potential structural unit in two dimensions, whereas these complexes are three-dimensional with many structural subunits.

DETAILED DESCRIPTION

Figure 1:
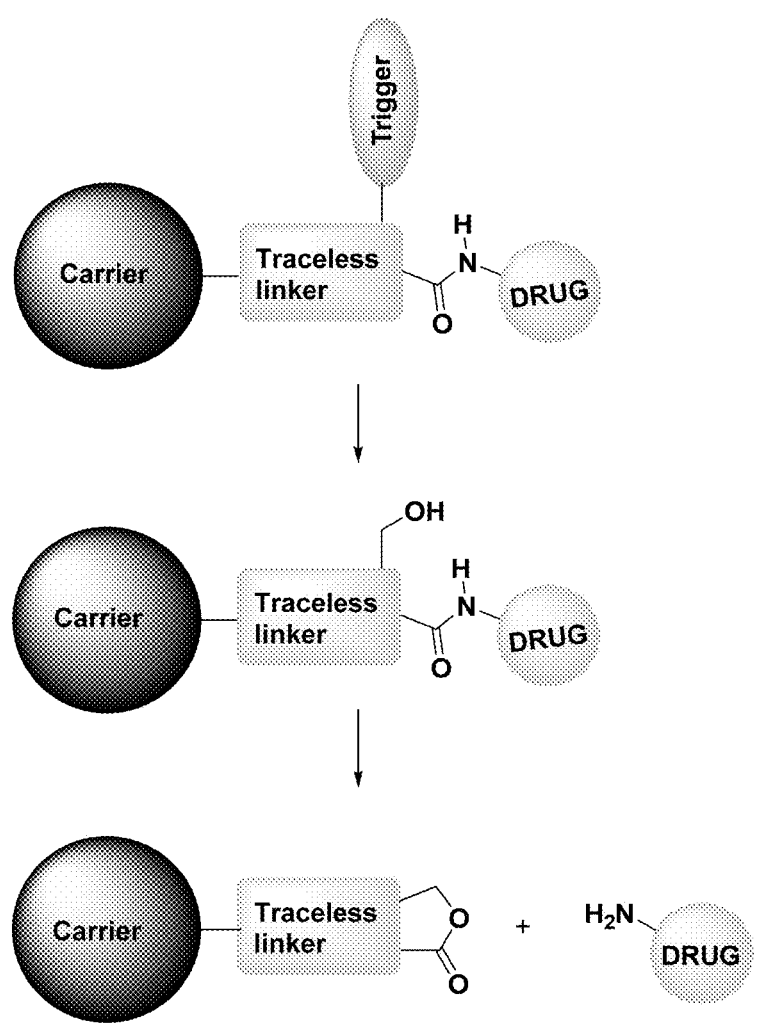
FIG. 1 shows a cartoon of a drug delivery system comprising a drug conjugated to a carrier by a traceless linker, and the drug after release. Reaction of the trigger generates a nucleophilic functional group that cleaves the amide bond linking the drug to the drug delivery system. In this non-limiting example, the drug is linked via a primary amine group.
Figure 2:
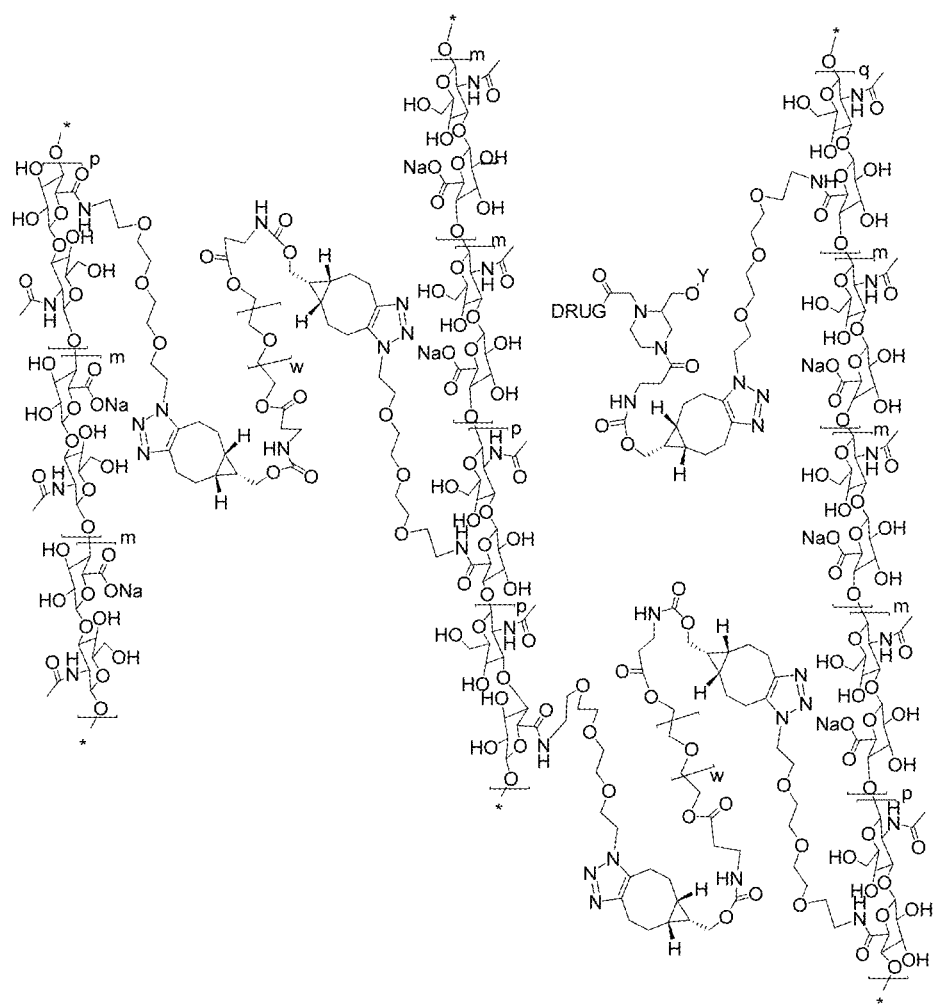
FIG. 2 shows a partial chemical representation of a hydrogel-drug conjugate, where the hydrogel is comprised of hyaluronic acid cross-linked with a PEG and drug is conjugated to the hydrogel by a traceless linker with trigger Y.
Figure 3A:
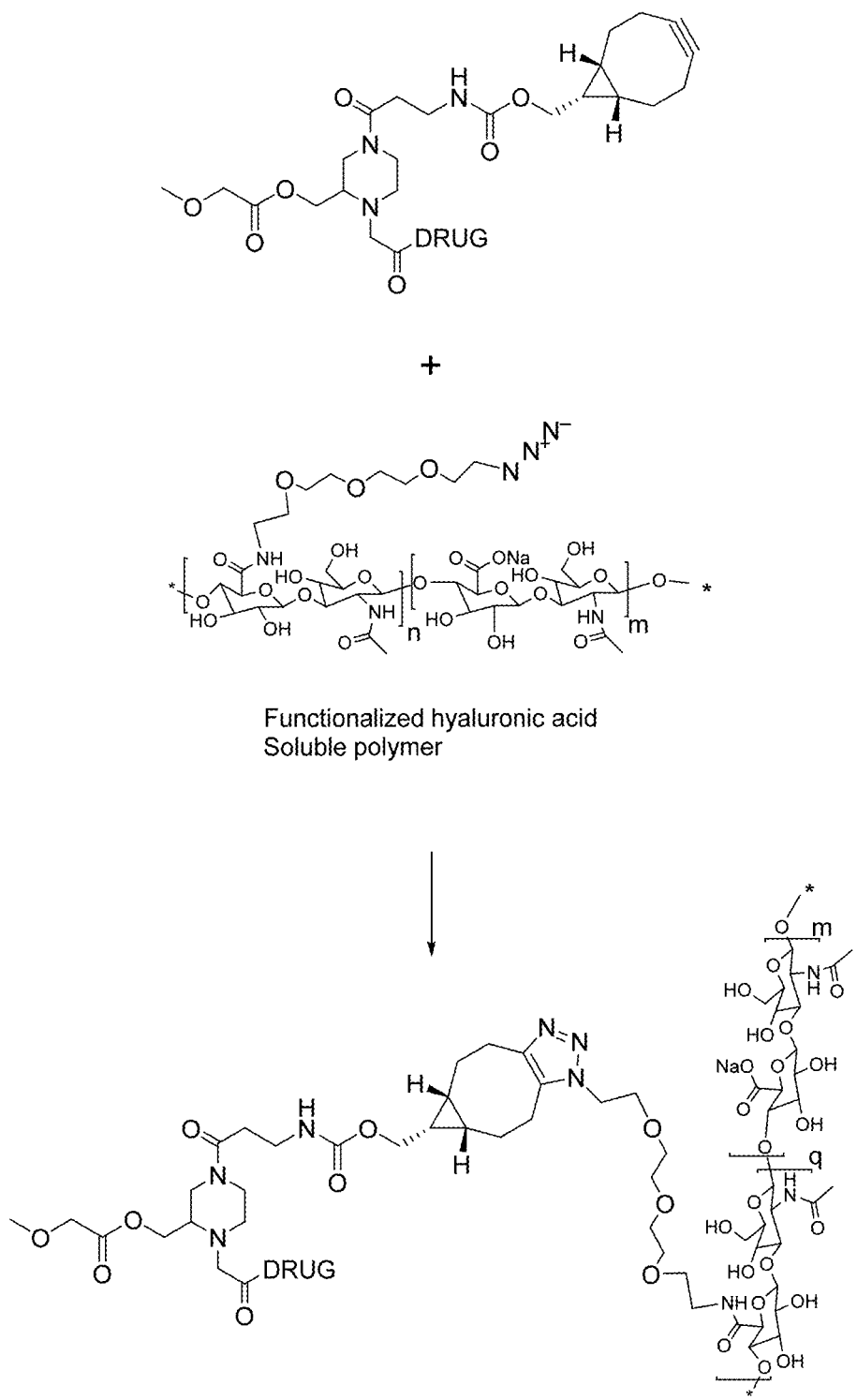
FIG. 3A shows an exemplary reaction of a traceless linker with an azide-functionalized hyaluronic acid polymer.
Figure 3B:
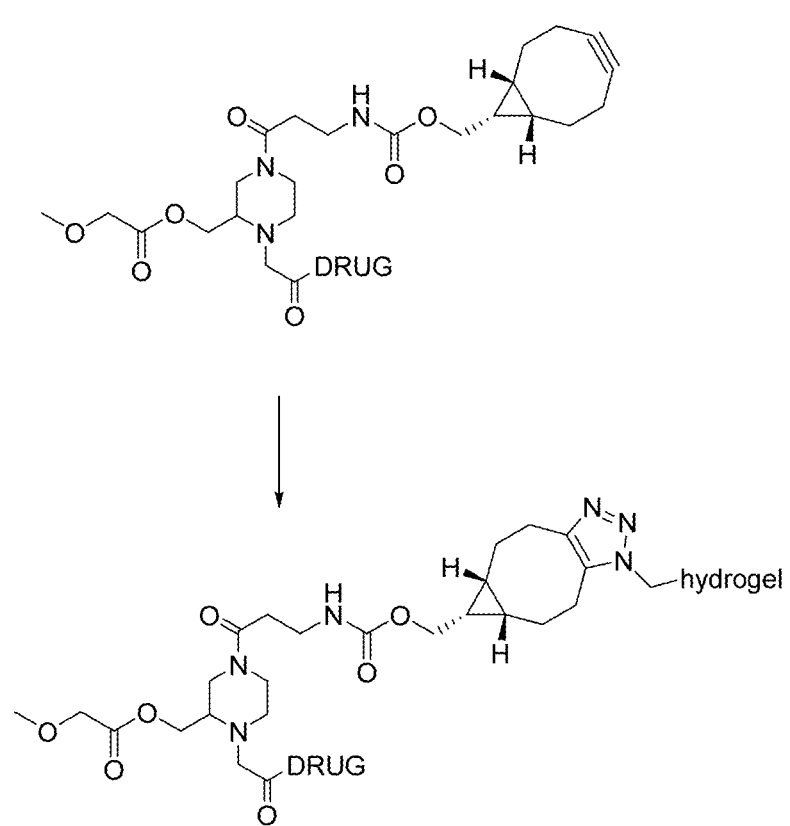
FIG. 3B shows an exemplary reaction of a traceless linker with an azide-functionalized hydrogel.

Described herein are drug delivery systems for delivering biologically active agents comprising primary or secondary amines, or a ring nitrogen atom of an azaheteroaryl ring, pharmaceutically acceptable salts thereof, drug delivery reagents related thereto, pharmaceutical compositions comprising the drug delivery systems, and the use of the drug delivery systems as sustained release therapeutics.

As used herein, the term "alkyl" refers to a straight chain, branched or cyclic carbon chain. Unless otherwise specified, one or more hydrogen atoms of an alkyl carbon may be replaced by a substituent. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. When two moieties of a molecule are linked by the alkyl group, it is referred to also as alkylene. "Lower alkyl" as used herein, is a subset of alkyl, in some embodiments preferred, and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like. The term "alkyl" or "lower alkyl" is intended to include both substituted and unsubstituted alkyl or lower alkyl unless otherwise indicated and these groups may be substituted with additional organic and/or inorganic groups, including but not limited to groups selected from halo (e.g., to form haloalkyl), alkyl, haloalkyl, alkenyl, alkynyl, cycloalkyl, cycloalkylalkyl, aryl, arylalkyl, heterocyclic, heterocycloalkyl, hydroxyl, alkoxy (thereby creating a polyalkoxy such as polyethylene glycol), alkenyloxy, alkynyloxy, haloalkoxy, cycloalkoxy, cycloalkylalkyloxy, aryloxy, arylalkyloxy, heterocyclooxy, heterocyclolalkyloxy, mercapto, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro, cyanoalkyl-$S(O)_m$, haloalkyl-$S(O)_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, or heterocycloalkyl-S(O)$_m$, where m=0, 1, 2, or 3.

As used herein, the term "alkenyl" alone or as part of another group, refers to a straight or branched chain hydrocarbon containing from 1 to 10, 20, or 30 or more carbon atoms (or in lower alkenyl 1 to 4 carbon atoms), which include 1 to 4, 5, or 6 or more double bonds in the normal chain. Representative examples of alkenyl include, but are not limited to, vinyl, 2-propenyl, 3-butenyl, 2-butenyl, 4-pentenyl, 3-pentenyl, 2-hexenyl, 3-hexenyl, 2,4-heptadiene, and the like. The term "alkenyl" or "lower alkenyl" is intended to include both substituted and unsubstituted alkenyl or lower alkenyl unless otherwise indicated and these groups may be substituted with groups as described in connection with alkyl and lower alkyl above.

As used herein, the term "alkynyl" As used herein, alone or as part of another group, refers to a straight or branched chain hydrocarbon containing from 1 to 10, 20, 30, or 40 or more carbon atoms (or in lower alkynyl 1 to 4 carbon atoms) which include 1, 2, or 3 or more triple bonds in the normal chain. Representative examples of alkynyl include, but are not limited to, 2-propynyl, 3-butynyl, 2-butynyl, 4-pentynyl, 3-pentynyl, and the like. The term "alkynyl" or "lower alkynyl" is intended to include both substituted and unsubstituted alkynyl or lower alknynyl unless otherwise indicated and these groups may be substituted with the same groups as set forth in connection with alkyl and lower alkyl above.

As used herein, the term "cycloalkynyl" refers to a cyclic hydrocarbon ring system having between 6 and 16 carbon atoms and 1, 2, or 3 rings that are fused or bridged including at least 1 or more triple bonds in the ring structure.

As used herein, the term "heterocycloalkynyl" refers to a cyclic hydrocarbon ring system having between 6 and 16 carbon atoms, 1, 2, 3, or 4 heteroatoms independently selected from oxygen, nitrogen and sulfur, and 1, 2 or 3 rings which are fused or bridged including at least 1 or more triple bonds in the ring structure.

As used herein, the term "cycloalkyl" alone or as part of another group, refers to a saturated or partially unsaturated cyclic hydrocarbon group containing from 3, 4, 5, 6, 7, or 8 carbons (which carbons may be replaced in a heterocyclic group as discussed below). Representative examples of cycloalkyl include cyclopropyl, cyclobutyl, cyclopentyl, cyclohexyl, cycloheptyl, and cyclooctyl. These rings may be optionally substituted with additional substituents as described herein such as halo or lower alkyl. The term "cycloalkyl" is generic and intended to include heterocyclic groups as discussed below unless specified otherwise.

As used herein, the term "heterocyclic" or "heterocyclyl" alone or as part of another group, refers to an aliphatic (e.g., fully or partially saturated heterocyclic) or aromatic (e.g., heteroaryl) monocyclic- or bicyclic-ring system. Monocyclic ring systems are exemplified by any 3- to 8-membered ring containing 1, 2, 3, or 4 heteroatoms independently selected from oxygen, nitrogen and sulfur. The 5-membered ring has from 0-2 double bonds and the 6-membered ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, purine, pyranopyridine, quinoline, quinolizine, quinoxaline, quinazoline, tetrahydroisoquinoline, tetrahydroquinoline, thiopyranopyridine, and the like. These rings include quaternized derivatives thereof and may be optionally substituted with additional organic and/or inorganic groups, including but not limited to groups selected from halo, alkyl, haloalkyl, alkenyl, alkynyl, cycloalkyl, cycloalkylalkyl, aryl, arylalkyl, heterocyclic, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro, cyano, alkyl-S(O)$_m$ haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, where m=0, 1, 2, or 3.

As used herein, the term "heteroaryl" is as described in connection with heterocyclic above.

As used herein, the term "cycloalkylalkyl," "cycloalkylalkenyl," and "cycloalkylalkynyl" As used herein, alone or as part of another group, refers to a cycloalkyl group, as defined herein, appended to the parent molecular moiety through an alkyl, alkenyl, or alkynyl group, respectively, as defined herein.

As used herein, the term "alkoxy" alone or as part of another group, refers to an alkyl or lower alkyl group, as defined herein (and thus including substituted versions such as polyalkoxy), appended to the parent molecular moiety through an oxy group, —O—. Representative examples of alkoxy include, but are not limited to, methoxy, ethoxy, propoxy, 2-propoxy, butoxy, tert-butoxy, pentyloxy, hexyloxy and the like. In some aspects, alkoxy groups, when part of a more complex molecule, comprise an alkoxy substituent attached to an alkyl or lower alkyl via an ether linkage.

As used herein, the term "halo" or "halogen" refers to any suitable halogen, including —F, —Cl, —Br, or —I.

As used herein, the term "acyl" alone or as part of another group refers to a —C(O)R' radical, wherein R' is any suitable substituent such as aryl, alkyl, alkenyl, alkynyl, cycloalkyl or other suitable substituent as described herein.

As used herein, the term "alkylthio" alone or as part of another group, refers to an alkyl group, as defined herein, appended to the parent molecular moiety through a thiol moiety, as defined herein. Representative examples of alkylthio include, but are not limited, methylthio, ethylthio, tert-butylthio, hexylthio, and the like.

As used herein, the term "amide", "amido", or "amidyl" As used herein, alone or as part of another group refers to a —C(O)NRaRb radical, where Ra and Rb are independently any suitable substituent such as alkyl, hydrogen, cycloalkyl, alkenyl, alkynyl or aryl.

As used herein, the term "ester" alone or as part of another group refers to a —C(O)OR' radical, where R' is any suitable substituent such as alkyl, cycloalkyl, alkenyl, alkynyl or aryl.

As used herein, the term "ether" alone or as part of another group refers to a —COR' radical where R' is any suitable substituent such as alkyl, cycloalkyl, alkenyl, alkynyl, or aryl.

As used herein, the term "sulfone" alone or as part of another group refers to a —S(O)(O)R' radical, where R' is any suitable substituent such as alkyl, cycloalkyl, alkenyl, alkynyl or aryl.

As used herein, the term "sulfonamide" alone or as part of another group refers to a —S(O)$_2$NR$_a$R$_b$ radical, where R$_a$ and R$_b$ are independently any suitable substituent such as H, alkyl, cycloalkyl, alkenyl, alkynyl or aryl.

As used herein, the term "carboxyl" refers to refers to the radical —C(O)OH.

As used herein, the term "hydroxyl" refers to the radical —OH.

As used herein, the term "amino" refers to the radical —NH$_2$.

As used herein, vinyl refers to the radical —CH$_2$CH$_2$.

As used herein, the term "sulfonate" refers to the radical —S(O)(O)OR', where R' is any suitable substituent such as alkyl, cycloalkyl, alkenyl, alkynyl or aryl.

As used herein, the term "sulfonyl" refers to the radical —S(O)(O)R', where R' is any suitable substituent such as alkyl, cycloalkyl, alkenyl, alkynyl or aryl.

As used herein, thiol refers to the radical —SH.

As used herein, oxyamine or aminoxy refers to the radical —ONH$_2$.

As used herein, "hydrazide" or "hydrazidyl" refers to the radical —C(O)—NH—NH$_2$.

As used herein, "maleimide or maleimidyl" refers to a cyclic compound with the molecular formula C$_2$H$_2$(C(O))$_2$NH or the radical —N(C(O))$_2$C$_2$H$_2$ having at least one C=C double bond.

As used herein, furan refers to a five-membered aromatic ring with four carbon atoms and one oxygen.

As used herein, "tetrazine" or "tetrazinyl" refers to a six-membered aromatic ring containing four nitrogen atoms with the molecular formula C$_2$H$_2$N$_4$ or the radical —C$_2$HN$_4$.

As used herein, the term "azide," "azidyl," or "azido" refers to an —N$_3$ group.

As used herein, the term "BCN" refers to a bicyclo[6.1.0]non-4-yn-9-yl)methyl radical, in which the exocyclic methylene can have an exo or endo orientation relative to the bicycle as shown:

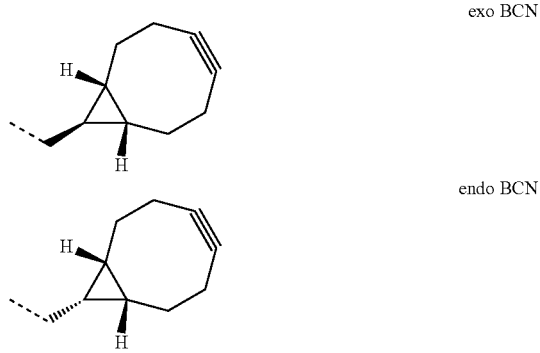

exo BCN endo BCN

As used herein, throughout the specification, as a matter of convenience most structures do not depict stereochemistry and thus represent all possible stereoisomers.

Specifically with regard to the structure of the triazole products of the reaction between a BCN and azido compound, As used herein, throughout the specification, the N-linked substitutent on the triazole ring is shown in a single regiochemistry position as a matter of convenience. One of ordinary skill in the art will recognize that the reaction of a BCN alkyne with an azido compound will result in a stereoisomeric mixture of products with the N-linked substituent on the 1- and 3-position of the triazole as shown:

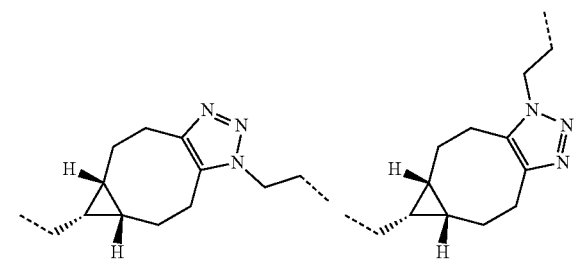

Stereoisomer reaction products of endo BCN with alkyl azide

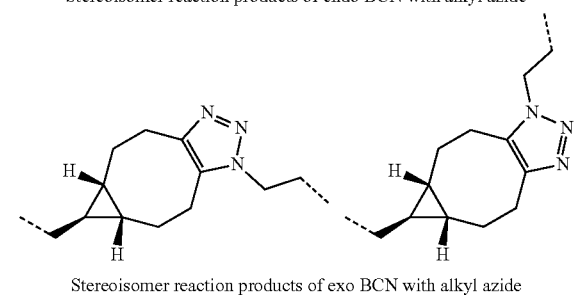

Stereoisomer reaction products of exo BCN with alkyl azide

As used herein, "reactive functional group" refers to a functional group, which is suitable for orthogonal coupling reactions. Suitable reactive functional groups are those that readily undergo orthogonal reactions. Exemplary and non-limiting orthogonal chemical reactions include functional groups shown in Table 2.

As used herein, "trigger" refers to a functional group present in the drug traceless linker adduct D-R, which is capable of undergoing a chemical reaction resulting in a new functional group. The presence of the new functional group substantially decreases the stability of the bond between the drug and the traceless linker relative and results in an increased probability of drug release.

The term "number average molecular weight" or "$M_n$" refers to the statistical average molecular weight of all molecules in the sample expressed in units of g/mol. The number average molecular weight may be determined by techniques known in the art, such as gel permeation chromatography (wherein $M_n$ can be calculated based on known standards based on an online detection system such as a refractive index, ultraviolet, or other detector), viscometry, mass spectrometry, or colligative methods (e.g., vapor pressure osmometry, end-group determination, or proton NMR). The number average molecular weight is defined by the equation below, $$M_n = \frac{\sum N_i M_i}{\sum N_i}$$

wherein $M_i$ is the molecular weight of a molecule and $N_i$ is the number of molecules of that molecular weight.

The term "weight average molecular weight" or "$M_w$" refers to the statistical average molecular weight of all molecules, taking into account the weight of each molecule in determining its contribution to the molecular weight average, expressed in units of g/mol. The higher the molecular weight of a given molecule, the more that molecule will contribute to the $M_w$ value. The weight average molecular weight may be calculated by techniques known in the art that are sensitive to molecular size, such as static light scattering, small angle neutron scattering, X-ray scattering, and sedimentation velocity. The weight average molecular weight is defined by the equation below, $$M_w = \frac{\sum N_i M_i^2}{\sum N_i M_i}$$

wherein '$M_i$' is the molecular weight of a molecule and '$N_i$' is the number of molecules of that molecular weight.

The term "viscosity average molecular weight" or "$M_v$" refers to the statistical average molecular weight of all molecules, taking into account the weight of each molecule in determining its contribution to the molecular weight average, expressed in units of g/mol. Large molecules or polymers have higher viscosities than smaller molecules. The viscosity average molecular weight is defined by the equation below, $$M_v = \left( \frac{\sum N_i M_i^{(1+a)}}{\sum N_i M_i} \right)^{1/a}$$

wherein '$M_i$' is the molecular weight of a molecule and '$N_i$' is the number of molecules of that molecular weight, and a is constant determined by the molecule, solvent, and temperature. Flexible polymeric molecules have a values of $0.5 \leq a \leq 0.8$. Semi-flexible polymeric molecules have $a \geq 0.8$. The viscosity average molecular weight can be determined from intrinsic viscosity experiments or size exclusion chromatography.

As used herein, a "drug" comprises one or more biologically active moieties comprising at least one primary or secondary amine or a ring nitrogen atom of an azaheteroaryl ring. The biologically active moieties may be small molecules, macromolecules such as proteins, peptides, or nucleic acids, or combinations thereof. With specific regard to a traceless linker, R, the drug or biologically active moiety comprises "D" in the D-R representation. The terms or phrases "drug", "biologically active molecule," "biologically active moiety," "biologically active agent," "active agent," or "D," refer to any substance that can affect any physical or biochemical properties of a biological organism, including but not limited to viruses, bacteria, fungi, plants, animals, and humans. In particular, drugs or biologically active molecules include any substance intended for diagnosis, cure, mitigation, treatment, or prevention of disease in humans or other animals, or to otherwise enhance physical or mental well-being of humans or animals.

In one embodiment, the biologically active moiety, D, comprises angiopoietin-like 3 (ANGPTL3) polypeptides. "ANGPTL3" refers to a member of the angoipoietin protein family. An amino acid sequence of human ANGPTL3 (GenBank Accession No. NP_055310.1) is set forth in SEQ ID NO:1; and the corresponding polynucleotide sequence of which is set forth as SEQ ID NO: 2 (NCBI reference sequence number NM014495.2, wherein the ANGPTL3 coding sequence comprises nucleotides 52-1434 of SEQ ID NO:2). See Table 1. For the purposes of the present disclosure, the numbering of an amino acid is typically determined with reference to the full-length wildtype human ANGPTL3 polypeptide sequence (SEQ ID NO:1). Thus, in embodiments in which a polypeptide of the invention contains only a C-terminal portion of full-length ANGPTL3, but not the N-terminal portion, although the peptide is less than 460 amino acids in length, the numbering of the positions is based on SEQ ID NO:1. For example, reference to amino acid position 423 of an ANGPTL3 polypeptide refers to position 423 of SEQ ID NO: 1, even though the ANGPTL3 polypeptide of the invention itself may only be 200 amino acids in length. In determining an amino acid in a sequence of interest that "corresponds to" a position in a reference sequence, such as SEQ ID NO: 1, this is performed by optimally aligning the sequences, e.g., using the default CLUSTAL alignment parameters or default BLAST 2 alignment parameters and comparing the sequences. For example, position 423 in a sequence of interest that is "determined with reference to SEQ ID NO: 1", or an amino acid that "corresponds to" position 423 of SEQ ID NO: 1, means the amino acid that aligns with position 423 of SEQ ID NO:1 when the sequence of interest is optimally aligned with SEQ ID NO: 1.

In one embodiment, the biologically active moiety, D, comprises the ANGPTL3 polypeptide D1. As used herein, D1 refers to the ANGPTL3 polypeptide having the sequence of SEQ ID NO: 19.

The terms "peptidomimetic" and "mimetic" refer to a synthetic chemical compound that has substantially the same functional characteristics of a naturally or non-naturally occurring polypeptide (e.g., ANGPTL3), but different (though typically similar) structural characteristics. Peptide analogs are commonly used in the field as non-peptide active compounds (e.g., drugs) with properties analogous to those of a template peptide. Such non-peptide compounds are termed "peptide mimetics" or "peptidomimetics." Fauchere, *J. Adv. Drug Res.* 15:29 (1986); Veber and Freidinger TINS p. 392 (1985); Evans et al. *J. Med. Chem.* 30:1229 (1987). Peptide mimetics that are structurally similar to therapeutically useful peptides may be used to produce an equivalent or enhanced therapeutic or prophylactic effect. Generally, peptidomimetics are structurally similar to a paradigm polypeptide (i.e., a polypeptide that has a biological or pharmacological activity), such as found in a polypeptide of interest, but have one or more peptide linkages optionally replaced by a linkage selected from the group consisting of, e.g., —CH$_2$NH—, —CH$_2$S—, —CH$_2$—CH$_2$—, —CH═CH— (cis and trans), —COCH$_2$—, —CH(OH)CH$_2$—, and —CH$_2$SO—. A mimetic can be either entirely composed of synthetic, non-natural analogues of amino acids, or, is a chimeric molecule of partly natural peptide amino acids and partly non-natural analogs of amino acids. A mimetic can also incorporate any amount of natural amino acid conservative substitutions as long as such substitutions also do not substantially alter the mimetic's structure and/or activity. For example, a mimetic composition is within the scope of the polypeptides described herein if it is capable of chondrogenic activity of an ANGPTL3 polypeptide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. Polypeptides, peptides, and proteins described herein comprise protease resistant ANGPTL3 peptidomimetics having chondrogenic activity.

The term "amino acid" refers to naturally occurring and synthetic amino acids, as well as amino acid analogs and amino acid mimetics that function in a manner similar to naturally occurring amino acids. Naturally occurring amino acids are those encoded by the genetic code, as well as those amino acids that are later modified, e.g., hydroxyproline, γ-carboxyglutamate, and O-phosphoserine Amino acid analogs refers to compounds that have the same basic chemical structure as a naturally occurring amino acid, i.e., an .alpha. carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) as well as pyrrolysine, pyrroline-carboxy-lysine, and selenocysteine.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG, and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every polypeptide sequence herein which is encoded by a polynucleotide encompasses every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

One of skill will recognize that individual substitutions, deletions or additions to a nucleic acid, peptide, polypeptide, or protein sequence which alters, adds or deletes a single amino acid or a small percentage of amino acids with reference to an original encoded amino acid sequence results in a "conservatively modified variant" where the alteration produces substitution of an amino acid with a chemically similar amino acid and/or a polypeptide sequence that produces a structurally similar protein having similar functional activity to the original protein. Conservative substitution tables providing functionally similar amino acids are well known in the art. Such conservatively modified variants are in addition to and do not exclude polymorphic variants, interspecies homologs, and alleles as described herein.

The term "conservative amino acid substitutions" refers to the substitution (conceptually or otherwise) of an amino acid from one such group with a different amino acid from the same group. One example of substitutions is based on analyzing the normalized frequencies of amino acid changes between corresponding proteins of homologous organisms. According to such analyses, groups of amino acids may be defined where amino acids within a group exchange preferentially with each other and, therefore, resemble each other most in their impact on the overall protein structure. See Schulz and Schirmer, Principles of Protein Structure, Springer-Verlag. One example of a set of amino acid groups defined in this manner include: (i) a charged group, consisting of Glu and Asp, Lys, Arg and His; (ii) a positively-charged group, consisting of Lys, Arg and His; (iii) a negatively-charged group, consisting of Glu and Asp; (iv) an aromatic group, consisting of Phe, Tyr and Trp; (v) a nitrogen ring group, consisting of His and Trp; (vi) a large aliphatic nonpolar group, consisting of Val, Leu and Ile; (vii) a slightly-polar group, consisting of Met and Cys; (viii) a small-residue group, consisting of Ser, Thr, Asp, Asn, Gly, Ala, Glu, Gln and Pro; (ix) an aliphatic group consisting of Val, Leu, Ile, Met and Cys; and (x) a small hydroxyl group consisting of Ser and Thr. Other examples of conservative substitutions based on shared physical properties are the substitutions within the following groups: (1) Alanine (A), Glycine (G); (2) Aspartic acid (D), Glutamic acid (E); (3) Asparagine (N), Glutamine (Q); (4) Arginine (R), Lysine (K); (5) Isoleucine (I), Leucine (L), Methionine (M), Valine (V); (6) Phenylalanine (F), Tyrosine (Y), Tryptophan (W); (7) Serine (S), Threonine (T); and (8) Cysteine (C), Methionine (M). See Creighton, *Proteins* (1984).

"Percentage of sequence identity" is determined by comparing two optimally aligned sequences over a comparison window, wherein the portion of the amino acid sequence or polynucleotide sequence in the comparison window may comprise additions or deletions (i.e., gaps) as compared to the reference sequence (e.g., an ANGPTL3 polypeptide), which does not comprise additions or deletions, for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same sequences. Two sequences are "substantially identical" if two sequences have a specified percentage of amino acid residues or nucleotides that are the same (i.e., 95% identity, optionally 96%, 97%, 98%, or 99% identity over a specified region, or, when not specified, over the entire sequence), when compared and aligned for maximum correspondence over a comparison window, or designated region as measured using one of the following sequence comparison algorithms or by manual alignment and visual inspection. Polypeptides that are substantially identical to the polypeptides, respectively, exemplified herein (e.g., any of SEQ ID NOs: 1, 3-45), as well as uses thereof including but not limited to use for treating or preventing arthritis or joint injury. Optionally, for nucleic acids, the identity exists over a region that is at least about 150 nucleotides in length, or more preferably over a region that is 300 to 450 or 600 or more nucleotides in length, or the entire length of the reference sequence. For amino acid sequence, optionally, identity exists over a region that is at least about 50 amino acids in length, or more preferably over a region that is 100 to 150 or 200 or more amino acids in length, or the entire length of the reference sequence.

For sequence comparison, typically one sequence acts as a reference sequence to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 50 to 600, usually about 75 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci.* USA 85:2444, by computerized implementations of these algorithms (GAP, BESTFIT, FASTA, and TFASTA), or by manual alignment and visual inspection. See e.g., Ausubel et al., Current Protocols in Molecular Biology (1995).

Two examples of algorithms that are suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix. See Henikoff and Henikoff, *Proc. Natl. Acad. Sci. USA* 89:10915 (1989) alignments (B) of 50, expectation (E) of 10, M=5, N=−4, and a comparison of both strands.

The BLAST algorithm also performs a statistical analysis of the similarity between two sequences. See Karlin and Altschul, *Proc. Natl. Acad. Sci. USA* 90:5873-5787 (1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The term "isolated," when applied to a nucleic acid or protein, denotes that the nucleic acid or protein is purified to be essentially free of other cellular components with which it is associated in the natural state. It is often in a homogeneous or nearly homogeneous state. It can be in either a dry or aqueous solution. Purity and homogeneity may be determined using analytical chemistry techniques known and used typically in the art, e.g., polyacrylamide gel electrophoresis, high performance liquid chromatography, etc. A protein that is the predominant species present in a preparation is substantially purified. The term "purified" in some aspects denotes that a protein gives rise to essentially one band in an electrophoretic gel. Typically, it means that a protein is at least 85% pure, more preferably at least 95% pure, and most preferably at least 99% pure.

As used herein, the ANGPTL3 polypeptide may be natural or recombinant and from any species; the ANGPTL3 peptide may also be synthetic. In one aspect, the ANGPTL3 polypeptide comprises the sequence of *Homo sapiens* ANGPTL3, mutant thereof, deletion thereof, or truncated version thereof. Particularly useful are ANGPTL3 polypeptides comprising mutants or deletions of amino acid K423 using the numbering for the full length wild-type human ANGPTL3 sequence (SEQ ID NO:1). In another aspect, the ANGPTL3 polypeptide is described in U.S. Pat. Nos. 9,301, 971; 9,649,359; 9,745,358; 9,868,771, or European Patent No. EP2 964 250, each of which are herein incorporated by reference for the specific teachings related to ANGPTL3 polypeptides and the sequences thereof. In another aspect, the ANGPTL3 polypeptide is a protease resistant polypeptide. In one aspect, the ANGPTL3 polypeptide is a protease-resistant polypeptide that has an amino acid substitution, relative to a native wildtype peptide sequence, at an R or a K residue. In another aspect, the ANGPTL3 polypeptide is D1 (SEQ ID NO: 19) which comprises a truncated version of human ANGPTL3 (e.g., amino acids 242-460) having a K423Q mutation using the numbering for the full length wild-type human ANGPTL3 sequence (SEQ ID NO: 1). In another aspect, the ANGPTL3 polypeptide comprises any of SEQ ID NO:1 or 3-45 as shown in Table 1. In another aspect, the ANGPTL3 polypeptide comprises the polypeptide encoded by the DNA sequence of SEQ ID NO:2 or mutations or deletions thereof. In one aspect, the ANGPTL3 polypeptide comprises a sequence having 80-99% identity to SEQ ID NO: 1 or 3-45, including all integers within the specified range. In another aspect, the ANGPTL3 polypeptide comprises an amino acid sequence that has at least 95% identity, at least 96% identity, at least 97% identity, at least 98% identity, or at least 99% identity to any Sequence shown in Table 1, wherein the polypeptide comprises an amino acid that is a polar amino acid other than K or R at position 423, as determined with reference to SEQ ID NO: 1. In one aspect, the ANGPTL3 polypeptides have chondrogenic activity. In another aspect, the ANGPTL3 polypeptide comprises the amino acid sequence that has at least 95% identity, at least 96% identity, at least 97% identity, at least 98% identity, or at least 99% identity to any one of SEQ ID NOs:1 or 3-45. In another aspect, the ANGPTL3 polypeptide comprises a polypeptide encoded by a DNA sequence having 90-100% identity to the coding portion of SEQ ID NO:2 (e.g., nucleotides 52-1434), including DNA sequences encoding mutations, truncations, or deletions.

TABLE 1

ANGPTL3 Sequences

| SEQ ID NO: | Description |
|---|---|
| 1 | *Homo sapiens* Angiopoietin-like 3 (ANGPTL3) |
| 2 | ANGPTL3 DNA Sequence |
| 3 | ANGPTL3 K423Q |
| 4 | ANGPTL3 K423S |
| 5 | ANGPTL3 207-460 K423Q |
| 6 | ANGPTL3 207-460 K423S |
| 7 | ANGPTL3 225-460 K423Q |
| 8 | ANGPTL3 225-460 K423S |
| 9 | ANGPTL3 225-460 S424T |
| 10 | ANGPTL3 226-460 K423Q |
| 11 | ANGPTL3 226-460 K423S |
| 12 | ANGPTL3 228-460 K423Q |
| 13 | ANGPTL3 228-460 K423S |
| 14 | ANGPTL3 228-460 S424T |
| 15 | ANGPTL3 233-460 K423Q |
| 16 | ANGPTL3 233-460 K423S |
| 17 | ANGPTL3 241-460 K423Q |
| 18 | ANGPTL3 241-460 K423S |
| 19 | ANGPTL3 242-460 K423Q |
| 20 | ANGPTL3 242-460 K423S |
| 21 | ANGPTL3 225-455 K423Q |
| 22 | ANGPTL3 225-455 K423S |
| 23 | ANGPTL3 226-455 K423Q |
| 24 | ANGPTL3 226-455 K423S |
| 25 | ANGPTL3 228-455 K423Q |
| 26 | ANGPTL3 228-455 K423S |
| 27 | ANGPTL3 233-455 K423Q |
| 28 | ANGPTL3 233-455 K423S |
| 29 | ANGPTL3 241-455 K423Q |
| 30 | ANGPTL3 241-455 K423S |
| 31 | ANGPTL3 242-455 K423Q |
| 32 | ANGPTL3 242-455 K423S |
| 33 | ANGPTL3 201-460 K423del |
| 34 | ANGPTL3 225-460 K423del |
| 35 | ANGPTL3 226-460 K423del |
| 36 | ANGPTL3 228-460 K423del |
| 37 | ANGPTL3 233-460 K423del |
| 38 | ANGPTL3 241-460 K423del |
| 39 | ANGPTL3 242-460 K423del |
| 40 | ANGPTL3 225-455 K423del |
| 41 | ANGPTL3 226-455 K423del |
| 42 | ANGPTL3 228-455 K423del |
| 43 | ANGPTL3 233-455 K423del |
| 44 | ANGPTL3 241-455 K423del |
| 45 | ANGPTL3 242-455 K423del |

As used herein, a "biologically active moiety comprising at least one primary amine, secondary amine, or ring nitrogen atom of an azaheteroaryl ring" refers to both the free biologically active moiety prior to attachment to a traceless linker or to the free biologically active moiety "D-H," which results after cleavage from the traceless linker adduct "D-R." In some aspects, the drug adduct, D-R, may have biological activity. In some aspects, biologically active moiety comprises an ANGPTL3 polypeptide as described herein.

As used herein, "free form" of a drug or biologically active moiety refers to the drug in its unmodified, pharmacologically active form, such as prior to being attached to a traceless linker or after being released from a traceless linker in a drug delivery system.

As used herein, a "traceless linker," R, is a linker that is represented by Formula (I) suitable for release of biologically active moiety D comprising at least one primary or secondary amine or a ring nitrogen atom of an azaheteroaryl ring:

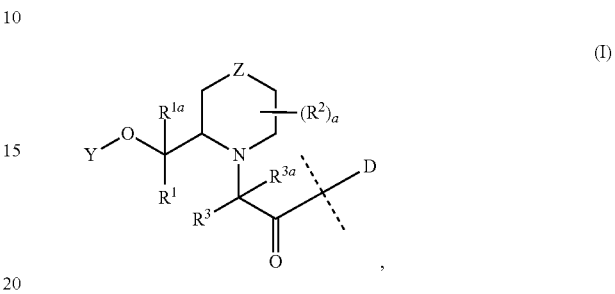

(I)

where the dashed line indicates attachment to the primary amine, secondary amine, or ring nitrogen atom of an azaheteroaryl ring;

$R^1$ is hydrogen or $C_1$-$C_4$alkyl;

$R^{1a}$ is hydrogen or $C_1$-$C_4$alkyl, or $CR^1R^{1a}$, taken in combination form a $C_3$-$C_6$cycloalk-1,1-diyl;

$R^2$ is independently selected at each occurrence from $C_1$-$C_4$alkyl or oxo, or two $R^2$ groups taken in combination form a fused $C_3$-$C_6$ cycloalkyl or spiro $C_3$-$C_6$cycloalk-1,1-diyl group;

a is 0, 1, 2, 3 or 4;

$R^3$ is hydrogen or $C_1$-$C_4$alkyl;

$R^{3a}$ is hydrogen, $C_1$-$C_4$alkyl, or $CR^3R^{3a}$, taken in combination form a $C_3$-$C_6$cycloalk-1,1-diyl; Y is $C(O)R^4$, $C(O)OR^4$, $C(O)NHR^4$, $C(O)NR^5R^6$, $SiR^5R^6R^7$, or $CR^{12}R^{12a}OR^{13}$;

$R^{12}$ is hydrogen or $C_1$-$C_4$alkyl;

$R^{12a}$ is hydrogen or $C_1$-$C_4$alkyl, or $CR^{12}R^{12a}$, taken in combination form a $C_3$-$C_6$cycloalk-1,1-diyl;

$R^{13}$ is $C_1$-$C_4$alkyl; or $CHR^{12}OR^{13}$, taken in combination form a 5, 6, or 7-member cyclic ether;

$R^4$ is $C_1$-$C_8$alkyl or $C_3$-$C_7$cycloalkyl, wherein cycloalkyl is optionally substituted with 0, 1, or 2 independently selected $C_1$-$C_4$alkyl groups and wherein alkyl is optionally substituted by $C_1$-$C_4$alkoxy;

$R^5$ and $R^6$ are each independently selected from $C_1$-$C_4$alkyl and $C_3$-$C_6$cycloalkyl;

$R^7$ is $C_1$-$C_8$alkyl, $C_3$-$C_7$cycloalkyl, $C_1$-$C_8$alkoxy, $C_3$-$C_7$cycloalkyloxy, heterocycloalkyloxy, or —(OCHR$^3$CH$_2$)$_b$O—C$_1$-C$_4$alkyl, wherein the heterocycloalkyloxy is a 4 to 7 member saturated heterocyclic ring having one ring heteroatom selected from N, O, and S and optionally substituted with 0, 1, or 2 independently selected $C_1$-$C_4$alkyl groups;

b is an integer of from 1 to 10;

Z is CH-L-A, CH-A, N-L-A, or N-A;

L is an optionally substituted bivalent linker;

A is hydrogen, $C_1$-$C_8$alkyl, $C(O)C_1$-$C_8$alkyl, $C(O)N(H)C_1$-$C_8$alkyl, $C(O)OC_1$-$C_8$alkyl, $R^{10}$, or $R^{11}$, wherein the alkyl group is optionally substituted with 0 or 1 $R^{10}$;

$R^{10}$ is a reactive functional group suitable for coupling Formula I to a carrier; and $R^{11}$ is a carrier.

In another embodiment, R, is a linker that is represented by Formula (I) suitable for release of biologically active moiety D comprising at least one primary or secondary amine or a ring nitrogen atom of an azaheteroaryl ring:

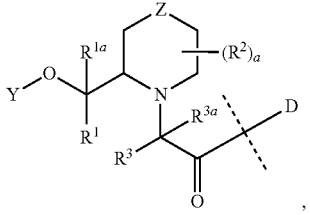

(I)

where the dashed line indicates attachment to the primary amine, secondary amine, or ring nitrogen atom of an azaheteroaryl ring;
$R^1$ is hydrogen or $C_1$-$C_4$alkyl;
$R^{1a}$ is hydrogen or $C_1$-$C_4$alkyl, or $CR^1R^{1a}$, taken in combination form a $C_3$-$C_6$cycloalk-1,1-diyl;
$R^2$ is independently selected at each occurrence from $C_1$-$C_4$alkyl or oxo, or two $R^2$ groups taken in combination form a fused $C_3$-$C_6$ cycloalkyl or spiro $C_3$-$C_6$cycloalk-1,1-diyl group;
a is 0, 1, 2, 3 or 4;
$R^3$ is hydrogen or $C_1$-$C_4$alkyl;
$R^{3a}$ is hydrogen, $C_1$-$C_4$alkyl, or $CR^3R^{3a}$, taken in combination form a $C_3$-$C_6$cycloalk-1,1-diyl; Y is $C(O)R^4$, $C(O)OR^4$, $C(O)NHR^4$, $C(O)NR^5R^6$, $SiR^5R^6R^7$, or $CR^{12}R^{12a}OR^{13}$;
$R^{12}$ is hydrogen or $C_1$-$C_4$alkyl;
$R^{12a}$ is hydrogen or $C_1$-$C_4$alkyl, or $CR^{12}R^{12a}$, taken in combination form a $C_3$-$C_6$cycloalk-1,1-diyl;
$R^{13}$ is $C_1$-$C_4$alkyl; or
$CHR^{12}OR^{13}$, taken in combination form a 5, 6, or 7-member cyclic ether;
$R^4$ is $C_1$-$C_8$alkyl or $C_3$-$C_7$cycloalkyl, wherein cycloalkyl is optionally substituted with 0, 1, or 2 independently selected $C_1$-$C_4$alkyl groups and wherein alkyl is optionally substituted by $C_1$-$C_4$alkoxy;
$R^5$ and $R^6$ are each independently selected from $C_1$-$C_4$alkyl and $C_3$-$C_6$cycloalkyl;
$R^7$ is $C_1$-$C_8$alkyl, $C_3$-$C_7$cycloalkyl, $C_1$-$C_8$alkoxy, $C_3$-$C_7$cycloalkyloxy, heterocycloalkyloxy, or —$(OCHR^3CH_2)_bO$—$C_1$-$C_4$alkyl, wherein the heterocycloalkyloxy is a 4 to 7 member saturated heterocyclic ring having one ring heteroatom selected from N, O, and S and optionally substituted with 0, 1, or 2 independently selected $C_1$-$C_4$alkyl groups;
b is an integer of from 1 to 10;
Z is CH-L-A, CH-A, N-L-A, or N-A;
L is an optionally substituted bivalent linker Q-[Sp-Q]$_h$-Q;
Q is independently selected at each occurrence from a bond, O, C(O), N(H), N($C_1$-$C_4$alkyl), C(O)NH, C(O)N($C_1$-$C_4$alkyl), N(H)C(O), N($C_1$-$C_4$alkyl)C(O), N(H)C(O)O, N($C_1$-$C_4$alkyl)C(O)O, OC(O)N(H), OC(O)N($C_1$-$C_4$alkyl), N(H)C(O)N(H), N($C_1$-$C_4$alkyl)C(O)N(H), N(H)C(O)N($C_1$-$C_4$alkyl), N($C_1$-$C_4$alkyl)C(O)N($C_1$-$C_4$alkyl), C(O)O, OC(O), OC(O)O, S, S(O)$_2$, N(H)S(O)$_2$, N($C_1$-$C_4$alkyl)S(O)$_2$, S(O)$_2$N(H), S(O)$_2$N($C_1$-$C_4$alkyl), $C_1$-$C_2$alkyl-C(O)N(H), N(H)C(O)$C_1$-$C_2$alkyl, $C_1$-$C_2$alkyl-C(O)O, OC(O)$C_1$-$C_2$alkyl, 1,2,3-triazole, OP(O)$_2$, P(O)$_2$O, $C_1$-$C_4$alkyl-P(O)$_2$—O, or O—P(O)$_2$—$C_{1-4}$alkyl;
Sp is independently selected at each occurrence from an optionally substituted $C_1$-$C_{20}$alkyl, $C_2$-$C_{20}$alkenyl, $C_2$-$C_{20}$alkynyl, [W—O]$_g$, $C_1$-$C_8$alkyl-[O—W]$_g$, [O—W]$_g$—O—$C_1$-$C_8$alkyl, $C_1$-$C_8$Calkyl-[O—W]$_g$—O—$C_1$-$C_8$alkyl, oligopeptide;

h is an integer of between 1 and 20;
g is a weighted average number of between about 2 and about 50;
W is $C_2$-$C_4$alkyl-1,2-diyl in which the hydrogen, methyl, or ethyl side chain may be present on either backbone carbon atom;
A is hydrogen, $C_1$-$C_8$alkyl, $C(O)C_1$-$C_8$alkyl, $C(O)OC_1$-$C_8$alkyl, $C(O)N(H)C_1$-$C_8$alkyl, $R^{10}$, or $R^{11}$, wherein the alkyl group is optionally substituted with 0 or 1 $R^{10}$;
$R^{10}$ is a reactive functional group suitable for coupling Formula I to a carrier; and
$R^{11}$ is a carrier.

In another embodiment, R, is a linker that is represented by Formula (I) suitable for release of biologically active moiety D comprising at least one primary or secondary amine or a ring nitrogen atom of an azaheteroaryl ring:

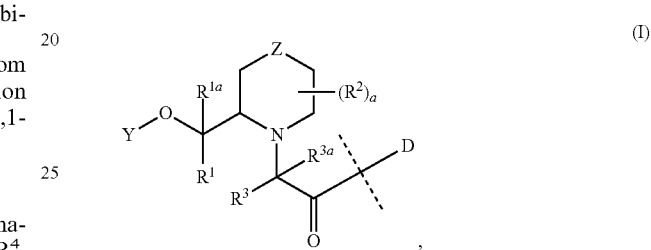

(I)

where the dashed line indicates attachment to the primary amine, secondary amine, or ring nitrogen atom of an azaheteroaryl ring;
$R^1$ is hydrogen or $C_1$-$C_4$alkyl;
$R^{1a}$ is hydrogen or $C_1$-$C_4$alkyl, or $CR^1R^{1a}$, taken in combination form a $C_3$-$C_6$cycloalk-1,1-diyl;
$R^2$ is independently selected at each occurrence from $C_1$-$C_4$alkyl or oxo, or two $R^2$ groups taken in combination form a fused $C_3$-$C_6$ cycloalkyl or spiro $C_3$-$C_6$cycloalk-1,1-diyl group;
a is 0, 1, 2, 3 or 4;
$R^3$ is hydrogen or $C_1$-$C_4$alkyl;
$R^{3a}$ is hydrogen, $C_1$-$C_4$alkyl, or $CR^3R^{3a}$, taken in combination form a $C_3$-$C_6$cycloalk-1,1-diyl;
Y is $C(O)R^4$, $C(O)OR^4$, $C(O)NHR^4$, $C(O)NR^5R^6$, $SiR^5R^6R^7$, or $CR^{12}R^{12a}OR^{13}$;
$R^{12}$ is hydrogen or $C_1$-$C_4$alkyl;
$R^{12a}$ is hydrogen or $C_1$-$C_4$alkyl, or $CR^{12}R^{12a}$, taken in combination form a $C_3$-$C_6$cycloalk-1,1-diyl;
$R^{13}$ is $C_1$-$C_4$alkyl; or
$CHR^{12}OR^{13}$, taken in combination form a 5, 6, or 7-member cyclic ether;
$R^4$ is $C_1$-$C_8$alkyl or $C_3$-$C_7$cycloalkyl, wherein cycloalkyl is optionally substituted with 0, 1, or 2 independently selected $C_1$-$C_4$alkyl groups and wherein alkyl is optionally substituted by $C_1$-$C_4$alkoxy;
$R^5$ and $R^6$ are each independently selected from $C_1$-$C_4$alkyl and $C_3$-$C_6$cycloalkyl;
$R^7$ is $C_1$-$C_8$alkyl, $C_3$-$C_7$cycloalkyl, $C_1$-$C_8$alkoxy, $C_3$-$C_7$cycloalkyloxy, heterocycloalkyloxy, or —$(OCHR^3CH_2)_bO$—$C_1$-$C_4$alkyl, wherein the heterocycloalkyloxy is a 4 to 7 member saturated heterocyclic ring having one ring heteroatom selected from N, O, and S and optionally substituted with 0, 1, or 2 independently selected $C_1$-$C_4$alkyl groups;
b is an integer of from 1 to 10;
Z is $CHR^8$ or $NR^9$;

$R^8$ and $R^9$ are each independently selected from hydrogen, $C_1$-$C_8$ alkyl, $C(O)C_1$-$C_8$ alkyl, or —$C(O)(CH_2)_q[O-W]_g$ $(NHC(O))_m(CH_2)_q[O-W]_p$-Q-A, wherein the alkyl group is optionally substituted with 0 or 1 Q-A;

q is independently at each occurrence 1, 2, or 3;

g and p each independently have a weighted average length of between about 2 and about 50;

m is 1 or 0;

W is $C_2$-$C_4$alkyl-1,2-diyl in which the hydrogen, methyl, or ethyl side chain may be present on either backbone carbon atom;

Q is a bond, O, N(H) or N($C_1$-$C_4$alkyl);

A is hydrogen, $C_1$-$C_8$alkyl, $C(O)C_1$-$C_8$alkyl, $C(O)N(H)C_1$-$C_8$alkyl, $C(O)OC_1$-$C_8$alkyl, $R^{10}$, or $R^{11}$, wherein the alkyl group is optionally substituted with 0 or 1 $R^{10}$;

$R^{10}$ is a reactive functional group suitable for coupling Formula I to a carrier; and $R^{11}$ is a carrier.

In one aspect, the traceless linker is a linker suitable for sustained release of a biologically active moiety. In one aspect, "R" is a traceless linker in the representation D-R, wherein "D" refers to a drug comprising a biologically active moiety comprising at least one primary amine, secondary amine, or ring nitrogen atom of an azaheteroaryl ring.

As used herein, a "drug adduct" is a drug, D linked to a traceless linker, R. With specific regard to a traceless linker, R, the drug adduct comprises "D-R."

As used herein, a "carrier" is a soluble polymer, biopolymer, or a cross-linked polymer or biopolymer. Carriers comprise proteins, nucleic acids, carbohydrates, or polyethylene glycols. In one aspects, the carrier or multiple carriers are cross-linked intermolecularly, intramolecularly, or a combination thereof. In one aspect, the cross-linked carrier comprises a hydrogel. With specific regard to a traceless linker, R, the carrier comprises $R^{11}$. In one aspect, Z is linked to a carrier, typically a polymer or a hydrogel. The carrier is attached to the traceless linker, R, either directly or via a non-cleavable spacer. As non-limiting examples, carriers can comprise polyethylene glycols, hyaluronic acid polymers, or cross-linked hyaluronic acid or polyethylene glycol that are capable of forming hydrogels.

As used herein, a "polymer" refers to a molecule comprised of repeating structural units (monomers) connected by chemical bonds in a linear, circular, branched, or dendrimeric way or a combination thereof, that can be of synthetic or biological origin or a combination of both. Typically, a polymer has an average molecular weight of at least 1 kDa. A copolymer is a polymer comprised of at least two chemically distinct monomers. Typically, a polymer is comprised of molecules having a distribution of molecular weights. One way to describe the molecular weight distribution of a polymer is the average molecular weight. Typically, a polymer is comprised of molecules having a distribution of degree of polymerization. One way to describe the degree of polymerization distribution of a polymer is the average degree of polymerization.

As described herein and depicted in the structures herein, polymeric molecules, such as polyethylene glycol or hyaluronic acid, are represented as $[P]_n$, where P represents the monomeric repeating unit and n represents the average degree of polymerization of the monomer in the polymer. One of ordinary skill in the art will understand that two polymeric molecules depicted with identical repeating unit P but different n are considered equivalent if the difference is about 10% or less of n. For the hyaluronic acid copolymers described and depicted in the structures herein, the distribution of monomers in the polymer is undefined and assumed to be random. In addition, the relative connectivity of the independent molecules for hydrogels or drug delivery systems described herein is random within a population. Structural depictions of hydrogels or drug delivery systems represent a single potential structural unit in two dimensions, whereas these complexes are three-dimensional with many structural subunits.

As described herein, the exact position of amide bond formation is not precisely known for a traceless linker-drug adduct, R-D. This can occur when D contains more than one primary or secondary amine, or ring nitrogen atom of an azaheteroaryl ring capable of forming an amide bond with a linker R (e.g., a protein or polypeptide). As a matter of convenience, adducts where the position of amide bond formation is not precisely known are depicted herein as follows:

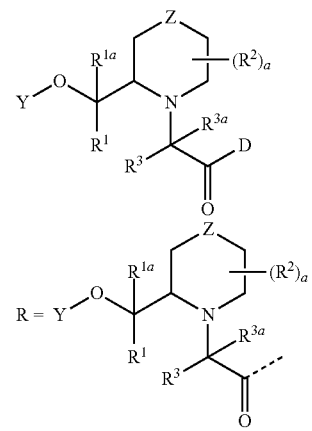

As used herein, a "hydrogel" refers to a three-dimensional, hydrophilic or amphiphilic polymeric network capable of taking up large quantities of water. The networks are composed of homopolymers or copolymers, and are insoluble due to the presence of covalent chemical or physical (ionic, hydrophobic interactions, entanglements) crosslinks. The crosslinks provide the network structure and physical integrity. Hydrogels exhibit a thermodynamic compatibility with water that allows them to swell in aqueous media. The chains of the network are connected in such a fashion that pores exist and water soluble solutes with dimensions smaller than the pores are able to diffuse in and out of the network.

As used herein, a "linker" or "non-biologically active linker" refers to a linker that does not produce any pharmacological effects. In some embodiments, the linker comprises a bi- or multi-valent organic linker that is compatible with biological systems. "Bivalent" refers to having a reactive group suitable for attachment to a traceless linker or drug, D, at each terminus of the polymer. "Multivalent" refers having a reactive group suitable for attachment to a traceless linker or drug, D, at each terminus of the polymer with additional reactive moieties interspersed along the linker molecule.

As used herein, a "drug delivery system" comprises a carrier linked to a drug adduct, D-R—$R^{11}$, wherein the carrier comprises $R^{11}$. The drug delivery system as described herein is the molecular conjugate comprising one or more drugs, D; one or more traceless linkers, R; and one or more carriers, $R^{11}$. In some embodiments, there can be multiple, distinct drug species conjugated to a drug delivery system. For example, two different drugs, such as D1 and another ANGPTL3 polypeptide as described herein may be conjugated in a single drug delivery system.

As used herein, the phrase "water-insoluble" refers to a swellable three-dimensionally crosslinked molecular network forming the hydrogel. The hydrogel if suspended in a large surplus of water or aqueous buffer of physiological osmolality may take up a substantial amount of water, e.g., up to 10-fold on a weight per weight basis, and is therefore swellable but after removing excess water still retains the physical stability of a gel and a shape. Such shape may be of any geometry and it is understood that such an individual hydrogel object is to be considered as a single molecule consisting of components wherein each component is connected to each other component through chemical bonds.

As used herein, "sustained release" or "sustained release rate" refers to the situation where the intervals between subsequent doses of the respective drug delivery system required to achieve a desired therapeutic effect are expanded. Drugs with a daily dosage may for example be turned into a sustained release form with a week-long or even longer interval between two administrations.

As used herein, a "functional group" refers to a group of atoms within molecules that exhibit a specific chemical activity. Examples are amides, amines, alcohols, carbonyls, carboxylic acids, thiols.

As used herein, a "protective group" refers to a moiety that temporarily protects a functional group of a molecule during synthesis to obtain chemoselectivity in subsequent chemical reactions. Protective groups for alcohols are, for example, benzyl and trityl, protective groups for amines are, for example, tert-butyloxycarbonyl, 9-fluorenylmethyloxycarbonyl and benzyl and for thiols examples of protective groups are 2,4,6-trimethoxybenzyl, phenylthiomethyl, acetamidomethyl, p-methoxybenzyloxycarbonyl, tert-butylthio, triphenylmethyl, 3-nitro-2-pyridylthio, 4-methyltrityl.

As used herein, a "protected functional group" means a functional group protected by one or more protective groups.

As used herein, "PBS" refers to phosphate buffered saline.

As used herein, the term "pharmaceutically acceptable salts" refers to salts that retain the biological effectiveness and properties of the biologically active agent and, that typically are not biologically or otherwise undesirable. In many cases, the biologically active agent is capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllinate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, subsalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine, or tromethamine.

The pharmaceutically acceptable salts can be synthesized from a parent compound, a basic or acidic moiety, by conventional chemical methods.

Generally, such salts can be prepared by reacting free acid forms of these compounds with a stoichiometric amount of the appropriate base (such as sodium, potassium, calcium, or magnesium hydroxides, carbonates, bicarbonates, or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", $18^{th}$ ed., Mack Publishing Company, Easton, Pa., (1990); and in "Handbook of Pharmaceutical Salts: Properties, Selection, and Use" by Stahl and Wermuth (Wiley-VCH, Weinheim, Germany, 2002).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, e.g., Remington's Pharmaceutical Sciences, $18^{th}$ ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a biologically active agent refers to an amount of the biologically active agent that will elicit the biological or medical response of a subject, for example, amelioration of a symptom, alleviation of a condition, slow or delay disease progression, or prevention of a disease, etc.

In another non-limiting embodiment, the term "a therapeutically effective amount" refers to the amount of the biologically active agent that, when administered to a cell, or a tissue, or a non-cellular biological material, or a medium, is effective to at least partially treat the disease or disorder. As will be appreciated by those of ordinary skill in the art, the absolute amount of a particular agent that is effective may vary depending on such factors as the desired biological endpoint, the agent to be delivered, the target tissue, etc. Those of ordinary skill in the art understand that "a therapeutically effective amount" may be administered in a single dose or may be achieved by administration of multiple doses. For example, in the case of an agent to treat heart failure, an effective amount may be an amount sufficient to result in clinical improvement of the patient, e.g., increased exercise tolerance/capacity, increased blood pressure, decrease fluid retention, and/or improved results on a quantitative test of cardiac functioning, e.g., ejection fraction, exercise capacity (time to exhaustion), etc.

As used herein, the term "subject" refers to an animal. Typically, the animal is a mammal. A subject also refers to for example, primates (e.g., humans and non-human primates), cows, sheep, goats, horses, dogs, cats, rabbits, rats, mice, fish, birds, and the like. In certain embodiments, the subject is a primate. In yet other embodiments, the subject is a human.

As used herein, the term "inhibit," "inhibition," or "inhibiting" refers to the reduction or suppression of a given condition, symptom, or disorder, or disease, or a significant decrease in the baseline activity of a biological activity or process.

As used herein, the term "treat," "treating," or "treatment" of any disease or disorder refers in one embodiment, to ameliorating the disease or disorder (i.e., slowing or arresting or reducing the development of the disease or at least one of the clinical symptoms thereof). In another embodiment "treat," "treating," or "treatment" refers to alleviating or ameliorating at least one physical parameter including those that may not be discernible by the patient. In yet another embodiment, "treat," "treating," or "treatment" refers to modulating the disease or disorder, either physically, (e.g., stabilization of a discernible symptom), physiologically, (e.g., stabilization of a physical parameter), or both. In yet another embodiment, "treat," "treating," or "treatment" refers to preventing or delaying the onset or development or progression of the disease or disorder. As used herein, the terms "prevent," "preventing," and "prevention" refer to the prevention of the recurrence, onset, or development of one or more symptoms of a disorder in a subject resulting from the administration of a therapy (e.g., a therapeutic agent), or the administration of a combination of therapies (e.g., a combination of therapeutic agents).

As used herein, a subject is "in need of" or "in need thereof" a treatment if such subject would benefit biologically, medically, or in quality of life from such treatment.

As used herein, the term "a," "an," "the" and similar terms used herein (especially in the context of the claims) are to be construed to cover both the singular and plural unless otherwise indicated herein or clearly contradicted by the context.

As used herein, the term "about" refers to any values, including both integers and fractional components that are within a variation of up to +10% of the value modified by the term "about."

The term "or" can be conjunctive or disjunctive such that "or" encompasses "and/or."

One embodiment described herein is a drug adduct comprising a drug and a traceless linker, D-R, wherein R, is a linker that is represented by Formula (I) suitable for release of D comprising an ANGPTL3 polypeptide comprising at least one primary or secondary amine or a ring nitrogen atom of an azaheteroaryl ring:

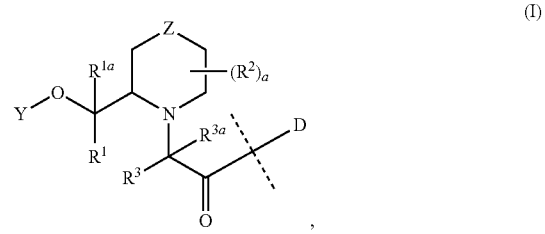

where the dashed line indicates attachment to the primary amine, secondary amine, or ring nitrogen atom of an azaheteroaryl ring;

$R^1$ is hydrogen or $C_1$-$C_4$alkyl;

$R^{1a}$ is hydrogen or $C_1$-$C_4$alkyl, or $CR^1R^{1a}$, taken in combination form a $C_3$-$C_6$cycloalk-1,1-diyl;

$R^2$ is independently selected at each occurrence from $C_1$-$C_4$alkyl or oxo, or two $R^2$ groups taken in combination form a fused $C_3$-$C_6$ cycloalkyl or spiro $C_3$-$C_6$cycloalk-1,1-diyl group;

a is 0, 1, 2, 3 or 4;

$R^3$ is hydrogen or $C_1$-$C_4$alkyl;

$R^{3a}$ is hydrogen, $C_1$-$C_4$alkyl, or $CR^3R^{3a}$, taken in combination form a $C_3$-$C_6$cycloalk-1,1-diyl;

Y is $C(O)R^4$, $C(O)OR^4$, $C(O)NHR^4$, $C(O)NR^5R^6$, $SiR^5R^6R^7$, or $CR^{12}R^{12a}OR^{13}$;

$R^{12}$ is hydrogen or $C_1$-$C_4$alkyl;

$R^{12a}$ is hydrogen or $C_1$-$C_4$alkyl, or $CR^{12}R^{12a}$, taken in combination form a $C_3$-$C_6$cycloalk-1,1-diyl;

$R^{13}$ is $C_1$-$C_4$alkyl; or $CHR^{12}OR^{13}$, taken in combination form a 5, 6, or 7-member cyclic ether;

$R^4$ is $C_1$-$C_8$alkyl or $C_3$-$C_7$cycloalkyl, wherein cycloalkyl is optionally substituted with 0, 1, or 2 independently selected $C_1$-$C_4$alkyl groups and wherein alkyl is optionally substituted by $C_1$-$C_4$alkoxy;

$R^5$ and $R^6$ are each independently selected from $C_1$-$C_4$alkyl and $C_3$-$C_6$cycloalkyl;

$R^7$ is $C_1$-$C_8$alkyl, $C_3$-$C_7$cycloalkyl, $C_1$-$C_8$alkoxy, $C_3$-$C_7$cycloalkyloxy, heterocycloalkyloxy, or —(OCHR$^3$CH$_2$)$_b$O—$C_1$-$C_4$alkyl, wherein the heterocycloalkyloxy is a 4 to 7 member saturated heterocyclic ring having one ring heteroatom selected from N, O, and S and optionally substituted with 0, 1, or 2 independently selected $C_1$-$C_4$alkyl groups;

b is an integer of from 1 to 10;

Z is CH-L-A, CH-A, N-L-A, or N-A;

L is an optionally substituted bivalent linker;

A is hydrogen, $C_1$-$C_8$alkyl, $C(O)C_1$-$C_8$alkyl, $C(O)N(H)C_1$-$C_8$alkyl, $C(O)OC_1$-$C_8$alkyl, $R^{10}$, or $R^{11}$, wherein the alkyl group is optionally substituted with 0 or 1 $R^{10}$;

$R^{10}$ is a reactive functional group suitable for coupling Formula I to a carrier; and $R^{11}$ is a carrier.

Another embodiment described herein is a drug adduct comprising a drug and a traceless linker, D-R, wherein R, is a linker that is represented by Formula (I) suitable for release of D comprising an ANGPTL3 polypeptide comprising at least one primary or secondary amine or a ring nitrogen atom of an azaheteroaryl ring:

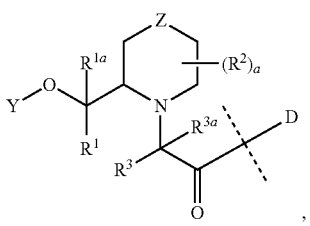

where the dashed line indicates attachment to the primary amine, secondary amine, or ring nitrogen atom of an azaheteroaryl ring;

$R^1$ is hydrogen or $C_1$-$C_4$alkyl;

$R^{1a}$ is hydrogen or $C_1$-$C_4$alkyl, or $CR^1R^{1a}$, taken in combination form a $C_3$-$C_6$cycloalk-1,1-diyl;

$R^2$ is independently selected at each occurrence from $C_1$-$C_4$alkyl or oxo, or two $R^2$ groups taken in combination form a fused $C_3$-$C_6$ cycloalkyl or spiro $C_3$-$C_6$cycloalk-1,1-diyl group;

a is 0, 1, 2, 3 or 4;

$R^3$ is hydrogen or $C_1$-$C_4$alkyl;

$R^{3a}$ is hydrogen, $C_1$-$C_4$alkyl, or $CR^3R^{3a}$, taken in combination form a $C_3$-$C_6$cycloalk-1,1-diyl;

Y is $C(O)R^4$, $C(O)OR^4$, $C(O)NHR^4$, $C(O)NR^5R^6$, $SiR^5R^6R^7$, or $CR^{12}R^{12a}OR^{13}$;

$R^{12}$ is hydrogen or $C_1$-$C_4$alkyl;

$R^{12a}$ is hydrogen or $C_1$-$C_4$alkyl, or $CR^{12}R^{12a}$, taken in combination form a $C_3$-$C_6$cycloalk-1,1-diyl;

$R^{13}$ is $C_1$-$C_4$alkyl; or $CHR^{12}OR^{13}$, taken in combination form a 5, 6, or 7-member cyclic ether;

$R^4$ is $C_1$-$C_8$alkyl or $C_3$-$C_7$cycloalkyl, wherein cycloalkyl is optionally substituted with 0, 1, or 2 independently selected $C_1$-$C_4$alkyl groups and wherein alkyl is optionally substituted by $C_1$-$C_4$alkoxy;

$R^5$ and $R^6$ are each independently selected from $C_1$-$C_4$alkyl and $C_3$-$C_6$cycloalkyl;

$R^7$ is $C_1$-$C_8$alkyl, $C_3$-$C_7$cycloalkyl, $C_1$-$C_8$alkoxy, $C_3$-$C_7$cycloalkyloxy, heterocycloalkyloxy, or —(OCHR$^3$CH$_2$)$_b$O—$C_1$-$C_4$alkyl, wherein the heterocycloalkyloxy is a 4 to 7 member saturated heterocyclic ring having one ring heteroatom selected from N, O, and S and optionally substituted with 0, 1, or 2 independently selected $C_1$-$C_4$alkyl groups;

b is an integer of from 1 to 10;

Z is CH-L-A, CH-A, N-L-A, or N-A;

L is an optionally substituted bivalent linker Q-[Sp-Q]$_h$-Q;

Q is independently selected at each occurrence from a bond, O, C(O), N(H), N(C$_1$-C$_4$alkyl), C(O)NH, C(O)N(C$_1$-C$_4$alkyl), N(H)C(O), N(C$_1$-C$_4$alkyl)C(O), N(H)C(O)O, N(C$_1$-C$_4$alkyl)C(O)O, OC(O)N(H), OC(O)N(C$_1$-C$_4$alkyl), N(H)C(O)N(H), N(C$_1$-C$_4$alkyl)C(O)N(H), N(H)C(O)N(C$_1$-C$_4$alkyl), N(C$_1$-C$_4$alkyl)C(O)N(C$_1$-C$_4$alkyl), C(O)O, OC(O), OC(O)O, S, S(O)$_2$, N(H)S(O)$_2$, N(C$_1$-C$_4$alkyl)S(O)$_2$, S(O)$_2$N(H), S(O)$_2$N(C$_1$-C$_4$alkyl), C$_1$-C$_2$alkyl-C(O)N(H), N(H)C(O)C$_1$-C$_2$alkyl, C$_1$-C$_2$alkyl-C(O)O, OC(O)C$_1$-C$_2$alkyl, 1,2,3-triazole, OP(O)$_2$, P(O)$_2$O, C$_1$-C$_4$alkyl-P(O)$_2$—O, or O—P(O)$_2$—C$_{1-4}$alkyl;

Sp is independently selected at each occurrence from an optionally substituted $C_1$-$C_{20}$alkyl, $C_2$-$C_{20}$alkenyl, $C_2$-$C_{20}$alkynyl, [W—O]$_g$, $C_1$-$C_8$alkyl-[O—W]$_g$, [O—W]$_g$—O—$C_1$-$C_8$alkyl, $C_1$-$C_8$Calkyl-[O—W]$_g$—O—$C_1$-$C_8$alkyl, oligopeptide;

h is an integer of between 1 and 20;

g is a weighted average number of between about 2 and about 50;

W is $C_2$-$C_4$alkyl-1,2-diyl in which the hydrogen, methyl, or ethyl side chain may be present on either backbone carbon atom;

A is hydrogen, $C_1$-$C_8$alkyl, $C(O)C_1$-$C_8$alkyl, $C(O)OC_1$-$C_8$alkyl, $C(O)N(H)C_1$-$C_8$alkyl, $R^{10}$, or $R^{11}$, wherein the alkyl group is optionally substituted with 0 or 1 $R^{10}$;

$R^{10}$ is a reactive functional group suitable for coupling Formula I to a carrier; and $R^{11}$ is a carrier.

Another embodiment described herein is a drug adduct comprising a drug and a traceless linker, D-R, wherein R, is a linker that is represented by Formula (I) suitable for release of D comprising an ANGPTL3 polypeptide comprising at least one primary or secondary amine or a ring nitrogen atom of an azaheteroaryl ring:

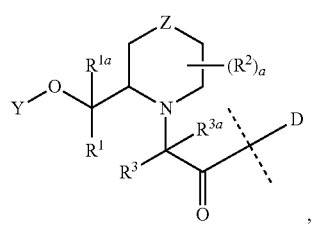

where the dashed line indicates attachment to the primary amine, secondary amine, or ring nitrogen atom of an azaheteroaryl ring;

$R^1$ is hydrogen or $C_1$-$C_4$alkyl;

$R^{1a}$ is hydrogen or $C_1$-$C_4$alkyl, or $CR^1R^{1a}$, taken in combination form a $C_3$-$C_6$cycloalk-1,1-diyl;

$R^2$ is independently selected at each occurrence from $C_1$-$C_4$alkyl or oxo, or two $R^2$ groups taken in combination form a fused $C_3$-$C_6$ cycloalkyl or spiro $C_3$-$C_6$cycloalk-1,1-diyl group;

a is 0, 1, 2, 3 or 4;

$R^3$ is hydrogen or $C_1$-$C_4$alkyl;

$R^{3a}$ is hydrogen, $C_1$-$C_4$alkyl, or $CR^3R^{3a}$, taken in combination form a $C_3$-$C_6$cycloalk-1,1-diyl;

Y is $C(O)R^4$, $C(O)OR^4$, $C(O)NHR^4$, $C(O)NR^5R^6$, $SiR^5R^6R^7$, or $CR^{12}R^{12a}OR^{13}$;

$R^{12}$ is hydrogen or $C_1$-$C_4$alkyl;

$R^{12a}$ is hydrogen or $C_1$-$C_4$alkyl, or $CR^{12}R^{12a}$, taken in combination form a $C_3$-$C_6$cycloalk-1,1-diyl;

$R^{13}$ is $C_1$-$C_4$alkyl; or $CHR^{12}OR^{13}$, taken in combination form a 5, 6, or 7-member cyclic ether;

$R^4$ is $C_1$-$C_8$alkyl or $C_3$-$C_7$cycloalkyl, wherein cycloalkyl is optionally substituted with 0, 1, or 2 independently selected $C_1$-$C_4$alkyl groups and wherein alkyl is optionally substituted by $C_1$-$C_4$alkoxy;

$R^5$ and $R^6$ are each independently selected from $C_1$-$C_4$alkyl and $C_3$-$C_6$cycloalkyl;

$R^7$ is $C_1$-$C_8$alkyl, $C_3$-$C_7$cycloalkyl, $C_1$-$C_8$alkoxy, $C_3$-$C_7$cycloalkyloxy, heterocycloalkyloxy, or —(OCHR$^3$CH$_2$)$_b$O—$C_1$-$C_4$alkyl, wherein the heterocycloalkyloxy is a 4 to 7 member saturated heterocyclic ring having one ring heteroatom selected from N, O, and S and optionally substituted with 0, 1, or 2 independently selected $C_1$-$C_4$alkyl groups;

b is an integer of from 1 to 10;

Z is CHR$^8$ or NR$^9$;

$R^8$ and $R^9$ are each independently selected from hydrogen, $C_1$-$C_8$ alkyl, C(O)$C_1$-$C_8$ alkyl, or —C(O)(CH$_2$)$_q$[O—W]$_g$(NHC(O))$_m$(CH$_2$)$_q$[O—W]$_p$-Q-A, wherein the alkyl group is optionally substituted with 0 or 1 Q-A;

q is independently at each occurrence 1, 2, or 3;

g and p each independently have a weighted average length of between about 2 and about 50;

m is 1 or 0;

W is $C_2$-$C_4$alkyl-1,2-diyl in which the hydrogen, methyl, or ethyl side chain may be present on either backbone carbon atom;

Q is a bond, O, N(H) or N($C_1$-$C_4$alkyl);

A is hydrogen, $C_1$-$C_8$alkyl, C(O)$C_1$-$C_8$alkyl, C(O)N(H)$C_1$-$C_8$alkyl, C(O)O$C_1$-$C_8$alkyl, $R^{10}$, or $R^{11}$, wherein the alkyl group is optionally substituted with 0 or 1 $R^{10}$;

$R^{10}$ is a reactive functional group suitable for coupling Formula I to a carrier; and $R^{11}$ is a carrier.

In some aspects, $R^1$-$R^8$ of Formula (I) have the following meanings. In one aspect, $R^1$ is hydrogen or methyl. In another aspect, $R^{1a}$ is hydrogen, or methyl. In another aspect, $R^1$ and $R^{1a}$, taken in combination form a $C_3$-$C_6$cycloalk-1,1-diyl. In another aspect, $R^2$ is methyl. In another aspect, two $R^2$ groups taken in combination form a fused or spiro $C_3$-$C_6$ cycloalkyl group. In another aspect, $R^3$ is hydrogen or methyl. In another aspect, $R^{3a}$ is hydrogen or methyl. In another aspect, $R^3$ and $R^{3a}$ taken in combination form a $C_3$-$C_6$cycloalk-1,1-diyl. In another aspect, Y is C(O)$R^4$ and $R^4$ is $C_1$-$C_6$alkyl, $C_1$-$C_2$alkoxy, $C_1$-$C_2$alkyl or $C_1$-$C_6$alkoxy. In another aspect, $R^4$ is methyl, ethyl, propyl, isopropyl, 1-methyl-cyclopropyl, or methoxymethyl. In another aspect, Y is SiR$^5$R$^6$OR$^7$; and $R^5$ and $R^6$ are each methyl, ethyl, propyl or isopropyl; and $R^7$ is ethyl, propyl, isopropyl, butyl, isobutyl, secbutyl, ethoxyethyl, ethoxyisopropyl, tetrahydropyranyl, or —(OCHR$^3$CH$_2$)$_b$O—$C_1$-$C_4$alkyl where b is 2, 3, or 4.

In some aspects, $R^8$ and $R^9$ of Formula (I) have the following meanings. In one aspect, $R^9$ is, C(O)$C_2$ carbamoyl. In another aspect, $R^9$ is C(O)$C_2$ amidyl. In another aspect, $R^9$ is C(O)$C_5$ alkyl. In another aspect, $R^9$ is C(O)$C_2$ alkyl. In another aspect, $R^9$ is C(O)$C_1$ alkyl. In another aspect, $R^9$ is C(O)CH$_2$CH$_2$NHC(O)CH$_2$CH$_2$CH$_2$CH$_2$. In another aspect, $R^9$ is C(O)(CH$_2$CH$_2$O)$_b$CH$_2$CH$_2$ where b is 1, 2, 3, or 4. In another aspect, $R^9$ is amidyl. In another aspect, $R^9$ is carbamoyl. In another aspect, $R^9$ is $C_1$ alkyl amidyl. In another aspect, $R^9$ is $C_2$ alkyl amidyl.

In some aspects, Z is CH-L-A, CH-A, N-L-A, or N-A;

L is an optionally substituted bivalent linker;

A is hydrogen, $C_1$-$C_8$alkyl, C(O)$C_1$-$C_8$alkyl, C(O)N(H)$C_1$-$C_8$alkyl, C(O)O$C_1$-$C_8$alkyl, $R^{10}$, or $R^{11}$, wherein the alkyl group is optionally substituted with 0 or 1 $R^{10}$;

$R^{10}$ is a reactive functional group suitable for coupling Formula I to a carrier; and $R^{11}$ is a carrier.

In some aspects, Z is CH-L-A, CH-A, N-L-A, or N-A;

L is an optionally substituted bivalent linker Q-[Sp-Q]$_h$-Q;

Q is independently selected at each occurrence from a bond, O, C(O), N(H), N($C_1$-$C_4$alkyl), C(O)NH, C(O)N($C_1$-$C_4$alkyl), N(H)C(O), N($C_1$-$C_4$alkyl)C(O), N(H)C(O)O, N($C_1$-$C_4$alkyl)C(O)O, OC(O)N(H), OC(O)N($C_1$-$C_4$alkyl), N(H)C(O)N(H), N($C_1$-$C_4$alkyl)C(O)N(H), N(H)C(O)N($C_1$-$C_4$alkyl), N($C_1$-$C_4$alkyl)C(O)N($C_1$-$C_4$alkyl), C(O)O, OC(O), OC(O)O, S, S(O)$_2$, N(H)S(O)$_2$, N($C_1$-$C_4$alkyl)S(O)$_2$, S(O)$_2$N(H), S(O)$_2$N($C_1$-$C_4$alkyl), $C_1$-$C_2$alkyl-C(O)N(H), N(H)C(O)$C_1$-$C_2$alkyl, $C_1$-$C_2$alkyl-C(O)O, OC(O)$C_1$-$C_2$alkyl, 1,2,3-triazole, OP(O)$_2$, P(O)$_2$O, $C_1$-$C_4$alkyl-P(O)$_2$—O, or O—P(O)$_2$—$C_{1-4}$alkyl;

Sp is independently selected at each occurrence from an optionally substituted $C_1$-$C_{20}$alkyl, $C_2$-$C_{20}$alkenyl, $C_2$-$C_{20}$alkynyl, [W—O]$_g$, $C_1$-$C_8$alkyl-[O—W]$_g$, [O—W]$_g$—O—$C_1$-$C_8$alkyl, $C_1$-$C_8$Calkyl-[O—W]$_g$—O—$C_1$-$C_8$alkyl, oligopeptide;

h is an integer of between 1 and 20;

g is a weighted average number of between about 2 and about 50;

W is $C_2$-$C_4$alkyl-1,2-diyl in which the hydrogen, methyl, or ethyl side chain may be present on either backbone carbon atom;

A is hydrogen, $C_1$-$C_8$alkyl, C(O)$C_1$-$C_8$alkyl, C(O)O$C_1$-$C_8$alkyl, C(O)N(H)$C_1$-$C_8$alkyl, $R^{10}$, or $R^{11}$, wherein the alkyl group is optionally substituted with 0 or 1 $R^{10}$;

$R^{10}$ is a reactive functional group suitable for coupling Formula I to a carrier; and $R^{11}$ is a carrier.

In certain aspects, g and h are 1 to about 25 or from 1 to about 10.

In some aspects, Z of Formula (I) is NR$^9$. In one aspect, $R^9$ is further substituted with $R^{10}$. In another aspect, $R^9$ is further substituted with $R^{11}$.

According to Formula (I), $R^{10}$ is a reactive functional group that is suitable for orthogonal coupling reactions. Suitable reactive functional groups are those that readily undergo orthogonal reactions. Exemplary and non-limiting orthogonal chemical reactions include functional groups shown in Table 2. For a given row in Table 2, a functional group X (left column) is suitable for a coupling reaction with a functional group Y (right column). Coupling reactions may be covalent bonds or intermolecular complexes. In most embodiments, the coupling reaction results in a covalent bond. In other reactions, such as adamantane with cyclodextran, the coupling is a non-covalent molecular association. In one aspect, the functional group is selected from azidyl, alkynyl, substituted or unsubstituted $C_6$-$C_{12}$ cycloalkynyl, $C_6$-$C_{12}$ heterocycloalkynyl, $C_6$-$C_{12}$ cycloalkenyl, norbornyl, vinyl carboxyl, vinyl sulfonyl, $C_2$-$C_8$ alkenyl, substituted or unsubstituted $C_1$-$C_8$ alkoxy, thiol, $C_1$-$C_8$ carboxyl, $C_1$-$C_8$ carbonyl, oxyamine, carbohydrazide, maleimide, alpha-halo carbonyl, furan, substituted or unsubstituted tetrazinyl, lysine, glutamine, cyclodextrin, and adamantanyl. In another aspect, the functional group is a substituted $C_6$-$C_{12}$ cycloalkynyl, wherein the substitution includes a fused cyclopropyl group. In another aspect, the functional group is bicyclo[6.1.0]non-4-yn-9-yl. In another aspect, the functional group is azidyl.

TABLE 2

Exemplary Orthogonal Chemistry

| Compound (or polymer) 1-X<br>X: | Compound (or polymer) 2-Y<br>Y: |
|---|---|
| —N₃ | —C≡H, cyclooctyne, difluorocyclooctyne, DBCO-amide, dibenzoazacyclooctyne-one, dibenzocyclooctynol |
| —C≡H, cyclooctyne, difluorocyclooctyne, DBCO-amide, dibenzoazacyclooctyne-one, dibenzocyclooctynol, BCN (exo and endo) | —N₃ |

TABLE 2-continued

Exemplary Orthogonal Chemistry

| Compound (or polymer) 1-X<br>X: | Compound (or polymer) 2-Y<br>Y: |
|---|---|
| —N₃ | bicyclononyne-OCH₂- (both stereoisomers) |
| —SH | maleimide |
| | acrylate ester |
| | vinyl sulfone |
| | CH=CH (trans alkene with H) |
| | CH=CH (alkene) |
| | X—CH₂—C(=O)— (X = halogen) |
| | norbornene |
| | —SH |
| maleimide | |
| acrylate ester | |
| vinyl sulfone | |
| CH=CH (trans alkene with H) | |
| CH=CH (alkene) | |
| X—CH₂—C(=O)— | |

TABLE 2-continued
Exemplary Orthogonal Chemistry
| Compound (or polymer) 1-X<br>X: | Compound (or polymer) 2-Y<br>Y: |
|---|---|
| 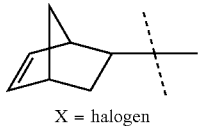<br>X = halogen | |
| 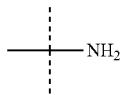 | 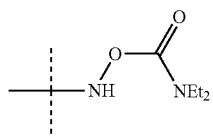 |
| —NH$_2$ | 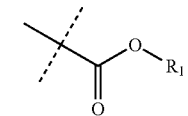<br>R$_1$ = H or activated ester |
| 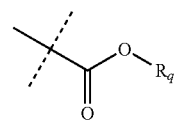<br>R$_q$ = H or activated ester | 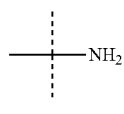<br>—NH$_2$ |
| 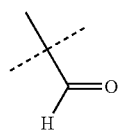 | 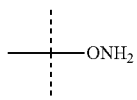<br>—ONH$_2$ |
| 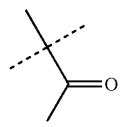 | 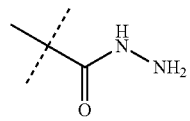 |
| 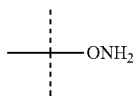<br>—ONH$_2$ | 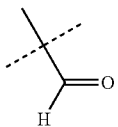 |
| 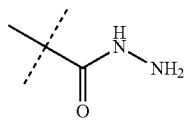 | 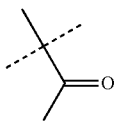 |
| 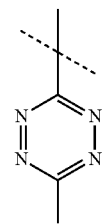 | 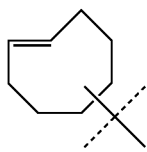 |

TABLE 2-continued

Exemplary Orthogonal Chemistry

| Compound (or polymer) 1-X<br>X: | Compound (or polymer) 2-Y<br>Y: |
|---|---|
| *trans-cyclooctene structure* | *tetrazine structure* |
| *furan structure* | *maleimide structure* |
| *maleimide structure* | *furan structure* |
| *substituted alkene with $R_y$, $R_x$, $R_z$* | *diene structure* |
| *diene structure* | *substituted alkene with $R_y$, $R_x$, $R_z$* |
| —Lys | —Gln |
| —Gln | —Lys |
| —cyclodextrin or other host molecule | —adamantane or other host molecule |
| —adamantane or other host molecule | —cyclodextrin or other host molecule |

In some embodiments, the traceless linker, R, comprises Formula (II):

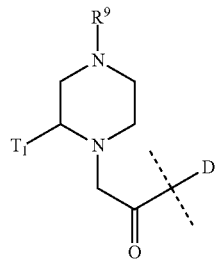

(II)

wherein, $R^9$ and D are both as defined for Formula (I) above and Ti comprises a substituted or unsubstituted $C_2$-$C_{10}$ ester, a substituted or unsubstituted $C_3$-$C_{10}$ silyl ether containing one or more heteroatoms selected from nitrogen or oxygen.

In some aspects, $T_1$ is —$CR^1R^{1a}OY$, which contains a trigger moiety and comprises one of the following structures in Table 3.

TABLE 3

Trigger Moieties

TABLE 3-continued

Trigger Moieties

In some embodiments, the traceless linker, R, according to either Formula I or II comprises any one of the following structures in Table 4.

TABLE 4
Exemplary Traceless Linkers
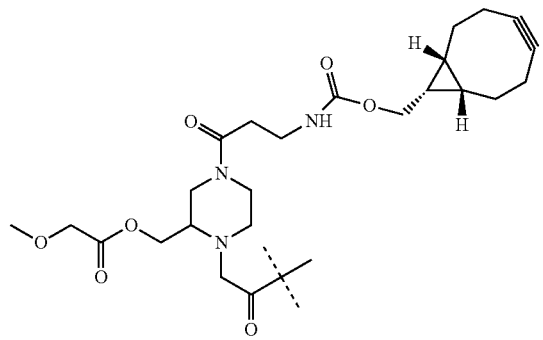
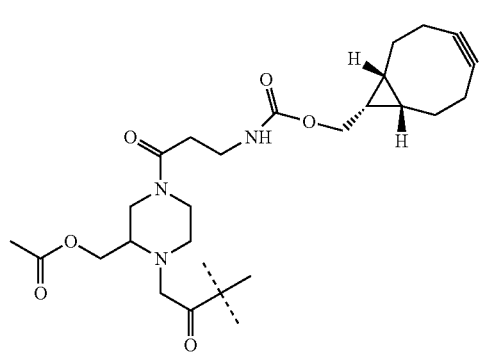
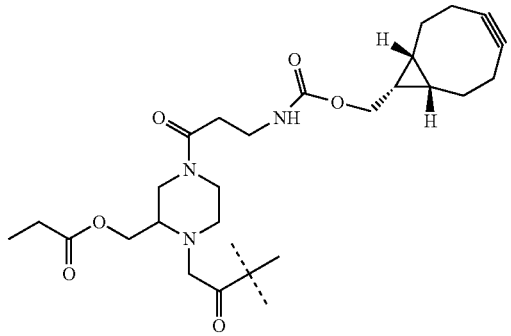
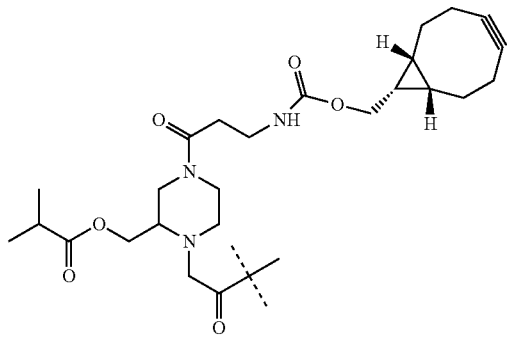
TABLE 4-continued
Exemplary Traceless Linkers
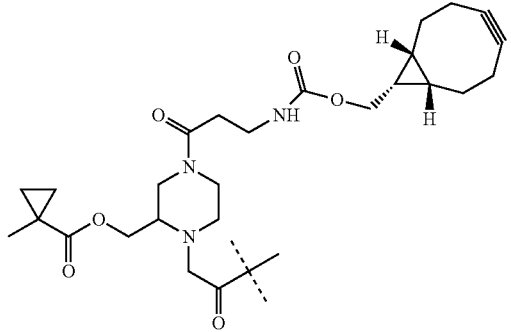
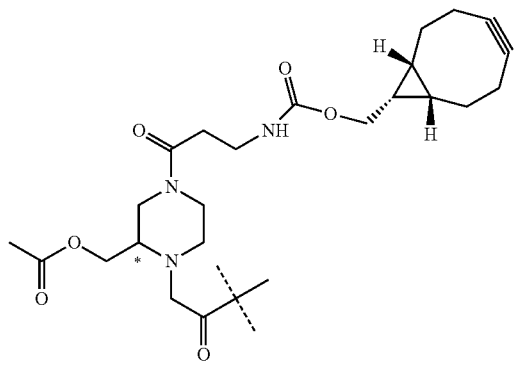
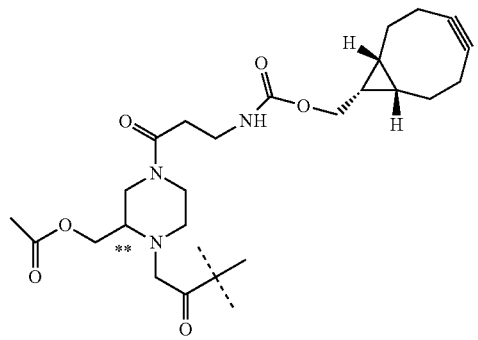
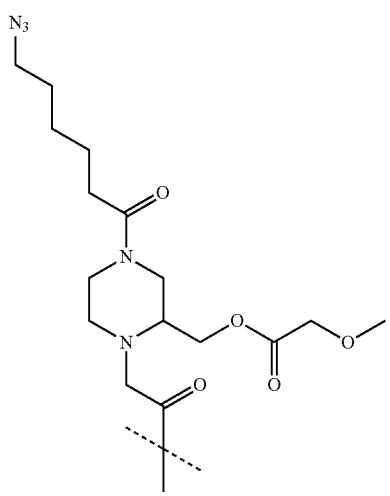

TABLE 4-continued
Exemplary Traceless Linkers
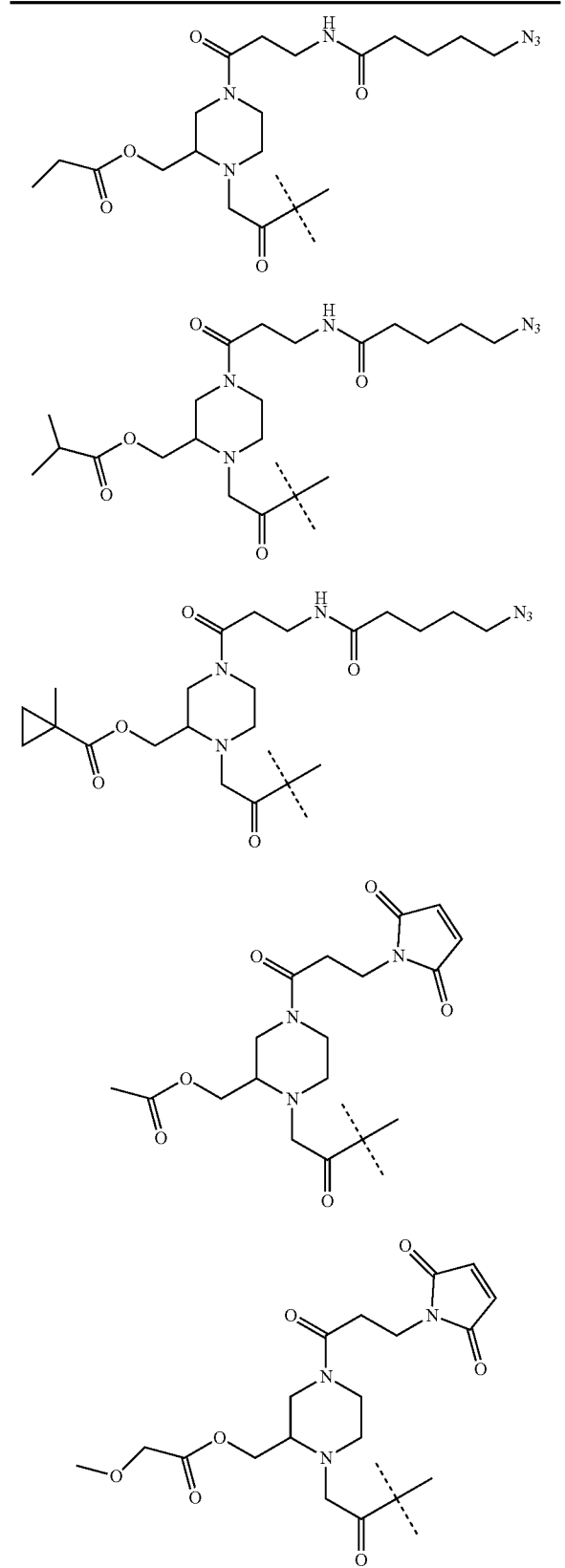
TABLE 4-continued
Exemplary Traceless Linkers
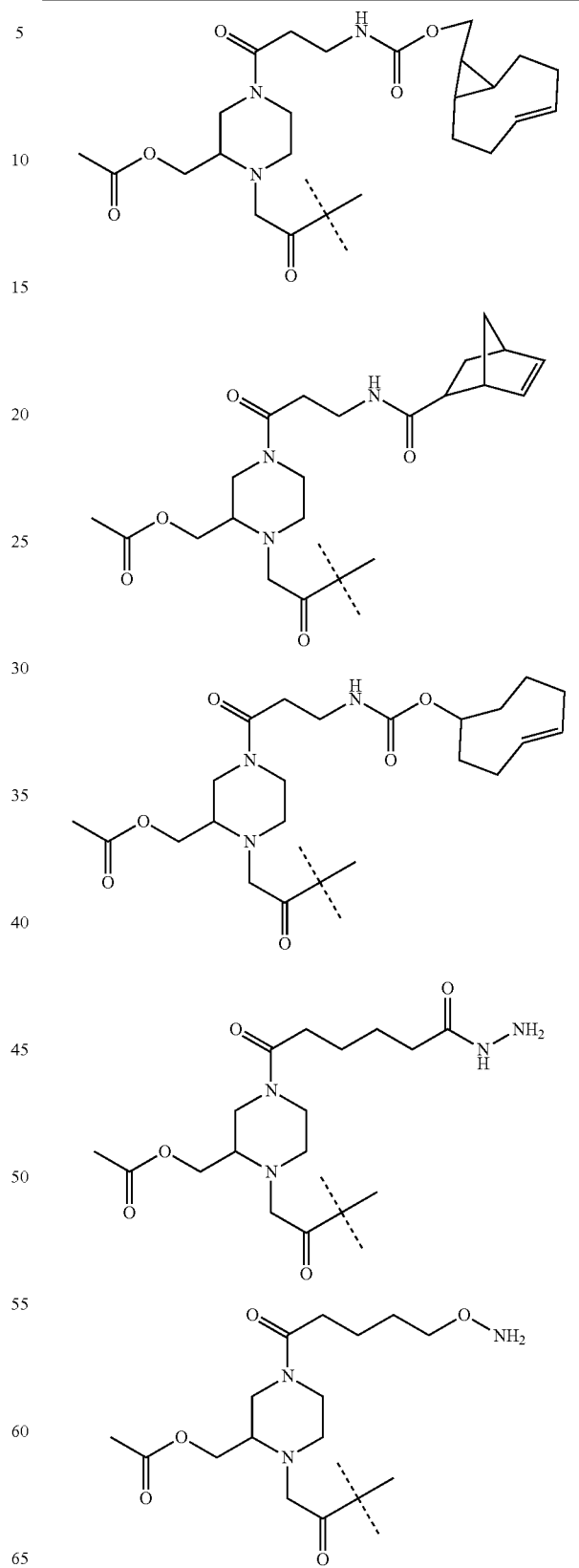

TABLE 4-continued

Exemplary Traceless Linkers

[Chemical structure: piperazine derivative with N-acyl group bearing SH (thiol) terminus, and acetoxymethyl substituent]

[Chemical structure: piperazine derivative with N-acyl linker terminating in BF₃⁻K⁺, and acetoxymethyl substituent]

In another embodiment, the traceless linker, R, of Formula (I) or Formula (II) is conjugated to a drug or bioactive moeity. In one aspect, the traceless linker, R, of Formula (I) or Formula (II) is conjugated to an ANGPTL3 polypeptide. In another aspect, the ANGPTL3 polypeptide comprises SEQ ID NOs:1, or 3-45. In another aspect, the ANGPTL3 polypeptide comprises D1 (SEQ ID NO:19).

Synthesis of a Traceless Linker, R

Another embodiment is a method for manufacturing a traceless linker, R, of Formula (I) comprising any one of the steps: (A) reacting the N4 nitrogen of a piperazine compound containing a nucleophilic group at the C2 position with a functionalized acyl linker compound to form an N4-acylpiperazine; (B) carboxymethylating the N1 nitrogen of the piperazine ring of the N4-acylpiperazine, wherein the carboxyl group is covalently attached to a suitable protecting group; (C) reacting the nucleophilic group of the N4-acylpiperazine with a trigger compound described herein; (D) if necessary, elaborating the functionalized acyl linker on N4 to contain a functional group suitable for attaching the traceless linker to a carrier compound. In one aspect, the nucleophilic group at the C2 position of the piperazine compound comprises a hydroxyl. In another aspect, the nucleophilic group at the C2 position of the piperazine compound is a primary alcohol. In another aspect, the primary alcohol present in the piperazine compound of step (A) or (D) is conjugated to a suitable protecting group or trigger group. In another aspect, the protecting group or trigger group comprises an ester, silyl ether, acetal, carbamate, carbonate, or a disiloxane containing compound. In one aspect, the N4 carboxymethyl ester protecting group is deprotected to form a carboxylic acid, which is suitable for forming an amide bond to a biologically active agent comprising at least one primary or secondary amine or a ring nitrogen atom of an azaheteroaryl ring. In another aspect, in the carboxymethylation step, the carboxyl group of the carboxymethylating reagent is covalently attached via an amide bond to a biologically active agent comprising at least one primary or secondary amine or a ring nitrogen atom of an azaheteroaryl ring. In one aspect, the functional group of step A is suitable for attaching the traceless linker to a carrier compound.

Another embodiment is a method for manufacturing a traceless linker, R, of Formula (I) comprising any one of the steps: (A) carboxymethylating the N1 nitrogen of a piperazine compound containing a nucleophilic group at the C2 position, wherein the carboxyl group is covalently attached to a suitable protecting group; (B) reacting the N4 nitrogen of the piperazine compound with a functionalized alkyl linker to form an N4-alkylpiperazine; (C) reacting the nucleophilic group of the N4-alkylpiperazine with a trigger compound described herein; (D) if necessary, elaborating the functionalized alkyl linker on N4 to contain functional group suitable for attaching the traceless linker to a carrier compound. In one aspect, the reactive group on the piperazine compound comprises a hydroxyl. In another aspect, the nucleophilic group at the C2 position of the piperazine compound is a primary alcohol. In another aspect, the primary alcohol present on the piperazine compound of step (A) or (D) is conjugated to a suitable protecting group or trigger group. In another aspect, the trigger compound comprises an ester, silyl ether, acetal, carbamate, carbonate, or a disiloxane containing compound. In one aspect, the $N_4$ carboxymethyl ester protecting group is deprotected to form a carboxylic acid, which is suitable for forming an amide bond to a biologically active agent comprising at least one primary or secondary amine or a ring nitrogen atom of an azaheteroaryl ring. In another aspect, in the carboxymethylation step, the carboxyl group of the carboxymethylating reagent is covalently attached via an amide bond to a biologically active agent comprising at least one primary or secondary amine or a ring nitrogen atom of an azaheteroaryl ring. In one aspect, the functional group of step A is suitable for attaching the traceless linker to a carrier compound.

Another embodiment is a method for manufacturing a traceless linker, R, of Formula (I) comprising any one of the steps: (A) introducing a functionalized linker at the C4-position of a pyridine compound containing a nucleophilic group at the C2 position via a cross coupling or substitution reaction; (B) hydrogenating the 4-substituted pyridine compound to form a 4-substituted piperidine compound; (C) carboxymethylating the N1 nitrogen of the 4-substituted piperidine compound, wherein the carboxyl group is covalently attached to a suitable protecting group; (D) reacting the nucleophilic group of the 4-substituted piperidine compound with a trigger compound described herein; (E) if necessary, elaborating the functionalized alkyl linker on C4 to contain a functional group suitable for attaching the traceless linker to a carrier compound. In one aspect, the nucleophilic group on the pyridine or piperidine compounds comprises a hydroxyl. In another aspect, the nucleophilic group at the C2 position of the pyridine or piperidine compounds is a primary alcohol. In another aspect, the trigger compound comprises an ester, silyl ether, acetal, carbamate, carbonate, or a disiloxane containing compound. In one aspect, the N4 carboxymethyl ester protecting group is deprotected to form a carboxylic acid, which is suitable for forming an amide bond to a biologically active agent comprising at least one primary or secondary amine or a ring nitrogen atom of an azaheteroaryl ring. In another aspect, in the carboxymethylation step, the carboxyl group of the carboxymethylating reagent is covalently attached via an amide bond to a biologically active agent comprising at least one primary or secondary amine or a ring nitrogen atom of an azaheteroaryl ring. In one aspect, the functional group of step A is suitable for attaching the traceless linker to a carrier compound.

Suitable protecting groups are moieties that are reversibly connected to reactive functional groups or chemical functional groups to render them incapable of reacting with for example other chemical functional groups. Exemplary and non-limiting amino protecting groups include a fluorenylmethylenoxy group (FMOC), tert-butyloxycarbonyl (BOC), carboxybenzyl (Cbz), and the like. Exemplary and non-limiting alcohol protecting groups include t-butyl ether, allyl ether, benzyl ether, tert-butyldimethylsilyl ethers (TBDMS), and the like. Deprotecting groups may be added or removed as needed throughout the synthesis to block and expose particular moieties.

In one embodiment, the method for manufacturing a traceless linker is according to reaction Schemes 1-3. The following schemes are general and non-limiting schemes for manufacturing traceless linkers. As shown in the Examples herein some synthesis routes do not specifically conform to these general schemes. In another aspect, the method for manufacturing a traceless linker according to the reaction schemes provided in Example 1.

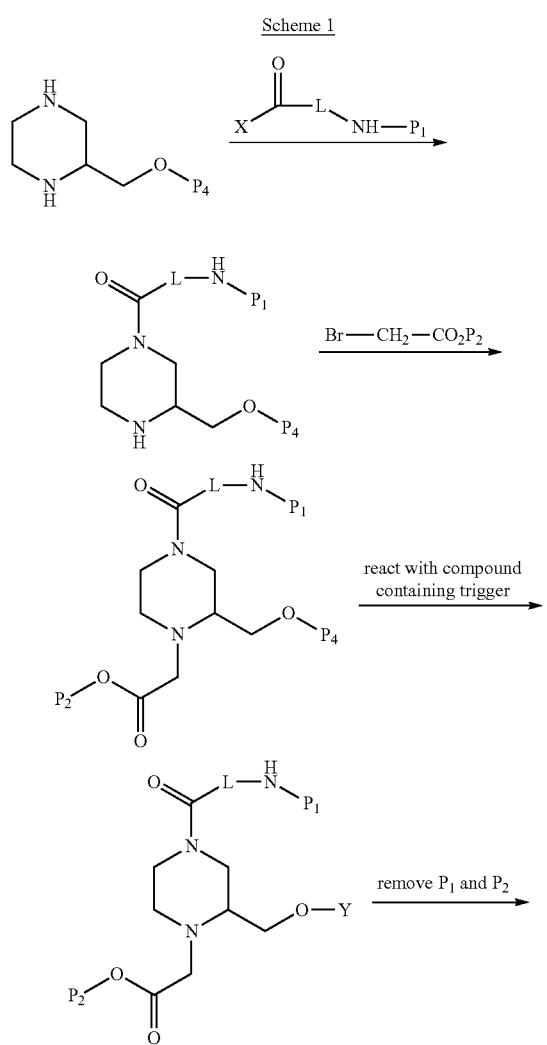

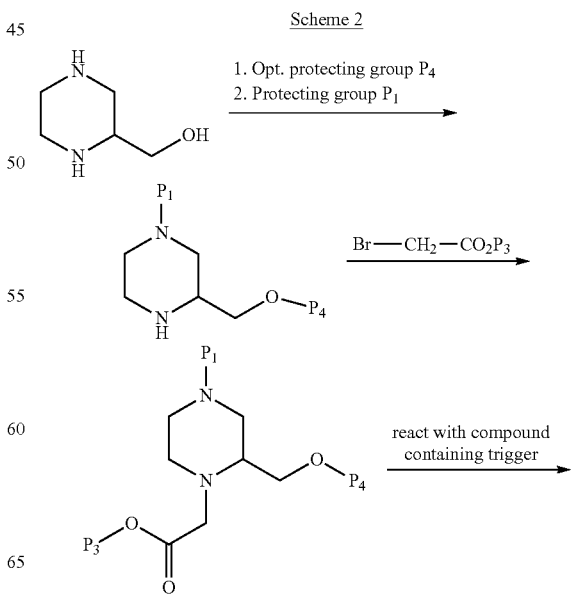

wherein one or more of the steps shown above may be performed in a different sequential order or omitted depending on the reagents utilized;

X is an activating group comprising Cl, O—NHS, O(C=O)—$R^{2a}$, or X—OH and the reaction includes standard peptide coupling reagents such as 1-[Bis(dimethylamino)methylene]-1H-1,2,3-triazolo[4,5-b]pyridinium 3-oxide hexafluorophosphate (HATU);

$R^{2a}$ is $C_1$-$C_8$ alkyl or aryl;

$P_4$ is a suitable protecting group or H;

L is an optionally substituted bivalent linker;

$P_1$ and $P_2$ are protecting groups that may be identical;

Y is a suitable trigger provided in Table 3; and

FG comprises a suitable functional group(s) capable of conjugating to a carrier described herein.

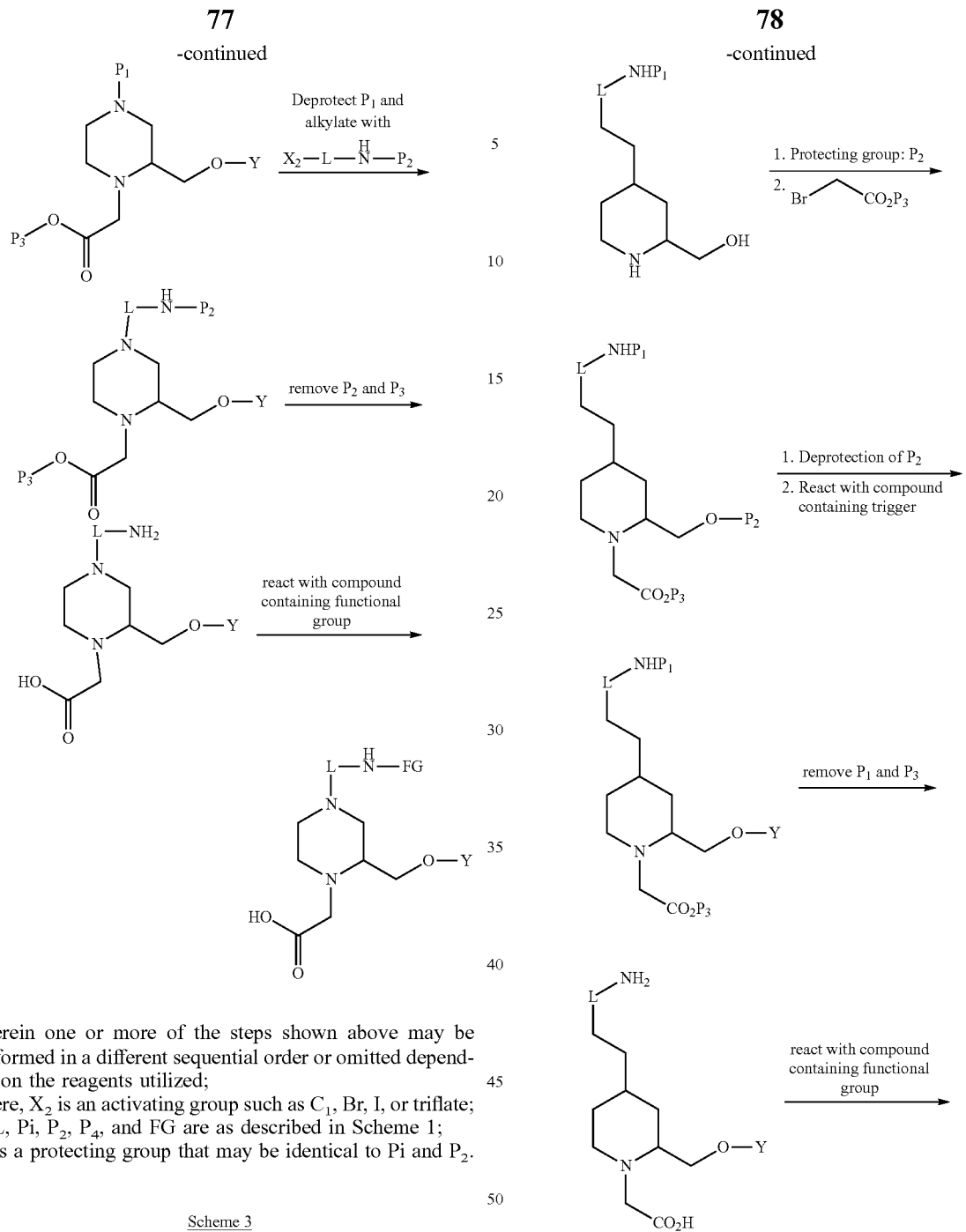
wherein one or more of the steps shown above may be performed in a different sequential order or omitted depending on the reagents utilized;
where, $X_2$ is an activating group such as $C_1$, Br, I, or triflate; Y, L, Pi, $P_2$, $P_4$, and FG are as described in Scheme 1; $P_3$ is a protecting group that may be identical to Pi and $P_2$.
Scheme 3
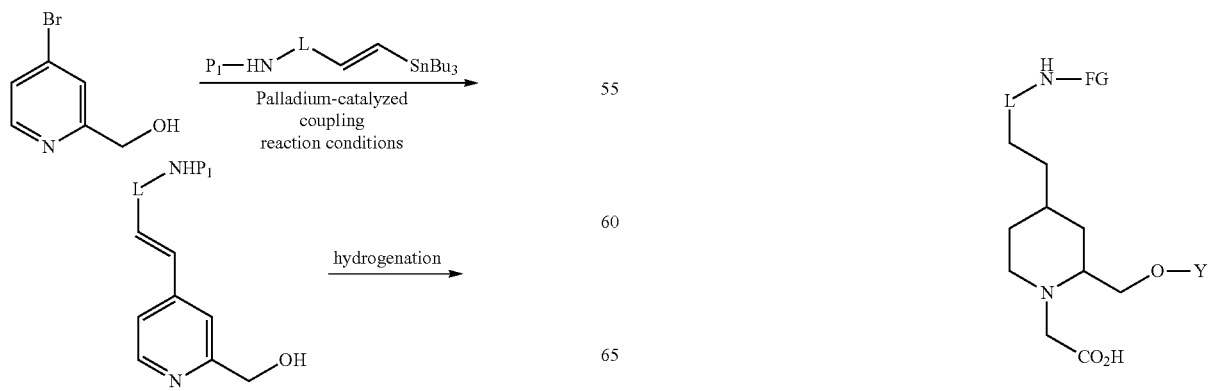

wherein one or more of the steps shown above may be performed in a different sequential order or omitted depending on the reagents utilized; and L, $P_1$, $P_2$, $P_3$, Y, and FG are as described in Scheme 2.

As described herein, the adduct D-R of Formula (I) or Formula (II) is prepared by reacting the carboxylic acid form of traceless linker R with an amino group of a biologically active agent comprising at least one primary or secondary amine or a ring nitrogen atom of an azaheteroaryl ring to form an amide bond. This process is described in Scheme 4. A suitable carboxylic acid activating agent is used to promote the amide bond forming reaction. As an example, the carboxylic acid may be converted to an amino-reactive form by the action of disuccinimidyl carbonate to form an NHS ester; the NHS ester of traceless linker R is then reacted with amino-containing drug D to form adduct D-R.

In Scheme 4, L, Y, and FG are as described in Schemes 1-3; D is a biologically active agent comprising at least one primary or secondary amine or a ring nitrogen atom of an azaheteroaryl ring.

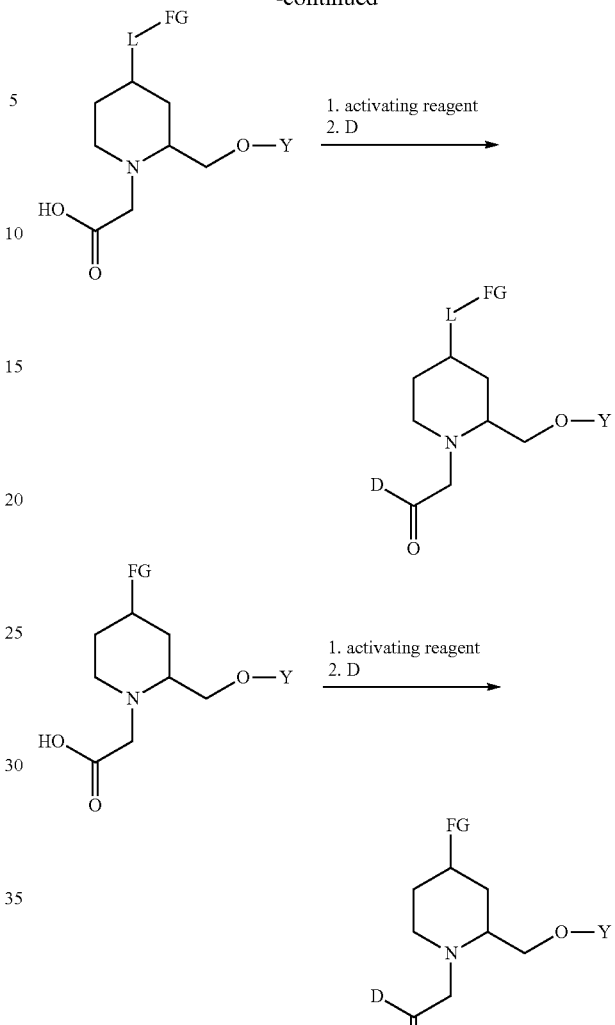

One embodiment described herein is a traceless linker, R, of Formula (I) or Formula (II) attached to a carrier composition through a linker having one or more functional groups. In one aspect, the carrier composition comprises $R^{11}$ of a traceless linker as described herein. In one aspect, $R^{11}$ comprises a polymer, biopolymer, or polyethylene glycol connected to $R^8$ or $R^9$ through a linker. In one aspect, the carrier composition is a hydrogel. In one aspect, the hydrogel composition comprises hyaluronic acid, polyethylene glycol, polypropylene glycol, polyethylene oxide, polyglutamate, polylysine, polysialic acid, polyvinyl alcohol, polyacrylate, polymethacrylate, polyacrylate/polymethacrylate copolymers, polyacrylamide, polymethacrylamide, polyvinylpyrrolidone, polyoxazoline, polyiminocarbonate, polyamino acid, hydrophilic polyester, polyamide, polyurethane, polyurea, dextran, agarose, xylan, mannan, carrageenan, alginate, gelatin, collagen, albumin, cellulose, methylcellulose, ethylcellulose, hydroxypropylmethylcellulose, hydroxyethyl starch, chitosan, nucleic acids, derivatives thereof, co-polymers thereof, or combinations thereof. In another aspect, $R^{11}$ comprises a nanoparticle or a molecular surface. In one aspect, the hydrogel comprises hyaluronic acid or polyethylene glycol. In another aspect, $R^{11}$ comprises a cross-linked hydrogel of hyaluronic acid or polyethylene glycol. In one aspect, where the drug delivery system is utilized in the eye or in the synovial joints, $R^{11}$ comprises hyaluronic acid or cross-linked hyaluronic acid.

As described herein, $R^{11}$ carrier compositions can be cross-linked to join multiple molecules together and facilitate hydrogel formation. Cross-linking can be accomplished using any means known in the art. See, for example, Liu et al., "Solution processable, cross-linked sulfur polymers as solid electrolytes in dye-sensitized solar cells," *Chem. Commun.* 51: 14660-14662 (2015). In one embodiment described herein, hyaluronic acid or polyethylene glycol are functionalized with one or more functional groups shown in Table 2 to provide reactive functional groups for cross-linking. In another aspect, the hyaluronic acid or polyethylene glycol are functionalized with a functional group selected from azidyl, alkynyl, substituted or unsubstituted $C_7$-$C_{12}$ cycloalkynyl, $C_7$-$C_{12}$ cycloalkenyl, substituted or unsubstituted $C_7$-$C_{12}$ heterocycloalkynyl, vinyl carboxyl, vinyl sulfonyl, $C_2$-$C_8$ alkenyl, amino, thiol, $C_1$-$C_8$ carboxyl, $C_1$-$C_8$ carbonyl, oxyamine, carbohydrazide, maleimide, alpha-halo carbonyl, furan, substituted or unsubstituted tetrazinyl, lysine, glutamine, cyclodextrin, and adamantanyl. In another aspect, the hyaluronic acid is functionalized with an azidyl group.

The degree of functionalization can determine the porosity of the hydrogel. In one aspect, about 5% to about 50% of the carrier polymer is functionalized, including all integers within the specified range. In one aspect, the carrier polymer is functionalized about 5%, about 10%, about 15%, about 20%, about 25%, about 30%, about 35%, about 40%, about 45%, about 50%, or even greater.

In one aspect, the carrier is hyaluronic acid. In another aspect, hyaluronic acid is reacted with 4-(4,6-dimethoxy-1,3,5-triazin-2-yl)-4-methylmorpholin-4-ium chloride (CAS number 3945-69-5) and 2-(2-(2-(2-azidoethoxy)ethoxy)ethoxy)ethanamine (CAS Number 134179-38-7) to form an azide functionalized hyaluronic acid ([HA-$N_3$]). In one aspect, the reaction is:

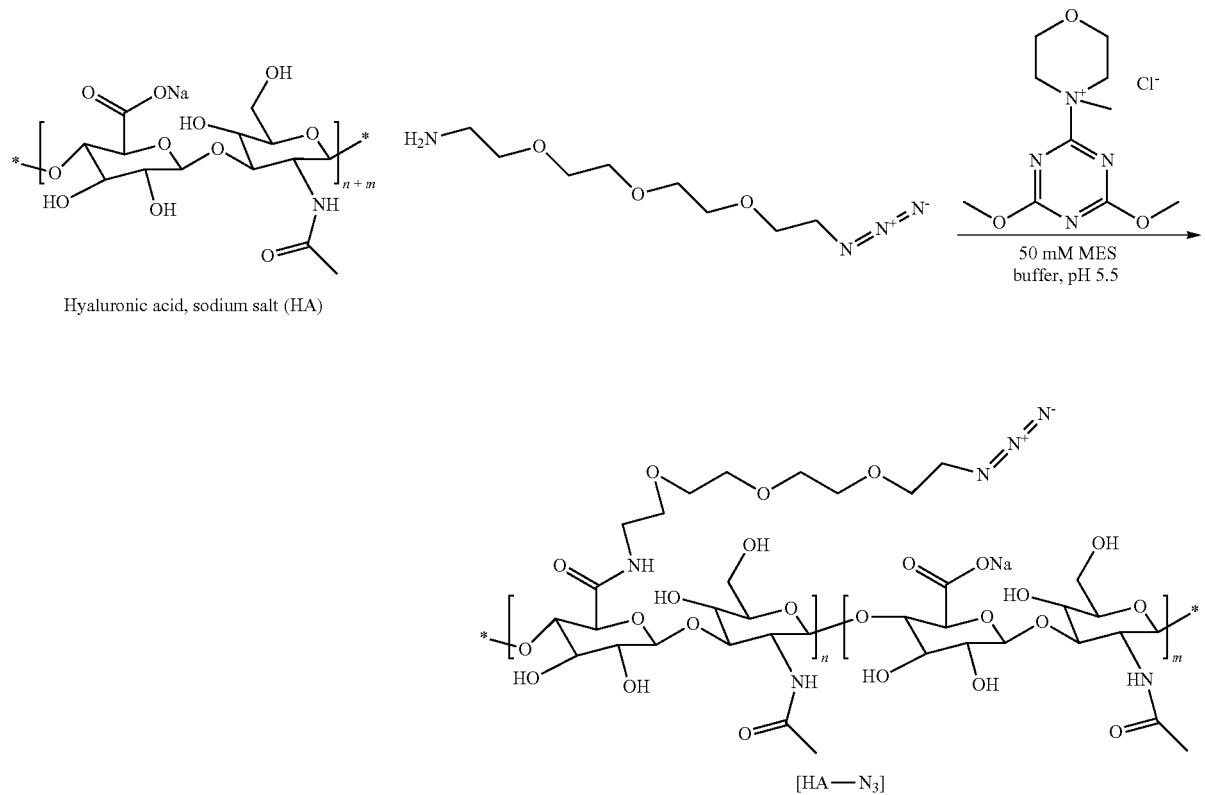

Experimental conditions are described in Example 3. In one aspect, about 5% to about 50% of the hyaluronic acid is functionalized, including all integers within the specified range. In one aspect, the hyaluronic acid is functionalized about 5%, about 10%, about 15%, about 20%, about 25%, about 30%, about 35%, about 40%, about 45%, about 50%, or even greater.

In another embodiment, polyethylene glycol is functionalized with various reagents to form cross-linkers for linking the functionalized hyaluronic acid monomers as discussed above.

Synthesis of 2 kDa 2-Arm PEG-BCN Crosslinker

In one aspect, $M_n$~2 kDa polyethylene glycol diamine hydrochloride is reacted as shown. Reaction conditions are described in Example 4.

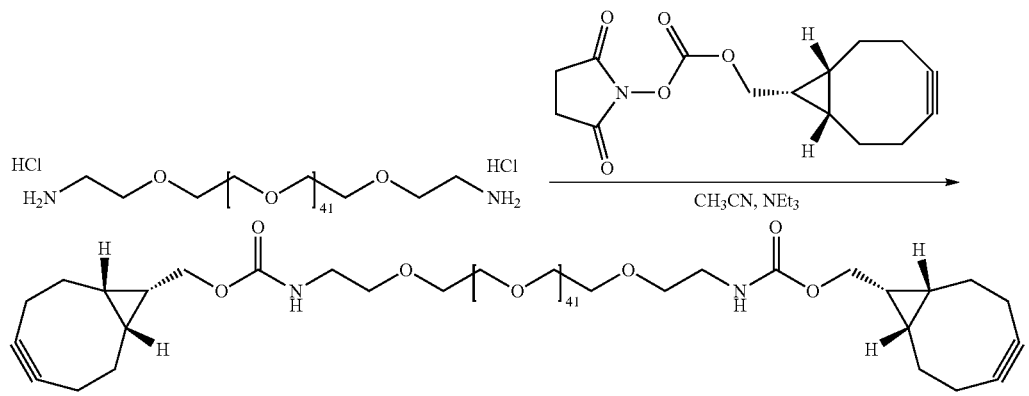

Synthesis of 10 kDa 4-Arm PEG-BCN Crosslinker

In another aspect, $M_n$~10 kDa 4-arm polyethylene glycol amine hydrochloride (pentaerythritol core, JenKem Technology) is reacted as shown. Reaction conditions are described in Example 4.

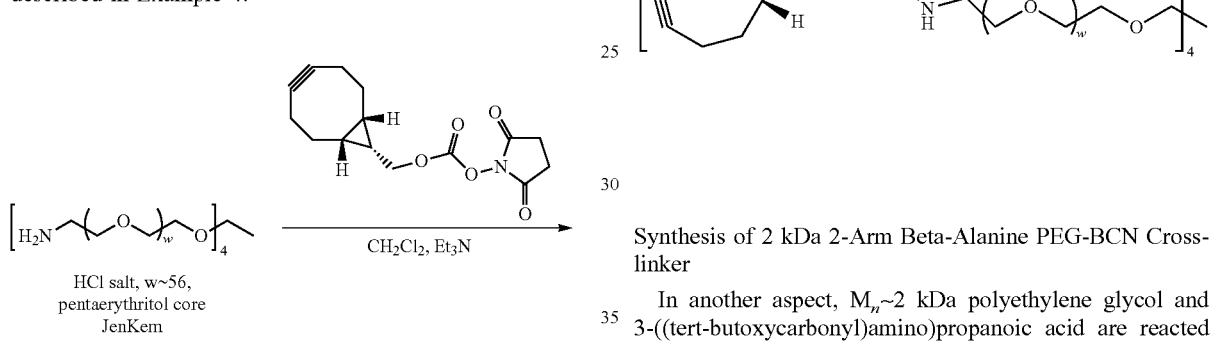

Synthesis of 2 kDa 2-Arm Beta-Alanine PEG-BCN Crosslinker

In another aspect, $M_n$~2 kDa polyethylene glycol and 3-((tert-butoxycarbonyl)amino)propanoic acid are reacted as shown. Reaction conditions are described in Example 4.

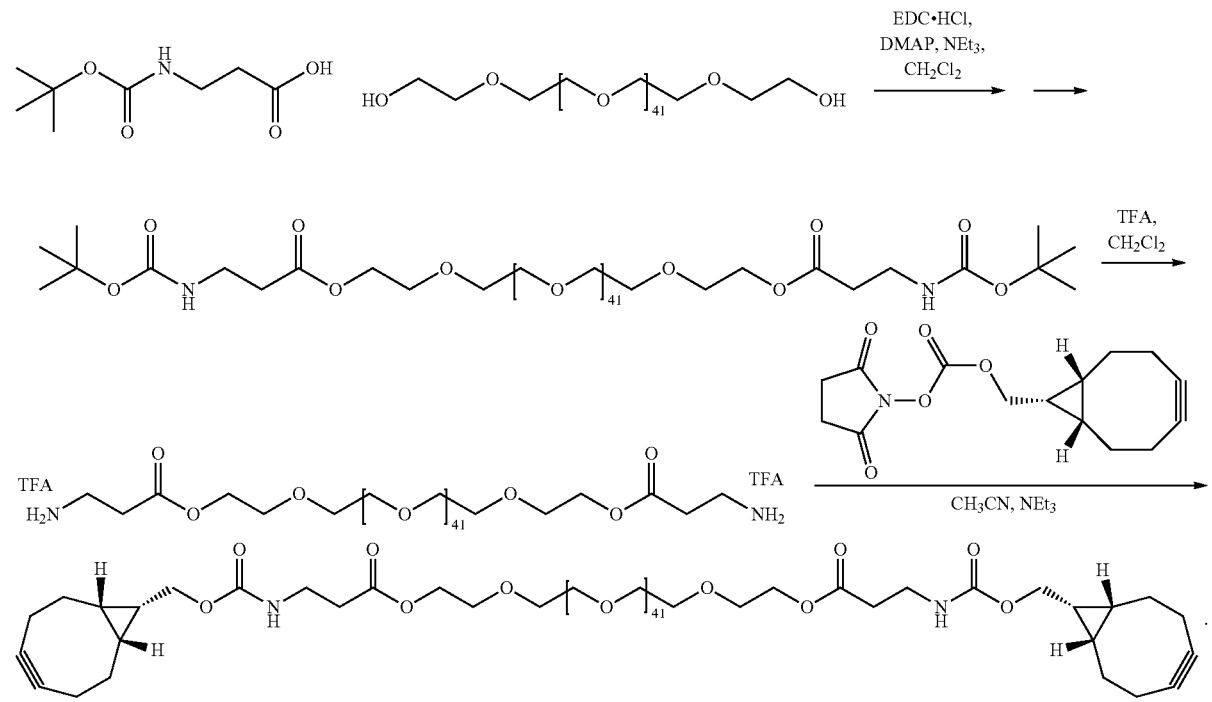

Synthesis of 2 kDa 2-Arm Aminocyclopropanecarboxylic Acid PEG-BCN Crosslinker

In another aspect, $M_n$~2 kDa polyethylene glycol and 1-((tert-butoxycarbonyl)amino)cyclopropane-1-carboxylic acid are reacted as shown. Reaction conditions are described in Example 4.

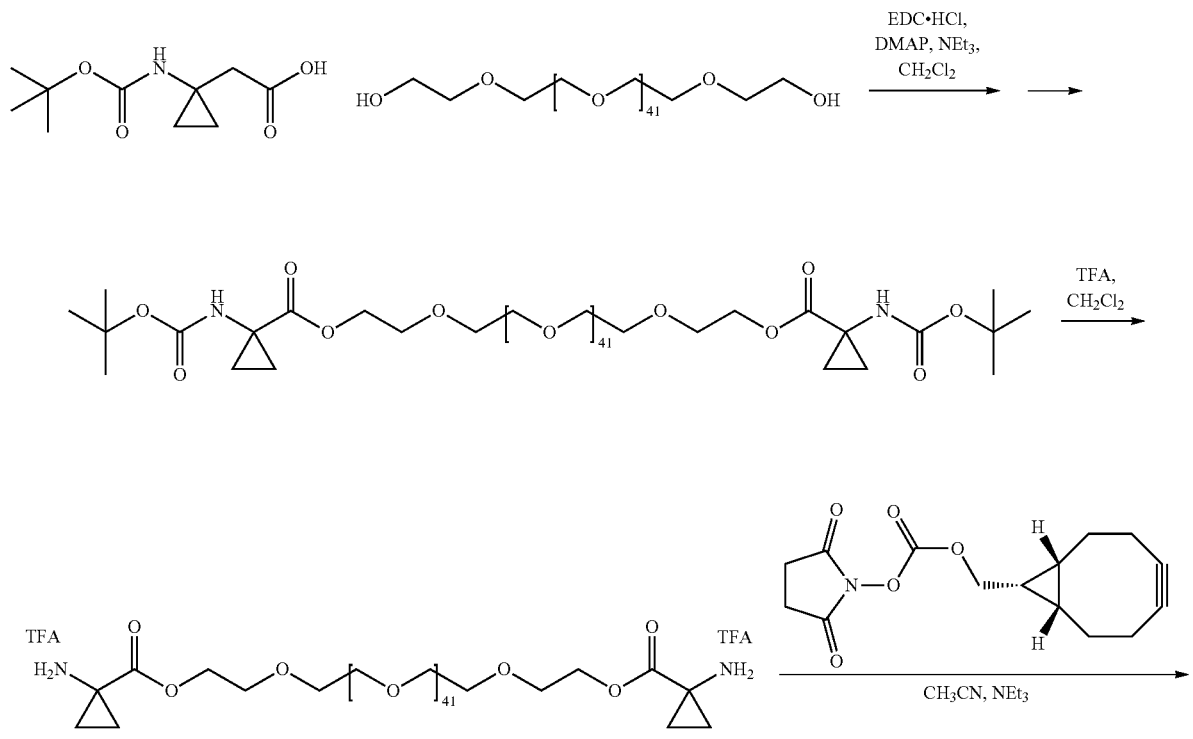

Another embodiment described herein is one or more cross-linking agents. In one aspect, the cross-linking agent comprises Formula V:

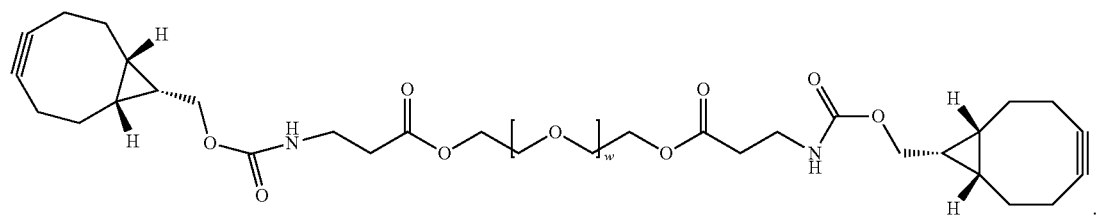

In another aspect, the cross-linking agent comprises Formula VI:
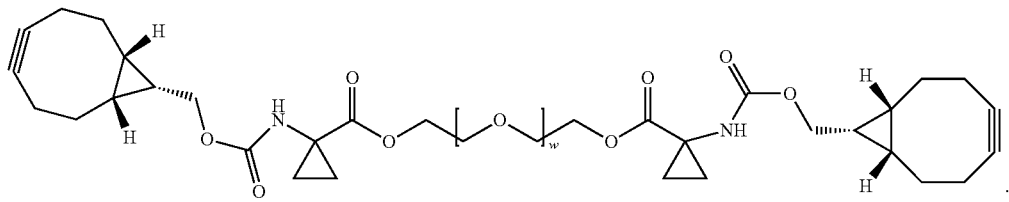
In another aspect, the cross-linking agent comprises Formula VIa:
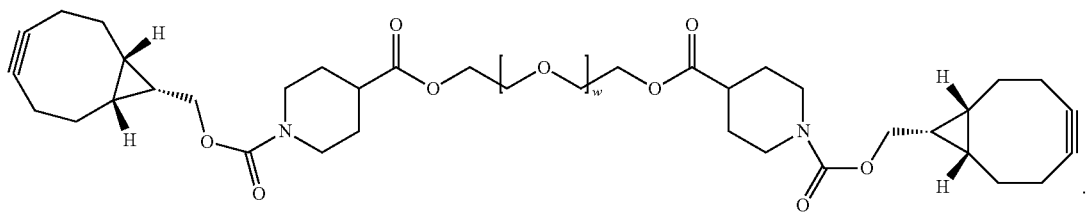
In another aspect, the cross-linking agent comprises Formula VIb:
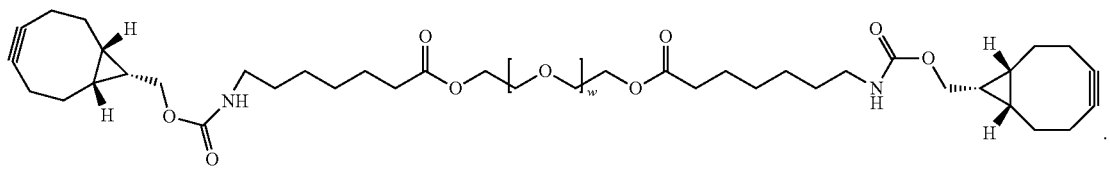
In another aspect, the cross-linking agent comprises Formula VIc:
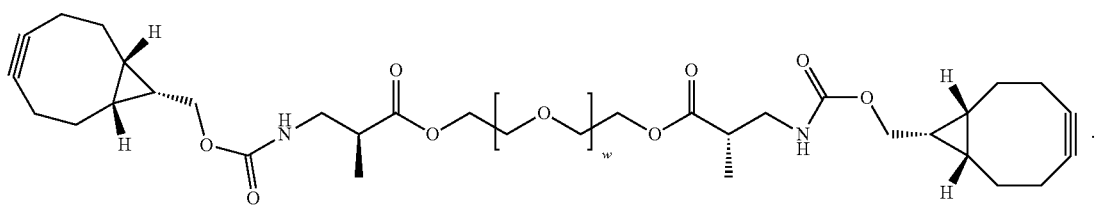

In another aspect, the cross-linking agent comprises Formula VII:
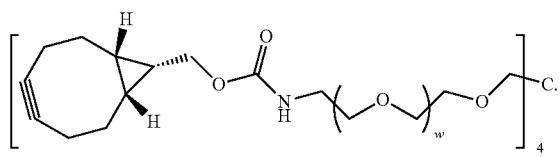
In another aspect, the cross-linking agent comprises Formula VIII:
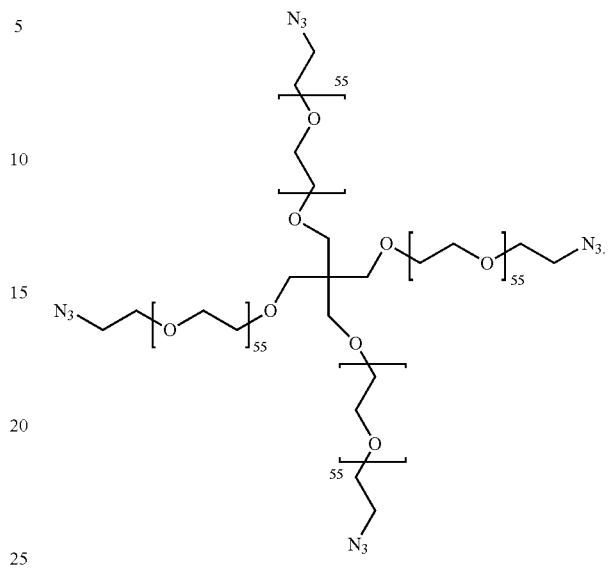
In another aspect, the cross-linking agent comprises Formula IX:
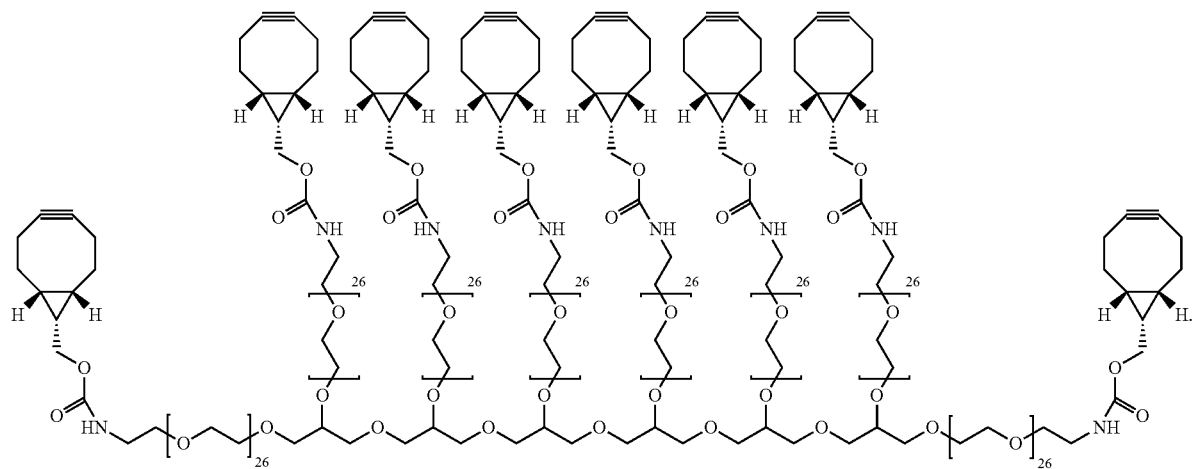

In another embodiment described herein, $R^{11}$ comprises a functionalized carrier that has been reacted with one or more cross-linking agents to form a cross-linked carrier. In one embodiment, the cross-linked carrier forms a hydrogel. In one aspect, the cross-linked carrier is hyaluronic acid that has been functionalized and cross-linked with one or more polyethylene glycol cross linkers as described herein to form a hydrogel.

In one embodiment, a cross-linked carrier comprising hyaluronic acid can be prepared by reacting appropriately functionalized polymers as shown:

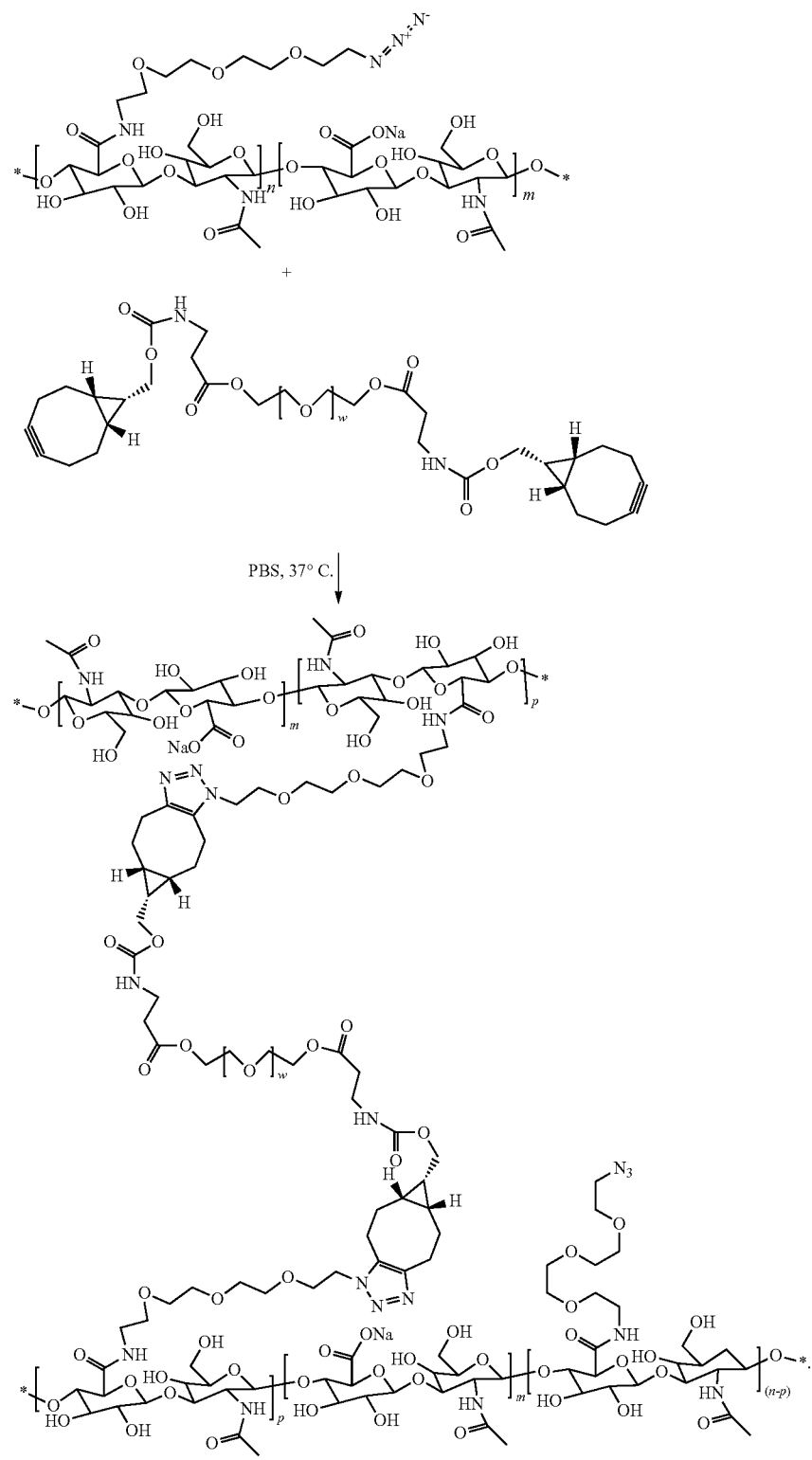

While not being bound by any particular example and by way of illustration, in one embodiment, hyaluronic acid sodium salt labeled by the supplier, Lifecore Biomedical (HA200K, Chaska, Minn.) as having a nominal average molecular weight varying from batch to batch in the range of 151-300 kDa, as determined by viscometry. For the purposes of this illustration, a molecule of hyaluronic acid sodium salt with an assumed nominal average molecular weight of 200 kDa would consist of an average of approximately 500 monomer units. In this and following structures the unmodified monomer unit is defined as "m," the monomer unit modified with an azido group as "n," the azido-monomer unit conjugated to the crosslinking molecule as "p" and the azido monomer unit conjugated to the traceless linker-drug adduct as "q." For a polymer chain comprising ≈500 monomer units, (n+m+p+q≈500). If the percent modification of the hyaluronic acid sodium salt molecule is 25%, then m=75% and (n+p+q)=25%.

Similarly, the PEG unit present in one embodiment of the cross linker is derived from a starting PEG described as having a nominal average molecular weight of 1 kDa, 2 kDa, 4 kDa, 6 kDa, 8 kDa, or 10 kDa, and would consist of approximately 22, 45, 91, 136, 181, or 226 repeating oxyethylene monomer units, respectively, described in these depicted structures as "w." In some aspects, w can be between about 5 and about 250. In other aspects, w comprises about 5, about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, or about 250 oxyethylene monomer units. In other aspects, w is about 20, about 45, about 90, about 140, about 180, or about 225.

In the following Formulae, in one embodiment, the sum of the unmodified disaccharide repeating unit of hyaluronic acid (m) plus the modified disaccharide repeating unit of hyaluronic acid (n+p+q) in a random distribution (=m+n+p+q) may comprise about 500 units for a nominal average molecular weight as determined by viscometry of approximately 200 kDa. This applies to Formulae X to XXII.

In one aspect, the cross-linked carrier comprises Formula X:

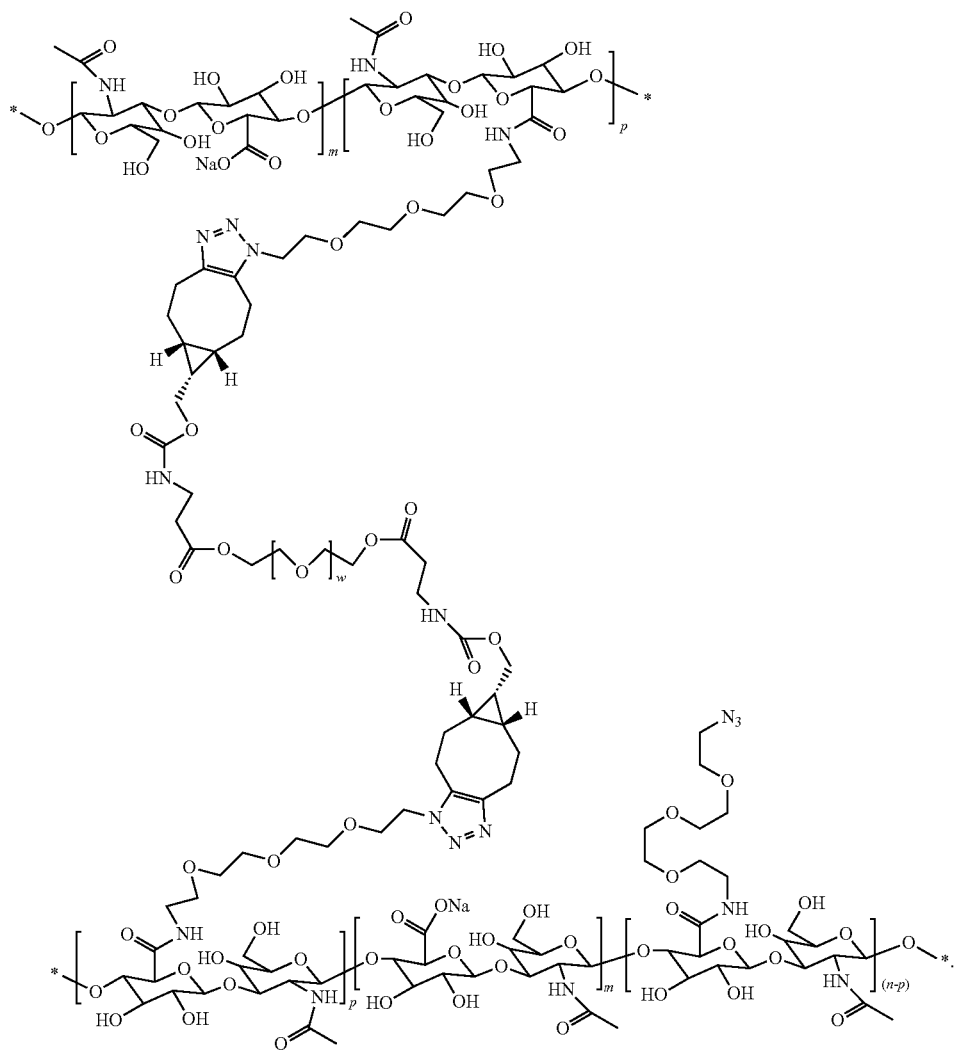

(X)

In another aspect, the cross-linked carrier comprises Formula XI:
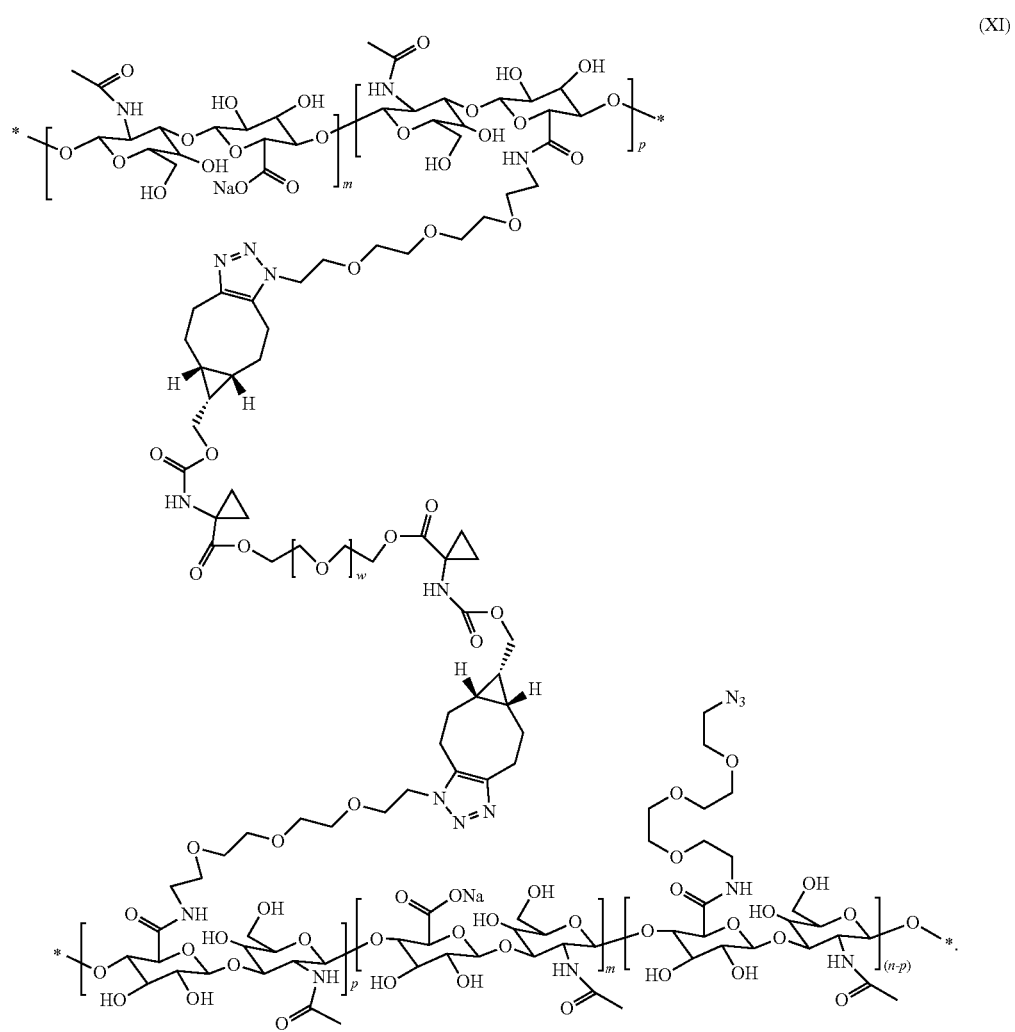
(XI)

In another aspect, the cross-linked carrier comprises Formula XII:
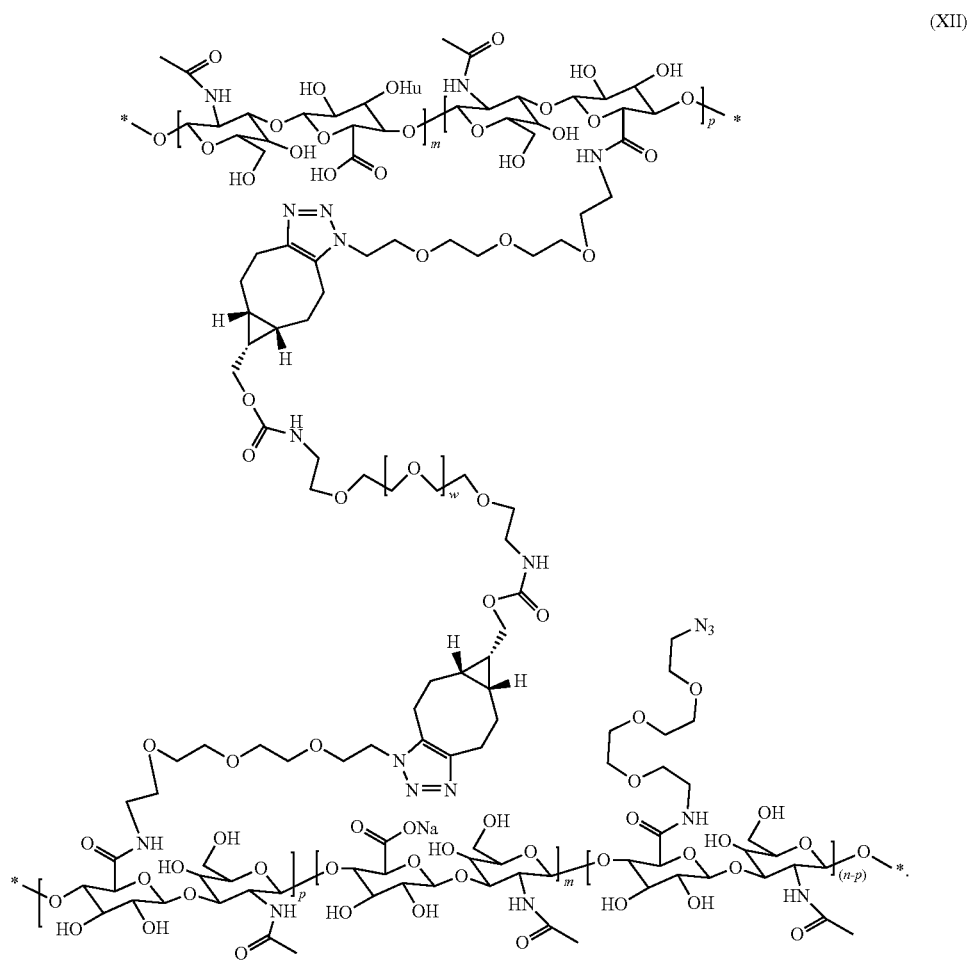
(XII)

In another aspect, the cross-linked carrier comprises Formula XIIa:
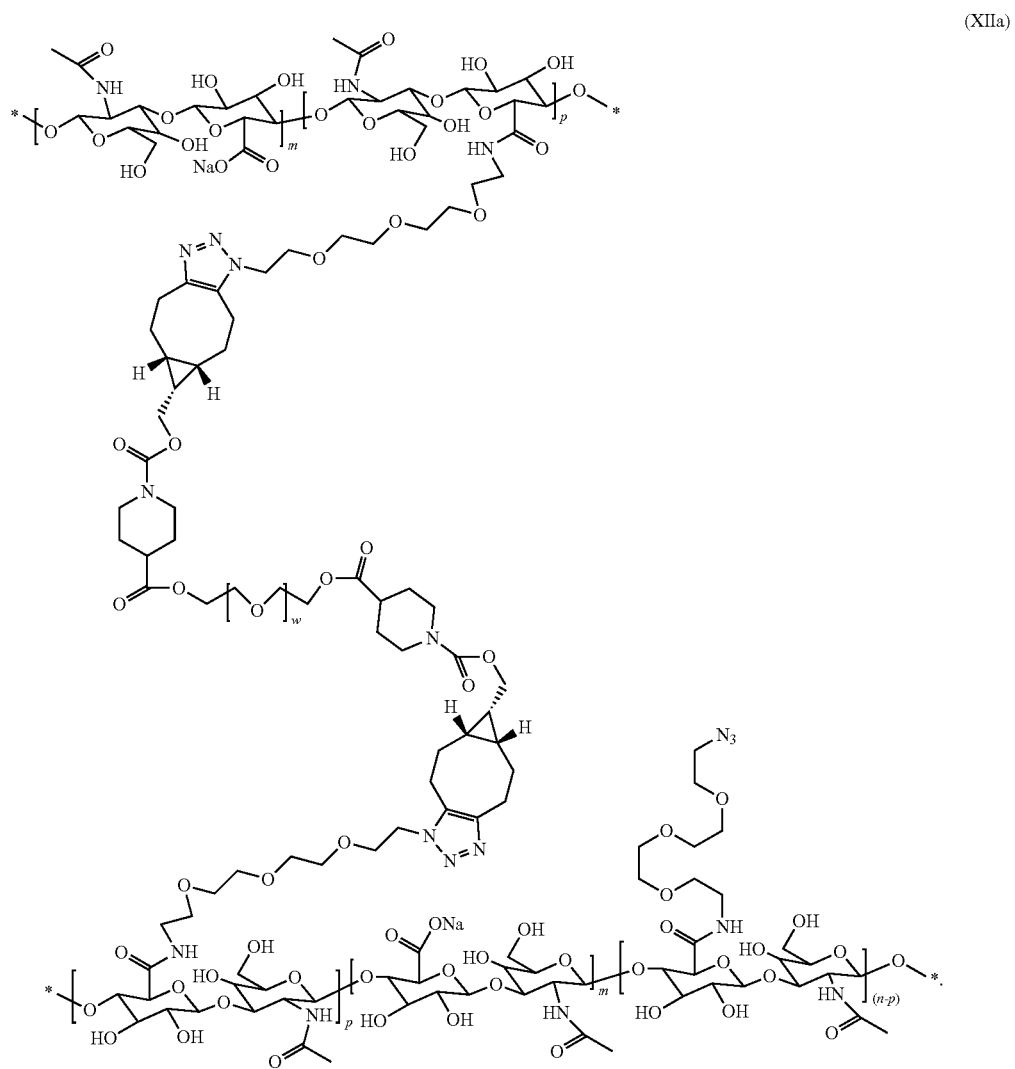
(XIIa)

In another aspect, the cross-linked carrier comprises Formula XIIb:
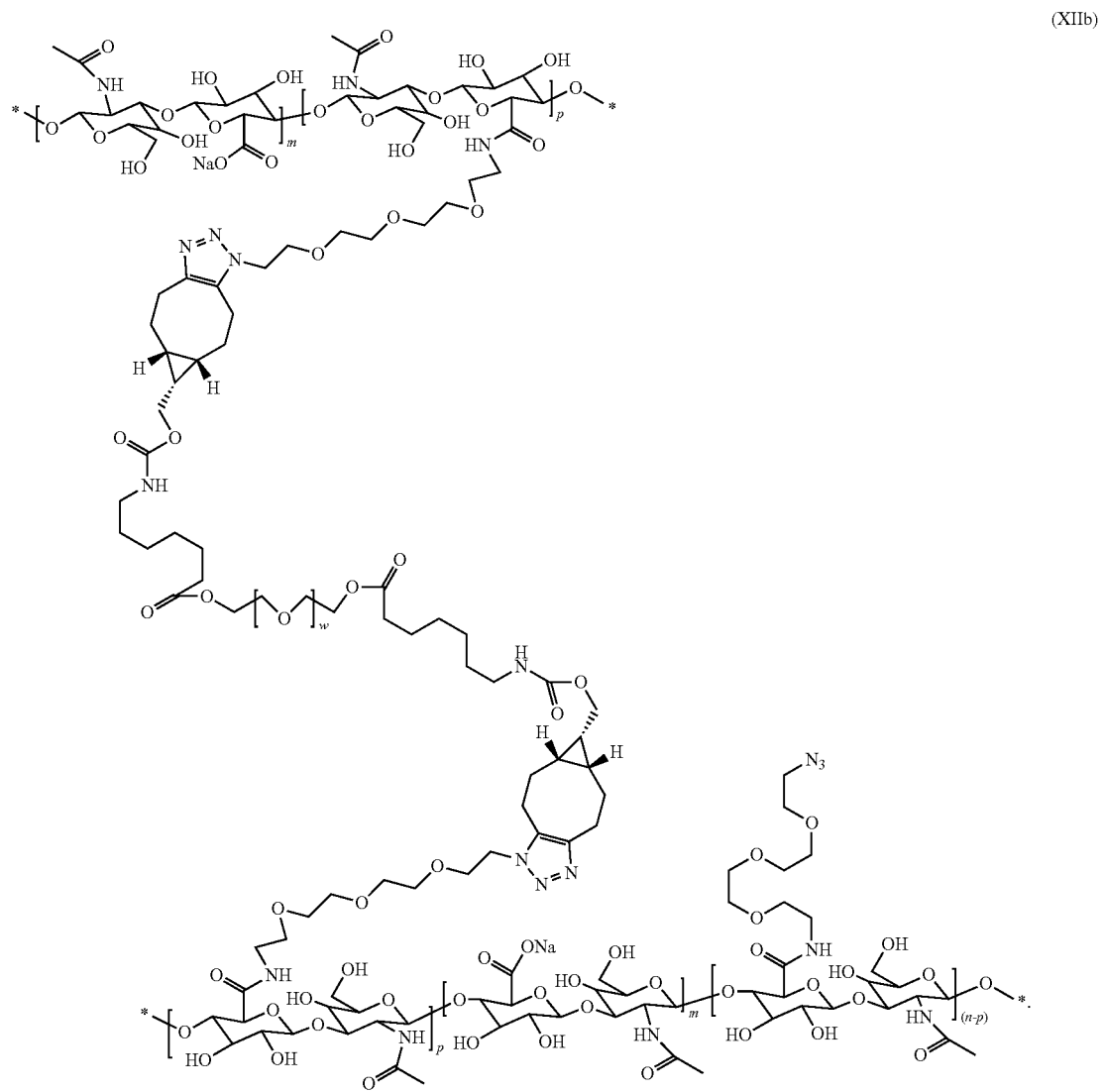
(XIIb)

In another aspect, the cross-linked carrier comprises Formula XIIc:
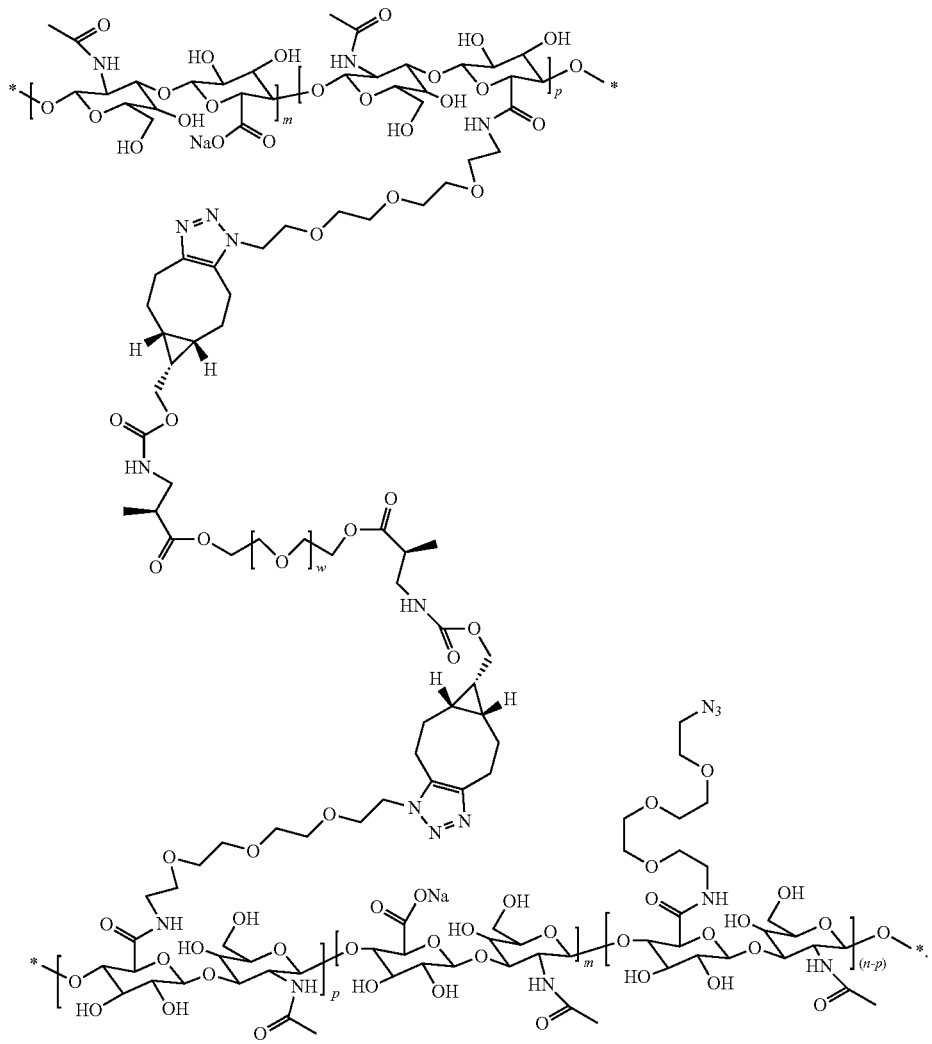
(XIIc)
In another aspect, the cross-linked carrier comprises Formula XIII:

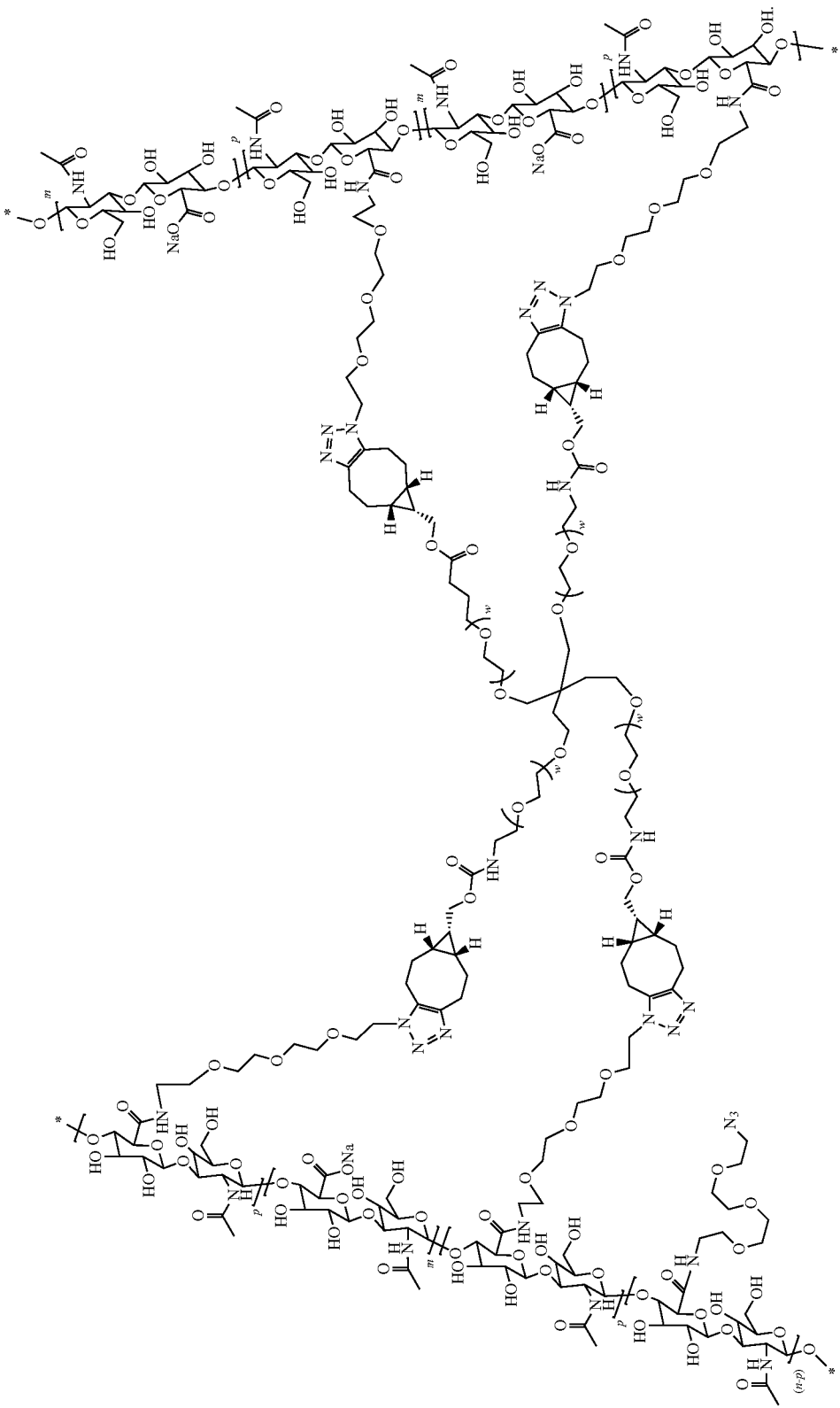

Another embodiment described herein is a drug adduct, D-R, wherein D is a biologically active moiety comprising at least one primary amine, secondary amine, or ring nitrogen atom of an azaheteroaryl ring; and R is a linker suitable for release of a biologically active moiety. In one aspect, D comprises a protein, nucleic acid, carbohydrate, peptide, nucleotide, oligosaccharide, or small molecule each of which has at least one primary or secondary amine and the small molecule has a molecular weight of between about 100 g/mol and about 2000 g/mol.

One embodiment described herein is a drug adduct, D-R, wherein D comprises an ANGPTL3 polypeptide. In one aspect, D comprises an ANGPTL3 polypeptide having at least 95% identity to any one of SEQ ID NO: 1 or 3-45. In another aspect, D comprises any one of SEQ ID NO:1 or 3-45. In another aspect, D comprises an ANGPTL3 polypeptide having a K423Q substitution or a K423 deletion. In another aspect, D comprises an ANGPTL3 polypeptide comprising amino acid residues 201-460; 207-460; 225-455; 225-455; 225-460; 225-460; 226-455; 226-455; 226-460; 226-460; 228-455; 228-455; 228-460; 228-460; 233-455; 233-455; 233-460; 233-460; 241-455; 241-455; 241-460; 241-460; 242-455; 242-455; 242-460; or 242-460, each in reference to SEQ ID NO: 1. In another aspect, D comprises an ANGPTL3 polypeptide comprising at least 95% identity to amino acid residues 242-460 in reference to SEQ ID NO: 1 and a K423Q substitution. In another aspect, D comprises an ANGPTL3 polypeptide comprising amino acid residues 242-460 in reference to SEQ ID NO:1 and a K423Q substitution, D1 (SEQ ID NO:19).

Another embodiment described herein is a drug delivery system comprising a carrier-traceless linker biologically-active agent conjugate, D-R—$R^{11}$, wherein D comprises a biologically active moiety comprising at least one primary amine, secondary amine, or ring nitrogen atom of an azaheteroaryl ring as described herein, R comprises a traceless linker as described herein attached to $R^{11}$, comprising a carrier polymer or hydrogel as described herein. In one aspect, $R^{11}$ comprises hyaluronic acid, cross-linked hyaluronic acid, polyethylene glycol, cross-linked polyethylene glycol or other suitable polymer as described herein. In another aspect, R comprises a traceless linker as described herein. In another aspect, D comprises an ANGPTL3 polypeptide as described herein. In one aspect, D comprises an ANGPTL3 polypeptide having at least 95% identity to any one of SEQ ID NO: 1 or 3-45. In another aspect, D comprises any one of SEQ ID NO:1 or 3-45. In another aspect, D comprises an ANGPTL3 polypeptide having a K423Q substitution or a K423 deletion. In another aspect, D comprises an ANGPTL3 polypeptide comprising amino acid residues 201-460; 207-460; 225-455; 225-455; 225-460; 225-460; 226-455; 226-455; 226-460; 226-460; 228-455; 228-455; 228-460; 228-460; 233-455; 233-455; 233-460; 233-460; 241-455; 241-455; 241-460; 241-460; 242-455; 242-455; 242-460; or 242-460, each in reference to SEQ ID NO: 1. In another aspect, D comprises an ANGPTL3 polypeptide comprising at least 95% identity to amino acid residues 242-460 in reference to SEQ ID NO: 1 and a K423Q substitution. In another aspect, D comprises an ANGPTL3 polypeptide comprising amino acid residues 242-460 in reference to SEQ ID NO:1 and a K423Q substitution, D1 (SEQ ID NO:19).

In another embodiment, D-R—$R^{11}$ comprises Formula XIV, wherein "Drug" comprises an ANGPTL3 polypeptide comprising one or more of SEQ ID NO: 1 or 3-45 or polypeptides having at least 90% identity thereto.

In some embodiments, D-R—$R^{11}$ comprises any of the species shown in Formulas XV-XXIII.

In one embodiment, the drug or biologically active agent D, comprises an ANGPTL3 polypeptide comprising one or more of SEQ ID NO: 1 or 3-45.

In one embodiment, the drug or biologically active agent D, comprises D1, which has the sequence of SEQ ID NO: 19.

One embodiment described herein is a peptide compositions for repairing cartilage. In particular ANGPTL3 peptides as described herein have increased protease-resistance as compared to a wildtype ANGPTL3 polypeptide.

Another embodiment described herein is a composition and method for administration of ANGPTL3 polypeptides to prevent or ameliorate arthritis or joint injury by administering a polypeptide of the invention into a joint, a cartilage tissue or a cartilage proximal tissue, or systemically. Also described are compositions and methods for induction of mesenchymal stem cell differentiation into chondrocytes.

Another embodiment described herein is a process for assembling a drug delivery system; the process may comprise one of the following sequence of steps:
(a) preparing a carrier molecule, $R^{11}$, where $R^{11}$ is a cross-linked hydrogel, then this step comprises the process used to prepare that hydrogel; the carrier molecule may optionally be purified at this stage;
(b) separately conjugating the traceless linker, R, to a biologically active agent, D, comprising a primary amine, secondary amine, or a ring nitrogen atom of an azaheteroaryl ring, thereby forming the traceless linker-D adduct; the traceless linker-D adduct may optionally be purified at this stage,
(c) conjugating the carrier molecule, $R^{11}$, with the traceless linker-D adduct; and
(d) purifying the drug delivery system from the reagents. This process is shown in Scheme 5A below.

Another embodiment described herein is a process for assembling a drug delivery system comprising the following steps:
(a) preparing a carrier molecule, $R^{11}$, where $R^{11}$ is a cross-linked hydrogel, then this step comprises the process used to prepare that hydrogel; the carrier molecule may optionally be purified at this stage;
(b) conjugating the traceless linker, R, to the carrier molecule, $R^{11}$, thereby forming the carrier molecule-traceless linker adduct, which may optionally be purified at this stage;
(c) conjugating the biologically active agent, D, comprising a primary amine, secondary amine, or a ring nitrogen atom of an azaheteroaryl ring, to the carrier molecule-traceless linker adduct; and
(d) purifying the drug delivery system from the reagents. This process is shown in Scheme 5B below.

Another embodiment described herein is a process for assembling a drug delivery system comprising the following steps:
(a) preparing a non-cross-linked carrier molecule, $R^{11}$, the carrier molecule may optionally be purified at this stage;
(b) separately conjugating the traceless linker, R, to a biologically active agent, D, comprising a primary amine, secondary amine, or a ring nitrogen atom of an azaheteroaryl ring, thereby forming the traceless linker-D adduct; the traceless linker-D adduct may optionally be purified at this stage;
(c) conjugating the carrier molecule, $R^{11}$, with the traceless linker-D adduct, which may optionally be purified at this stage;

(d) preparing the cross-linked hydrogel by incubating the non-cross-linked carrier molecule-traceless linker-biologically active agent, $R^{11}$—R-D, with the appropriate cross-linking reagent to form the hydrogel; and
(e) purifying the drug delivery system from the reagents. This process is shown in Scheme 5C below.

Another embodiment described herein is a process for assembling a drug delivery system comprising the following steps:
(a) preparing a non-cross-linked carrier molecule, $R^{11}$, the carrier molecule may optionally be purified at this stage;
(b) conjugating the traceless linker, R, to the carrier molecule, $R^{11}$, thereby forming the carrier molecule-traceless linker adduct, which may optionally be purified at this stage; and
(c) conjugating the biologically active agent, D, comprising a primary amine, secondary amine, or a ring nitrogen atom of an azaheteroaryl ring, to the carrier molecule-traceless linker adduct;
(d) preparing the cross-linked hydrogel by incubating the non-cross-linked carrier molecule-traceless linker-biologically active agent, $R^{11}$—R-D, with the appropriate cross-linking reagent to form the hydrogel; and
(e) purifying the drug delivery system from the reagents. This process is shown in Scheme 5D below.

Another embodiment described herein is a process for assembling a drug delivery system comprising the following steps:
(a) preparing a non-cross-linked carrier molecule, $R^{11}$, the carrier molecule may optionally be purified at this stage;
(b) conjugating the traceless linker, R, to the carrier molecule, $R^{11}$, thereby forming the carrier molecule-traceless linker adduct, which may optionally be purified at this stage;
(c) preparing the cross-linked hydrogel by incubating the non-cross-linked carrier molecule-traceless linker-adduct, $R^{11}$—R, with the appropriate cross-linking reagent to form the hydrogel, which may optionally be purified at this stage;
(d) conjugating the biologically active agent, D, comprising a primary amine, secondary amine, or a ring nitrogen atom of an azaheteroaryl ring, to the cross-linked carrier molecule-traceless linker adduct, which may optionally be purified at this stage; and
(e) purifying the drug delivery system from the reagents. This process is shown in Scheme 5E below.
Schemes 5A-E. Scheme 5 shows five processes, A-E, for assembling drug delivery systems as described herein.
Legend:

$\xi$ Carrier molecule, $R^{11}$, non-crosslinked
⟋⟋⟋⟋ crosslinker

▢ Carrier molecule, $R^{11}$, crosslinked hydrogel
▬ traceless linker, R

◯ biologically active agent, D

Scheme 5A

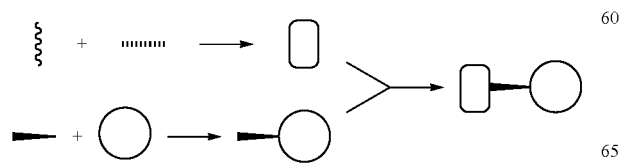

Scheme 5B

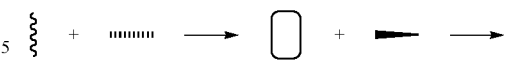

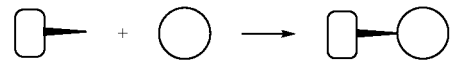

Scheme 5C

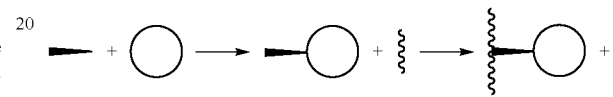

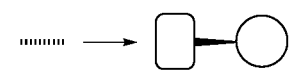

Scheme 5D

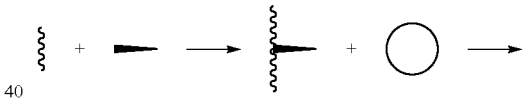

Scheme 5E

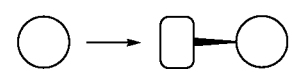

In one embodiment, the drug delivery system can comprise Formula (XIV):

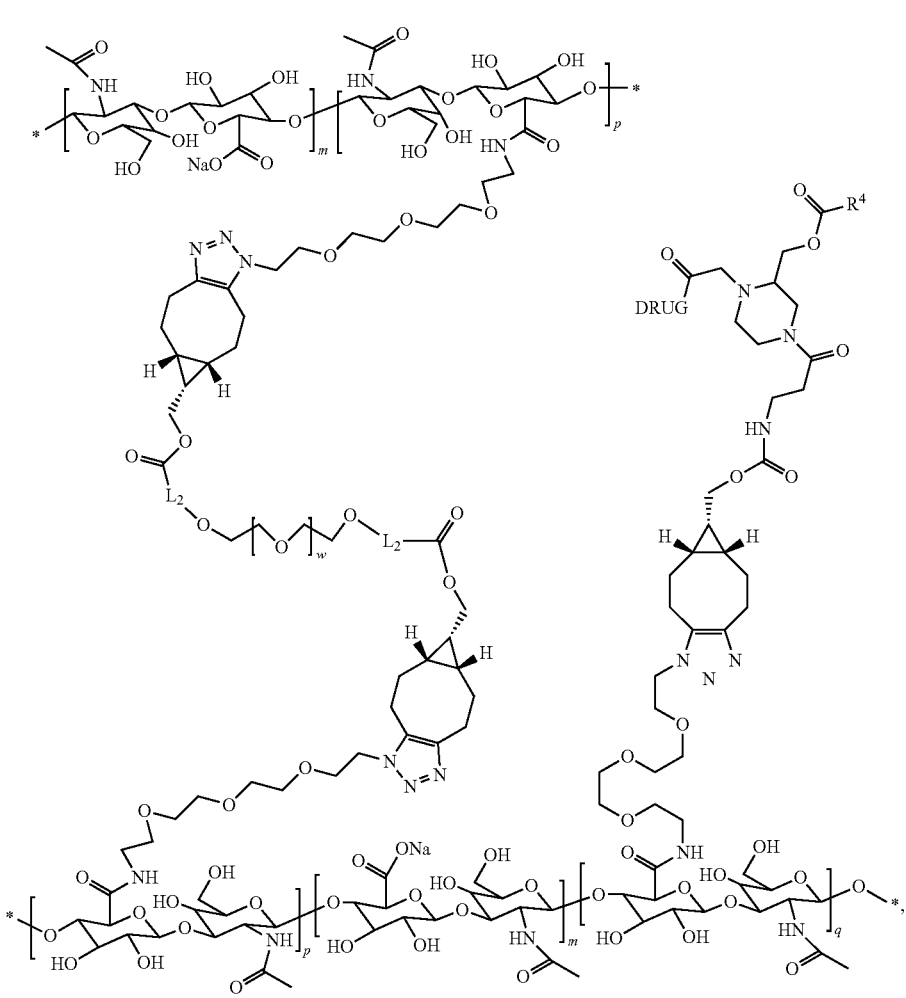

(XIV)

wherein L₂ represents a spacer group, which can be specific to a particular cross-linker, and "DRUG" represents a biologically active molecule comprising at least one primary amine, secondary amine, or ring nitrogen atom of an aza-heteroaryl ring that modulates at least one biologically relevant target in a therapeutically beneficial manner. In one aspect, "DRUG" comprises an ANGPTL3 polypeptide as described herein. In another aspect, "DRUG" comprises an ANGPTL3 polypeptide having at least 95% identity to any one of SEQ ID NO: 1 or 3-45. In another aspect, "DRUG" comprises any one of SEQ ID NO: 1 or 3-45. In another aspect, "Drug" comprises an ANGPTL3 polypeptide having a K423Q substitution or a K423 deletion. In another aspect, "DRUG" comprises an ANGPTL3 polypeptide comprising amino acid residues 201-460; 207-460; 225-455; 225-455; 225-460; 225-460; 226-455; 226-455; 226-460; 226-460; 228-455; 228-455; 228-460; 228-460; 233-455; 233-455; 233-460; 233-460; 241-455; 241-455; 241-460; 241-460; 242-455; 242-455; 242-460; or 242-460, each in reference to SEQ ID NO: 1. In another aspect, "DRUG" comprises an ANGPTL3 polypeptide comprising at least 95% identity to amino acid residues 242-460 in reference to SEQ ID NO: 1 and a K423Q substitution. In another aspect, "DRUG" comprises an ANGPTL3 polypeptide comprising amino acid residues 242-460 in reference to SEQ ID NO: 1 and a K423Q substitution, e.g., D1 (SEQ ID NO: 19).

In one embodiment, spacers, L₂, comprise any species shown in Table 5.

TABLE 5

Exemplary L₂ Spacers

In the table below, L₂ represents the spacer between O and C(O)O. For example:

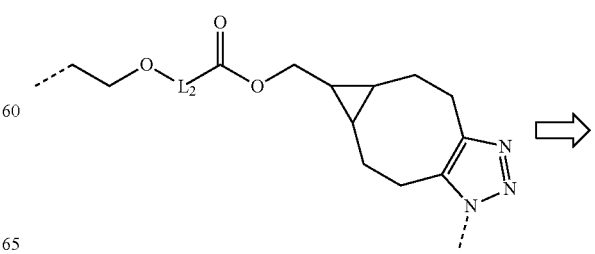

TABLE 5-continued
Exemplary L$_2$ Spacers
In the table below, L$_2$ represents the spacer between O and C(O)O. For example:
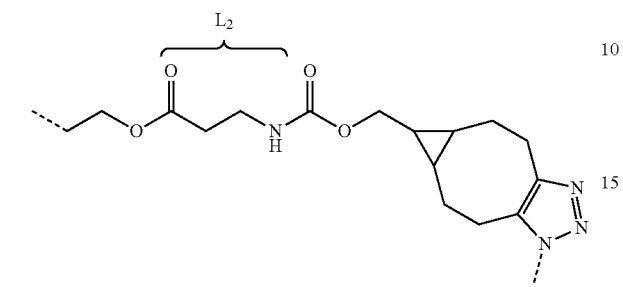
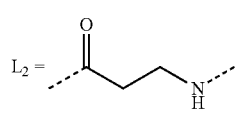
n = 1-10
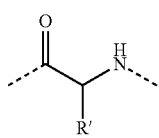
R' = Me, Et, Pr, iPr, C1-C6 alky, C1-C6 cycloalkyll
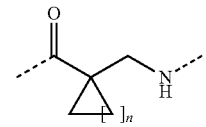
n = 1-6
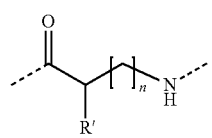
R' = Me, Et, Pr, iPr, C1-C6 alkyl, C1-C6 cycloalkyl
n = 1-5
TABLE 5-continued
Exemplary L$_2$ Spacers
In the table below, L$_2$ represents the spacer between O and C(O)O. For example:
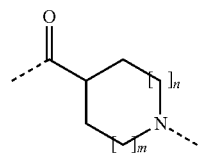
n = 0-2
m = 0-2
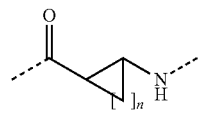
n = 1-5
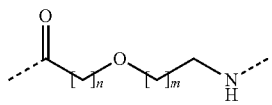
n = 1-6
m = 1-6
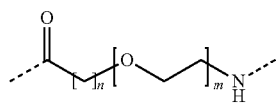
n = 1-6
m = 1-6
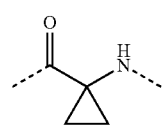
Cp-Glycine In another embodiment, the drug delivery system can comprise Formula (XV) with the DRUG being an ANGPTL3 polypeptide as described herein:
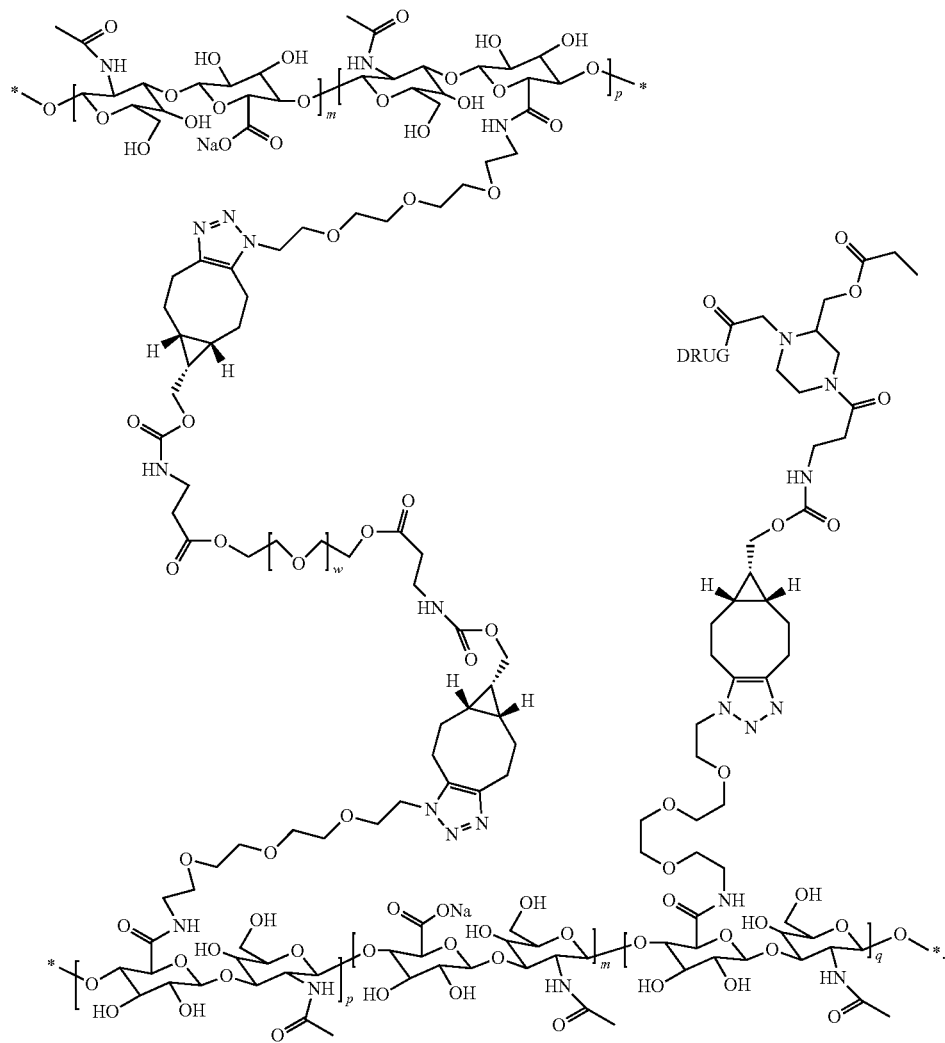
(XV)

In another embodiment, the drug delivery system can comprise Formula (XVI) with DRUG being an ANGPTL3 polypeptide as described herein:
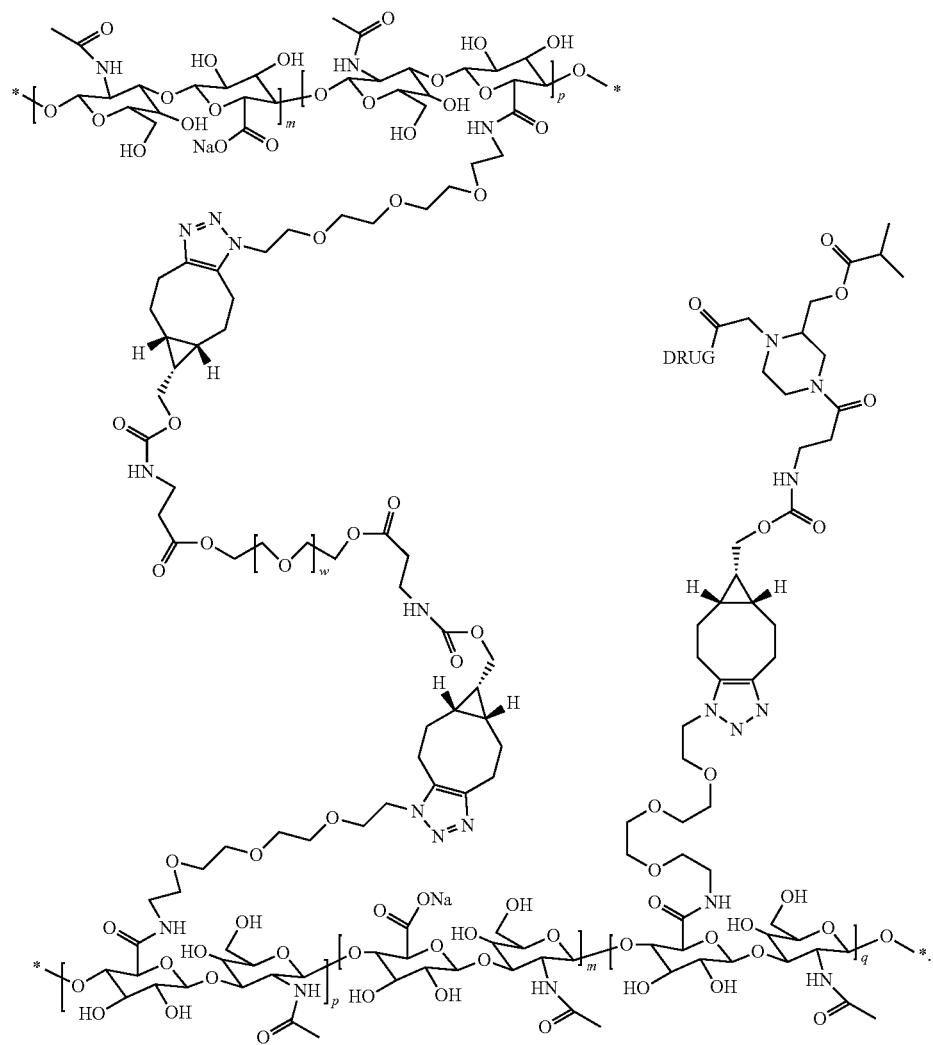
(XVI)

In another embodiment, the drug delivery system can comprise Formula (XVII) with DRUG being an ANGPTL3 polypeptide as described herein:
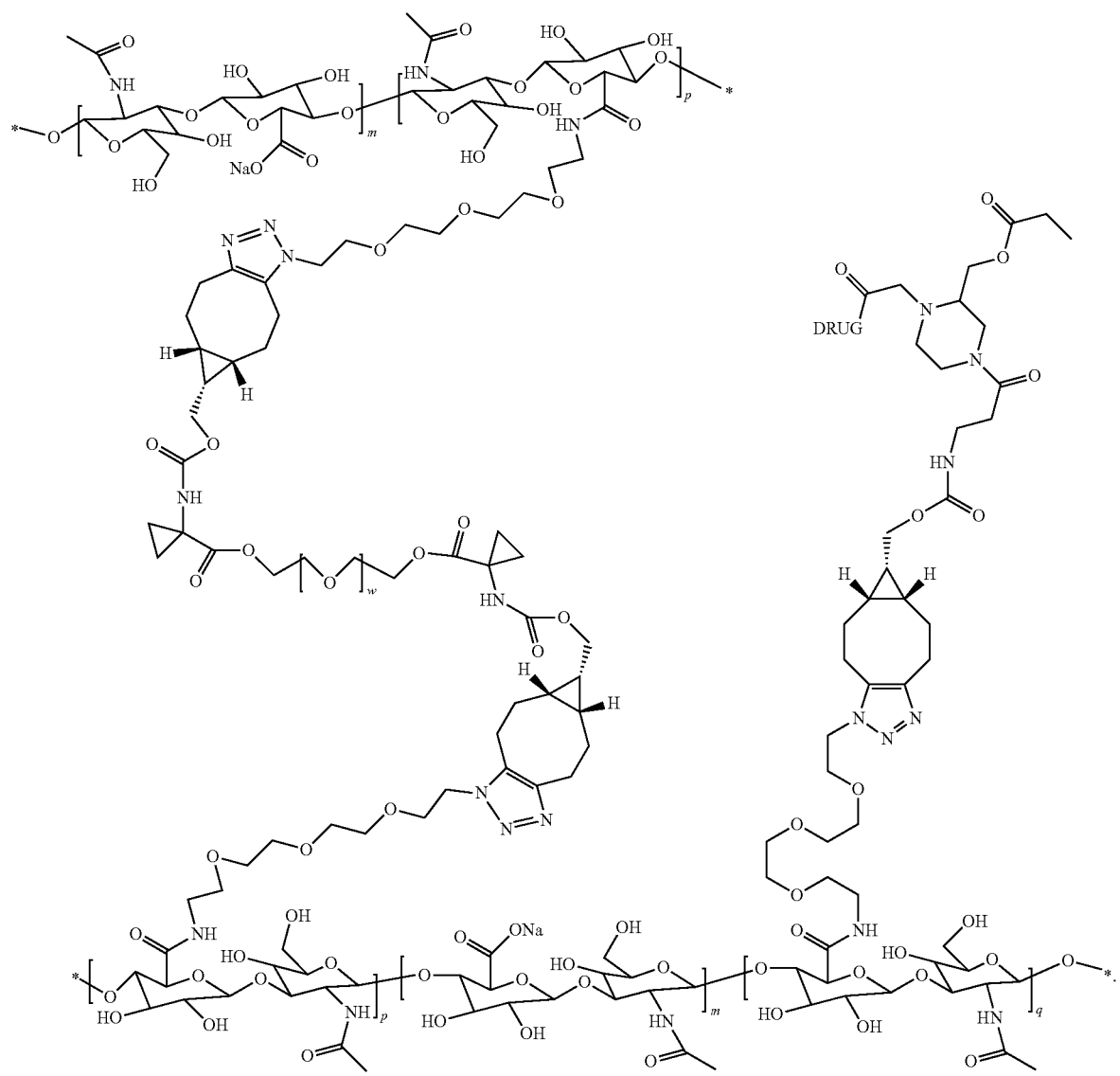
(XVII)

In another embodiment, the drug delivery system can comprise Formula (XVIII) with DRUG being an ANGPTL3 polypeptide as described herein:
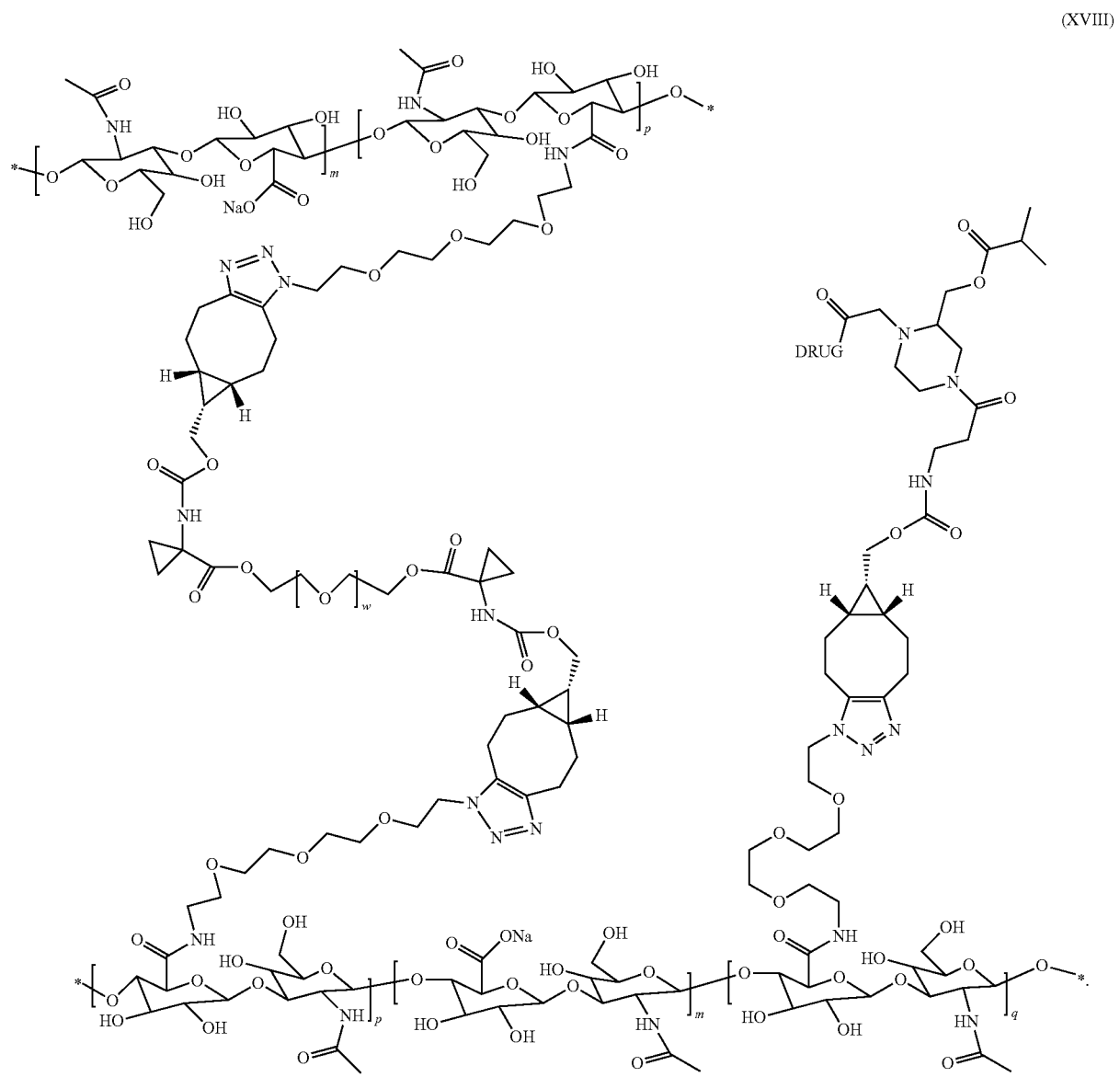
(XVIII)

In another embodiment, the drug delivery system can comprise Formula (XVIIIa) with DRUG being an ANGPTL3 polypeptide as described herein:
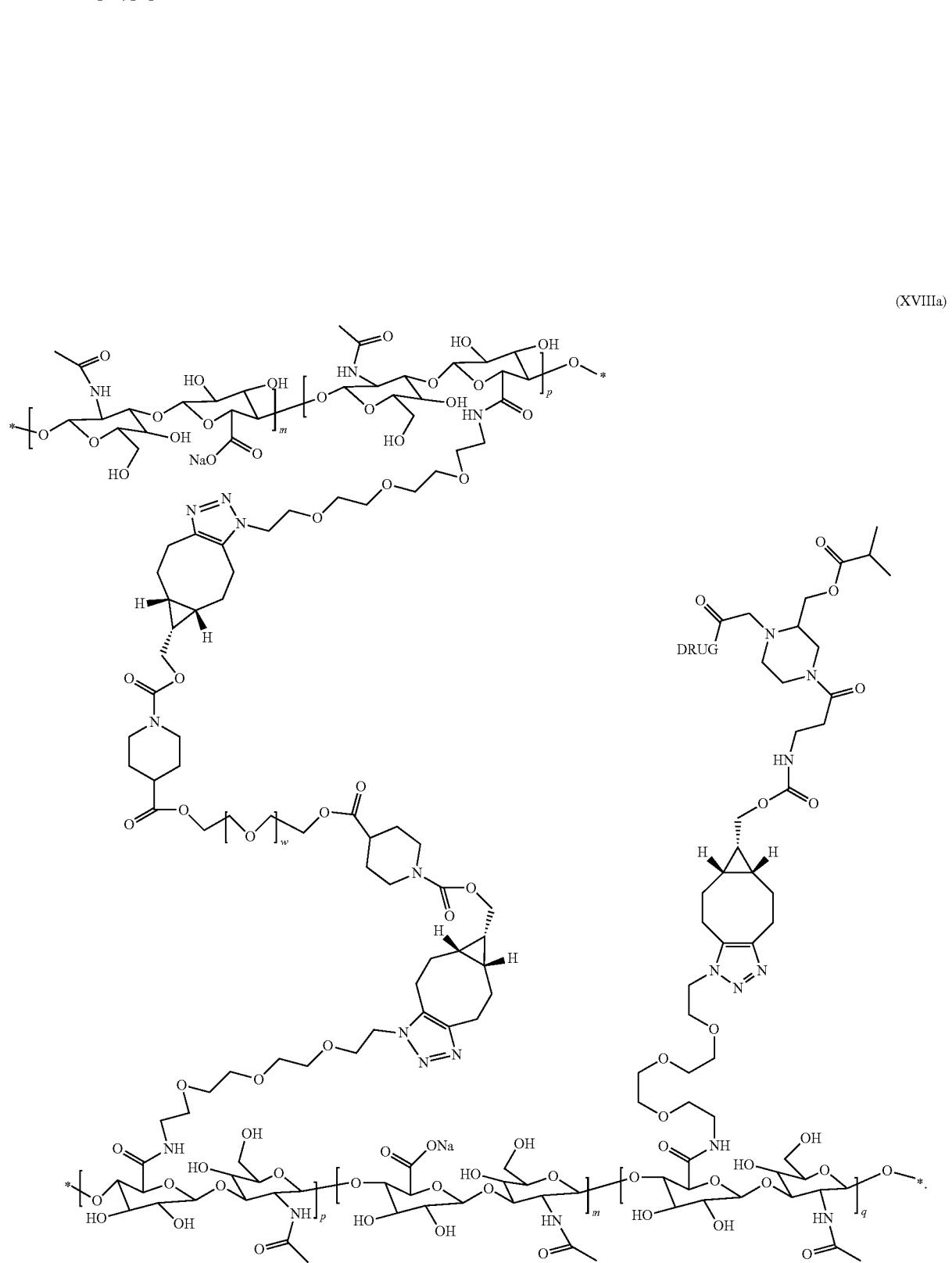
(XVIIIa)

In another embodiment, the drug delivery system can comprise Formula (XVIIIb) with DRUG being an ANGPTL3 polypeptide as described herein:
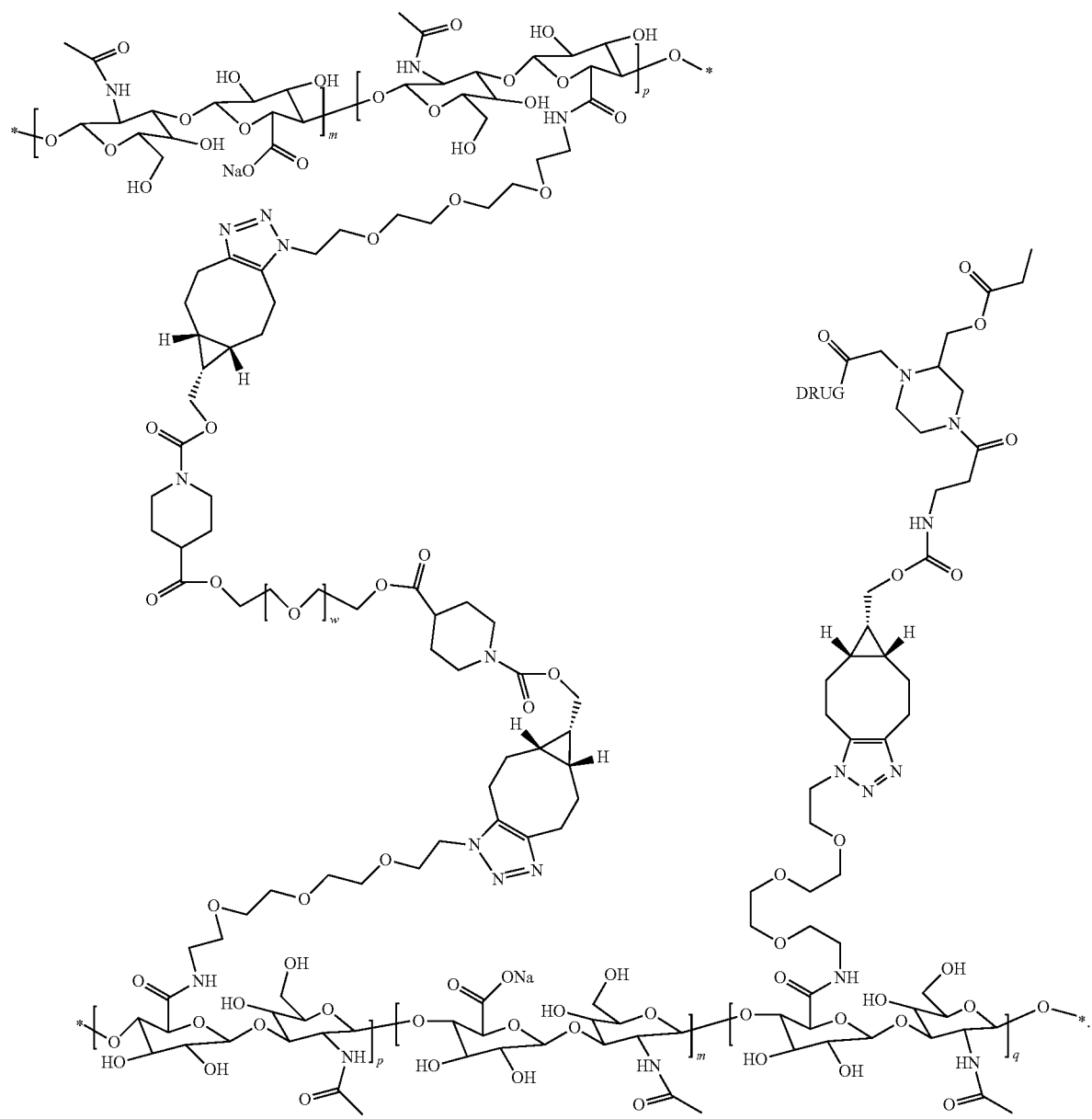
(XVIIIb)

In another embodiment, the drug delivery system can comprise Formula (XVIIIc) with DRUG being an ANGPTL3 polypeptide as described herein:
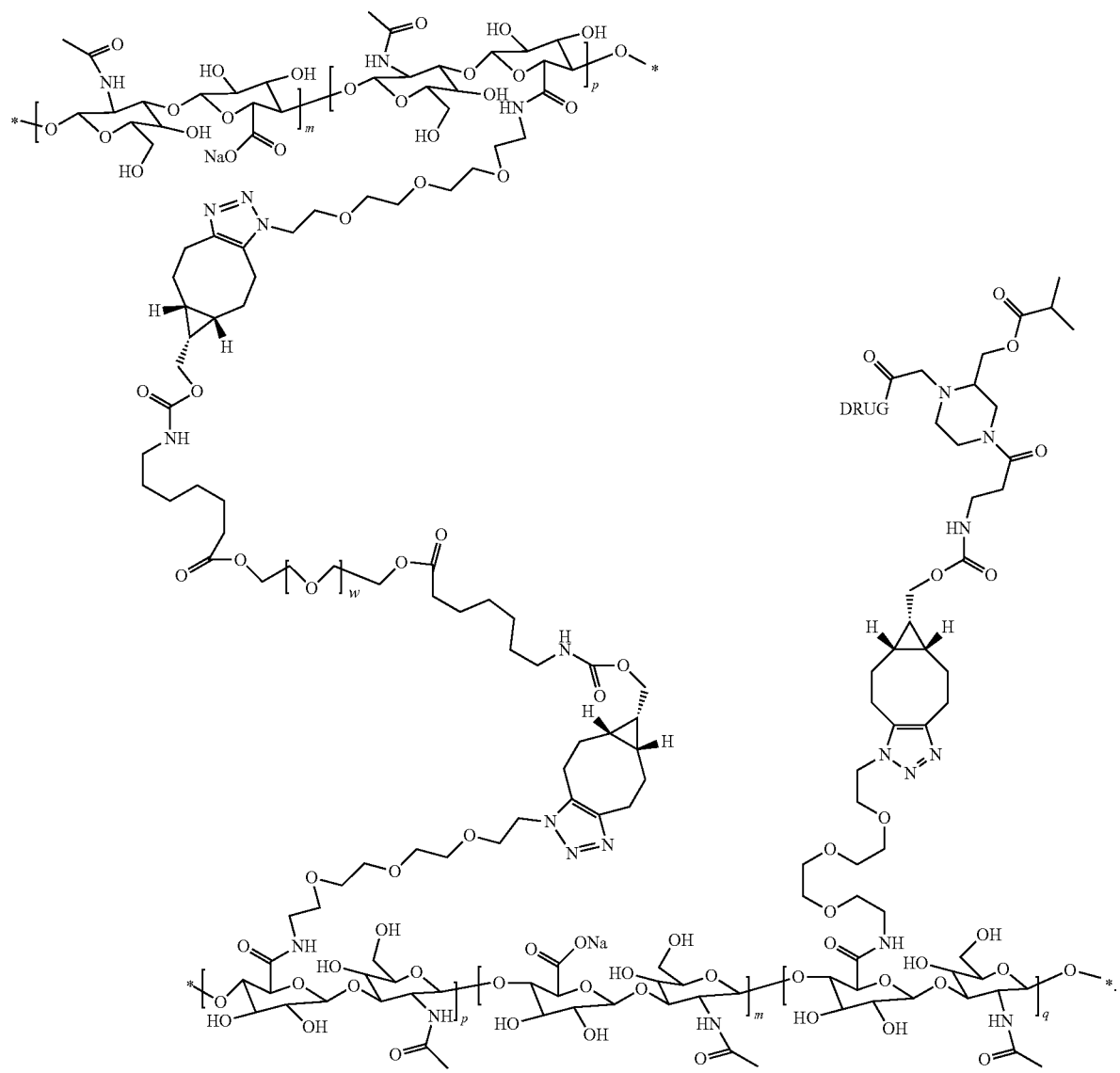
(XVIIIc)

In another embodiment, the drug delivery system can comprise Formula (XVIIId) with DRUG being an ANGPTL3 polypeptide as described herein:
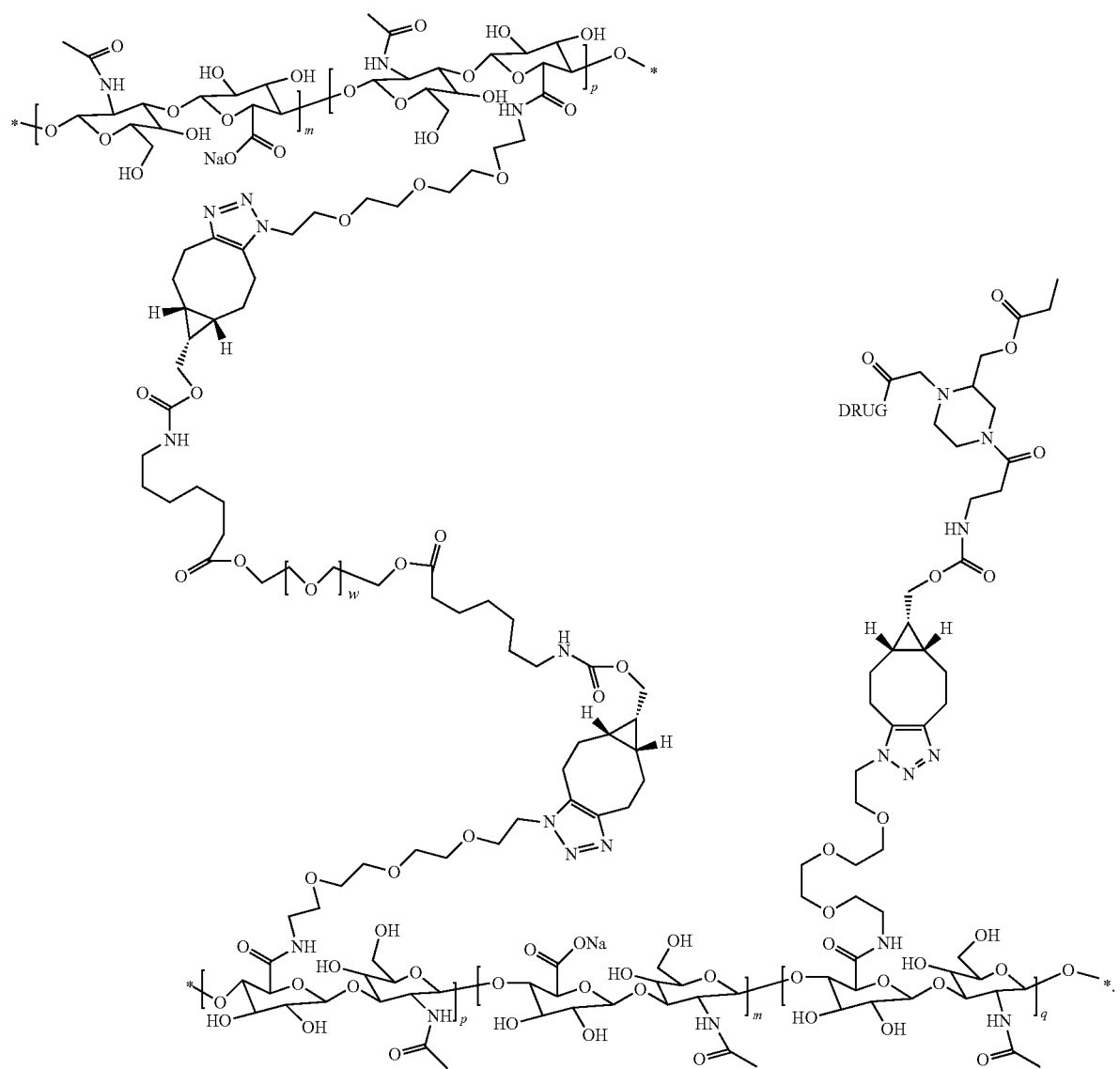
(XVIIId)

In another embodiment, the drug delivery system can comprise Formula (XVIIIe) with DRUG being an ANGPTL3 polypeptide as described herein:
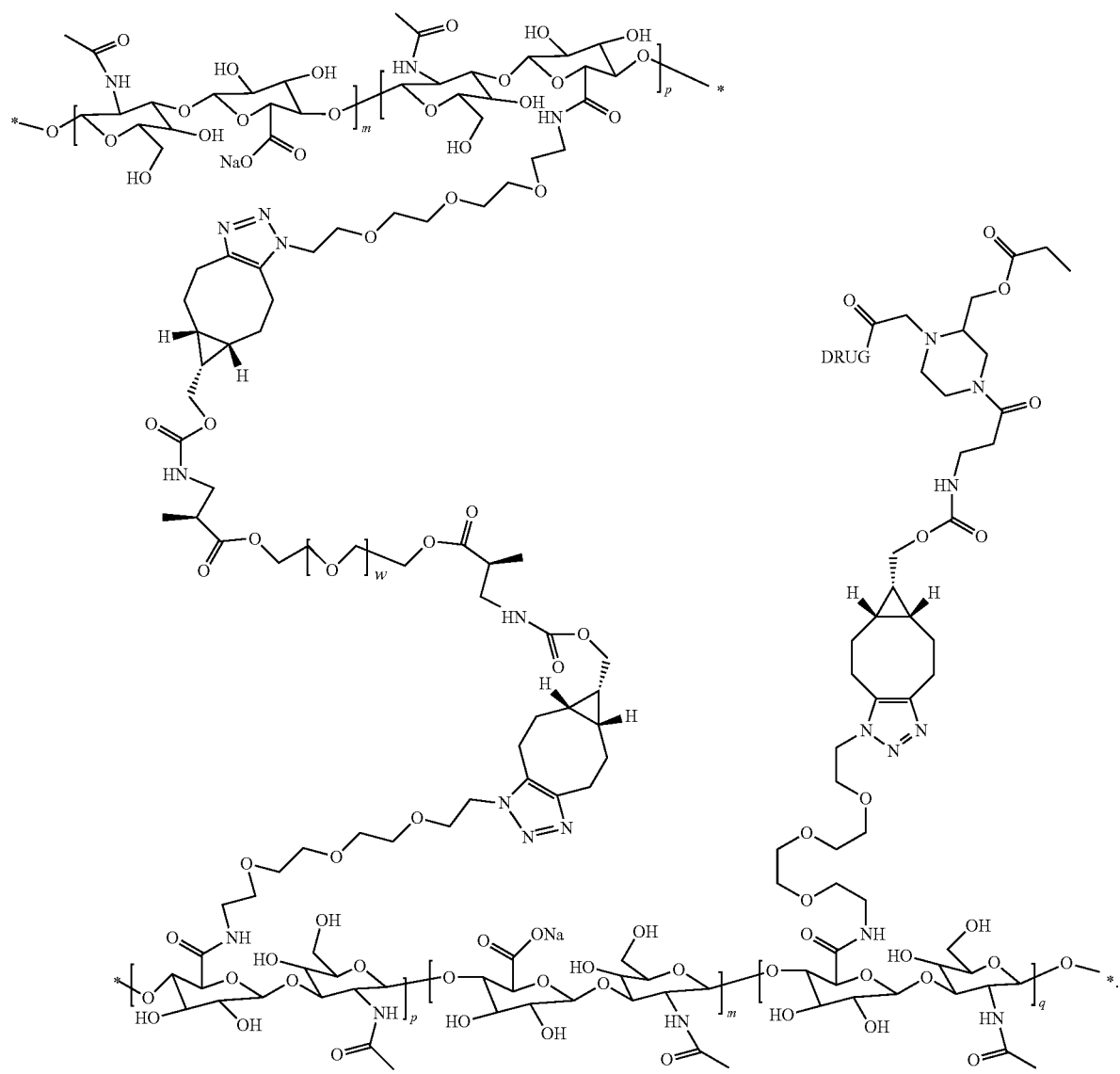
(XVIIIe)

In another embodiment, the drug delivery system can comprise Formula (XVIIIf) with DRUG being an ANGPTL3 polypeptide as described herein:
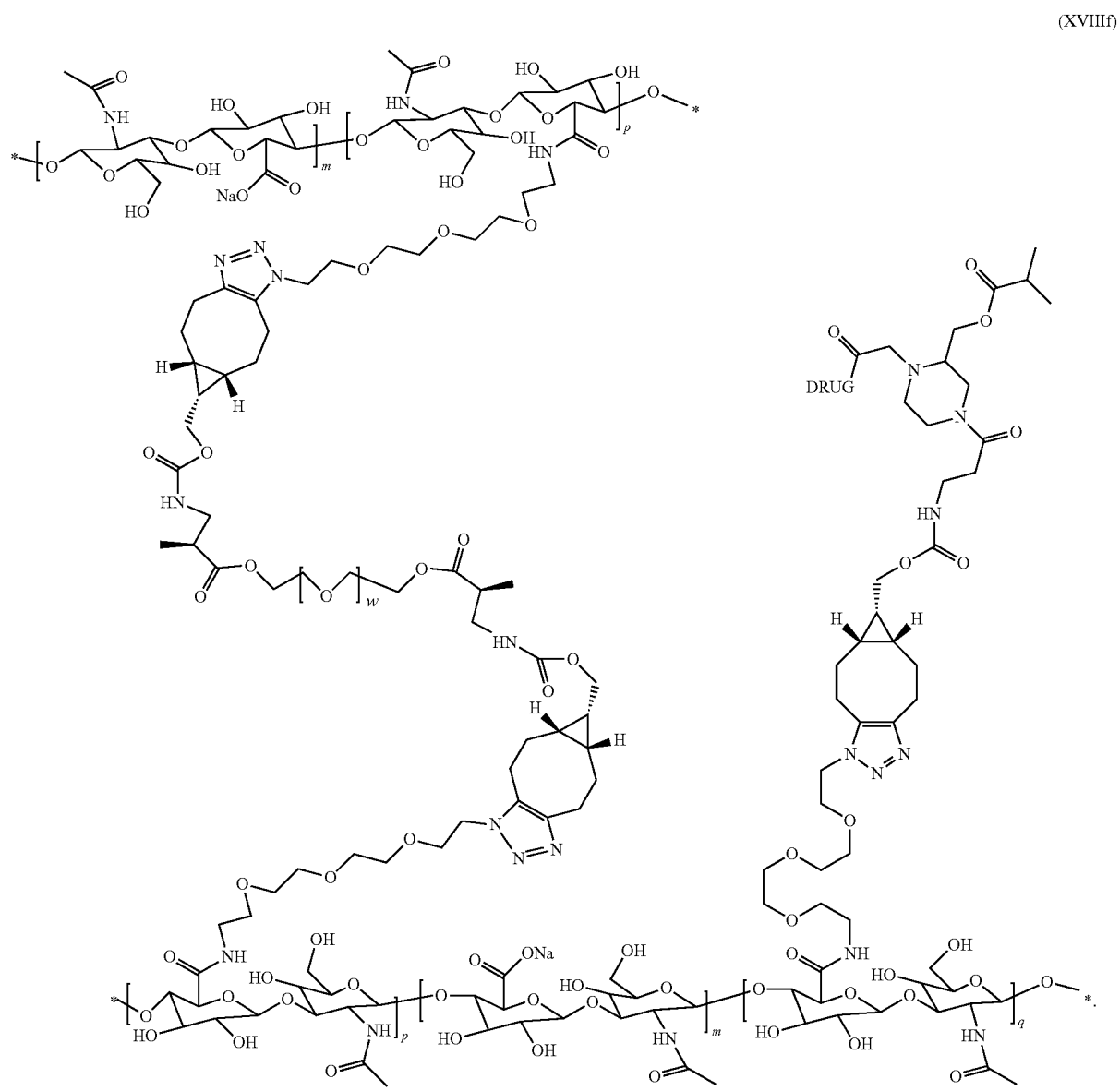
(XVIIIf)

In another embodiment, the drug delivery system can comprise Formula (XXIII) with the drug being an ANGPTL3 polypeptide as described herein:

Another embodiment described herein relates to the drug delivery system or a pharmaceutically acceptable salt thereof comprising D-R represented by Formula (I), wherein (XXIII)

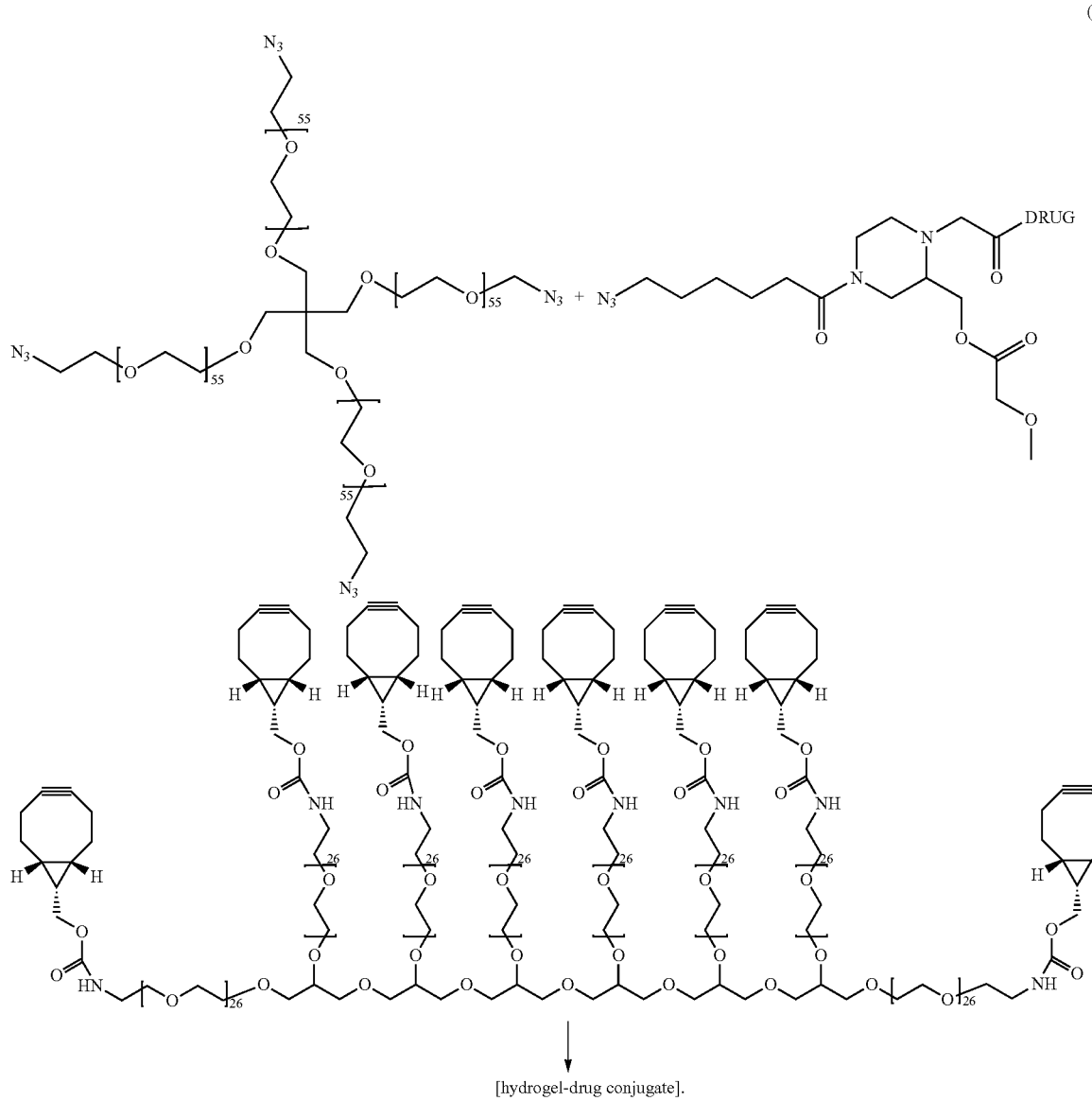

[hydrogel-drug conjugate].

Another embodiment described herein is a method for treating diseases or disorders using the drug delivery systems described herein. Another embodiment described herein relates to the drug delivery system or a pharmaceutically acceptable salt thereof comprising D-R represented by Formula (I) for use as a medicament. Another embodiment is the use of the drug delivery system or a pharmaceutically acceptable salt thereof comprising D-R represented by Formula (I) for the manufacture of a medicament for the treatment of joint damage or disease including arthritis, osteoarthritis, traumatic arthritis, or acute joint injury or trauma. In one aspect, pharmaceutical compositions of the drug delivery systems described herein can be administered to a subject in need thereof by injection. In one aspect, administration may be made by injection or surgical implantation.

D comprises an ANGPTL3 polypeptide comprising at least 95% sequence identity to one or more of SEQ ID NOs:1, 3-45 for use in the treatment of joint damage or disease including arthritis, osteoarthritis, traumatic arthritis, acute joint injury, or trauma. In one aspect, D comprises D1 (SEQ ID NO:19). In one aspect, the composition is a solution or suspension that is injected into the joint. In another aspect, the composition is a gel or semi-solid composition that is implanted in the joint using surgical means or by large-bore injection. In another aspect, the composition is in the form of particles that are injected into a joint or in the proximity of a joint. In another aspect, the composition is implanted in or around the joint as a biodegradable mesh or gauze that is eventually absorbed or processed in situ. In another aspect, the composition is impregnated into sutures, staples, plates, meshes, or similar articles that are utilized during surgery to reattach or repair tendons, ligaments, cartilage, bone, or other joint components following trauma or disease. In another aspect, the composition is a solution or suspension that is delivered intravenously, intraarterially, subcutaneously, intramuscularly, or intraperitoneally. In another aspect, the composition is a gel or semi-solid composition that is implanted using surgical means or large-bore injection. In another aspect, the composition is a gel or semi-solid composition that is applied topically or directly to cutaneous wounds.

In one embodiment, the drug delivery system as described herein releases the biologically active agent at a particular release rate. In one aspect, the release rate can be tuned or modulated by the "trigger" component of the traceless linker, R. Without being bound by any theory, it is believed that reaction of the trigger under physiological conditions generates a nucleophilic functional group, for example a hydroxyl functional group that in an intramolecular fashion cleaves the amide bond linking the drug to the drug delivery system. In one embodiment, the reaction of the trigger is a hydrolysis reaction resulting in the formation of a hydroxyl functional group. Without being bound by any theory, it is believed that steric hindrance of the trigger moiety is correlated with slower reaction of the trigger and the presence and proximity of electron withdrawing groups is correlated with faster reaction of the trigger.

In one embodiment the half-life for the release of the biologically active moiety is about 0.5 hours, about 1 hour, about 2 hours, about 4 hours, about 6 hours, about 8 hours, about 10 hours, about 12 hours, about 14 hours, about 16 hours, about 18 hours, about 20 hours, about 22 hours, about 24 hours, about 1 day, about 2 days, about 3 days, about 4 days, about 5 days, about 6 days, about 7 days, about 1 week, about 2 weeks, about 3 weeks, about 4 weeks, about 1 month, about 2 months, about 3 months, about 4 months, about 5 months, about 6 months, about 7 months, about 8 months, about 9 months, about 10 months, about 11 months, about 12 months, about 1 year, about 1.5 years, about 2 years, about 2.5 years, about 3 years, about 3.5 years, about 4, or greater than 4 years. In one aspect, the biologically active moiety release half-life is about 2.5 days, about 4.5 days, about 7 days, about 10 days, about 11 days, about 12 days, about 14 days, about 15 days, about 21 days, about 28 days, about 30 days, about 31 days, about 32 days, about 40 days, about 58 days, about 60 days, about 65 days, about 70 days, about 80 days, about 125 days, about 165 days, about 380 days, about 940 days, or even greater.

In one embodiment the half-life for the traceless linker trigger ester hydrolysis is about 0.5 hours, about 1 hour, about 2 hours, about 4 hours, about 6 hours, about 8 hours, about 10 hours, about 12 hours, about 14 hours, about 16 hours, about 18 hours, about 20 hours, about 22 hours, about 24 hours, about 1 day, about 2 days, about 3 days, about 4 days, about 5 days, about 6 days, about 7 days, about 1 week, about 2 weeks, about 3 weeks, about 4 weeks, about 1 month, about 2 months, about 3 months, about 4 months, about 5 months, about 6 months, about 7 months, about 8 months, about 9 months, about 10 months, about 11 months, about 12 months, about 1 year, about 1.5 years, about 2 years, about 2.5 years, about 3 years, about 3.5 years, about 4, or greater than 4 years. In one aspect, the traceless linker trigger ester hydrolysis half-life is about 1 day, about 1.5 days, about 2 days, about 2.5 days, about 4 days, about 5 days, about 10 days, about 12 days, about 15 days, about 20 days, about 30 days, about 32 days, about 35 days, about 40 days, about 55 days, about 60 days, about 90 days, about 120 days, about 150 days, about 180 days, about 200 days, about 300 days, about 400 days, or even longer.

In another embodiment the half-life for the clearance of the drug delivery system, $R—R^{11}$, following release of the drug, D (e.g., $D-R—R^{11} \rightarrow R—R^{11}+D$), from the tissue, organ, or compartment into which the drug delivery system was dosed is about 0.5 hours, about 1 hour, about 2 hours, about 4 hours, about 6 hours, about 8 hours, about 10 hours, about 12 hours, about 14 hours, about 16 hours, about 18 hours, about 20 hours, about 22 hours, about 24 hours, about 1 day, about 2 days, about 3 days, about 4 days, about 5 days, about 6 days, about 7 days, about 1 week, about 2 weeks, about 3 weeks, about 4 weeks, about 1 month, about 2 months, about 3 months, about 4 months, about 5 months, about 6 months, about 7 months, about 8 months, about 9 months, about 10 months, about 11 months, about 12 months, about 1 year, about 1.5 years, about 2 years, about 2.5 years, about 3 years, about 3.5 years, about 4, or greater than 4 years.

Other embodiments described herein are pharmaceutical compositions comprising the drug delivery system, D-R—$R^1$, as described herein. In one aspect, the pharmaceutical compositions are suitable for injection or implantation in a subject in need thereof.

Pharmaceutical compositions suitable for administration by injection or implantation include sterile aqueous solutions, suspensions, or dispersions and sterile powders or lyophilisates for the extemporaneous preparation of sterile injectable solutions or dispersion.

For intravenous administration, suitable carriers include phosphate buffered saline (PBS), physiological saline, Ringer's solution, or water for injection. In all cases, the composition should be sterile and should be fluid to the extent that easy syringability exists. Preferred pharmaceutical formulations are stable under the conditions of manufacture and storage and must be preserved against the contaminating action of microorganisms such as bacteria and fungi. In general, the relevant carrier can be a solvent or dispersion medium containing, for example, water, buffers, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, amino acids, sorbitol, sodium chloride, or combinations thereof in the composition. Prolonged absorption of the injectable compositions can be brought about by including in the composition an agent that delays absorption, for example, aluminum monostearate and gelatin.

Certain injectable compositions are aqueous isotonic solutions or suspensions, and suppositories are advantageously prepared from fatty emulsions or suspensions. Said compositions may be sterilized and/or contain adjuvants, such as preservatives, stabilizers, wetting agents, emulsifying agents, solution promoters, salts for regulating the osmotic pressure, buffers, or combinations thereof. In addition, they may also contain other therapeutically valuable substances. Said compositions are prepared according to conventional mixing, granulating or coating methods, respectively, and contain about 0.1-75%, or contain about 1-50%, of the active ingredient.

Sterile injectable solutions or suspensions can be prepared by incorporating the drug delivery system in the required amount in an appropriate solvent with one or a combination of ingredients, as required, followed by filtration sterilization. Generally, solutions or suspensions are prepared by incorporating the active compound into a sterile vehicle such as sterile PBS and any excipients. In the case of sterile powders for the preparation of sterile injectable solutions, the preferred preparation methods are vacuum drying and freeze-drying which yields a powder of the active ingredient plus any additional desired ingredient from a previously sterile-filtered solution thereof.

Transmucosal or transdermal administration means are also possible. Suitable compositions for transdermal application include an effective amount of a biologically active agent with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin, eyes, or joints, include aqueous solutions, suspensions, ointments, creams, gels or sprayable formulations, e.g., for delivery by aerosol or the like. Such topical delivery systems will in particular be appropriate for dermal application. They are thus particularly suited for use in topical, including cosmetic, formulations well known in the art. Such may contain solubilizers, stabilizers, tonicity enhancing agents, buffers, or preservatives.

As used herein, a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

Also described herein are pharmaceutical compositions and dosage forms comprising one or more agents that reduce the rate by which the compositions described herein as active ingredients will decompose. Such agents, which are referred to herein as "stabilizers," include, but are not limited to, antioxidants such as ascorbic acid, pH buffers, or salt buffers, etc.

The effective amount of a pharmaceutical composition to be employed therapeutically will depend, for example, upon the therapeutic context and objectives. One skilled in the art will appreciate that the appropriate dosage levels for treatment will thus vary depending, in part, upon the therapeutic agent incorporated into the drug delivery system, the indication for which the drug delivery system is being used, the route of administration, and the size (body weight, body surface, or organ size) and condition (the age and general health) of the patient. Accordingly, the clinician can titer the dosage and modify the route of administration to obtain the optimal therapeutic effect.

The frequency of dosing will depend upon the pharmacokinetic parameters of the therapeutic agent incorporated into the drug delivery system being used. Typically, a clinician will administer the composition until a dosage is reached that achieves the desired effect. The composition can therefore be administered as a single dose, as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages can be ascertained through use of appropriate dose-response data.

The drug delivery system can be prepared as solutions or suspensions of micro-particles. In one aspect, the carrier is formed into microparticulate which can be administered by a standard syringe to the target tissue, e.g., administration subcutaneously, intra-articularly, intra tendon, or intramuscularly. Such particles may have a mean particle size distribution of between 1 µm and 5000 µm. Other aspects comprise biodegradable gauze, mesh, or sutures that have been impregnated with drug delivery systems as described herein.

In some embodiments, microparticles of the drug delivery systems described herein can be produced by emulsion polymerization, lithography, spinning, molding, spray drying, milling, extrusion, mechanical comminution, or similar procedures known in the art. In one embodiment, the drug delivery systems, carrier polymers, or hydrogels as described herein can be divided into microparticles by extrusion through mesh or screens. In one aspect, the extrusion can be repeated multiple times and/or through successively smaller meshes to achieve the desired particle distribution size.

In one embodiment, based on laser diffraction to measure particle size, the drug delivery system has a mean particle size distribution of between 1 µm and 5000 µm when suspended in an isotonic aqueous formulation buffer. In some aspects, the drug delivery system has a mean particle size distribution of between 10 µm and 1000 µm when suspended in isotonic buffer. In another aspect, the drug delivery system has a mean particle size distribution of between 50 µm and 500 µm when suspended in an isotonic aqueous buffer. In another aspect, the drug delivery system has a mean particle size distribution of between 100 µm and 300 µm when suspended in an isotonic aqueous buffer. In another aspect, the drug delivery system has a mean particle size distribution of between 200 µm and 300 µm when suspended in an isotonic aqueous buffer. In some embodiments, the mean particle size distribution comprises about 10 µm, about 50 µm, about 100 µm, about 150 rpm, about 200 µm, about 250 µm, about 300 µm, about 350 µm, about 400 rpm, about 450 µm, about 500 µm, about 750 µm, about 1000 µm, about 1500 µm, about 2000 µm, about 2500 µm, or about 5000 µm.

The particle sizes may be determined using standard techniques known to one of ordinary skill in the art. The exemplary techniques that can be used for measuring the particle size distributions of drug delivery system particles may include laser diffraction analysis, light scattering (e.g., dynamic light scattering), microscopic particle image analysis, elutriation, or aerosol mass spectrometry. The sample of drug delivery system particles may be measured as a dry sample or a wet sample. Any commercially available instrument for measuring particle sizes may be used, including instruments from Cilas; Brookhaven Instruments Corporation; Malvern Instruments; Horiba Scientific; or Wyatt following the recommended operating procedures according to the manufacturer's instructions.

The measured particle sizes using the techniques described herein may be expressed as a derived diameter with a normal distribution or non-normal distribution with a mean, median (e.g., mass median diameter), and mode of particle diameter sizes. The particle size distribution may be expressed as a diameter number distribution, a surface area distribution, or a particle volume distribution. The mean of the particle size distribution may be calculated and expressed in various ways, such as the volume mean diameter (D[4,3] or $d_{43}$), mean surface area diameter (D[3,2] or $d_{32}$) or the mean number particle diameter (D[1,0] or $d_{10}$). Because the particle size distribution values vary depending on the measurement methodology and how the distribution is expressed, the comparison of different mean particle size distributions must be calculated by the same methodology in order to yield an accurate comparison. For example, a sample with a measured and calculated volume mean diameter must be compared with a second sample having a measured and calculated volume mean diameter, ideally measured using the same measuring instrument under the same conditions. Thus, the specific particle size distributions described herein are not intended to be limited to any one type of method for measuring or calculating a particle size distribution (e.g., a diameter number distribution, a surface area distribution, or a particle volume distribution), but rather indicate particle size values and distributions thereof for each method of measuring particle sizes described herein.

In one embodiment drug delivery systems can be administered by injection through a needle smaller than 0.6 mm inner diameter (e.g., 20 gauge), preferably through a needle smaller than 0.3 mm inner diameter (e.g., 25 gauge), more preferably through a needle smaller than 0.25 mm inner diameter (e.g., 27 gauge), even more preferably through a needle smaller than 0.2 mm inner diameter (e.g., 28 gauge), and most preferably through a needle smaller than 0.16 mm inner diameter (e.g., 30 gauge). For example when a 100 µm to 300 µm particle size distribution of a drug delivery system is injected a 20 gauge needle may be optimal for delivery. Because the particle morphology is flexible, however, needle sizes narrower than the drug delivery system particle size may be used successfully.

The phrases and terms "can be administered by injection," "injectable," or "injectability" refer to a combination of factors such as a certain force applied to a plunger of a syringe containing the drug delivery systems described herein swollen in a liquid at a certain concentration (w/v) and at a certain temperature, a needle of a given inner diameter connected to the outlet of such syringe, and the time required to extrude a certain volume of the drug delivery systems from the syringe through the needle.

In one embodiment, an injectability measurement is carried out for the drug delivery system suspended in PBS or physiological saline to a concentration of about 0.1% to about 20% (w/v) including all integers within the specified percentage range.

Consequently, the drug delivery systems show the beneficial effect of a controlled release rate in respect of the released drug D-H. Preferably, a sustained release rate is obtained. Sustained release means that the administration intervals of the respective drug delivery systems described herein are expanded compared to administration of the drug in the absence of the drug delivery system. For example, drug delivery systems that are based on drugs commonly administered once or several times a day provide therapeutically effective levels for at least three days, at least one week, for at least one month, for several months, or for years.

Another embodiment described herein is a pharmaceutical composition of the drug delivery systems described herein. The pharmaceutical compositions can comprise one or more excipients, such as:

(i) Buffering agents: physiologically tolerated buffers to maintain pH in a desired range, such as sodium phosphate, bicarbonate, succinate, histidine, citrate and acetate, sulphate, nitrate, chloride, pyruvate. Antacids such as $Mg(OH)_2$ or $ZnCO_3$ may be also used. Buffering capacity may be adjusted to match the conditions most sensitive to pH stability.

(ii) Isotonicity modifiers: to minimize pain that can result from cell damage due to osmotic pressure differences at the injection depot. Glycerin and sodium chloride are examples. Effective concentrations can be determined by osmometry using an assumed osmolality of 285-315 mOsmol/kg for serum.

(iii) Preservatives and/or antimicrobials: multidose parenteral preparations may require the addition of preservatives at a sufficient concentration to minimize the risk of subjects becoming infected upon injection and corresponding regulatory requirements have been established. Typical preservatives include m-cresol, phenol, methylparaben, ethylparaben, propylparaben, butylparaben, chlorobutanol, benzyl alcohol, phenylmercuric nitrate, thimerosol, sorbic acid, potassium sorbate, benzoic acid, chlorocresol, and benzalkonium chloride.

(iv) Stabilizers: Stabilization is achieved by strengthening of the protein-stabilising forces, by destabilization of the denatured state, or by direct binding of excipients to the protein. Stabilizers may be amino acids such as alanine, arginine, aspartic acid, glycine, histidine, lysine, proline, sugars such as glucose, sucrose, trehalose, polyols such as glycerol, mannitol, sorbitol, salts such as potassium phosphate, sodium sulphate, chelating agents such as EDTA, hexaphosphate, ligands such as divalent metal ions (zinc, calcium, etc.), other salts or organic molecules such as phenolic derivatives. In addition, oligomers or polymers such as cyclodextrins, dextran, dendrimers, polyethylene glycol, polyvinylpyrrolidone, protamine, or human serum albumin may be used.

(v) Anti-adsorption agents: Mainly ionic or ion-ionic surfactants or other proteins or soluble polymers are used to coat or adsorb competitively to the inner surface of the composition's container, e.g., poloxamer (Pluronic F-68), PEG dodecyl ether (Brij 35), polysorbate 20 and 80, dextran, polyethylene glycol, PEG-polyhistidine, BSA and HSA and gelatines. Chosen concentration and type of excipient depends on the effect to be avoided but typically, a monolayer of surfactant is formed at the interface just above the CMC value.

(vi) Lyophilization or cryoprotectants: During freeze- or spray drying, excipients may counteract the destabilising effects caused by hydrogen bond breaking and water removal. For this purpose, sugars and polyols may be used, but corresponding positive effects have also been observed for surfactants, amino acids, non-aqueous solvents, and other peptides. Trehalose is particularly efficient at reducing moisture-induced aggregation and also improves thermal stability potentially caused by exposure of protein hydrophobic groups to water. Mannitol and sucrose may also be used, either as sole lyo/cryoprotectant or in combination with each other where higher ratios of mannitol or sucrose are known to enhance physical stability of a lyophilized cake. Mannitol may also be combined with trehalose. Trehalose may also be combined with sorbitol or sorbitol may be used as the sole protectant. Starch or starch derivatives may also be used.

(vii) Oxidation protection agents: antioxidants such as ascorbic acid, ectoine, methionine, glutathione, monothioglycerol, morin, polyethylenimine (PEI), propyl gallate, vitamin E, chelating agents such aus citric acid, EDTA, hexaphosphate, thioglycolic acid.

(viii) Viscosifiers or viscosity enhancers: retard settling of the particles in the vial and syringe and are used in order to facilitate mixing and resuspension of the particles and to make the suspension easier to inj ect (i.e., low force on the syringe plunger). Suitable viscosifiers or viscosity enhancers are, for example, carbomer viscosifiers like Carbopol 940, Carbopol Ultrez 10, cellulose derivatives like hydroxypropylmethylcellulose (hypromellose, HPMC) or diethylaminoethyl cellulose (DEAE or DEAE-C), colloidal magnesium silicate (Veegum) or sodium silicate, hydroxyapatite gel, tricalcium phosphate gel, xanthans, carrageenans like Satiagum UTC 30, aliphatic poly(hydroxy acids), such as poly (D,L- or L-lactic acid) (PLA) and poly(glycolic acid) (PGA) and their copolymers (PLGA), terpolymers of D,L-lactide, glycolide and caprolactone, poloxamers, hydrophilic poly (oxyethylene) blocks and hydrophobic poly(oxypropylene) blocks to make up a triblock of poly(oxyethylene)-poly (oxypropylene)-poly(oxyethylene) (e.g., Pluronic.™), polyetherester copolymer, such as a polyethylene glycol terephthalate/polybutylene terephthalate copolymer, sucrose acetate isobutyrate (SAB), dextran or derivatives thereof, combinations of dextrans and PEG, polydimethylsiloxane, collagen, chitosan, polyvinyl alcohol (PVA) and derivatives, polyalkylimides, poly (acrylamide-co-diallyldimethyl ammonium (DADMA)), polyvinylpyrrolidone (PVP), glycosaminoglycans (GAGs) such as dermatan sulfate, chondroitin sulfate, keratan sulfate, heparin, heparan sulfate, hyaluronan, ABA triblock or AB block copolymers composed of hydrophobic A-blocks, such as polylactide (PLA) or poly(lactide-co-glycolide) (PLGA), and hydrophilic B-blocks, such as polyethylene glycol (PEG) or polyvinyl pyrrolidone. Such block copolymers as well as the above-mentioned poloxamers may exhibit reverse thermal gelation behavior (fluid state at room temperature to facilitate administration and gel state above sol-gel transition temperature at body temperature after injection).

(ix) Diffusion agents: modifies the permeability of connective tissue through the hydrolysis of components of the extracellular matrix in the interstitial space such as, but not limited to, hyaluronic acid, a polysaccharide found in the intercellular space of connective tissue. A spreading agent such as, but not limited to, hyaluronidase temporarily decreases the viscosity of the extracellular matrix and promotes diffusion of injected drugs.

(x) Other auxiliary agents: such as wetting agents, viscosity modifiers, antibiotics, hyaluronidase. Acids and bases such as hydrochloric acid and sodium hydroxide are auxiliary agents necessary for pH adjustment during manufacture.

The drug delivery system may be provided as a liquid, a suspension, or as a dry composition.

In one embodiment, the drug delivery system is a dry composition. Suitable methods of drying are, for example, spray drying and lyophilization (freeze-drying). In one aspect, the drug delivery system is dried by lyophilization.

In one embodiment, the drug delivery system is sufficiently dosed in the composition to provide therapeutically effective amounts of biologically active agent for at least 12 hours in one application. In one aspect, one application of drug delivery system is sufficient for about 1 day, about 2 days, about 3 days, about 4 days, about 5 days, about 1 week, about 2 weeks, about 3 weeks, about 4 weeks, one month, 2 months, 3 months, 4 months, 6 months, 9 months, one year, 2 years, 3 years, 4 years, or even longer.

In one embodiment, the drug delivery system is provided as a single dose, meaning that the container in which it is supplied contains one pharmaceutical dose.

In another embodiment, the composition is provided as a multiple dose composition, meaning that it contains more than one therapeutic dose. Preferably, a multiple dose composition contains at least 2 doses. Such multiple dose drug delivery systems can either be used for different subjects in need thereof or is intended for use in one subject, wherein the remaining doses are stored after the application of the first dose until needed.

In another embodiment, the drug delivery system is comprised in one or more containers. For liquid or suspension compositions, the container is preferably a single chamber syringe. For dry compositions, preferably the container is a dual-chamber syringe. The dry composition is provided in a first chamber of the dual-chamber syringe and reconstitution solution is provided in a second chamber of the dual-chamber syringe.

Prior to applying the dry drug delivery system to a subject in need thereof, the dry composition is reconstituted. Reconstitution can take place in the container in which the dry drug delivery system is provided, such as in a vial, syringe, dual-chamber syringe, ampoule, and cartridge. Reconstitution is done by adding a predefined amount of reconstitution solution to the dry composition. Reconstitution solutions are sterile liquids, such as phosphate buffered saline, isotonic saline, water for injection, or other buffers, which may contain further excipients, such as preservatives and/or antimicrobials, such as, for example, benzylalcohol and cresol. Preferably, the reconstitution solution is sterile phosphate buffered saline (PBS) or physiological saline. Alternatively, the reconstitution solution is sterile water for injection.

Another embodiment is a method of preparing a reconstituted composition comprising a therapeutically effective amount of a drug delivery system, and optionally one or more pharmaceutically acceptable excipients, the method comprising the step of contacting the composition with a volume of reconstitution vehicle. The reconstituted drug delivery system may then be administered by injection or other routes.

Another embodiment is a reconstituted composition comprising a therapeutically effective amount of a drug delivery system, a reconstitution vehicle, and optionally one or more pharmaceutically acceptable excipients.

Another embodiment is a pre-filled syringe comprising a solution or a suspension comprising a therapeutically effective amount of a drug delivery system, and optionally one or more pharmaceutically acceptable excipients. In one aspect, the syringe is filled with between about 0.01 mL and about 5 mL of a drug delivery system as described herein. In one aspect, the syringe is filled with between about 0.05 mL and about 5 mL, between about 1 mL and about 2 mL, between about 0.1 mL and about 0.15 mL, between about 0.1 mL, about 0.5 mL, between about 0.15 mL and about 0.175 mL, or about 0.5 to about 5 mL. In one embodiment, the syringe is filled with 0.165 mL of a drug delivery system as described herein. In some aspects, a syringe is filled with about 0.01 mL, about 0.02 mL, about 0.03 mL, about 0.04 mL, about 0.05 mL, about 0.06 mL, about 0.07 mL, about 0.08 mL, about 0.09 mL, about 0.1 mL, about 0.2 mL, about 0.3 mL, about 0.4 mL, about 0.5 mL, about 0.6 mL, about 0.7 mL, about 0.8 mL, about 0.9 mL, about 1 mL, about 1.2 mL, about 1.5 mL, about 1.75 mL, about 2 mL, about 2.5 mL, about 3 mL, about 4 mL, or about 5 mL of a drug delivery system as described herein. A syringe is often filled with more than the desired dose to be administered to the patient, to take into account wastage due to "dead space" within the syringe and needle. There may also be a predetermined amount of waste when the syringe is primed by the physician, so that it is ready to inject the patient.

In one embodiment, a syringe is filled with a dosage volume (i.e., the volume of medicament intended for delivery to the patient) of between about 0.01 mL and about 5 mL depending on the route of injection (e.g., between about 0.01 mL and about 0.1 mL, between about 0.1 mL and about 0.5 mL, between about 0.2 mL and about 2 mL, between about 0.5 mL and about 5 mL, or between about 1 mL and about 5 mL) of a drug delivery system as described herein. In one embodiment intended for intra-articular injection, a syringe is filled with a dosage volume of between about 0.05 mL and about 5.0 mL of a drug delivery system solution or suspension with a drug concentration of 1 mg/mL to 40 mg/mL as described herein. In one embodiment intended for subcutaneous injection, a syringe is filled with a dosage volume of between about 0.1 mL and about 5.0 mL of a drug delivery system solution or suspension with a drug concentration of 0.1 mg/mL to 40 mg/mL as described herein. In other embodiments intended for injection by other routes, a syringe is filled with a dosage volume of between about 0.01 mL and about 5.0 mL of a drug delivery system solution or suspension with a drug concentration of 0.1 mg/mL to 40 mg/mL as described herein. In some aspects, a syringe is filled with about 0.01 mL, about 0.02 mL, about 0.03 mL, about 0.04 mL, about 0.05 mL, about 0.06 mL, about 0.07 mL, about 0.08 mL, about 0.09 mL, about 0.1 mL, about 0.2 mL, about 0.3 mL, about 0.4 mL, about 0.5 mL, about 0.6 mL, about 0.7 mL, about 0.8 mL, about 0.9 mL, about 1 mL, about 1.2 mL, about 1.5 mL, about 1.75 mL, about 2 mL, about 2.5 mL, about 3 mL, about 4 mL, or about 5 mL of a drug delivery system as described herein for delivery to a patient in need thereof.

As the syringe contains a medicament solution, the outlet may be reversibly sealed to maintain sterility of the medicament. This sealing may be achieved by a sealing device as is known in the art, such as a luer lock or a tamper resistant seal.

Another embodiment is a kit comprising one or more pre-filled syringes comprising a solution or suspension of one or more drug delivery systems as described herein. In one embodiment, such a kit comprises a pre-filled syringe comprising drug delivery systems as described herein in a blister pack or a sealed sleeve. The blister pack or sleeve may be sterile on the inside. In one aspect, pre-filled syringes as described herein may be placed inside such blister packs or sleeves prior to undergoing sterilization, for example terminal sterilization.

Such a kit may further comprise one or more needles for administration of drug delivery systems as described herein. Such kits may further comprise instructions for use, a drug label, contraindications, warnings, or other relevant information. One embodiment described herein is a carton or package comprising one or more pre-filled syringes comprising one or more drug delivery systems as described herein contained within a blister pack, a needle, and optionally instructions for administration, a drug label, contraindications, warnings, or other relevant information.

A terminal sterilization process may be used to sterilize the syringe and such a process may use a known process such as an ethylene oxide or a hydrogen peroxide ($H_2O_2$) sterilization process. Needles to be used with the syringe may be sterilised by the same method, as may kits described herein. In one aspect, a package is exposed to the sterilising gas until the outside of the syringe is sterile. Following such a process, the outer surface of the syringe may remain sterile (whilst in its blister pack) for up to 6 months, 9 months, 12 months, 15 months, 18 months, 24 months or longer. Thus, in one embodiment, a pre-filed syringe as described herein (in its blister pack) may have a shelf life of up to 6 months, 9 months, 12 months, 15 months, 18 months, 24 months, or even longer. In one embodiment, less than one syringe in a million has detectable microbial presence on the outside of the syringe after 18 months of storage. In one aspect, the pre-filled syringe has been sterilised using ethylene oxide with a Sterility Assurance Level of at least $10^{-6}$. In another aspect, the pre-filled syringe has been sterilised using hydrogen peroxide with a Sterility Assurance Level of at least $10^{-6}$. Significant amounts of the sterilising gas should not enter the variable volume chamber of the syringe. The term "significant amounts" As used herein, refers to an amount of gas that would cause unacceptable modification of the drug delivery system solution or suspension within the variable volume chamber. In one embodiment, the sterilization process causes $\leq 10\%$ (preferably $\leq 5\%$, $\leq 3\%$, $\leq 1\%$) alkylation of the drug delivery system. In one embodiment, the pre-filled syringe has been sterilised using ethylene oxide, but the outer surface of the syringe has $\leq 1$ ppm, preferably $\leq 0.2$ ppm ethylene oxide residue. In one embodiment, the pre-filled syringe has been sterilised using hydrogen peroxide, but the outer surface of the syringe has $\leq 1$ ppm, preferably $\leq 0.2$ ppm hydrogen peroxide residue. In another embodiment, the pre-filled syringe has been sterilised using ethylene oxide, and the total ethylene oxide residue found on the outside of the syringe and inside of the blister pack is $\leq 0.1$ mg. In another embodiment, the pre-filled syringe has been sterilised using hydrogen peroxide, and the total hydrogen peroxide residue found on the outside of the syringe and inside of the blister pack is $\leq 0.1$ mg.

Another aspect is a kit of parts. For liquid and suspension compositions, and when the administration device is simply a hypodermic syringe, the kit may comprise the syringe, a needle and a container comprising the drug delivery system composition for use with the syringe. In case of a dry composition, the container may have one chamber containing the dry drug delivery system composition, and a second chamber comprising a reconstitution solution. In one embodiment, the injection device is a hypodermic syringe adapted so the separate container with drug delivery system composition can engage with the injection device such that in use the liquid or suspension or reconstituted dry composition in the container is in fluid connection with the outlet of the injection device. Examples of administration devices include but are not limited to hypodermic syringes and pen injector devices. Particularly preferred injection devices are the pen injectors, in which case the container is a cartridge, preferably a disposable cartridge.

Another embodiment comprises a kit comprising a needle and a container containing the drug delivery system composition and optionally further containing a reconstitution solution, the container being adapted for use with the needle. In one aspect, the container is a pre-filled syringe. In another aspect, the container is dual chambered syringe.

Another embodiment is a cartridge containing a composition of drug delivery system as hereinbefore described for use with a pen injector device. The cartridge may contain a single dose or plurality of doses of drug delivery system.

In another embodiment the drug delivery system solution or suspension comprises a drug delivery system and one or more excipients, and also other biologically active agents, either in their free form or as drugs or combined with other drug delivery systems such as pegylated drugs or hydrogel linked drugs. In one aspect, such additional one or more biologically active agents is a free form drug or a second drug delivery system.

In another embodiment, one or more drug delivery systems are simultaneously administered, with each drug delivery system having either separate or related biological activities.

In an alternative embodiment, the drug delivery system is combined with a second biologically active compound in such way that the drug delivery system is administered to a subject in need thereof first, followed by the administration of the second compound. Alternatively, the drug delivery system composition is administered to a subject in need thereof after another compound has been administered to the same subject.

Another embodiment is a drug delivery system or a pharmaceutically acceptable salt thereof comprising D-R represented by Formula (I) for use as a medicament.

Another embodiment is a drug delivery system or pharmaceutically acceptable salt thereof comprising D-R represented by Formula (I) for use in the treatment of a musculoskeletal disorder.

Another embodiment is the use of drug delivery system or a pharmaceutically acceptable salt thereof comprising D-R represented by Formula (I) for the manufacture of a medicament for the treatment of a musculoskeletal disorders.

Another embodiment is a drug delivery system or a pharmaceutical composition for use in a method of treating or preventing diseases or disorders which can be treated by the biologically active moiety released from the drug delivery system.

Another embodiment is a method of manufacturing a solution or suspension composition of drug delivery system. In one embodiment, such composition is made by:
(i) admixing the drug delivery system with one or more excipients;
(ii) transferring amounts of the liquid or suspension composition equivalent to single or multiple doses into suitable containers; and
(iii) sealing the containers.

Another embodiment is the method of manufacturing a dry composition of a drug delivery system. In one embodiment, such composition is made by:
(i) admixing the drug delivery system with one or more excipients;
(ii) transferring amounts equivalent to single or multiple doses into suitable containers;
(iii) drying the composition in said containers; and
(iv) sealing the containers.

Suitable containers are vials, syringes, dual-chamber syringes, ampoules, and cartridges.

Another embodiment is a method for the synthesis of a drug delivery system or a pharmaceutically acceptable salt thereof as defined above. Drug delivery systems or precursors of drug delivery systems may be prepared by known methods or in accordance with the reaction sequences as described below. The starting materials used in the preparation (synthesis) of drug delivery systems or precursors thereof are known or commercially available, or can be prepared by known methods or as described below.

It will be readily apparent to one of ordinary skill in the relevant arts that suitable modifications and adaptations to the compositions, methods, and applications described herein can be made without departing from the scope of any embodiments or aspects thereof. The compositions and methods provided are exemplary and are not intended to limit the scope of any of the specified embodiments. All of the various embodiments, aspects, and options disclosed herein can be combined in any and all variations or iterations. The scope of the compositions, formulations, methods, and processes described herein include all actual or potential combinations of embodiments, aspects, options, examples, and preferences herein described.

EXAMPLES

Abbreviations

Ac Acetyl
ACN Acetonitrile
AcOH acetic acid
$Ac_2O$ acetic anhydride
aq. Aqueous
atm Atmosphere
Boc, BOC tertiary butyl carboxy
Boc-anhydride di-tert-butyl dicarbonate
$(Boc)_2O$, $(BOC)_2O$ di-tert-butyl dicarbonate
br. Broad
BSA bovine serum albumin
BuOH Butanol
CAD charged aerosol detector
calcd. Calculated
Cat, cat Catalytic
CBZ, Cbz Carbobenzyloxy
$Cu(OTf)_2$ copper(II) trifluoromethane sulfonate
d Doublet
dd doublet of doublets
DCM Dichloromethane
DIAD diisopropyl azodicarboxylate
DIPEA, DIEA N,N-diisopropylethylamine
DMAP 4,4-dimethylaminopyridine
DMF N,N-dimethylformamide
DMSO Dimethylsulfoxide
DOSY-NMR One dimensional diffusion ordered NMR
DSC N,N'-disuccinimidyl carbonate
ECL Electrochemiluminescence
Elem. Anal. Elemental analysis
ELSD evaporative light scattering detector
N-(3-Dimethylaminopropyl)-N'-ethylcarbodiimide hydrochloride
ESI electrospray ionization
EtOAc, AcOEt ethyl acetate
Et Ethyl
EtOH Ethanol
FCC flash column chromatography
FITC fluorescein isothiocyanate
g Grams
G Gauge
h hour(s)
2-(1H-7-azabenzotriazol-1-yl)-1,1,3,3-tetramethyl uronium hexafluorophosphate methanaminium
HC HPLC condition
HOBt 1-Hydroxybenzotriazole hydrate
HPLC high performance liquid chromatography
IPA 2-propanol
IR infrared spectroscopy
i or iso Iso
$K_2CO_3$ potassium carbonate
kD, kDa Kilodalton
L liter(s)
LCMS liquid chromatography-mass spectrometry
M Molar
MHz mega Hertz
m Multiplet Me Methyl
MeCN Acetonitrile
MeOH Methanol
MES 2-(N-morpholino)ethanesulfonic acid
mg milligram(s)
g Microgram
mM Millimolar
mm millimeter(s)
min Minutes
mL milliliter(s)
mmol Millimoles
L Microliter
mol Micromoles
MOPS 3-(N-morpholino)propanesulfonic acid
MS mass spectrometry
MsCl methanesulfonyl chloride
MsOH methanesulfonic acid
MWCO molecular weight cut off
m/z mass to charge ratio
N normal
NA not available
NaBH$_4$ sodium borohydride
NaBH$_3$CN sodium cyanoborohydride
Na(AcO)$_3$BH sodium triacetoxyborohydride
ng nanogram
NH$_4$C$_1$ ammonium chloride
NHS N-hydroxysuccinimide
nM nanomolar
NMR nuclear magnetic resonance
OMe methoxy
PBS phosphate buffered saline
1×PBS phosphate buffered saline, typically about 10 mM PO$_4$$^{3-}$
Pd/C palladium on carbon
Pd(dppf)Cl$_2$ 1,1'-bis(diphenylphosphino)ferrocene-palladium(II)dichloride
1,1'-bis(diphenylphosphino)ferrocene-palladium(II)dichloride
Pd(dppf)Cl$_2$.CH$_2$Cl$_2$ adduct
dichloromethane complex
Pd(PPh$_3$)$_4$ tetrakis(triphenylphosphine)palladium(0)
Ph phenyl
ppm parts per million
psi pounds per square inch
rac racemic
rcf relative centrifugal force
RP reverse phase
rt, RT room temperature
s singlet
sat. saturated
SDS-page sodium dodecyl sulfate polyacrylamide gel electrophoresis
SEC size exclusion chromatography
SFC Supercritical Fluid Chromatography
t triplet
t-Bu, tBu tertiary-butyl
t$_{1/2}$ half life
t$_r$ or ret. time retention time
TBAF tetra-n-butylammonium fluoride
TBSCl, TBDMSCl tert-butyldimethylsilyl chloride
TEA, Et$_3$N, NEt3 triethylamine
tert-tertiary
TFA trifluoroacetic acid
Tf$_2$O trifluoromethanesulfonic anhydride
THF tetrahydrofuran
TLC Thin Layer Chromatography
TMS trimethylsilyl TMSOTf trimethylsilyl trifluoromethanesulfonate
Tris tris(hydroxymethyl)aminomethane
Triton X-100 t-octylphenoxypolyethoxyethanol (CAS 9002-93-1)
Ts p-toluenesulfonyl
TsOH p-toluenesulfonic acid
Tween 20 polysorbate 20, Polyoxyethylene (20) sorbitan monolaurate
UPLC ultra performance liquid chromatography
UV ultraviolet
v/v volume per volume
w/v weight per volume
w/w weight per weight
Methods
Synthesis of

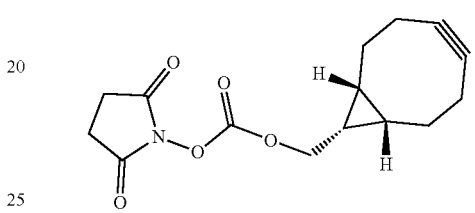

((1R,8S,9s)-bicyclo[6.1.0]non-4-yn-9-yl)methyl (2,5-dioxopyrrolidin-1-yl) carbonate used in some following examples was described by A. M. Jawalekar, et al; *Molecules*, 2013, 18, 7346-7363.

Synthesis of

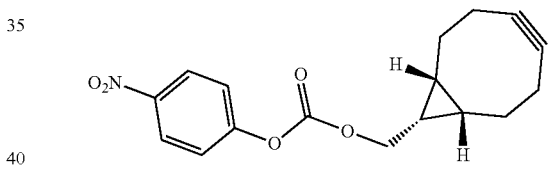

((1R,8S,9s)-bicyclo[6.1.0]non-4-yn-9-yl)methyl (4-nitrophenyl) carbonate used in some following examples was described by J. Dommerholt, et al; *Angew. Chem. Int. Ed.* 2010, 49, 9422-9425.

All other intermediates and reagents not specifically described as synthesized herein are commercially available and were used as delivered.

LCMS Methods

Method 1

Column SunFire C18 3.5 μm 3.0×30 mm; Column Temperature 40° C.; Flow 2.0 mL/min; Stop Time 2.20 min; pH 2.2; Eluent A1 0.05% TFA in Water; Eluent B1 Acetonitrile; Gradient Time (min)/% A (Eluent A1): % B (Eluent B1); 0.00/95:5; 1.70/5:95; 2.00/5:95; 2.10/95:5.

Method 2

Column AcQuity UPLC BEH C18 1.7 μm 2.1×30 mm; Column Temperature 50° C.; Flow 1.0 mL/min; Stop Time 2.00 min; pH 2.6; Eluent A1 0.1% Formic Acid in Water; Eluent B1 0.1% Formic Acid in Acetonitrile; Gradient Time (min)/% A (Eluent A1): % B (Eluent B1) 0.00/98:2; 0.10/98:2; 1.50/2:98; 1.80/2:98; 1.90/98:2; 2.00/98:2.

Method 3

Column: Kinetex C18 100A (2.6 μm 100×4.6 mm); mobile phase A (0.1% formic acid in water), B (acetonitrile); gradient (time (min)/% B): 0/5, 1/30, 3/95, 4/95, 4.1/5, 6/5.

Method 4
Column: AcQuity UPLC BEH C18 1.7 μm 2.1×30 mm; column temperature 50° C.; Flow 1.0 mL/min; Stop time: 2.00 min; pH 2.6; Eluent A1 0.1% formic acid in Water; Eluent B1 0.1% formic acid in Acetonitrile; Gradient Time (min)/% A (Eluent A1): % B (Eluent B1); 0.00/98:2; 0.10/98:2; 1.50/2:98; 1.80/2:98; 1.90/98:2; 2.00/98:2.

Method 5
Column: SunFire C18 3.5 μm 3.0×30 mm; Column Temperature 40° C.; Flow 2.0 mL/min; Stop Time 2.20 min; pH 2.2; Eluent A1 5 mM Ammonium Hydroxide in Water; Eluent B1 Acetonitrile; Gradient Time (min)/% A (Eluent A1): % B (Eluent B1); 0.00/95:5; 1.70/5:95; 2.00/5:95; 2.10/95:5.

Method 6
Column: Kinetex C18 100A, (2.6 μm 100×4.60 mm); Gradient/(Time (min)/% B) 0/5, 1/30, 3/95, 4/95, 4.1/5, 6/5; mobile phase: 0.1% Formic acid in Water (A)/acetonitrile (B); Flow: 1.4 mL/min; Column Temperature: 40° C.

Method 7
Column: Synergi MAX-RP 100A Mercury (2.5 μm 100×4.6 mm); mobile phase A (0.1% formic acid in water), B (acetonitrile); gradient (time (min)/% B): 0/30, 0.5/30, 1.5/95, 2.4/95, 2.5/30, 3.0/30.

Method 8
Column: Kinetex C18 100A (2.6 μm 100×4.6 mm); mobile phase A (0.1% formic acid in water), B (acetonitrile); gradient (time (min)/% B): 0/50, 1/70, 2/100, 4/100, 4.1/50, 6/50. The ESI-MS data was recorded on an Acquity G2 Xevo-QTOF-MS. The positive ion mass spectrum was deconvoluted using MaxEnt 1 program in the MassLynx software package.

Method 9
Column: Acclaim PepMap C4, 5 μm, 300 Å, (300 m×15 cm); mobile phase A (0.1% formic acid in water/acetonitrile (95/5%)), B (0.1% formic acid in acetonitrile/isopropanol/water (47.5/47.5/5%); gradient (time (min)/% B): 0/5, 2/5, 10/40, 11/95, 13/95, 14/5, 20/5. Samples were diluted 1/100 in MeOH/H$_2$O (50/50%) and ESI-MS data was recorded on a Lumos Orbitrap MS system coupled to an Ultimate 3000 CapLC. The positive ion mass spectrum was deconvoluted using BioPharma Finder 3.0 (Thermo Fisher Scientific) and the mass was reported.

Method 10
Column AcQuity UPLC HSS T3 C18 (1.8 μm 2.1×50 mm); Column Temperature 60° C.; Flow 1.0 mL/min; Stop Time 2.00 min; Eluent A1 0.05% Formic Acid+3.75 mM Ammonium acetate in Water; Eluent B 1 0.04% Formic Acid in Acetonitrile; Gradient Time (min)/% A (Eluent A1): % B (Eluent B1) 0.00/95:5; 1.40/2:98; 1.80/2:98; 1.90/95:5; 2.00/95:5. The UPLC instrument was coupled to a single-stage quadrupole mass spectrometry using electrospray ionization (ESI) in both positive and negative modes. The deconvoluted m/z for (M+H)$^+$ was reported.

Example 1

Traceless Linkers

This example describes the synthesis of a number of traceless linkers, capable of being conjugated to both an amine-containing drug and to a carrier.

TABLE 6

Traceless Linkers L1-L5

| Structure | Number |
|---|---|
| 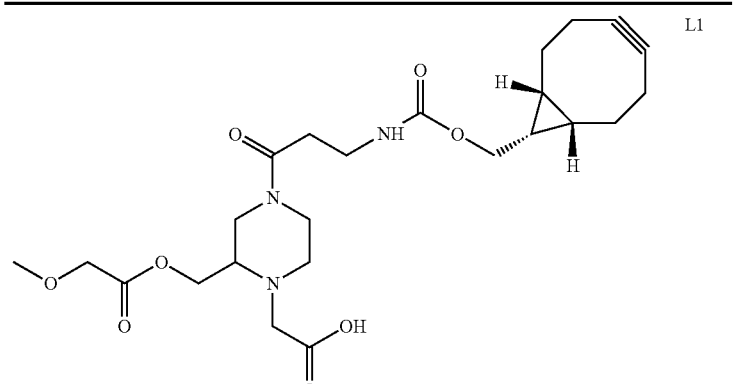 | L1 |
| 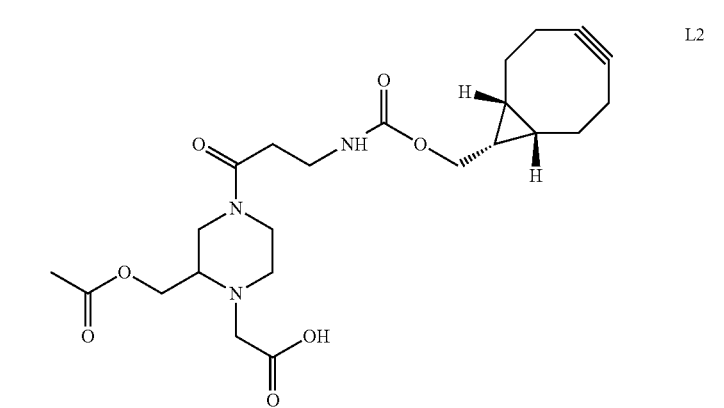 | L2 |

TABLE 6-continued

Traceless Linkers L1-L5

| Structure | Number |
|---|---|
| 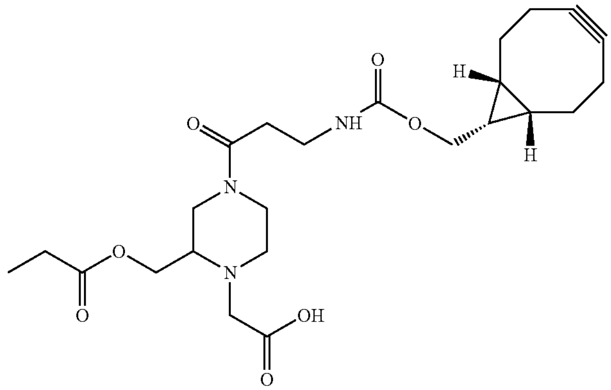 [SMILES: CCC(=O)OCC1CN(C(=O)CCNC(=O)OC[C@@H]2[C@@H]3CCC#CCC[C@@H]32)CCN1CC(=O)O] | L3 |
| 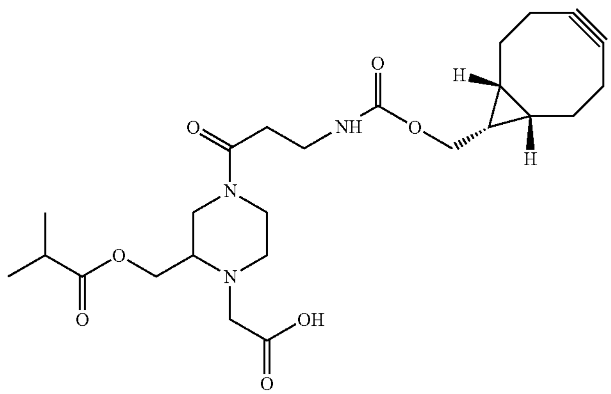 [SMILES: CC(C)C(=O)OCC1CN(C(=O)CCNC(=O)OC[C@@H]2[C@@H]3CCC#CCC[C@@H]32)CCN1CC(=O)O] | L4 |
| 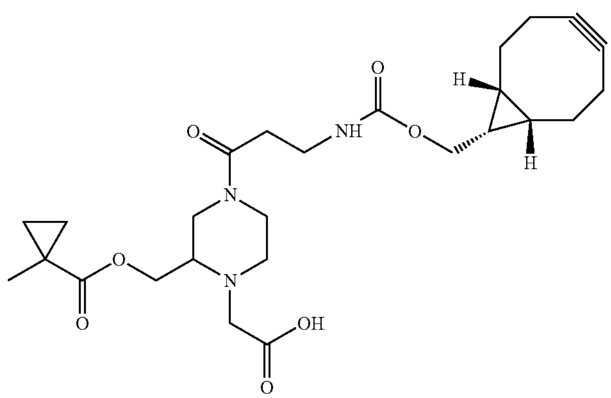 [SMILES: CC1(C(=O)OCC2CN(C(=O)CCNC(=O)OC[C@@H]3[C@@H]4CCC#CCC[C@@H]43)CCN2CC(=O)O)CC1] | L5 |

Synthesis of Traceless Linkers
Common Intermediate: L-INT-1c

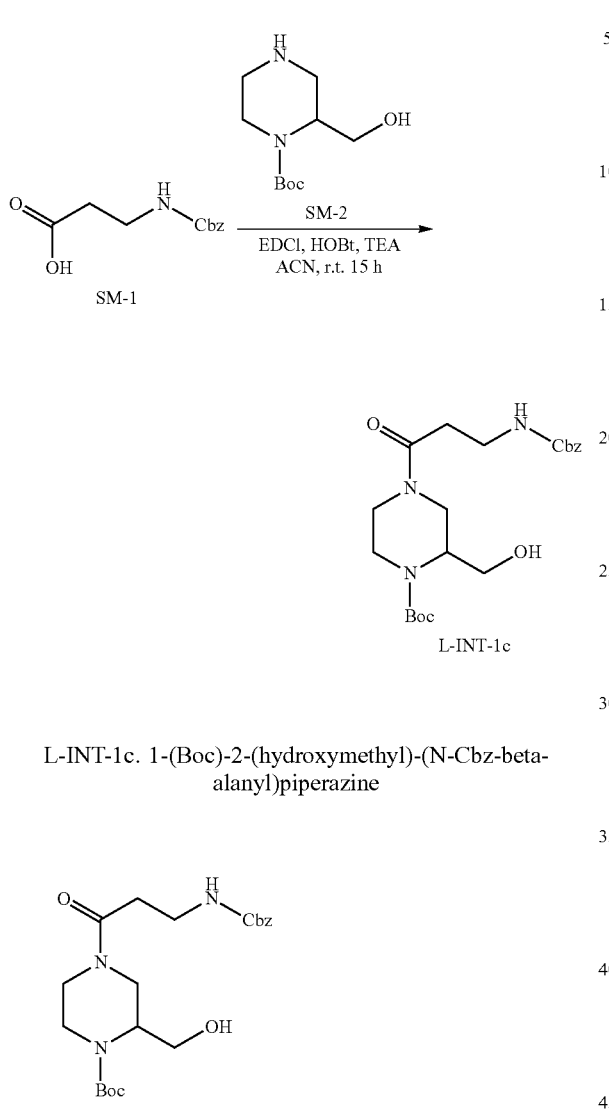

L-INT-1c. 1-(Boc)-2-(hydroxymethyl)-(N-Cbz-beta-alanyl)piperazine

In a 250-mL flask were charged tert-butyl 2-(hydroxymethyl)piperazine-1-carboxylate SM-2 (5.81 g, 26.9 mmol), 3-(((benzyloxy)carbonyl)amino)propanoic acid SM-1 (5 g, 22.4 mmol) and acetonitrile (100 mL). To this suspension was successively added triethylamine (9.37 mL, 67.2 mmol), HOBt (0.686 g, 4.48 mmol) and EDC.HCl (6.44 g, 33.6 mmol). The reaction mixture was stirred at room temperature for 15 hr. After this time, the mixture was diluted with water and extracted three times with ethyl acetate. The combined organic layer was successively washed with a solution of 1M HCl, a saturated solution of NaHCO$_3$ and finally with brine. The organic layer was dried over anhydrous magnesium sulfate, filtered and concentrated on vacuo using a rotoevaporator to afford L-INT-1c (8.75 g, 83% yield) as a colorless oil. The material was used in the next step without further purification. MS (ESI+; method 10) m/z 422.5 (M+H). $^1$H NMR (500 MHz, MeOH-d$_4$) δ 7.49-7.27 (m, 5H), 5.15-4.98 (m, 2H), 4.56-4.27 (m, 1H), 4.19-3.83 (m, 3H), 3.61-3.37 (m, 4H), 3.29-2.55 (m, 5H), 1.49 (s, 9H).

Linker Intermediate Xc

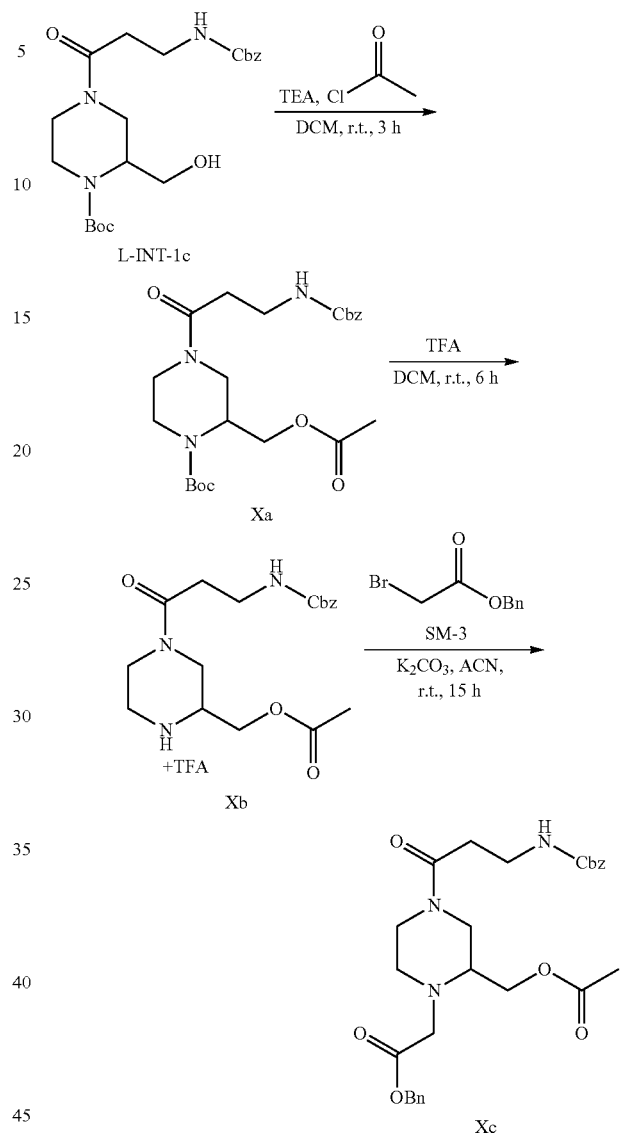

Xa. 1-(Boc)-2-(acetoxymethyl)-4-(N-Cbz-beta-alanyl)piperazine

In a 500 mL flask was prepared a solution of L-INT-1c (8.6 g, 20.4 mmol) in dichloromethane (160 mL). The solution was cooled down to 0° C. using an ice bath, then triethylamine (7.11 mL, 51.0 mmol) was added followed by acetyl chloride (1.74 mL, 24.48 mmol). The reaction mixture was stirred at room temperature for 4 hr. After this time, the mixture was quenched with water and extracted with dichloromethane. The combined organic layer was successively washed with brine, dried over anhydrous magnesium sulfate, filtered, and concentrated on vacuo using a rotoevaporator to afford Xa (10.6 g, 95% yield) as a yellow oil. The material was used in the next step without further purification. MS (ESI+; method 10) m/z 464.3 (M+H). $^1$H NMR (500 MHz, MeOH-d$_4$) δ 7.48-7.27 (m, 5H), 5.18-5.01 (m, 2H), 4.54-3.84 (m, 6H), 3.47-3.36 (m, 2H), 3.19-2.51 (m, 5H), 2.33-2.01 (m, 3H), 1.49 (s, 9H). Exchangeable protons are not visible in MeOD.

Xb.
1-(N-Cbz-beta-alanyl)-3-(acetoxymethyl)piperazine, trifluoroacetic acid salt

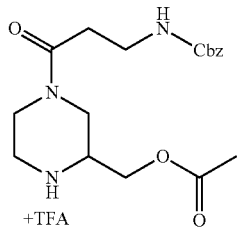

To a 0° C. solution of Xa (10.6 g, 19.44 mmol) in dichloromethane (160 mL) was slowly added trifluoroacetic acid (22.46 mL, 292 mmol). The ice bath was removed and the solution was stirred at room temperature for 6 hr. After this time, the mixture was concentrated to dryness to provide the trifluoroacetic acid salt Xb, which was used without further purification. MS (ESI+) m/z 364.3 (M+H). $^1$H NMR (500 MHz, MeOH-d$_4$) δ 7.52-7.22 (m, 5H), 5.09 (s, 2H), 4.62-4.04 (m, 4H), 3.71-3.38 (m, 5H), 3.17-2.59 (m, 4H), 2.27-2.10 (m, 3H). Exchangeable protons are not visible in MeOD.

Xc. 2-(acetoxymethyl)-4-(N-Cbz-beta-alanyl)-1-piperazineacetic acid benzyl ester

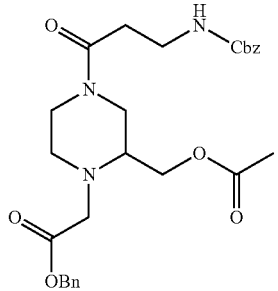 [SMILES: CC(=O)OCC1CN(C(=O)CCNC(=O)OCc2ccccc2)CCN1CC(=O)OCc1ccccc1]

In a 250 mL flask were charged Xb (16 g, 18.1 mmol), potassium carbonate (7.50 g, 54.3 mmol) and acetonitrile (160 mL). Then, benzyl 2-bromoacetate SM-3 (4.26 mL, 27.1 mmol) was added and the reaction mixture was stirred at room temperature for 15 hr. After this time, the reaction mixture was quenched with water and extracted with ethyl acetate. The combined organic layer was successively washed with brine, dried over anhydrous magnesium sulfate, filtered and concentrated on vacuo using a rotoevaporator. The crude mixture was purified by flash chromatography (Biotage isolera, RediSep column: silica 220 g, Eluent A: dichloromethane, Eluent B: dichloromethane+MeOH (9:1), gradient from 0 to 100% B in 20 min) to afford a mixture, which was not pure enough. A second purification was performed using flash chromatography (Biotage isolera, RediSep column: silica SI KP-NH 44 g, Eluent A: cyclohexane, Eluent B: ethyl acetate, gradient from 0 to 100% B in 20 min) to obtain Xc (6.52 g, 63% yield) as a colorless oil. MS (ESI+) m/z 512.3 (M+H). $^1$H NMR (500 MHz, MeOH-d$_4$) δ 7.49-7.15 (m, 10H), 5.17 (s, 2H), 5.08 (s, 2H), 4.19-3.96 (m, 3H), 3.82-3.54 (m, 3H), 3.40 (m, 2H), 3.27-3.08 (m, 2H), 3.06-2.94 (m, 1H), 2.88-2.73 (m, 2H), 2.69-2.52 (m, 2H), 1.99 (d, J=5.1 Hz, 3H). Exchangeable protons are not visible in MeOD.

Xd. 2-(1'-methylcyclopropylcarbonyloxymethyl)-4-(N-Cbz-beta-alanyl)-1-piperazineacetic acid benzyl ester

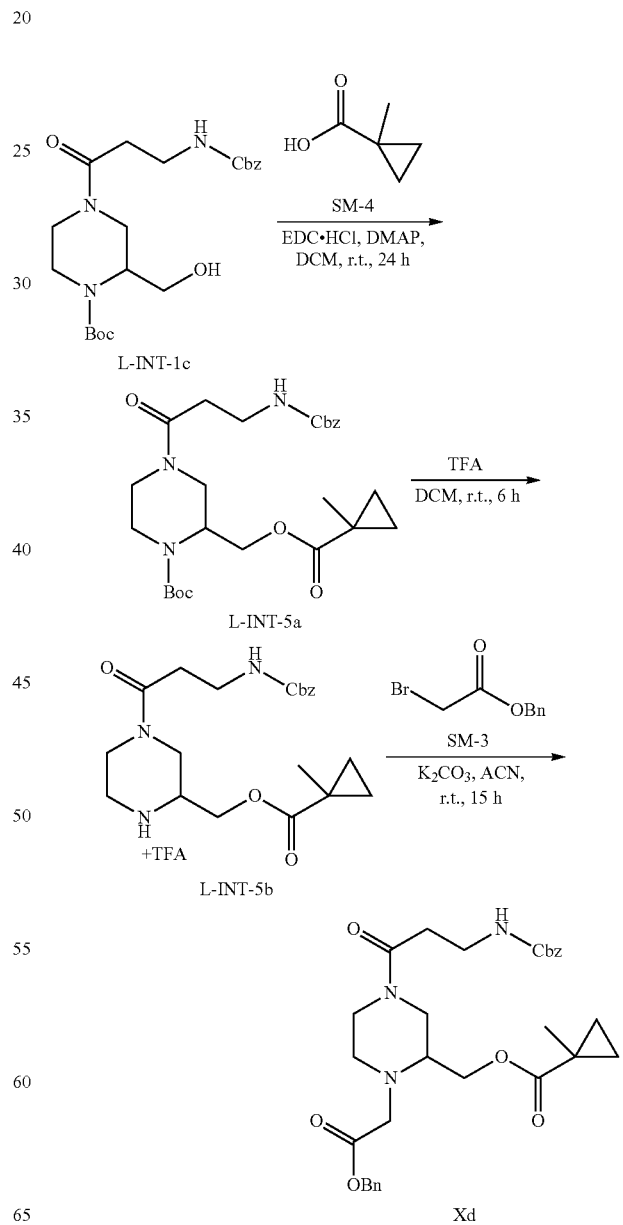

159

L-INT-5a. 1-(Boc)-2-(1'-methylcyclopropylcarbonyloxymethyl)-4-(N-Cbz-beta-alanyl)piperazine

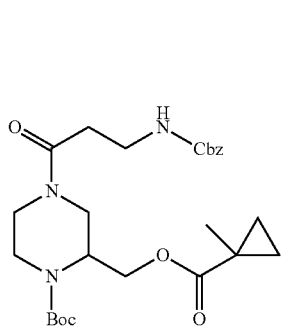 [SMILES: CC(C)(C)OC(=O)N1CCN(C(=O)CCNC(=O)OCc2ccccc2)CC1COC(=O)C1(C)CC1]

To a solution of 1-methylcyclopropane carboxylic acid SM-4 (47.5 mg, 0.475 mmol) in dichloromethane (2 mL) was added EDC-HCl (91 mg, 0.475 mmol) and DMAP (58.0 mg, 0.475 mmol). The reaction was stirred for 30 min at room temperature and L-INT-1c (100 mg, 0.237 mmol) was added. The reaction mixture was stirred at room temperature for 15 hr. After this time, the reaction mixture was quenched with a saturated solution of ammonium chloride and extracted with ethyl acetate. The combined organic layer was successively dried over anhydrous magnesium sulfate, filtered, and concentrated to dryness using a rotavap. The crude residue was purified by flash chromatography (Teledyne Isco, column: RediSep 4 g. Eluent A: dichloromethane, Eluent B: dichloromethane/MeOH 8:2, gradient from 0 to 100% B in 20 min) to afford the desired compound (97 mg, 77% yield) as a light yellow oil. MS (ESI+; method 10) m/z 504.2 (M+H).

Xd. 2-(1'-methylcyclopropylcarbonyloxymethyl)-4-(N-Cbz-beta-alanyl)-1-piperazineacetic acid benzyl ester

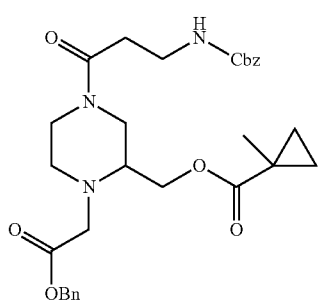 [SMILES: CC1(C(=O)OCC2CN(C(=O)CCNC(=O)OCc3ccccc3)CCN2CC(=O)OCc2ccccc2)CC1]

Xd was prepared in two steps from L-INT-5a following the general methods described for the synthesis of Xb and Xc. L-INT-5: UPLC-MS (method 10): retention time=1.18 min; MS (ESI+) m/z 552.4 (M+H). $^1$H NMR (400 MHz, DMSO-d6) δ 7.40-7.30 (m, 10H), 7.19-7.17 (m, 1H), 5.14-5.06 (m, 2H), 5.05-5.00 (m, 2H), 4.07-3.97 (m, 2H), 3.91-3.79 (m, 1H), 3.67-3.56 (m, 3H), 3.23-3.18 (m, 2H), 3.10-2.88 (m, 3H), 2.78-2.57 (m, 3H), 2.45-2.39 (m, 2H), 1.20 (m, 3H), 1.08-1.07 (m, 2H), 0.72-0.71 (m, 2H).

160

Traceless Linkers; L1-L7

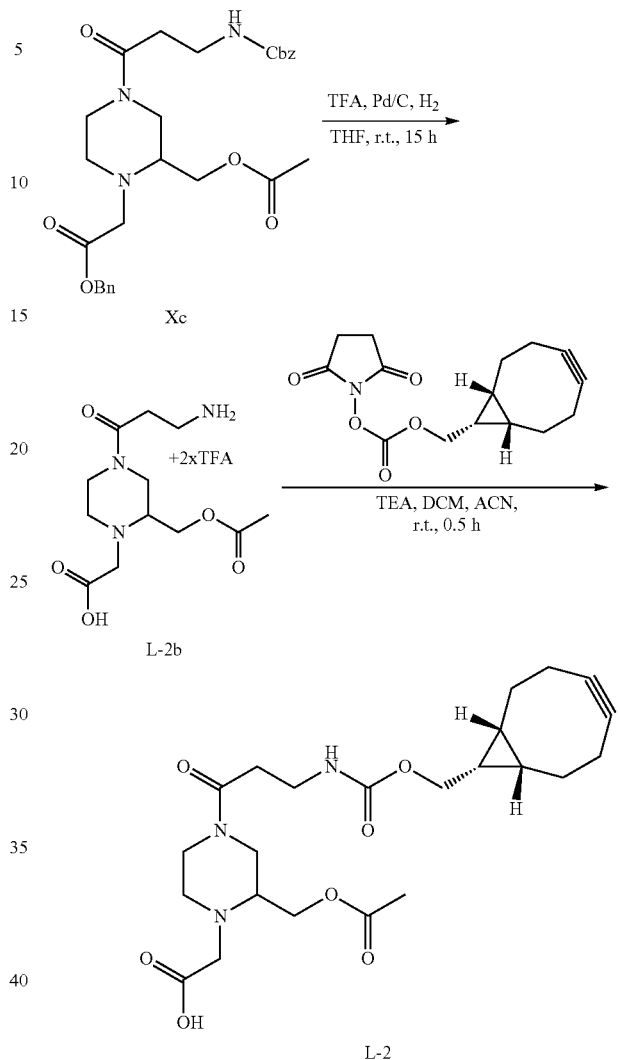

L-2b: 2-(acetoxymethyl)-4-(beta-alanyl)-1-piperazineacetic acid, bis trifluoroacetic acid salt

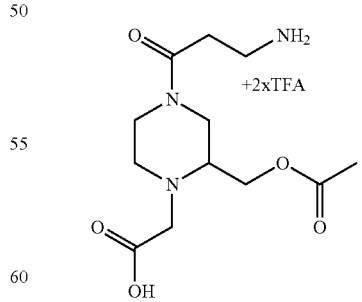

Xc (3 g, 5.86 mmol) was dissolved in tetrahydrofuran (60 mL) and trifluoroacetic acid (1.04 mL, 13.49 mmol) was added followed by Palladium on charcoal (0.624 g, 5.86 mmol). The flask was successively put under vacuum and backfilled with hydrogen. The operation was repeated three times and the reaction mixture was stirred at room temperature for 15 hr. After this time, the mixture was diluted with a dichloromethane/methanol mixture (9:1, 50 mL) and filtered through a pad of Celite. The Celite was carefully washed with methanol (50 mL) and the combined filtrate was concentrated on vacuo to provide crude title material L-2b (3.2 g, 95% yield) as a yellowish foam. MS (ESI+) m/z 288.3 (M+H). $^1$H NMR (500 MHz, MeOH-$d_4$) δ 4.50-4.16 (m, 3H), 4.10-3.82 (m, 3H), 3.72-3.39 (m, 4H), 3.29-3.20 (m, 3H), 2.92-2.76 (m, 2H), 2.11 (d, J=5.1 Hz, 3H). Exchangeable protons are not visible in MeOD.

L2. 2-(acetoxymethyl)-4-(N-(((1R,8S,9s)-bicyclo[6.1.0]non-4-yn-9-yl)methoxycarbonyl)-beta-alanyl)-1-piperazineacetic acid

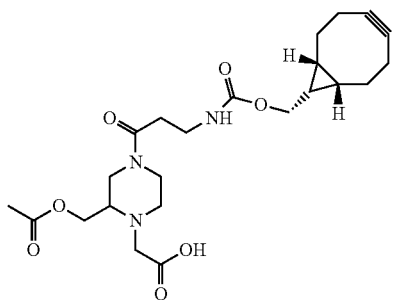

Crude L-2b (200 mg, 0.349 mmol) was taken up in dichloromethane (2 mL) and acetonitrile (3 mL) to provide a faintly cloudy mixture. Addition of triethylamine (0.195 mL, 1.397 mmol) and ((1R,8S,9s)-bicyclo[6.1.0]non-4-yn-9-yl)methyl (2,5-dioxopyrrolidin-1-yl) carbonate (112 mg, 0.384 mmol) resulted in a solution, which was evaporated after 1 hr. The crude material was either: (i) Dissolved in 6 mL 3:1 acetonitrile:water and purified by HPLC (Column: Waters XBridge BEH 5 μm 19×150 mm; method: 15-30% acetonitrile 10 min gradient (10 mM ammonium hydroxide) in water 30 mL/min). The fractions were evaporated, flash frozen and lyophilized to provide L2; or (ii) Directly adsorbed on Isolute and purified by reverse phase chromatography (Teledyne Isco, column: RediSep C18 15.5 gold, Eluent A: water, Eluent B: acetonitrile, gradient from 10 to 100% B in 20 min) to afford L2 after lyophilization. White powder. UPLC-MS (method 10): retention time=0.71 min; MS (ESI+) m/z 464.3 (M+H). $^1$H NMR (500 MHz, MeOH-d4) δ 4.31-4.11 (m, 4H), 4.06-3.96 (m, 1H), 3.84-3.64 (m, 1H), 3.55-3.36 (m, 5H), 3.29-3.00 (m, 2H), 2.98-2.74 (m, 2H), 2.66-2.54 (m, 2H), 2.32-2.16 (m, 6H), 2.10-2.03 (m, 3H), 1.69-1.57 (m, 2H), 1.46-1.35 (m, 1H), 1.03-0.89 (m, 2H). Exchangeable protons are not visible in MeOD.

Species shown in Table 7 were prepared using methods analogous to those used in the synthesis of L2.

TABLE 7

Exemplary Traceless Linker Species

| Structure | Number (starting intermediate) | LCMS: [M + H]; retention time; method | $^1$H-NMR (400 MHz, CD$_3$OD) |
|---|---|---|---|
| 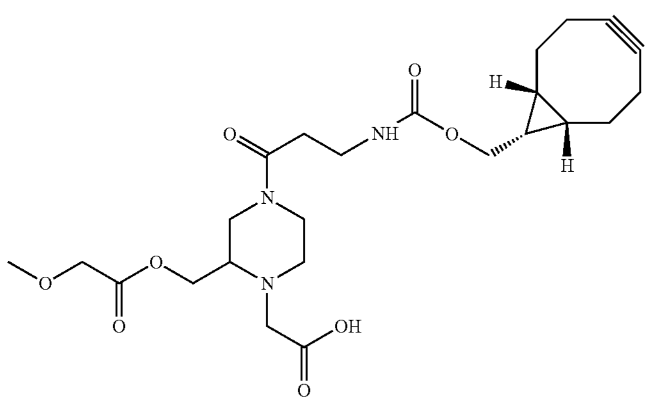 | L1 (L-INT-1) | 494.1; 0.98 min; 1 | 4.25 (m, 2H); 4.14 (m, 4H); 4.0-3.44 (m, 5H), 3.42 (s, 3H), 3.3-3.1 (m, 2H), 2.96 (m, 1H), 2.83 (m, 1H), 2.69 (m, 1H), 2.62 (m, 2H), 2.21 (m, 6H), 1.61 (m, 2H), 1.37 (m, 1H), 0.93 (m, 2H) |

2-(2'-methoxyacetoxymethyl)-4-(N-(((1R,8S,9s)-bicyclo[6.1.0]non-4-yn-9-yl)methoxycarbonyl)-beta-alanyl)-1-piperazineacetic acid TABLE 7-continued Exemplary Traceless Linker Species

| Structure | Number (starting intermediate) | LCMS: [M + H]; retention time; method | $^1$H-NMR (400 MHz, CD$_3$OD) |
|---|---|---|---|
| 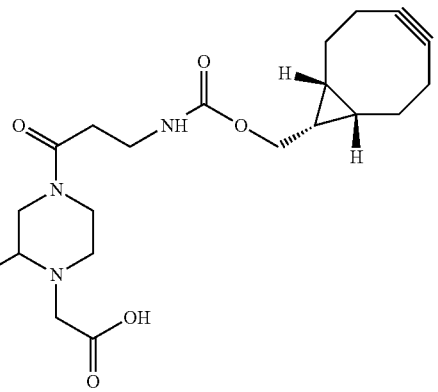<br>2-(propanoyloxymethyl)-4-(N-(((1R,8S,9s)-bicyclo[6.1.0]non-4-yn-9-yl)methoxycarbonyl)-beta-alanyl)-1-piperazineacetic acid | L3 (L-INT-3) | 478.2; 1.03 min; 1 | 4.17 (m, 3H); 3.99 (dd, 1H), 3.76 (dd, 1H), 3.47 (m, 2H), 3.37 (M, 2H), 3.06 (dd, 1H), 2.91 (m, 1H), 2.79 (m, 1H), 2.60 (t, 2H), 2.36 (m, 2H), 2.19 (m, 6H), 1.59 (m, 2H), 1.38 (m, 1H), 1.12 (t, 3H), 0.96 (m, 2H) |
| 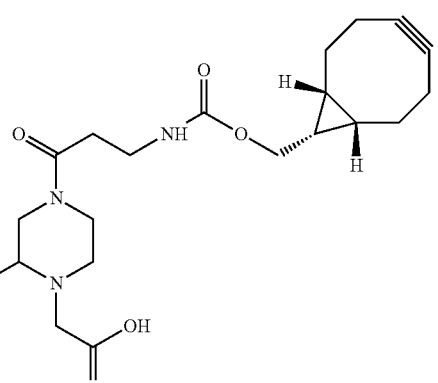<br>2-(isobutanoyloxymethyl)-4-(N-(((1R,8S,9s)-bicyclo[6.1.0]non-4-yn-9-yl)methoxycarbonyl)-beta-alanyl)-1-piperazineacetic acid | L4 (L-INT-4) | 492.7; 0.82 min; 2 | 4.17 (m, 3H); 3.99 (dd, 1H), 3.76 (dd, 1H), 3.41 (m, 4H), 3.06 (dd, 1H), 2.90 (m, 1H), 2.79 (m, 1H), 2.58 (m, 3H), 2.19 (m, 6H), 1.60 (m, 2H), 1.37 (m, 1H), 1.16 (d, 6H), 0.96 (t, 2H) |

TABLE 7-continued

Exemplary Traceless Linker Species

| Structure | Number (starting intermediate) | LCMS: [M + H]; retention time; method | ¹H-NMR (400 MHz, CD₃OD) |
|---|---|---|---|
| 2-(1'-methylcyclopropylcarbonyloxymethyl)-4-(N-(((1R,8S,9s)-bicyclo[6.1.0]non-4-yn-9-yl)methoxycarbonyl)-beta-alanyl)-1-piperazineacetic acid | L5 (L-INT-5) | 504.2; 1.09 min; 1 | 4.16 (m, 4H); 3.99 (m, 1H), 3.76 (m, 1H), 3.5-3.35 (m, 5H), 3.06 (m, 1H), 2.93 (m, 1H), 2.88 (dt, 1H), 2.77 (m, 1H), 2.61 (m, 2H), 2.19 (m, 6H), 1.60 (m, 2H), 1.38 (m, 1H), 1.29 (s, 3H), 1.22 (d, 2H), 0.93 (t, 2H), 0.73 (dq, 2H) |
| Isomer 1. 2-(acetoxymethyl)-4-(N-(((1R,8S,9s)-bicyclo[6.1.0]non-4-yn-9-yl)methoxycarbonyl)-beta-alanyl)-1-piperazineacetic acid | L6 (L-INT-6) | 464.2; 0.95 min; 1 | Used as a crude, no NMR |

TABLE 7-continued

Exemplary Traceless Linker Species

| Structure | Number (starting intermediate) | LCMS: [M + H]; retention time; method | ¹H-NMR (400 MHz, CD₃OD) |
|---|---|---|---|
| 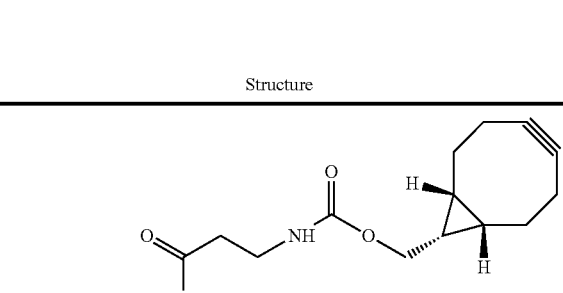<br>Isomer 2.<br>2-(acetoxymethyl)-4-(N-(((1R,8S,9s)-bicyclo[6.1.0]non-4-yn-9-yl)methoxycarbonyl)-beta-alanyl)-1-piperazineacetic acid | L7<br>(L-INT-7) | 464.2;<br>0.96 min;<br>1 | Used as a crude, no NMR |

Traceless Linker L8. 2-(2'-methoxyacetoxymethyl)-4-(6'-azidohexanoyl)-1-piperazineacetic acid

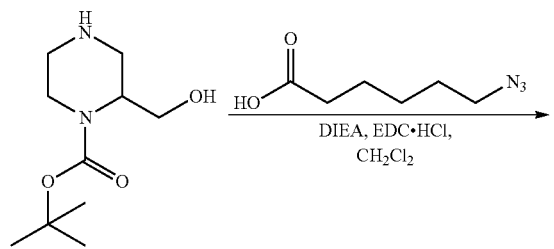

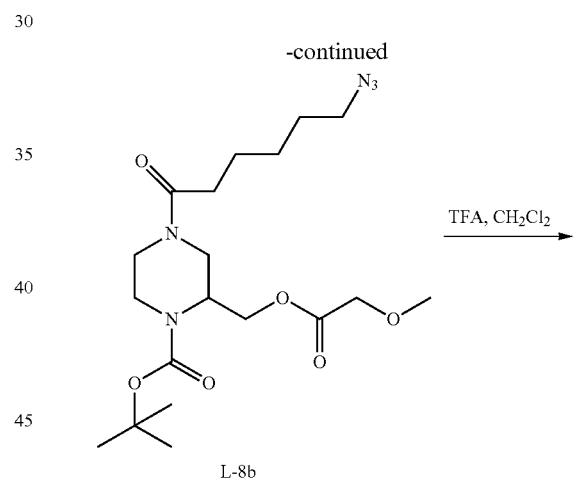

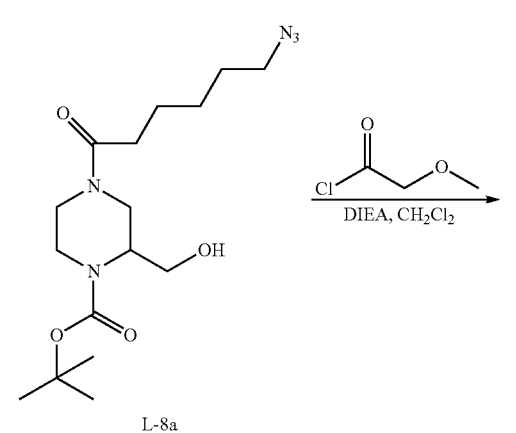

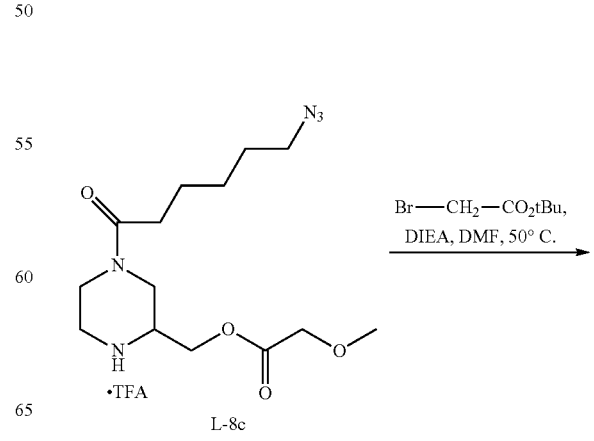

-continued

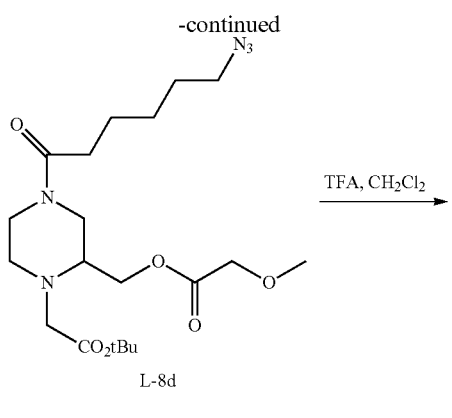

L-8d

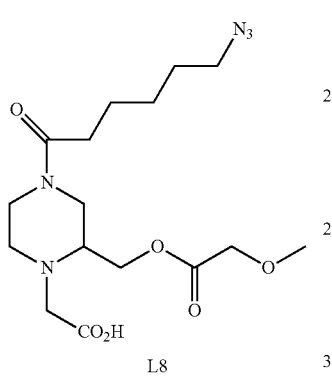

L-8

L-8a. 1-(Boc)-2-(hydroxymethyl)-4-(6'-azido-hexanoyl)piperazine

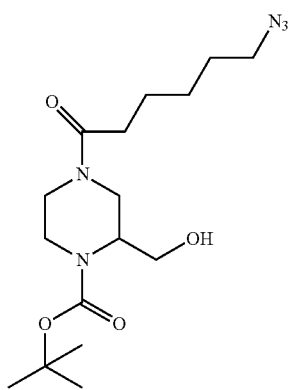 [SMILES: CC(C)(C)OC(=O)N1CCN(C(=O)CCCCCN=[N+]=[N-])CC1CO]

6-azidohexanoic acid (743 mg, 4.73 mmol) and N-(3-dimethylaminopropyl)-N'-ethylcarbodiimide hydrochloride (1.0 g, 5.22 mmol) were weighed into a round-bottomed flask and dissolved in dichloromethane (20 mL). After 5 min, solid tert-butyl 2-(hydroxymethyl)piperazine-1-carboxylate (0.98 g, 4.53 mmol) and diisopropylethylamine (1.0 mL, 5.73 mmol) were added and the solution was stored at room temperature overnight. The next day, the reaction mixture was diluted with 100 mL dichloromethane and washed with 1 M HCl (2×50 mL), 1 M NaOH (1×50 mL), and brine (1×50 mL). The organic phase was concentrated to provide L-8a. MS (ESI+) m/z 356.3 (M+H).

L-8b. 1-(Boc)-2-(2'-methoxyacetoxymethyl)-4-(6''-azidohexanoyl)piperazine

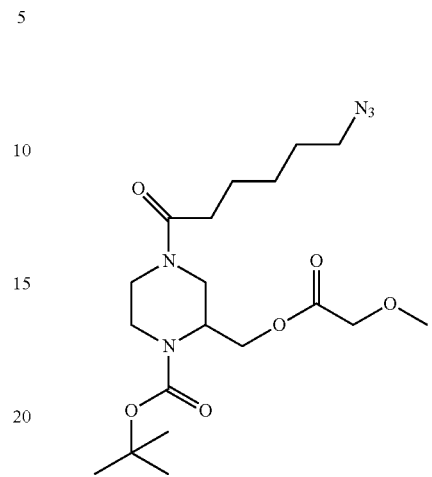

L-8a (959 mg, 2.70 mmol) was dissolved in dichloromethane (12 mL) in a round-bottomed flask. A stir bar and diisopropylethylamine (1 mL, 5.73 mmol) were added, followed by 2-methoxyacetyl chloride (0.32 mL, 3.51 mmol), and the flask was capped. The reaction was stirred at room temperature. After 6 h, 100 µL additional 2-methoxyacetyl chloride was added. After 30 min, the reaction mixture was diluted with 90 mL ethyl acetate and washed with 1 M HCl (2×25 mL) and brine (1×20 mL). The organic phase was concentrated using a rotoevaporator. The product was purified by flash column chromatography on silica with an ethyl acetate:heptanes gradient. Product containing fractions were combined and concentrated to provide L-8b. MS (ESI+) m/z=428.3 (M+H).

L-8c. 1-(6'-azidohexanoyl)-3-(2''-methoxyacetoxymethyl)piperazine, trifluoroacetic acid salt

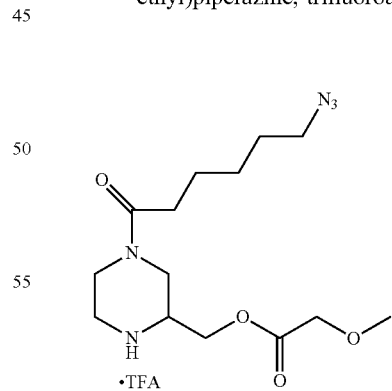

L-8b (846 mg, 1.979 mmol) was dissolved in trifluoroacetic acid (10 mL, 130 mmol) and dichloromethane (10 mL). The solution was stirred at room temperature. After 1 h, the solvents were removed using a rotoevaporator and the product dried under vacuum to provide L-8c. MS (ESI+) m/z 328.2 (M+H).

L-8d. 2-(2'-methoxyacetoxymethyl)-4-(6"-azido-hexanoyl)-1-piperazineacetic acid t-butyl ester

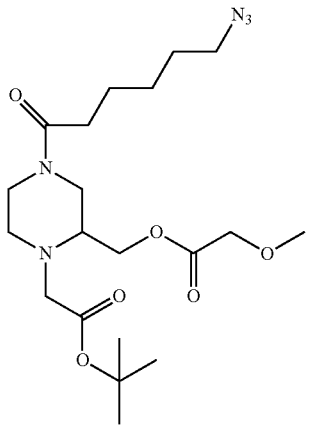 [SMILES: COCC(=O)OCC1CN(C(=O)CCCCCN=[N+]=[N-])CCN1CC(=O)OC(C)(C)C]

L-8c (439 mg, 0.994 mmol) was dissolved in dimethylformamide (5 mL) in a glass vial with a stirbar. t-Butyl bromoacetate (0.220 mL, 1.491 mmol) and diisopropylethylamine (0.868 mL, 4.97 mmol) were added, and the vial was capped. The reaction was stirred at 50° C. overnight. The next day, the reaction mixture was removed from the heat source and stored at −20 OC until purification the following day. The reaction mixture was purified without extractive work up by flash column chromatography on silica with a heptane:ethyl acetate gradient. Product containing fractions were combined, and concentrated to provide L-8d. MS (ESI−) m/z=486.5 (M+formate).

L8. 2-(2'-methoxyacetoxymethyl)-4-(6"-azido-hexanoyl)-1-piperazineacetic acid

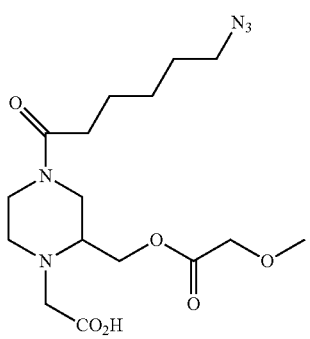 [SMILES: COCC(=O)OCC1CN(C(=O)CCCCCN=[N+]=[N-])CCN1CC(=O)O]

L-8d (150 mg, 0.317 mmol) was dissolved in dichloromethane (5 mL) and trifluoroacetic acid (5 mL) and the reaction was stirred at room temperature overnight. The next day, the solution was concentrated using a rotoevaporator and the residue was redissolved in 4 mL acetonitrile. The solution was filtered and purified by preparative reverse phase HPLC with mass directed fraction collection (method below). Product containing fractions were pooled, frozen, and lyophilized to provide L8. MS (ESI+) m/z=386.5 (M+H). Preparative HPLC conditions: Waters Sunfire C18; particle size: 5 μm; column size: 30×50 mm; eluent/gradient: 10% $CH_3CN/H_2O$/0.7 min, 10-30% $CH_3CN/H_2O$/3.5 min, 30-95% $CH_3CN/H_2O$ 0.5 min ($CH_3CN$ and $H_2O$ containing 0.1% TFA); flow rate: 75 mL/min; column temperature: room temperature; collection m/z: +385.

Traceless Linkers: L9-L11

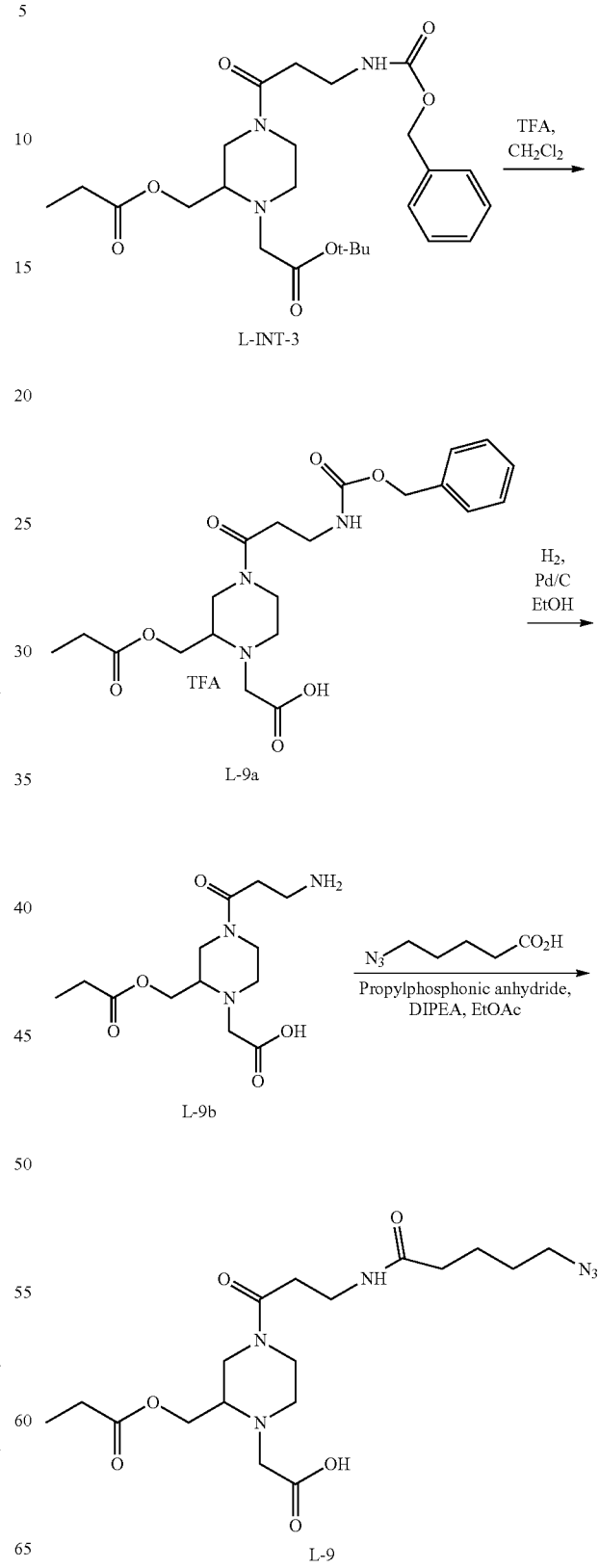

L-9a. 2-(propanoyloxymethyl)-4-(N-Cbz-beta-alanyl)-1-piperazineacetic acid, trifluoroacetic acid salt

L9.

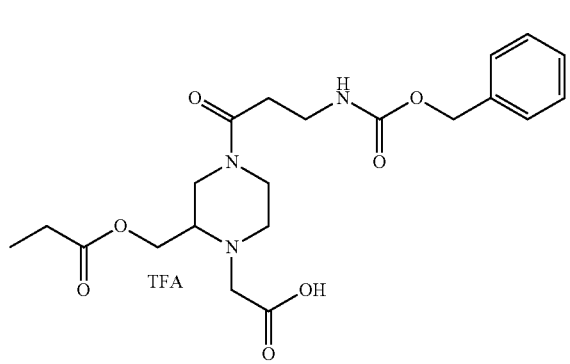 [SMILES: CCC(=O)OCC1CN(C(=O)CCNC(=O)OCc2ccccc2)CCN1CC(=O)O]

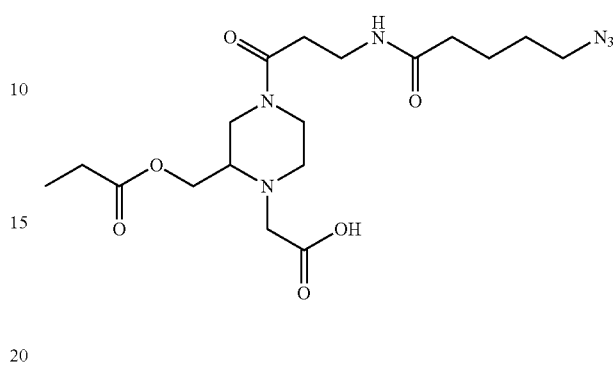

L-INT-3 (250 mg, 0.51 mmol) was dissolved in dichloromethane (5 mL) at 0° C., then treated with trifluoroacetic acid (2.5 mL) and stirred at room temperature 6 h under argon. The reaction was evaporated, washed with pentane and dried to provide crude L-9a as a trifluoroacetic acid salt. LCMS (method 5): retention time=0.262 min; MS (ESI+) m/z 436.2 (M+H).

L-9b. 2-(propanoyloxymethyl)-4-(beta-alanyl)-1-piperazineacetic acid

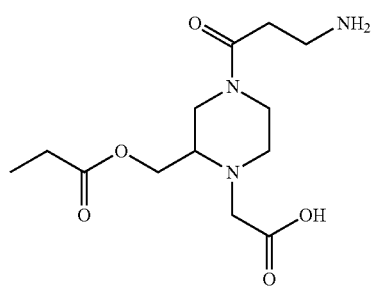 [SMILES: CCC(=O)OCC1CN(C(=O)CCN)CCN1CC(=O)O]

L-9a (250 mg, 0.57 mmol) was dissolved in ethanol (5 mL), to which was added 10% palladium on carbon (25 mg). The solution was stirred under a balloon of hydrogen gas for 6 h and then filtered through Celite®, washing with ethanol. The combined filtrates were evaporated to provide compound L-9b. LCMS (method 5): retention time=0.774 min; MS (ESI+) m/z 302.2 (M+H).

L-9b (100 mg, 0.33 mmol) and 5-azidopentanoic acid (57 mg, 0.40 mmol) in ethyl acetate (5 mL) at 0° C. were treated with diisopropylethylamine (107 mg, 0.83 mmol) and propylphosphonic anhydride (50% solution in ethyl acetate, 158 mg, 0.50 mmol). The reaction was stirred at room temperature 16 h under argon, then quenched with water and evaporated. Initial flash chromatography (SiO$_2$, 10% methanol:dichloromethane) was followed by preparative HPLC (column: zorbax C-18 4.6×150 mm; Mobile phase A=:methanol (1:1) 0.01% TFA in water, mobile phase B=acetonitrile:methanol (1:1); time=0 min: 30% B; 1 min: 70% B; 6 min: 100% B; 1 mL/min) to provide L$_9$. LCMS (method 5): retention time=0.18 min; MS (ESI+) m/z 427.1 (M+H). $^1$H-NMR (MeOH-d$_4$, ppm) (all assignments provisional) 4.23-4.17 (m, 2H), 4.16-3.98 (m, 1H), 3.78-3.62 (m, 1H), 3.54 (s, 2H), 3.46-3.43 (t, J=4, 3H), 3.26-3.20 (m, 1H), 3.18-3.05 (m, 1H), 3.03-2.76 (m, 2H), 2.64-2.61 (t, J=8, 2H), 2.43-2.36 (m, 2H), 2.24-2.21 (t, J=8, 2H), 1.75-1.58 (m, 4H), 1.15-1.12 (t, J=8, 3H). Exchangeable protons are not visible in MeOD.

Species shown in Table 8 were prepared using methods analogous to those used in the synthesis of L-9:

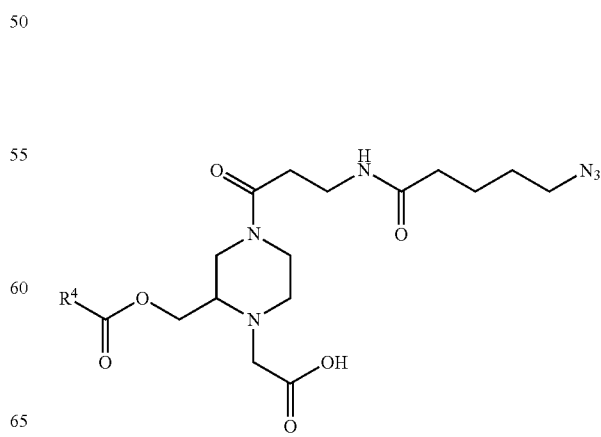

TABLE 8

Exemplary Traceless Linker Species

| R[4], Name | Number (starting intermediate) | LCMS: [M + H]; retention time; method | $^1$H-NMR (300 MHz, CD$_3$OD) |
|---|---|---|---|
| R[4] = (CH$_3$)$_2$CH— 2-(isobutanoyl-oxymethyl)-4-(N-(5'-azidopentanoyl)-beta-alanyl)-1-piperazineacetic acid | L10 (L-INT-4) | 441.1 0.16 min 5 | 4.21-4.15 (m, 2H), 4.04-3.84 (t, J = 16, 1H), 3.81-3.73 (m, 1H), 3.55 (s, 2H), 3.49-3.45 (t, J = 8, 3H), 3.34 (s, 1H), 3.27-3.22 (m, 1H), 3.14-3.10 (m, 2H), 2.99-2.80 (m, 2H), 2.70-2.57 (m, 3H), 1.72-1.58 (m, 4H), 1.19-1.17 (d, J = 8, 6H). |
| R[4] = H$_3$C⟨cyclopropyl⟩ 2-(1'-methylcyclopropyl-carbonyloxymethyl)-4-(N-(5''-azidopentanoyl)-beta-alanyl)-1-piperazineacetic acid | L11 (L-INT-5) | 453.2 0.21 min 5 | 4.21-4.16 (dd, J = 16,4, 2H), 4.05-3.99 (t, J = 12, 1H), 3.83-3.72 (m, 1H), 3.56 (s, 2H), 3.49-3.45 (t, J = 8, 3H), 3.28-3.20 (m, 1H), 3.18-3.04 (m, 1H), 3.02-2.76 (m, 2H), 2.72-2.54 (m, 2H), 2.24-2.21 (t, J = 8, 2H), 1.72-1.56 (m, 5H), 1.13 (s, 3H), 1.26-1.21 (m, 2H), 1.07-0.90 (m, 1H), 0.76-0.74 (t, J = 4, 2H) |

Traceless Linkers: L12 and L13

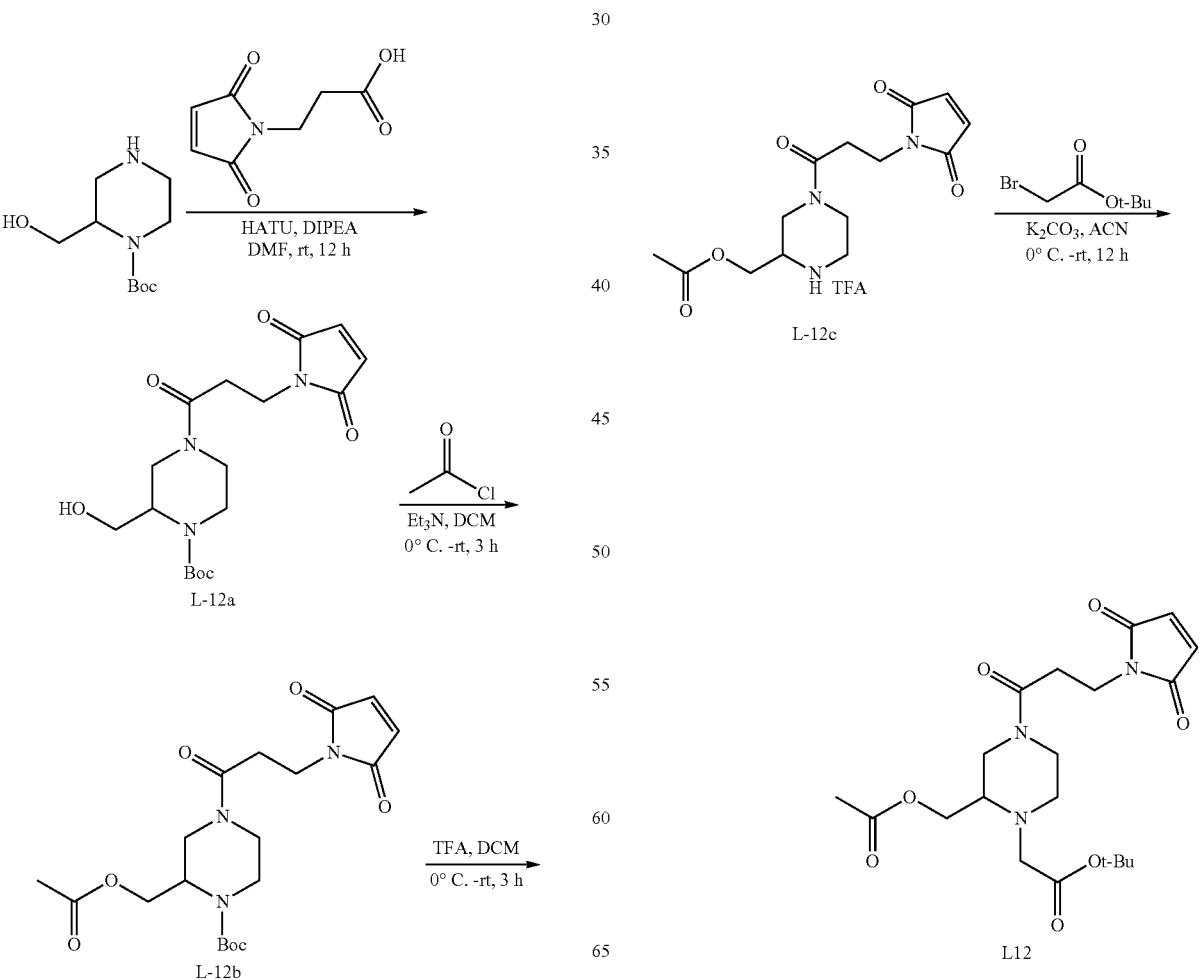

L-12a. 1-(Boc)-2-(hydroxymethyl)-4-(N-maleoyl-beta-alanyl)piperazine

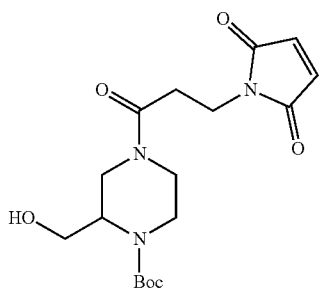 [SMILES: CC(C)(C)OC(=O)N1CCN(C(=O)CCN2C(=O)C=CC2=O)CC1CO]

tert-Butyl 2-(hydroxymethyl)piperazine-1-carboxylate (200 mg, 0.93 mmol) was dissolved in dichloromethane (10 mL) at 0° C. Diisopropylethylamine (359 mg, 2.78 mmol) and HATU (422 mg, 1.11 mmol) were added and the solution was stirred 15 min at 0° C. 3-maleimidopropionic acid (187 mg, 1.11 mmol) was added, and then the reaction was stirred 12 h at room temperature under argon. The reaction was diluted with water and extracted with dichloromethane. The organic layer was washed with brine, dried over sodium sulfate and concentrated. Purification by flash chromatography (neutral alumina, 2% methanol:ethyl acetate provided the title material L-12a. LCMS (method 6): retention time=2.87 min.

L-12b. 1-(Boc)-2-(acetoxymethyl)-4-(N-maleoyl-beta-alanyl)piperazine

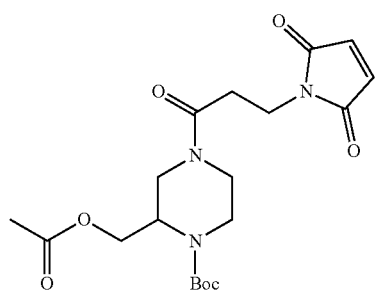 [SMILES: CC(=O)OCC1CN(C(=O)CCN2C(=O)C=CC2=O)CCN1C(=O)OC(C)(C)C]

To L-12a (300 mg, 0.82 mmol) and triethylamine (330 mg, 3.27 mmol) in dichloromethane (4 mL) at 0° C. under argon was dropwise added acetyl chloride (125 mg, 1.64 mmol). The reaction was stirred at room temperature for 3 h, then treated with water and extracted with dichloromethane. The organic layer was dried (sodium sulfate), concentrated and purified by flash chromatography (neutral alumina, 2% methanol:ethyl acetate) to provide the title material L-12b. LCMS (method 6): retention time=3.2 min.

L-12c. 1-(N-maleoyl-beta-alanyl)-3-(acetoxymethyl)piperazine, trifluoroacetic acid salt

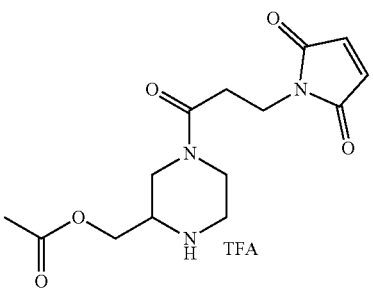 [SMILES: CC(=O)OCC1CN(C(=O)CCN2C(=O)C=CC2=O)CCN1]

L-12b (200 mg, 0.49 mmol) was dissolved in dichloromethane (5 mL) at 0° C., then treated dropwise with trifluoroacetic acid (0.4 mL) and stirred at room temperature 3 h under argon. The reaction was evaporated, washed with pentane and dried to provide crude title material L-12c. LCMS (method 6): retention time=1.709 min; MS (ESI+) m/z 310 (M+H).

L12. 2-(acetoxymethyl)-4-(N-maleoyl-beta-alanyl)-1-piperazineacetic acid t-butyl ester

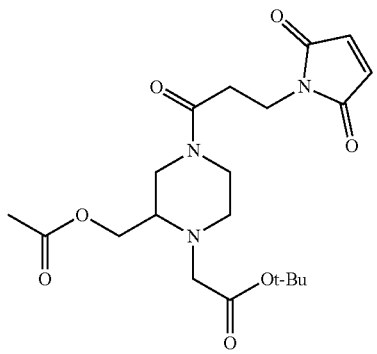 [SMILES: CC(=O)OCC1CN(C(=O)CCN2C(=O)C=CC2=O)CCN1CC(=O)OC(C)(C)C]

To L-12c (140 mg, 0.45 mmol) and potassium carbonate (156 mg, 1.13 mmol) in acetonitrile (5 mL) at 0° C. was dropwise added tert-butyl bromoacetate (100 mg, 0.54 mmol). The reaction was warmed to 10-15° C., then allowed to stir for 12 h at room temperature under argon. The reaction was diluted with water and extracted with ethyl acetate. The organic layer was dried (sodium sulfate), concentrated and purified by preparative HPLC (column: zorbax eclipse XDB C18, 21.2×150 mm, 5 μm; Mobile phase A=water, mobile phase B=acetonitrile; time=0 min: 30% B; 2 min: 40% B; 10 min: 60% B) to provide L12. LCMS (method 6): retention time=3.08 min; MS (ESI+) m/z 424 (M+H). $^1$H-NMR (CDCl$_3$, ppm) 6.69 (s, 2H), 4.25-4.14 (m, 2H), 4.09-3.96 (m, 2H), 3.88-3.83 (t, J=9, 2H), 3.65-3.54 (m, 1H), 3.46-3.33 (m, 2H), 3.31-3.17 (m, 2H), 3.05-2.98 (m, 2H), 2.84-2.75 (m, 2H), 2.68-2.63 (t, J=9, 2H), 2.09-2.07 (d, J=6, 3H), 1.45 (s, 9H).

L13 was prepared using methods analogous to those used in the synthesis of L12:

L13. 2-(2'-methoxyacetoxymethyl)-4-(N-maleoyl-beta-alanyl)-1-piperazineacetic acid t-butyl ester (1-(2-(tert-butoxy)-2-oxoethyl)-4-(3-(maleimidyl)propanoyl)piperazin-2-yl)methyl 2-methoxyacetate

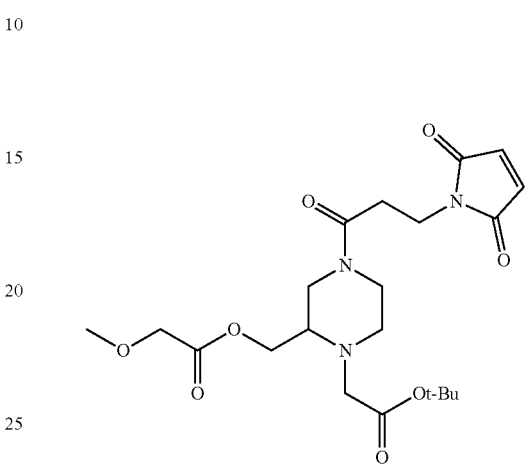

L13. LCMS (method 6): retention time=3.04 min; MS (ESI+) m/z 454.5 (M+H). $^1$H-NMR (CDCl$_3$, ppm) 6.70 (s, 2H), 4.40-4.24 (m, 1H), 4.20-4.10 (m, 1H), 4.07-4.60 (d, J=4, 2H), 4.02-3.94 (m, 1H), 3.87-3.83 (t, J=8, 2H), 3.70-3.60 (m, 1H), 3.68-3.60 (m, 1H), 3.58-3.51 (m, 1H), 3.45 (s, 3H), 3.41-3.39 (d, J=8, 1H), 3.36-3.32 (s, 1H), 3.32-3.28 (s, 1H), 3.18-3.10 (m, 1H), 3.04-2.97 (m, 1H), 2.83-2.81 (t, J=4, 1H), 2.79-2.75 (m, 1H), 2.67-2.64 (t, J=8, 2H), 1.46 (s, 9H).

Traceless Linkers; L14-L16

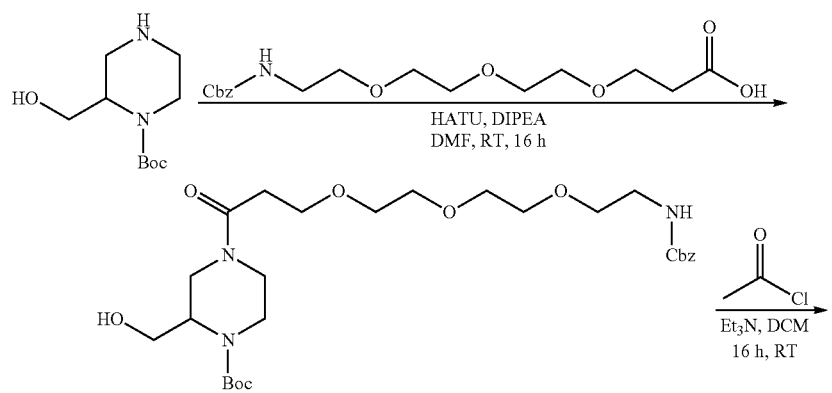

L-14a

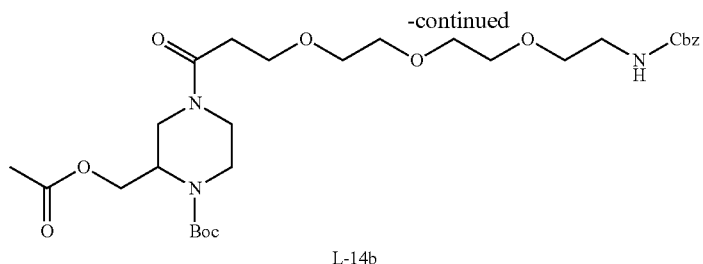

L-14b

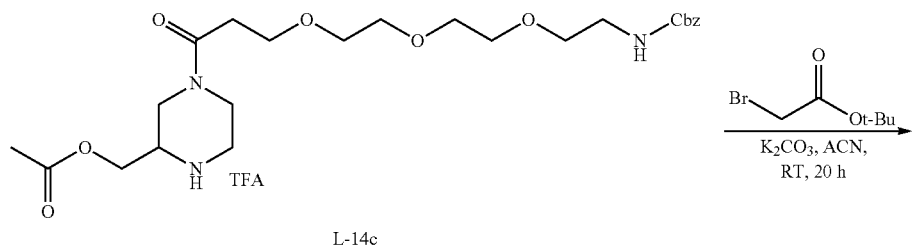

L-14c

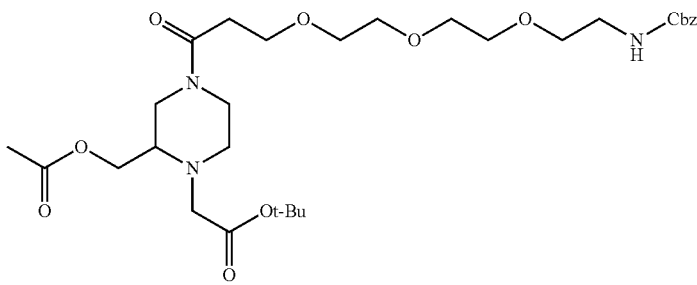

L14

L14a. 1-(Boc)-2-(hydroxymethyl)-4-(3'-(2''-(2'''-(2''''-((N-Cbz)-amino)ethoxy)ethoxy)ethoxy)propanoyl)piperazine

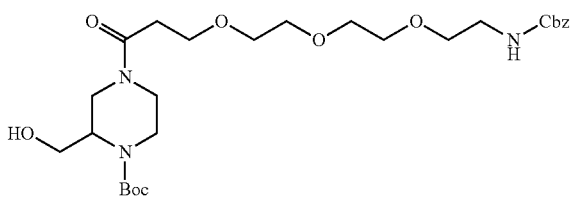 [SMILES: CC(C)(C)OC(=O)N1CCN(C(=O)CCOCCOCCOCCNC(=O)OCc2ccccc2)CC1CO]

To tert-butyl 2-(hydroxymethyl)piperazine-1-carboxylate (1.0 g, 4.63 mmol) dissolved in dichloromethane (20 mL) at 0° C. was added diisopropylethylamine (1.79 g, 13.9 mmol) and HATU (2.10 g, 5.55 mmol). The solution was stirred 15 min at 0° C. 3-(2'-(2''-(2'''-((N-Cbz)-amino)ethoxy)ethoxy)ethoxy)propanoic acid (1.64 g, 4.63 mmol) was added and the reaction was stirred 16 h at room temperature under argon. The reaction was diluted with water and extracted with ethyl acetate. The organic layer was washed with brine, dried over sodium sulfate and concentrated. Purification by flash chromatography (SiO₂, 1-4% methanol:dichloromethane) provided the title material L-14a. LCMS (method 5): retention time=1.27 min; MS (ESI+) m/z 554.3 (M+H).

L-14b. 1-(Boc)-2-(acetoxymethyl)-4-(3'-(2''-(2'''-(2''''-((N-Cbz)-amino)ethoxy)ethoxyethoxy)propanoyl)piperazine To L-14a (500 mg, 0.90 mmol) and triethylamine (228 mg, 2.26 mmol) dissolved in dichloromethane (20 mL) at 0° C. was dropwise added acetyl chloride (83 mg, 1.08 mmol). The reaction was stirred at room temperature under argon for 16 h. The reaction was diluted with water and extracted with dichloromethane. The combined organic layer was dried over sodium sulfate and concentrated, then purified by flash chromatography (SiO₂, 1-4% methanol dichloromethane) to provide the title material L-14b. LCMS (method 7): retention time=1.54 min; MS (ESI+) m/z 595.8 (M+H).

L-14c. 1-(3'-(2''-(2'''-(2''''-((N-Cbz)-amino)ethoxy)ethoxy)ethoxy)propanoyl)-3-(acetoxymethyl)piperazine, trifluoroacetic acid salt

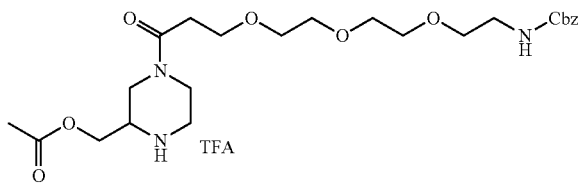 [SMILES: CC(=O)OCC1CN(C(=O)CCOCCOCCOCCNC(=O)OCc2ccccc2)CCN1]

L-14b (500 mg, 0.84 mmol) was dissolved in dichloromethane (10 mL) at 0° C., then treated dropwise with trifluoroacetic acid (3 mL) and stirred at room temperature 3 h under argon. The reaction was evaporated, washed with pentane and dried to provide crude title material L-14c, which was carried into the next reaction without further purification or analysis.

L14. 2-(acetoxymethyl)-4-(3'-(2''-(2'''-(2''''-((N-Cbz)-amino)ethoxy)ethoxy)ethoxy)propanoyl)-1-piperazineacetic acid t-butyl ester To L-14c (500 mg, 1.0 mmol) and potassium carbonate (418 mg, 3.03 mmol) in acetonitrile (10 mL) at 0° C. was dropwise added tert-butyl bromoacetate (295 mg, 1.51 mmol). The reaction was stirred for 20 h at room temperature under argon. The reaction was diluted with water and extracted with ethyl acetate. The organic layer was dried (sodium sulfate), concentrated and purified by an initial flash chromatography ($SiO_2$, 1-5% methanol:dichloromethane), followed by preparative HPLC (column: zorbax eclipse XDB C18, 4.6×150 mm, 5 μm; Mobile phase A=0.01% TFA in water, mobile phase B=acetonitrile:methanol (1:1), 1 mL/min; time=0 min: 30% B; 1 min: 70% B; 6 min: 100% B) to provide L14. LCMS (method 5): retention time=3.43 min; MS (ESI+) m/z 610.35 (M+H). $^1$H-NMR (CDCl$_3$, ppm) 7.36-7.31 (m, 5H), 5.49 (s, 1H), 5.09 (s, 2H), 4.26-4.16 (m, 1H), 4.07-3.98 (m, 1H), 3.78-3.74 (t, J=6, 2H), 3.60-3.53 (m, 11H), 3.39-3.32 (m, 4H), 2.84-2.72 (m, 2H), 2.61-2.57 (t, J=3, 2H), 2.08-2.06 (d, J=6, 2H), 1.45 (s, 9H).

Species shown in Table 9 were prepared using methods analogous to those used in the synthesis of L14:

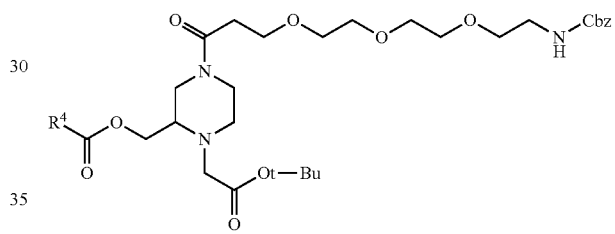

TABLE 9

Exemplary Traceless Linker Species

| $R^4$, Name | Number | LCMS: [M + H]; Retention Time; Method | $^1$H-NMR (300 MHz, CDCl$_3$) |
|---|---|---|---|
| $R^4$ = CH$_3$CH$_2$— 2-(propanoyloxymethyl)-4-(3'-(2''-(2'''-(2''''-((N-Cbz)-amino)ethoxy)ethoxy)ethoxy)propanoyl)-1-piperazineacetic acid t-butyl ester | L15 | 624.35; 3.60 min; 5 | 7.36-7.30 (m, 5H), 5.41 (s 1H), 5.09 (s, 2H), 4.28-3.96 (m, 3H), 3.78-3.74 (t, J = 6, 3H), 3.60-3.53 (m, 12H), 3.43-3.22 (m, 6H), 3.10-2.92 (m, 2H), 2.81-2.74 (m, 2H), 2.61-2.56 (t, J = 9, 2H), 2.39-20 (m, 2H), 1.63 (s, 3H), 1.45 (s, 9H), 1.16-1.10 (t, J = 6, 3H). |
| $R^4$ = (CH$_3$)$_2$CH— 2-(isobutanoyloxymethyl)-4-(3'-(2''-(2'''-(2''''-((N-Cbz)-amino)ethoxy)ethoxy)ethoxy)propanoyl)-1-piperazineacetic acid t-butyl ester | L16 | 638.35; 3.60 min; 5 | 7.36-7.30 (m, 5H), 4.95 (s, 1H), 5.10 (s, 2H), 4.26-4.12 (m, 2H), 4.08-3.96 (m, 2H), 3.81-3.76 (m, 3H), 3.61 (s, 8H), 3.57-3.54 (t, J = 4, 3H), 3.41-3.19 (m, 6H), 3.11-3.04 (m, 1H), 3.02-2.88 (m, 1H), 2.84-2.72 (m, 2H), 2.60-2.57 (m, 3H), 1.45 (s, 9H), 1.18-1.16 (d, J = 8, 6H). |

TABLE 10

Exemplary Traceless Linker Synthetic Intermediates

| Structure | Number | Analogous compounds |
|---|---|---|
| (structure) | L-2b | L-1b, L-3b, L-4b, L-5b, L-6b, L-7b |
| (structure) | L-2a | L-1a, L-3a, L-4a, L-5a, L-6a, L-7a |
| (structure) | L-INT-1 | L-INT-2, L-INT-3, L-INT-4 |
| (structure) | L-INT-1b | L-INT-2b, L-INT-3b, L-INT-4b |
| (structure) | L-INT-1c | L-INT-2c, L-INT-3c, L-INT-4c |

TABLE 10-continued

Exemplary Traceless Linker Synthetic Intermediates

| Structure | Number | Analogous compounds |
|---|---|---|
| (structure) | L-INT-1d | L-INT-2c, L-INT-3c, L-INT-4c |
| (structure) | L-INT-1e | L-INT-2c, L-INT-3c, L-INT-4c |
| (structure) | L-INT-5a | |
| (structure) | L-INT-5b | |
| (structure) | L-8a | |

TABLE 10-continued

Exemplary Traceless Linker Synthetic Intermediates

| Structure | Number | Analogous compounds |
|---|---|---|
| 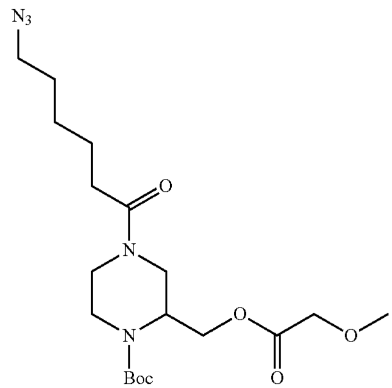 [SMILES: COCC(=O)OCC1CN(C(=O)CCCCCN=[N+]=[N-])CCN1C(=O)OC(C)(C)C] | L-8b | |
| 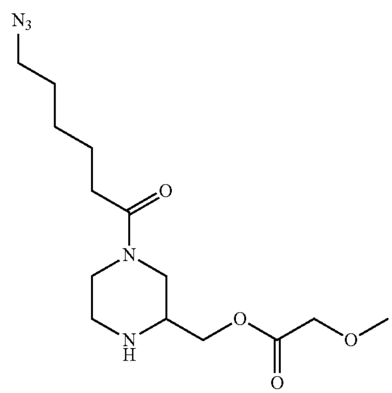 [SMILES: COCC(=O)OCC1CN(C(=O)CCCCCN=[N+]=[N-])CCN1] | L-8c | |
| 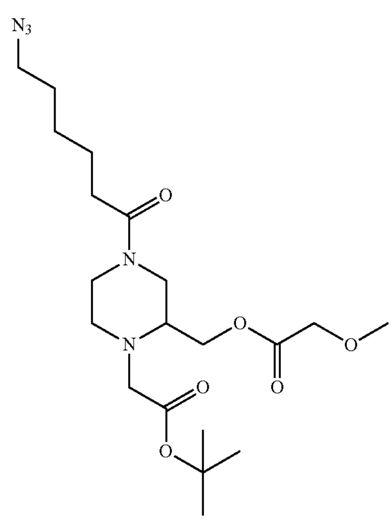 [SMILES: COCC(=O)OCC1CN(C(=O)CCCCCN=[N+]=[N-])CCN1CC(=O)OC(C)(C)C] | L-8d | |

TABLE 10-continued

Exemplary Traceless Linker Synthetic Intermediates

| Structure | Number | Analogous compounds |
|---|---|---|
| 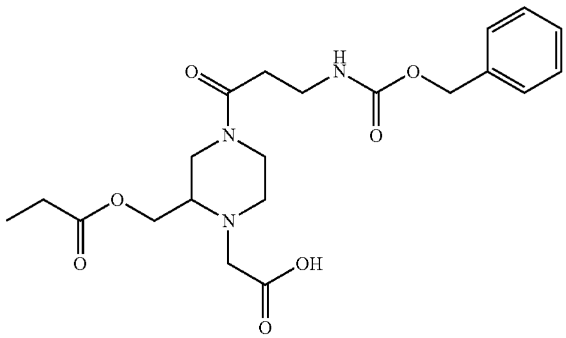 [SMILES: CCC(=O)OCC1CN(C(=O)CCNC(=O)OCc2ccccc2)CCN1CC(=O)O] | L-9a | L-10a, L-11a |
| 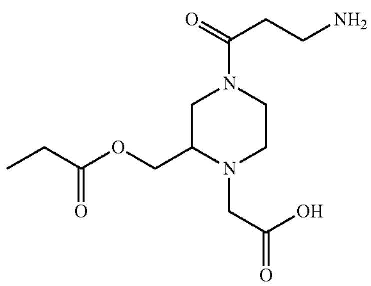 [SMILES: CCC(=O)OCC1CN(C(=O)CCN)CCN1CC(=O)O] | L-9b | L-10b, L-11b |
| 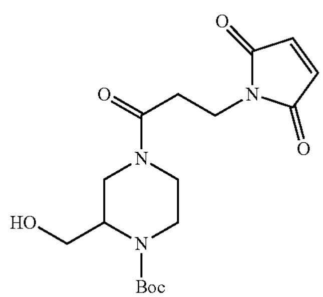 [SMILES: CC(C)(C)OC(=O)N1CCN(C(=O)CCN2C(=O)C=CC2=O)CC1CO] | L-12a | L-13a |
| 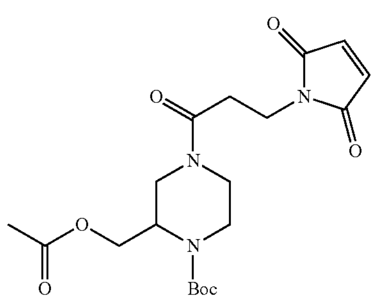 [SMILES: CC(=O)OCC1CN(C(=O)CCN2C(=O)C=CC2=O)CCN1C(=O)OC(C)(C)C] | L-12b | L-13b |
| 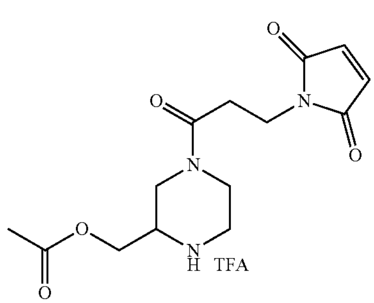 [SMILES: CC(=O)OCC1CN(C(=O)CCN2C(=O)C=CC2=O)CCN1] | L-12c | L-13c |

194

TABLE 10-continued

Exemplary Traceless Linker Synthetic Intermediates

| Structure | Number | Analogous compounds |
|---|---|---|
| 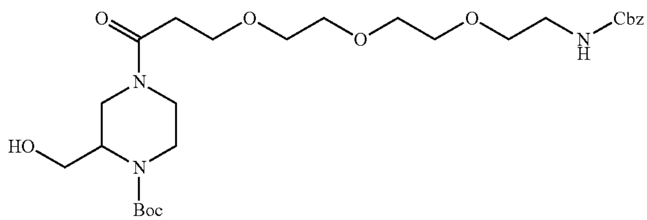 [SMILES: CC(C)(C)OC(=O)N1CCN(C(=O)CCOCCOCCOCCNC(=O)OCc2ccccc2)CC1CO] | L-14a | L-15a, L-16a |
| 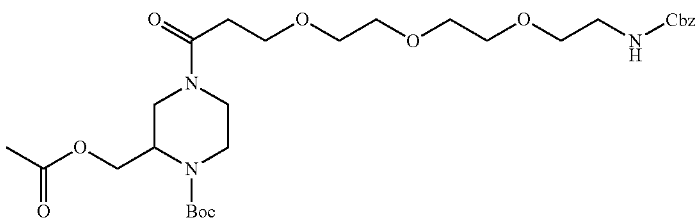 [SMILES: CC(=O)OCC1CN(C(=O)CCOCCOCCOCCNC(=O)OCc2ccccc2)CCN1C(=O)OC(C)(C)C] | L-14b | L-15b, L-16b |
| 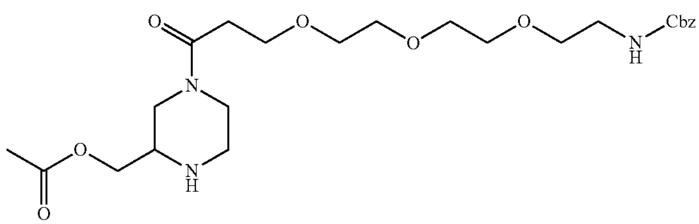 [SMILES: CC(=O)OCC1CN(C(=O)CCOCCOCCOCCNC(=O)OCc2ccccc2)CCN1] | L-15c | L-15c, L-16c |

Example 2

Adducts of Traceless Linkers with Biologically Active Moieties

This example describes the synthesis of a number of traceless linker-drug adducts, which are also capable of being conjugated to a carrier. D1 as depicted below comprises an ANGPTL3 polypeptide comprising amino acid residues 242-460 in reference to SEQ ID NO: 1 and a K423Q substitution (SEQ ID NO: 19).

TABLE 11

Exemplary Traceless Linker-Drug Adducts

| Number | Structure | Traceless linker | Drug (D) |
|---|---|---|---|
| L1D1 | 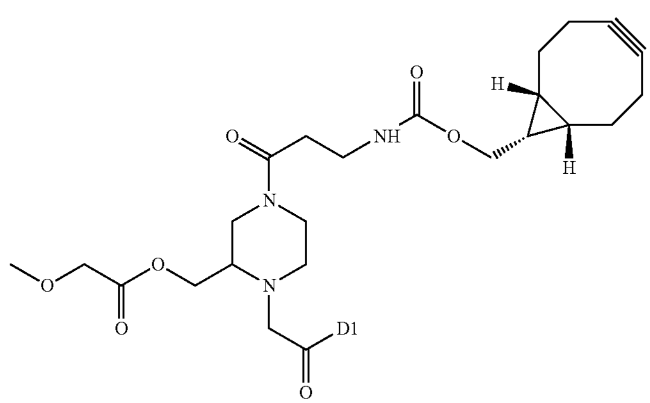 | L1 | D1 |

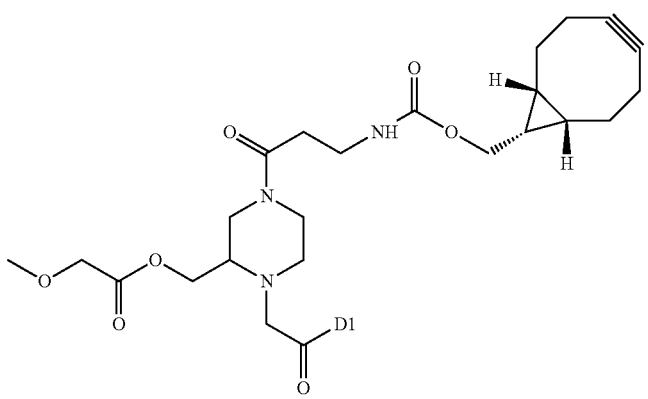

TABLE 11-continued

Exemplary Traceless Linker-Drug Adducts

| Number | Structure | Traceless linker | Drug (D) |
|---|---|---|---|
| L2D1 | 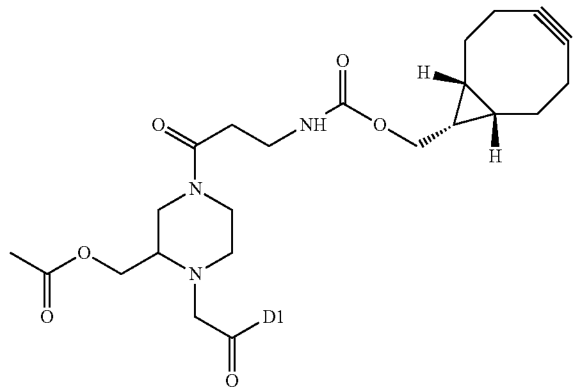 | L2 | D1 |
| L3D1 | 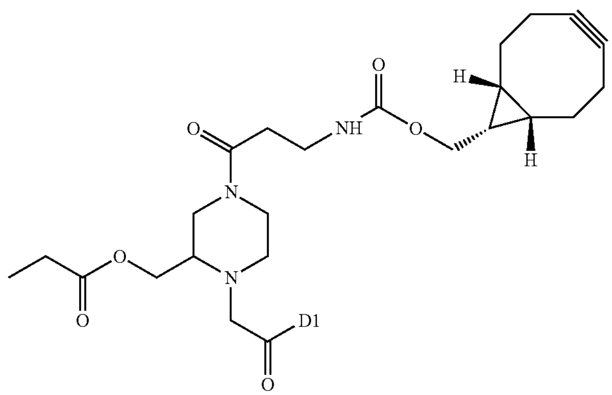 | L3 | D1 |
| L4D1 | 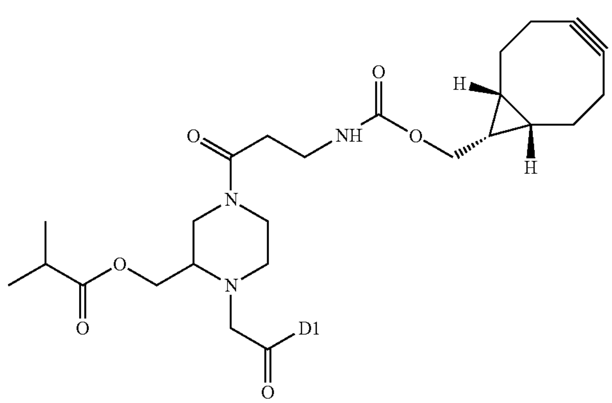 | L4 | D1 |

TABLE 11-continued
Exemplary Traceless Linker-Drug Adducts
| Number | Structure | Traceless linker | Drug (D) |
|---|---|---|---|
| L5D1 | 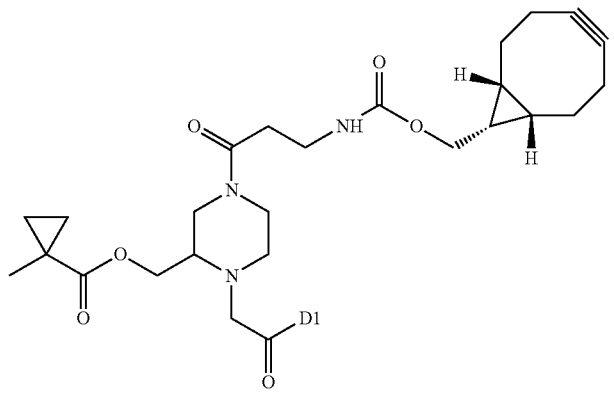 | L5 | D1 |
Synthesis of Adducts
Acylation of biologically active moieties with a traceless linker:
L2-NHS. 2-(acetyloxymethyl)-4-(N-(((1R',8'S,9's)-bicyclo[6.1.0]non-4'-yn-9'-yl)methoxycarbonyl)-beta-alanyl)-1-piperazineacetic acid N-hydroxysuccinimidyl ester
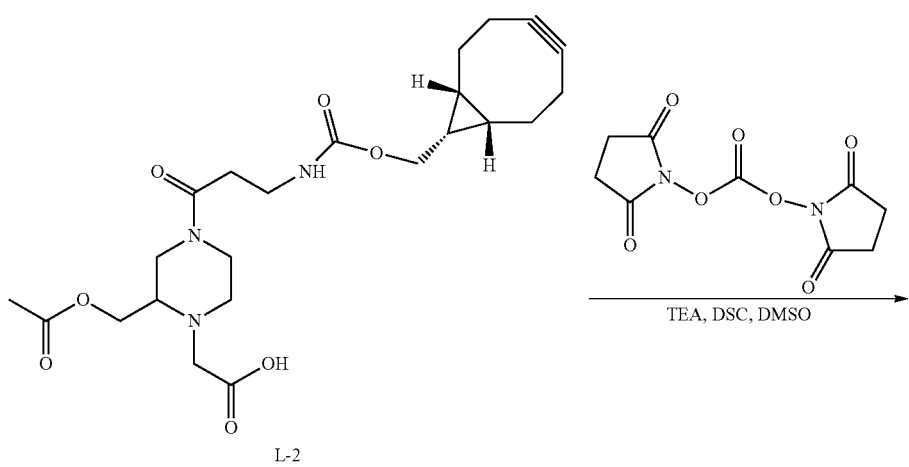

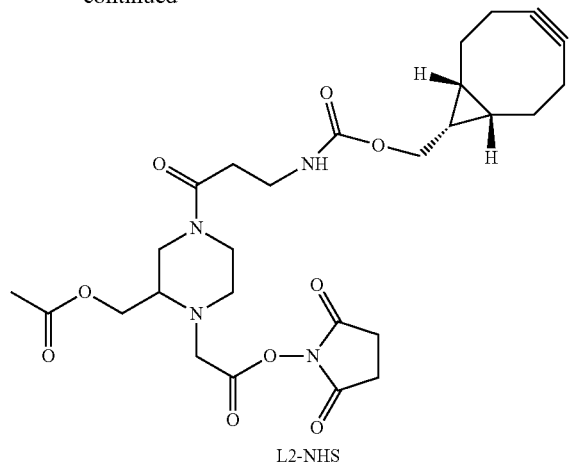

L2-NHS

L2 (16 mg, 0.031 mmol) was dissolved in dimethylsulfoxide (0.818 mL) to reach a 38 mM concentration. Triethylamine (3.46 µL, 0.025 mmol) was added followed by N,N'-disuccinimidyl carbonate (11.94 mg, 0.047 mmol) and the resulting clear solution was stirred for 1 h at room temperature under argon. The solution was used in the next step as such without further purification. LCMS (method 10): retention time=0.93 min; MS (ESI+) m/z 561.4 (M+H).

The species in Table 12 were prepared using methods analogous to those used in the synthesis of L2-NHS.

TABLE 12

Exemplary Activated Traceless Linker Species

| Structure | Number (starting intermediate) | Name | MS (ESI+) m/z (M + H) retention time; method |
|---|---|---|---|
| (structure shown) | L1-NHS (L1) | 2-(2'-methoxyacetoxymethyl)-4-(N-(((1''R,8''S,9''s)-bicyclo[6.1.0]non-4''-yn-9''-yl)methoxycarbonyl)-beta-alanyl)-1-piperazeacetic acid N-hydroxysuccinimidyl ester | 591.4; 0.87 min; 2 |
| (structure shown) | L2-NHS (L2) | 2-(acetoxymethyl)-4-(N-(((1'R,8'S,9's)-bicyclo[6.1.0]non-4'-yn-9'-yl)methoxycarbonyl)-beta-alanyl)-1-piperazineacetic acid N-hydroxysuccinimidyl ester | 561.4; 0.93 min; 10 |

TABLE 12-continued

Exemplary Activated Traceless Linker Species

| Structure | Number (starting intermediate) | Name | MS (ESI+) m/z (M + H) retention time; method |
|---|---|---|---|
| 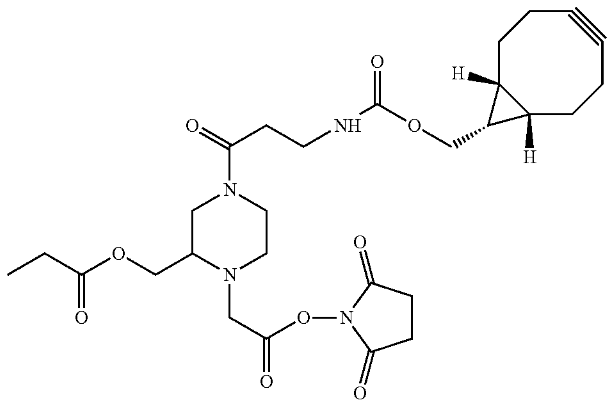 [SMILES: CCC(=O)OCC1CN(C(=O)CCNC(=O)OC[C@@H]2[C@@H]3CCC#CCC[C@@H]32)CCN1CC(=O)ON1C(=O)CCC1=O] | L3-NHS (L3) | 2-(propanoyloxymethyl)-4-(N-(((1'R,8'S,9's)-bicyclo[6.1.0]non-4'-yn-9'-yl)methoxycarbonyl)-beta-alanyl)-1-piperazineacetic acid N-hydroxysuccinimidyl ester | 575.5; 0.91 min; 4 |
| 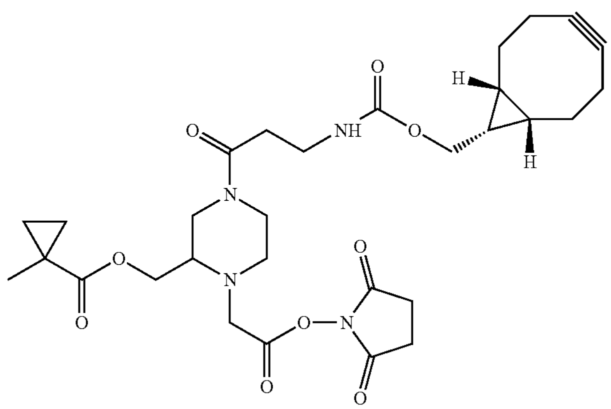 [SMILES: CC1(C(=O)OCC2CN(C(=O)CCNC(=O)OC[C@@H]3[C@@H]4CCC#CCC[C@@H]43)CCN2CC(=O)ON2C(=O)CCC2=O)CC1] | L5-NHS (L5) | 2-(1'-methylcyclopropyl-carbonyloxymethyl)-4-((N-(((1"R,8"S,9"s)-bicyclo[6.1.0]non-4"-yn-9"-yl)methoxycarbonyl)-beta-alanyl)-1-piperazineacetic acid N-hydroxysuccinimidyl ester | 601.4; 0.99 min; 4 |

L2-D1 (SEQ ID NO:19) (L2D1)

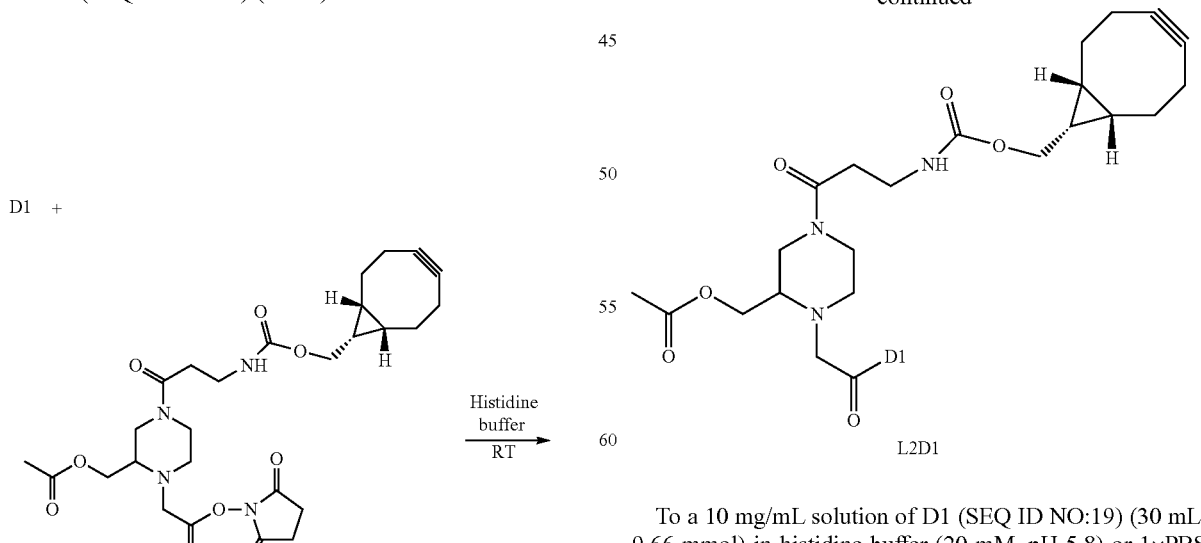

To a 10 mg/mL solution of D1 (SEQ ID NO:19) (30 mL, 9.66 mmol) in histidine buffer (20 mM, pH 5.8) or 1×PBS (pH 7.4) was slowly added a 38 mM solution of L2-NHS in DMSO (0.508 mL, 19.32 mmol). The reaction mixture was vigorously vortexed, and then shaken at room temperature for 2 h at 200 tr/min. Purification was performed by ultracentrifugation (Amicon filter, 3 kDa MWCO, 2000 rcf, 45 min, RT), washing with Histidine buffer or 1×PBS (3 times) removed residual small molecule impurities, resulting in a mixture of L2D1 and unmodified D1. MS (method 9) deconvoluted m/z 29969 (D1, M+H); deconvoluted m/z 30415 (L2D1, M+H, expected MW=MW (D1)+446).

An important analytical parameter is determination of ratio of (unmodified D1, n=0): (mono-acylated D1, n=1): (poly-acylated D1, n>1). Comparison of relative peak heights for the various species in a mass spectrum allows an estimate of the product ratio to be made.

An additional method for estimating the ratio of reaction products utilizes SEC (size exclusion chromatography) analysis of derivatized reaction products; derivitization is required in order to achieve separation of the reaction products.

L2D1 Derivatization Reaction

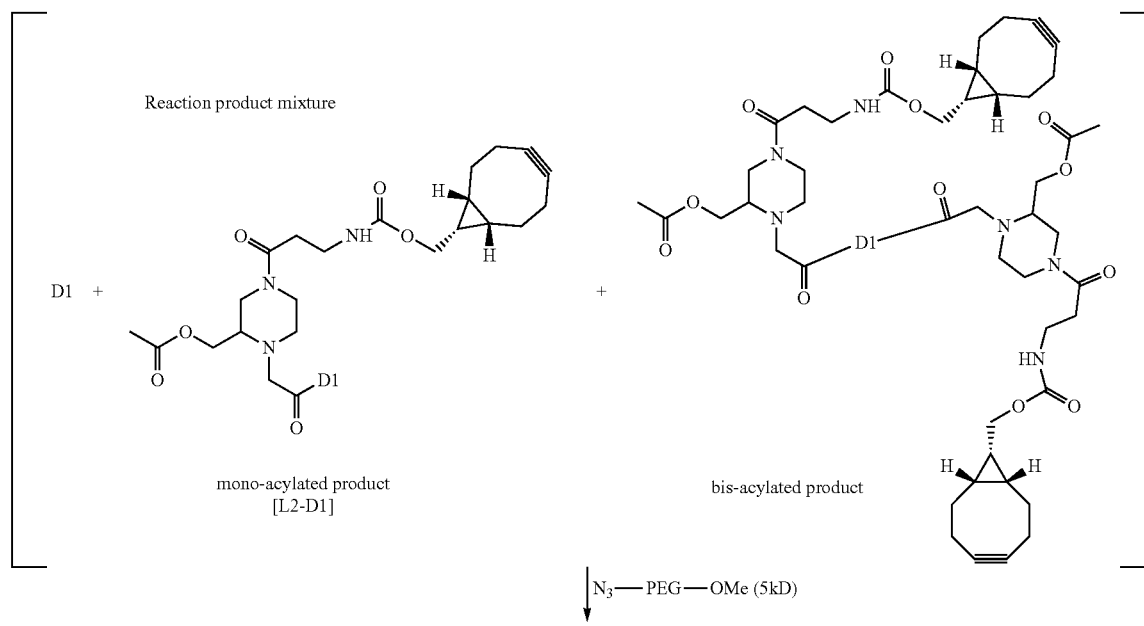

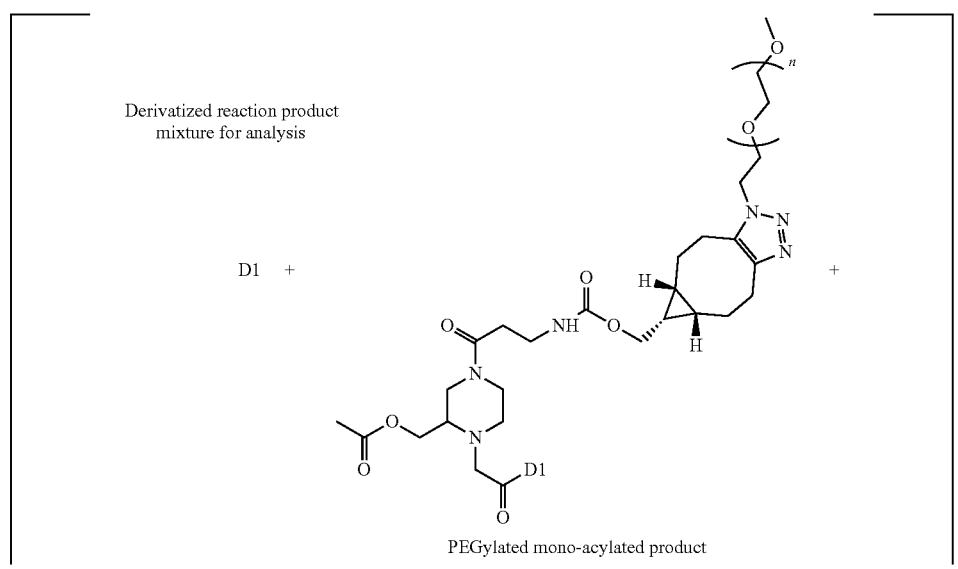

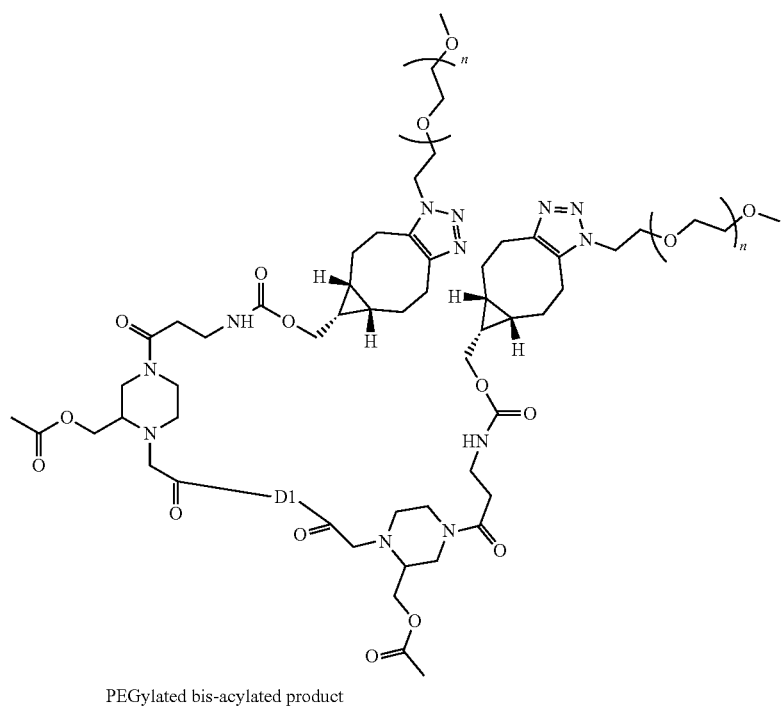

PEGylated bis-acylated product

An aliquot from the reaction mixture (10 mg/mL L2D1 solution, 0.020 mL, 0.060 µmol) was treated with a $M_n$~5 kDa methoxy-PEG-azide (Sigma-Aldrich, 689475, 0.014 mL of a 100 mg/mL solution in 1×PBS, 0.28 µmol), vortexed, shaken at 37° C. for 30 min and diluted with PBS (0.066 mL).

Analysis of L2D1-Derivative

SEC: (Instrument: Agilent LC 1260 Infinity; column: Superdex 200 increase 10/300GL (28-9909-44); Column temperature: r.t., flow rate: 0.75 mL/min; injection volume: 10 µL; mobile phase: 1/9 PBS/water preliminary filtered through a 0.10 membrane filter (isocratic); run time: 40 min; detection wavelengths: 214 nm). L2D1-derivative determination of ratio of (unmodified D1, n=0, retention time=20.90 min): (mono-acylated D1, n=1, retention time=18.23 min): (bis-acylated D1, n=2, retention time=16.64 min)=[(n=0):(n=1):(n=2)]=87:12:1.

Example 3

Functionalization of Hyaluronic Acid

This example describes the synthesis of a functionalized hyaluronic acid, which may itself be a carrier or may also be reacted with a crosslinking moiety to form a hydrogel.

Synthesis of Hyaluronic Acid Intermediate [HA-N$_3$]:

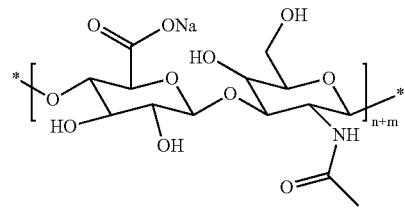

Hyaluronic acid (HA), 200 kD

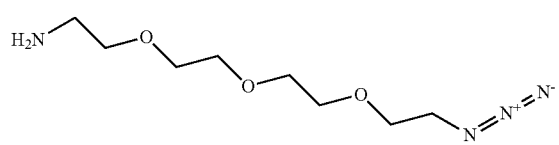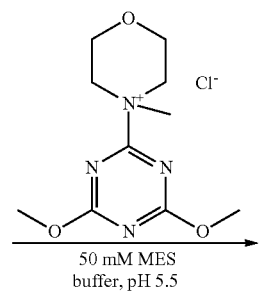

50 mM MES buffer, pH 5.5

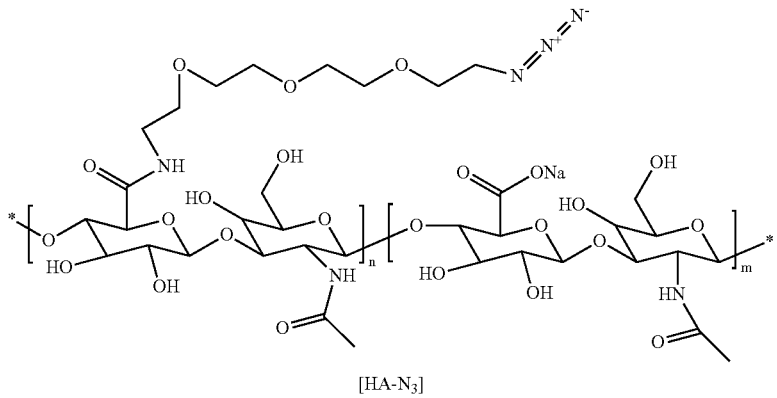

[HA-N3]

Hyaluronic acid sodium salt is a linear polymer consisting of repeating dimeric units of glucuronic acid and N-acetylgalactosamine, with a repeating unit molecular weight of 401.3 Da. In this example the moles of hyaluronic acid reported refers to the moles of repeating unit and the equivalents of reagents used in the reaction with hyaluronic acid are reported relative to the moles of hyaluronic acid repeating unit. The average molecular weight of the polymer determines the average number of repeat units per polymer strand. Hyaluronic acid sodium salt labeled by the supplier, Lifecore Biomedical (HA200K, Chaska, Minn.) as having a nominal average molecular weight of 200 kDa may vary from batch to batch in the range of 151-300 kDa, as determined by viscometry. In this example, such a molecule of hyaluronic acid sodium salt with an assumed nominal average molecular weight of 200 kDa would have an average length of approximately 500 monomer units.

Synthesis of [HA-N$_3$]-23%

A solution of hyaluronic acid, sodium salt (nominal average molecular weight 200 kD; 250.1 mg, 0.623 mmol; Lifecore Biomedical, LLC; product number HA200K) was fully dissolved in 25 mL of MES buffer (50 mM, pH 5.5). To this solution was added 4-(4',6'-dimethoxy-1',3',5'-triazin-2'-yl)-4-methylmorpholin-4-ium chloride (DMTMM, 295 mg, 1.07 mmol, 1.71 eq), followed after 5 min by addition of 11-azido-3,6,9-trioxaundecan-1-amine (N3-PEG3-NH2, 196 mg, 0.90 mmol). The reaction was stirred overnight, then diluted with 25 mL of 0.25 M NaCl solution and purified by tangential flow filtration.

Tangential flow filtration was carried out using a 30 kDa MWCO Vivaflow-50R hydrosart cartridge from Sartorius, eluting with 400 mL of 0.25 M NaCl solution, then 400 mL of water.

The product was flash frozen and lyophilized to provide the title material [HA-N$_3$]-23%.

$^1$H NMR (400 MHz, D20) δ 4.45 (bs, 2H), 4.0-3.1 (m, 15.5H), 1.95 (s, 3H).

DOSY-NMR. One dimensional diffusion ordered NMR spectra (DOSY) were collected using the stimulated echo with one spoil gradient pulse sequence (stegplsld) on a Bruker AVANCE III 400 MHz (for $^1$H) instrument with 5 mm DCH cryoprobe. The diffusion time and the diffusion gradient time were set to 50 ms and 4 ms, respectively. Two spectra were collected with gradient strength (gpz6) set to 2% and 95%. Comparison of the two spectra showed no differences apart from the solvent peak, indicating no small molecule impurities were present in the polymer.

Elem. Anal: C: 40.05%: H: 5.67%; N: 5.70%.

The degree of substitution of the [HA-N3] is defined as the % of repeat units in which the carboxylate moiety has undergone reaction to give the depicted amide. Elemental analysis was used to determine the degree of substitution. The [% C/% N] ratio determined by elemental analysis of a purified sample is entered into the following formula to provide the degree of substitution. Where y=[(% C)/(% N)]) then:

$$\text{Degree of substitution} = 100 \times \frac{\frac{14 \times 12.01}{14.01 \times y} - 1}{4 - \frac{8 \times 12.01}{14.01 \times y}}$$

In this example, the degree of substitution (DS) of [HA-N3] was 23%.

This 200 kDa hyaluronic acid, functionalized with 23% of the azide linker is labeled [HA-N3]-23%.

In the rest of the examples, a 200 kDa hyaluronic acid, functionalized with X % of the azide linker is labeled [HA-N3]-X %.

The species in Table 13 were prepared and characterized using methods analogous to those used in the synthesis of [HA-N3]-23%. We find that the degree of substitution achieved depends on the given stock of DMTMM reagent used and can be idiosyncratic. In general, for a given stock of DMTMM, the degree of substitution increases as the number of equivalents of DMTMM used increases, and the degree of substitution decreases as the number of equivalents of DMTMM used decreases. Some of the [HA-N3] intermediates were purified by dialysis instead of tangential flow filtration ([HA-N3]-23% b, [HA-N3]-37%). In these cases, a crude reaction mixture was filled into a regenerated cellulose dialysis membrane (MWCO 1-25 kD), and dialyzed 1-3 days against 0.25 M-1 M NaCl, with several changes of the dialysis solution, followed by 1-3 day's dialysis against deionized water, also with multiple changes of the dialysis solution. Upon completion, the sample was removed from the dialysis tubing, flash-frozen, and lyophilized.

TABLE 13

Exemplary Functionalized Hyaluronic Acid Species

| Hyaluronic acid derivative | DS | Equivalents of DMTMM/ N3-PEG3-NH2 used in reaction | Elemental analysis |
|---|---|---|---|
| [HA-N3]-15% | 15% | 1.66/1.42 | C: 39.80<br>H: 5.52<br>N: 4.93 |
| [HA-N3]-19% | 19% | 1.63/1.08 | C: 37.19<br>N: 4.88 |
| [HA-N3]-22% | 22% | 1.65/1.42 | C: 39.89<br>H: 5.76<br>N: 5.53 |
| [HA-N3]-23% | 23% | 1.71/1.44 | C: 40.05<br>H: 5.67<br>N: 5.70 |
| [HA-N3]-23%b | 23% | 4.08/3.04 | C: 36.93<br>H: 5.97<br>N: 5.18 |
| [HA-N3]-23%c | 23% | 1.60/1.02 | C: 36.85<br>H: 6.44<br>N: 5.19 |
| [HA-N3]-26% | 26% | 1.90/1.44 | C: 39.78<br>H: 5.72<br>N: 5.92 |
| [HA-N3]-33% | 33% | 1.75/1.43 | C: 40.60<br>H: 5.97<br>N: 6.63 |
| [HA-N3]-37% | 37% | 3.84/2.88 | C: 39.87<br>H: 5.92<br>N: 6.82 |

Example 4

Preparation of PEG Polymers, XL-1-XL-10

This example describes the synthesis of crosslinkers that may be reacted with other functionalized polymers to form hydrogels.

PEG-Based Cross-Linking Polymers

General Structure 1.

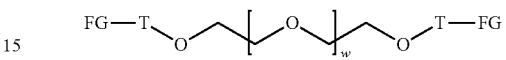

In some aspects, w can be 22, 45, 91, 136, 181, or 226 and correspond to a PEG having a nominal average molecular weight of about 1 kDa, about 2 kDa, about 4 kDa, about 6 kDa, about 8 kDa, or about 10 kDa, respectively.

General Structure 2.

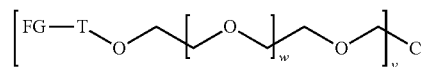

TABLE 14

Exemplary Crosslinking Species

| Number | General structure | FG | T | v | $M_n$~ starting PEG (Da) |
|---|---|---|---|---|---|
| XL-1 | 1 | BCN | —HN—CH2CH2—C(O)O— | NA | 2000 (w~45) |
| XL-2 | 1 | BCN | —HN—C(cyclopropyl)—C(O)O— | NA | 2000 (w~45) |
| XL-3 | 1 | BCN | —HN—CH2—C(cyclopropyl)—C(O)O— | NA | 2000 (w~45) |

TABLE 14-continued
Exemplary Crosslinking Species
| Number | General structure | FG | T | v | $M_n\sim$ starting PEG (Da) |
|---|---|---|---|---|---|
| XL-4 | 1 | 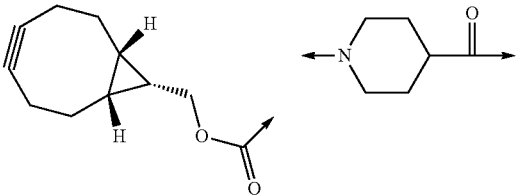 | 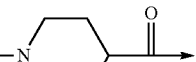 | NA | 2000 (w~45) |
| XL-5 | 1 | 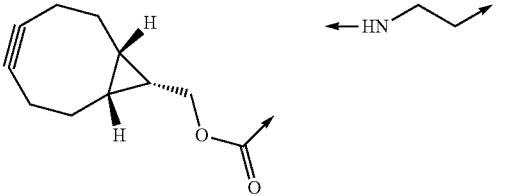 | 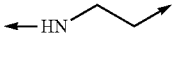 | NA | 2000 (w~45) |
| XL-6 | 2 | 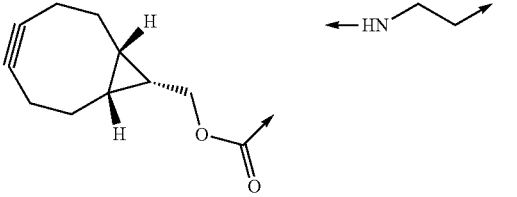 | 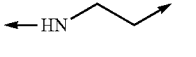 | 4 | 10000 (w~226) |
| XL-7 (commercial product) | 2 | N$_3$ | —CH$_2$CH$_2$— | 4 | 10000 (w~226) |
| XL-8 (shown below) | 1 | 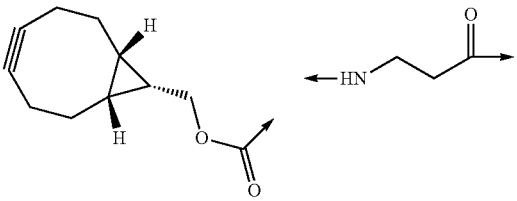 |  | NA | 10000 (w~226) |
| XL-9 | 1 | 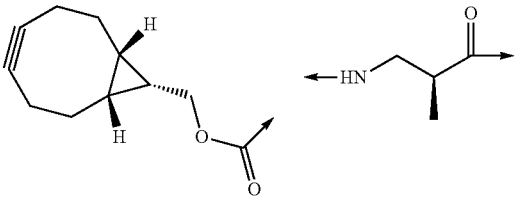 |  | NA | 2000 (w~45) |
| XL-10 | 1 | 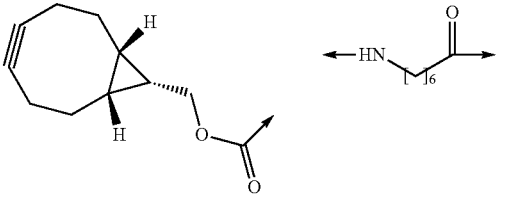 |  | NA | 2000 (w~45) |

TABLE 14-continued
Exemplary Crosslinking Species
| Number | General structure | FG | T | v | $M_n$~ starting PEG (Da) |
|---|---|---|---|---|---|
| XL-11 | 1 | 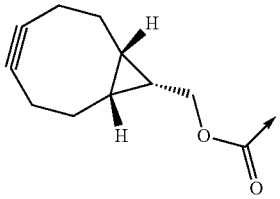 | 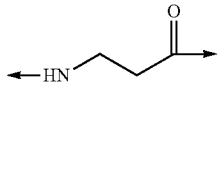 | NA | 1000 (w~22) |
| XL-12 | 1 | 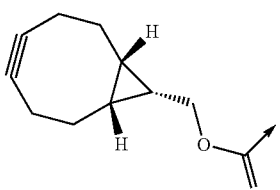 | 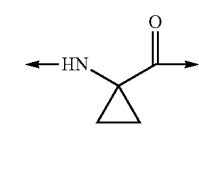 | NA | 4000 (w~90) |
| XL-13 | 1 | 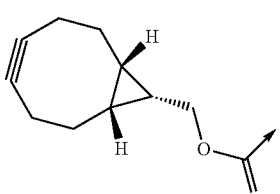 | 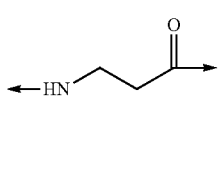 | NA | 6000 (w~136) |
| XL-14 | 1 | 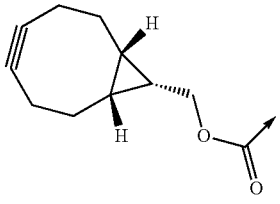 | 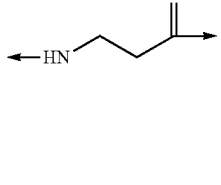 | NA | 8000 (w~181) |
The structure of XL-8:
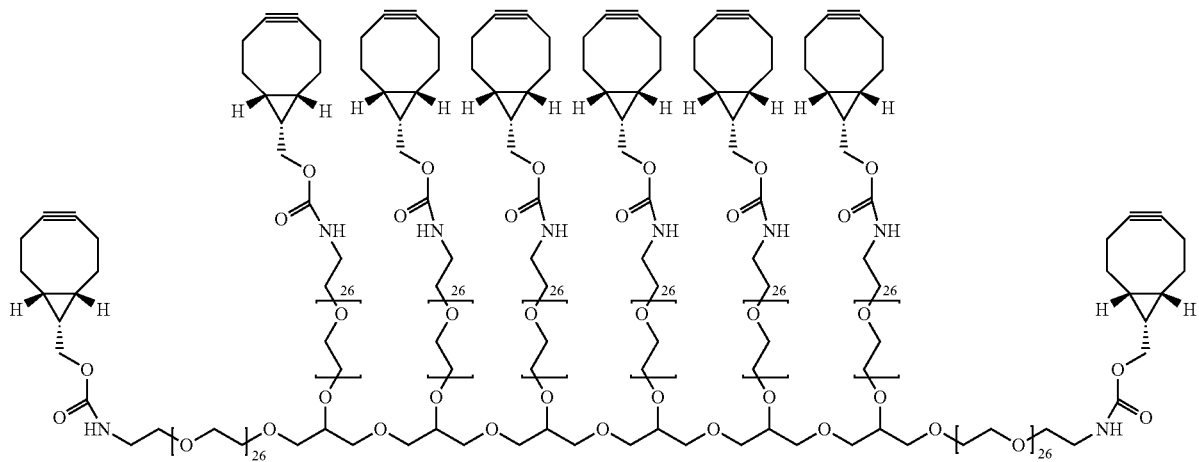

MW of starting PEG: $M_n$~10,000 kDa.

Synthesis of PEG-Based Cross-Linking Polymers

Degree of substitution is an important parameter for PEG-derived cross-linkers and is defined as the percentage of PEG end groups substituted with the desired introduced functional group. Degree of substitution was determined using $^1$H-NMR to compare the integration of a methylene group specific to the PEG end group to the integration of protons specific to the introduced functional group. For XL-1-XL-6, the methylene group specific to the PEG moiety was the ester or carbamate methylene [—(C=O)—O—CH$_2$—], which was compared to the integration of protons in the bicyclo[6.1.0]non-4-yne moiety. Degree of substitution=((moles introduced functional group by $^1$H-NMR)/(moles PEG end group by $^1$H-NMR))×100.

XL-1. PEG(2000)-bis-[3-(((((1R,8S,9s)-bicyclo[6.1.0]non-4-yn-9-yl)methoxy)carbonyl)amino)propanoate]

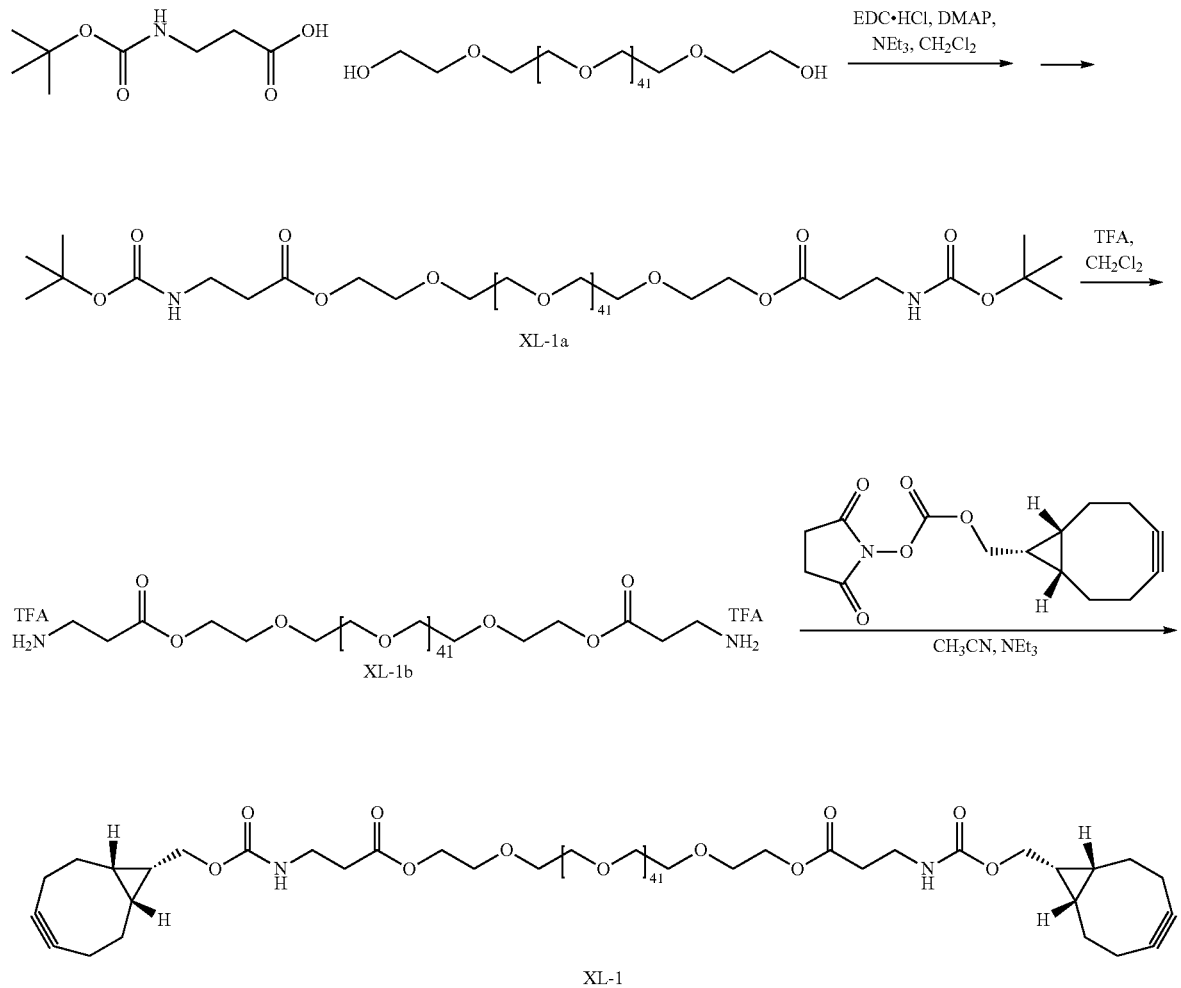

XL-1a. PEG(2000)-bis-[3-((tert-butoxycarbonyl)amino)propanoate]

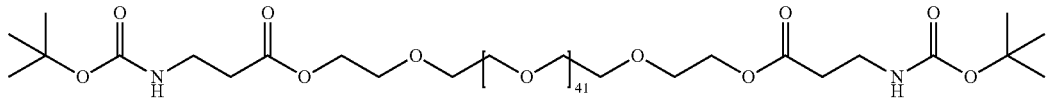

3-((tert-butoxycarbonyl)amino)propanoic acid (1.15 g, 6.0 mmol) and $M_n$~2 kDa PEG (3 g, 1.500 mmol) were dissolved in 30 mL dichloromethane. Dimethylaminopyridine (0.092 g, 0.750 mmol) and EDC-HCl (1.211 g, 6.0 mmol) were added and the reaction mixture was stirred at room temperature overnight. The crude product was purified by flash column chromatography (with a ELSD detector) on silica with a 0-20% dichloromethane:dichloromethane/methanol (4:2) gradient. The product containing fractions were pooled and concentrated to dryness to provide XL-1a. $^1$H NMR (500 MHz, DMSO-$d_6$) δ 6.83 (t, J=5.7 Hz, 2H), 4.16-4.09 (m, 4H), 3.61-3.56 (m, 5H), 3.51 (s, 184H), 3.15 (q, J=6.7 Hz, 4H), 2.43 (t, J=7.0 Hz, 4H), 1.37 (s, 18H).

XL-1b. PEG(2000)-bis-[3-(amino)propanoate], bis-trifluoroacetic acid

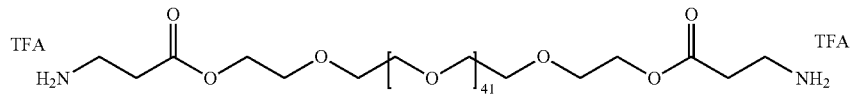

XL-1a (3.12 g, 1.357 mmol) was dissolved in dichloromethane (36 mL). Trifluoroacetic acid was added (36 mL) and the reaction mixture was stirred at room temperature for 2 hours. The solvent was removed under reduced pressure. The crude product was successively triturated with diethyl ether and filtered off. The operation was repeated three times and the resulting solid was dried under vacuum to provide XL-1b. $^1$H NMR (500 MHz, DMSO-$d_6$) δ 7.80 (s, 4H), 4.24-4.11 (m, 4H), 3.72-3.32 (m, 182H), 3.09-2.95 (m, 4H), 2.67 (t, J=6.9 Hz, 4H).

XL-1-1. PEG(2000)-bis-[3-(((((1R,8S,9s)-bicyclo[6.1.0]non-4-yn-9-yl)methoxy)carbonyl)amino)propanoate]

XL-1b (600 mg, 0.286 mmol) was dissolved in acetonitrile (7 mL). Triethylamine (1.99 mL, 14.3 mmol) was added followed by ((1R,8S,9s)-bicyclo[6.1.0]non-4-yn-9-yl)methyl (2,5-dioxopyrrolidin-1-yl) carbonate (333 mg, 1.14 mmol) and the reaction mixture was stirred at room temperature for 2 hours. The reaction mixture was directly purified by flash column chromatography (with a ELSD detector) on silica with a 0-40% dichloromethane dichloromethane/methanol (4:2) gradient. The product containing fractions were pooled and concentrated to dryness to afford XL-1-1. For storage purposes, XL-1-1 was kept as a solution in acetonitrile (50 mg/mL) in placed in a freezer. Analytical UPLC (method B, see below): retention time=1.19 min. $^1$H NMR (500 MHz, MeOH-$d_4$) δ 4.23 (m, 4H), 4.14 (m, 4H), 3.64 (br s, 214H), 2.55 (m, 4H), 2.22 (m, 12H), 1.61 (m, 4H), 1.35 (m, 2H), 0.92 (m, 4H).

Method A: analytical HPLC with CAD detector: Waters XBridge BEH300 C18; particle size: 3.5 μm; column size: 4.6×100 mm; eluent/gradient: 2% $CH_3CN/H_2O$/0.5 min, 2-98% $CH_3CN/H_2O$/17.5 min ($CH_3CN$ containing 0.05% TFA and $H_2O$ containing 0.1% TFA); flow rate: 1 mL/min; column temperature: 50° C.

Method B: analytical UPLC with ELSD detector: Waters ACQUITY UPLC HSS T3;
particle size: 1.8 μm; column size: 2.1×50 mm; eluent/gradient: 5-98% $CH_3CN/H_2O$ in 1.4 min ($CH_3CN$ containing 0.04% FA and $H_2O$ containing 0.05% FA+3.75 mM AA); flow rate: 1 mL/min; column temperature: 60° C.

Method C: analytical UPLC with CAD: Waters ACQUITY BEH C18; particle size: 1.7 m; pore size: 130 Å; column size: 2.1×50 mm; eluent/gradient: 5% $CH_3CN/H_2O$/

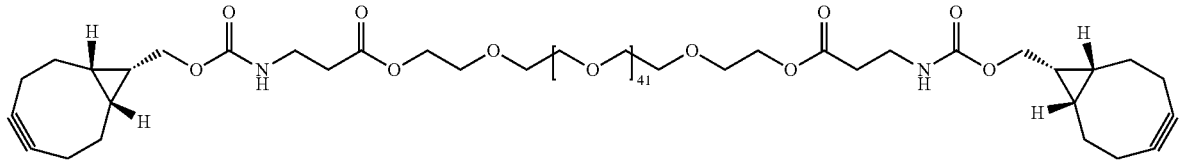

1.2 min, 5-95% $CH_3CN/H_2O$/1.8 min ($CH_3CN$ containing 0.1% TFA and $H_2O$ containing 0.1% TFA); flow rate: 1 mL/min; column temperature: 45° C.

The species in Table 15 were prepared using methods analogous to those used in the synthesis of XL-1 (except for XL-1-2):

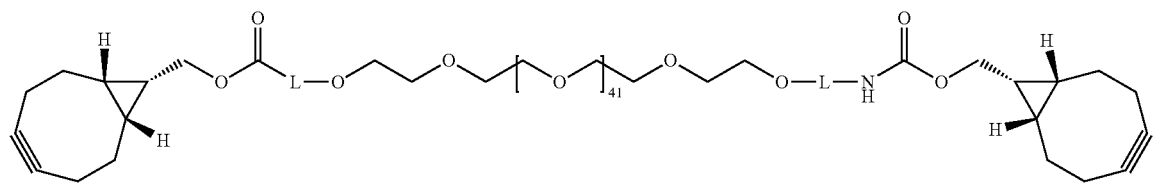

TABLE 15

| Number | T | Number of PEG-end groups substituted with functional group | Anal Method/ Retention time (min) | $^1$H NMR (400 MHz, Methanol-d4) |
|---|---|---|---|---|
| XL-1-1 | −HN−CH$_2$CH$_2$−C(=O)− | 2 of 2 100% | B 1.19 min | (500 MHz) δ 4.23 (m, 4H), 4.14 (m, 4H), 3.64 (br s, 214H), 2.55 (m, 4H), 2.22 (m, 12H), 1.61 (m, 4H), 1.35 (m, 2H), 0.92 (m, 4H). |
| XL-1-2 | −HN−CH$_2$CH$_2$−C(=O)− | (1.5-1.8) of 2 75% | NA | δ 4.23 (m, 4H), 4.14 (m, 3.3H), 3.63 (br s, 156H), 2.55 (m, 4H), 2.21 (m, 9.6H), 1.60 (m, 3.6H), 0.94 (m, 3.9H). |
| XL-2 | −HN−C(cyclopropyl)−C(=O)− | 2 of 2 100% | B 1.20 min | δ 4.30-4.14 (m, 8H), 3.66 (s, 186H), 2.35-2.13 (m, 12H), 1.64 (d, J = 12.2 Hz, 4H), 1.51 (m, 4H), 1.41 (m, 2H), 1.17 (m, 4H), 1.02-0.93 (m, 4H). |
| XL-3 | −HN−CH$_2$−C(cyclopropyl)−C(=O)− | 2 of 2 100% | A 12.93 min | δ 4.19 (m, 8H), 3.85-3.43 (m, 192H), 3.36 (br s, 4H), 2.22 (m, 12H), 1.60 (m, 4H), 1.38 (m, 2H), 1.19 (m, 4H), 0.95 (m, 8H). |
| XL-4 | piperidine-N,4-diyl C(=O) | 2 of 2 100% | A 13.25 min | δ 4.22 (m, 8H), 4.02 (m, 4H), 3.84-3.43 (m, 194H), 3.00 (br s, 4H), 2.60 (m, 2H), 2.23 (m, 12H), 1.91 (m, 4H), 1.61 (m, 8H), 1.42 (m, 2H), 0.97 (m, 4H). |
| XL-9 | −HN−CH$_2$−CH(CH$_3$)−C(=O)− | 2 of 2 100% | C 1.85 min | δ 4.29-4.19 (m, 4H), 4.14 (d, J = 8.1 Hz, 4H), 3.87-3.41 (m, 179H), 3.28-3.18 (m, 3H), 2.78-2.62 (m, 2H), 2.37-2.06 (m, 12H), 1.72-1.51 (m, 4H), 1.47-1.31 (m, 2H), 1.21-1.09 (m, 6H), 1.04-0.87 (m, 4H). |
| XL-10 | −HN−(CH$_2$)$_6$−C(=O)− | 2 of 2 100% | C 1.96 min | δ 4.25-4.18 (m, 4H), 4.13 (d, J = 8.3 Hz, 4H), 3.85-3.40 (m, 178H), 3.09 (t, J = 7.0 Hz, 4H), 2.34 (t, J = 7.5 Hz, 4H), 2.31-2.09 (m, 11H), 1.72-1.54 (m, 8H), 1.54-1.44 (m, 4H), 1.44-1.25 (m, 11H), 1.03-0.85 (m, 4H). |

Intermediates Used in the Synthesis of PEG-Based Cross-Linking Polymers:

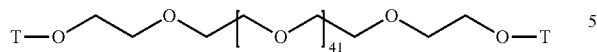

TABLE 16

Exemplary PEG-based Cross-Linking Polymers

| Number | T | Number of PEG-end groups substituted with functional group | $^1$H NMR (400 MHz) |
|---|---|---|---|
| XL-2a | | 2 of 2 100% | (chloroform-d) δ 4.23 (m, 4H), 3.64 (br s, 165H), 1.52 (br m, 4H), 1.45 (br s, 18H), 1.16 (br m, 4H). |
| XL-3a | | 2 of 2 100% | (methanol-d4) δ 4.23 (m, 4H), 3.83-3.41 (m, 181H), 1.44 (br s, 18H) 1.17 (m, 4H), 0.94 (m, 4H). |
| XL-4a | | 2 of 2 100% | (methanol-d4) δ 4.23 (m, 4H), 3.95 (m, 4H), 3.85-3.41 (m, 180H), 2.92 (br s, 4H), 2.57 (m, 2H), 1.89 (m, 4H), 1.56 (m, 4H), 1.45 (m, 18H). |
| XL-9a | | 2 of 2 100% | (methanol-d$_4$) δ 4.31-4.17 (m, 4H), 3.83-3.44 (m, 179H), 3.27-3.15 (m, 4H), 2.72-2.61 (m, 2H), 1.50-1.39 (m, 18H), 1.14 (d, J = 7.2 Hz, 6H). |
| XL-10a | | 2 of 2 100% | (methanol-d$_4$) δ 4.27-4.15 (m, 4H), 3.83-3.44 (m, 180H), 3.04-2.99 (m, 4H), 2.34 (t, J = 7.3 Hz, 4H), 1.68-1.57 (m, 4H), 1.55-1.40 (m, 22H), 1.39-1.27 (m, 9H). |
| XL-2b | Bis-TFA salt | 2 of 2 100% | (chloroform-d) δ 4.23 (m, 4H), 3.64 (br s, 165H), 1.55 (br m, 4H), 1.19 (br m, 4H). |
| XL-3b | Bis-TFA salt | 2 of 2 100% | (methanol-d4) δ 4.33 (m, 4H), 3.88-3.42 (m, 184H), 2.91 (br m, 4H), 3.22 (br s, 2H), 1.41 (m, 4H), 1.15 (m, 4H), |
| XL-4b | Bis-TFA salt | 2 of 2 100% | (methanol-d4) δ 4.30 (m, 4H), 3.85-3.54 (m, 178H), 3.39 (m, 4H), 3.15, (m, 4H), 2.79 (m, 2H), 2.14 (m, 4H), 1.95 (m, 4H). |

TABLE 16-continued

Exemplary PEG-based Cross-Linking Polymers

| Number | T | Number of PEG-end groups substituted with functional group | $^1$H NMR (400 MHz) |
|---|---|---|---|
| XL-9b | ![H2N-CH(CH3)-C(=O)-] Bis-TFA Salt | 2 of 2 100% | (methanol-d$_4$) δ 4.56-4.43 (m, 2H), 4.32-4.20 (m, 2H), 3.92-3.41 (m, 180H), 3.25-3.12 (m, 4H), 2.99-2.84 (m, 2H), 1.28 (d, J = 7.0 Hz, 6H). |
| XL-10b | ![H2N-(CH2)6-C(=O)-] Bis-TFA Salt | 2 of 2 100% | (methanol-d$_4$) δ 4.25-4.19 (m, 4H), 4.10-3.41 (m, 180H), 3.04-2.90 (m, 4H), 2.44-2.30 (m, 4H), 1.77-1.55 (m, 8H), 1.54-1.33 (m, 8H). |

XL-5. PEG(2000)-bis-[3-(((((1R,8S,9s)-bicyclo[6.1.0]non-4-yn-9-yl)methylcarbamoyl]

HPLC-CAD (method below): retention time=11.85 min. NMR (400 MHz, MeOH-d4) δ 4.14 (m, 4H), 3.63 (br s, 186H), 3.54 (m, 4H), 2.22 (m, 12H), 1.61 (m, 4H), 1.38 (m,

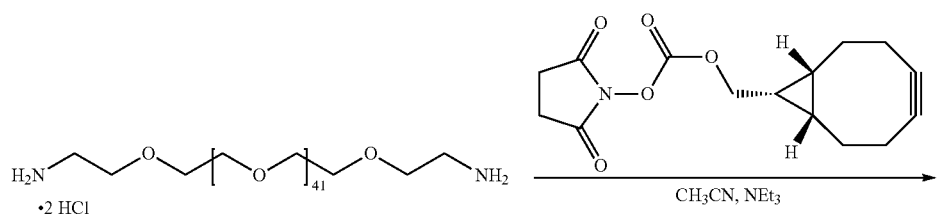

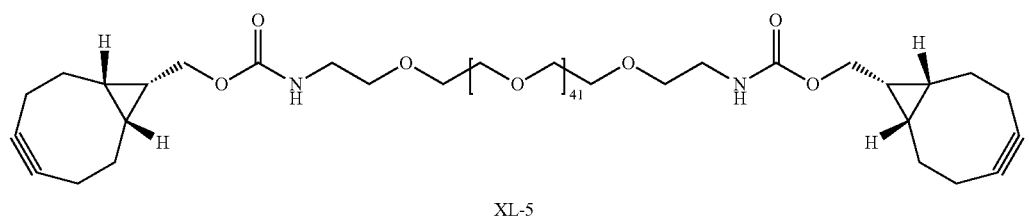

XL-5

$M_n$~2 kDa PEG diamine hydrochloride (JenKem Technology, 300 mg, 0.148 mmol) was dissolved in acetonitrile (3 mL). Triethylamine (0.413 mL, 2.96 mmol) was added, followed by ((1R,8S,9s)-bicyclo[6.1.0]non-4-yn-9-yl)methyl (2,5-dioxopyrrolidin-1-yl) carbonate (345 mg, 1.184 mmol) and the reaction mixture was stirred at room temperature for 4 h. The reaction mixture was directly purified by preparative reverse phase HPLC with ELSD triggered fraction collection (method below). The product containing fractions were pooled, frozen, and lyophilized to provide XL-5. For storage purposes, XL-5 was kept as an acetonitrile, DMSO, or methanol solution in a freezer. Analytical 2H), 0.94 (m, 4H). Exchangeable protons are not visible in MeOD.

Preparative HPLC conditions: Waters XBridge C18; particle size: 5 μm; column size: 19×250 mm; eluent/gradient: 5% CH$_3$CN/H$_2$O/0.5 min, 5-95% CH$_3$CN/H$_2$O/12.5 min, 95% CH$_3$CN/H$_2$O/3 min; flow rate: 30 mL/min; column temperature: room temperature.

Analytical HPLC-CAD conditions: Waters XBridge BEH300 C18; particle size: 3.5 μm; column size: 4.6×100 mm; eluent/gradient: 2% CH$_3$CN/H$_2$O/0.5 min, 2-98% CH$_3$CN/H$_2$O/17.5 min (CH$_3$CN containing 0.05% TFA and H$_2$O containing 0.1% TFA); flow rate: 1 mL/min; column temperature: 50° C.

225

XL-6. PEG(10000)-tetra-[3-(((((1R,8S,9s)-bicyclo[6.1.0]non-4-yn-9-yl)methylcarbamoyl]

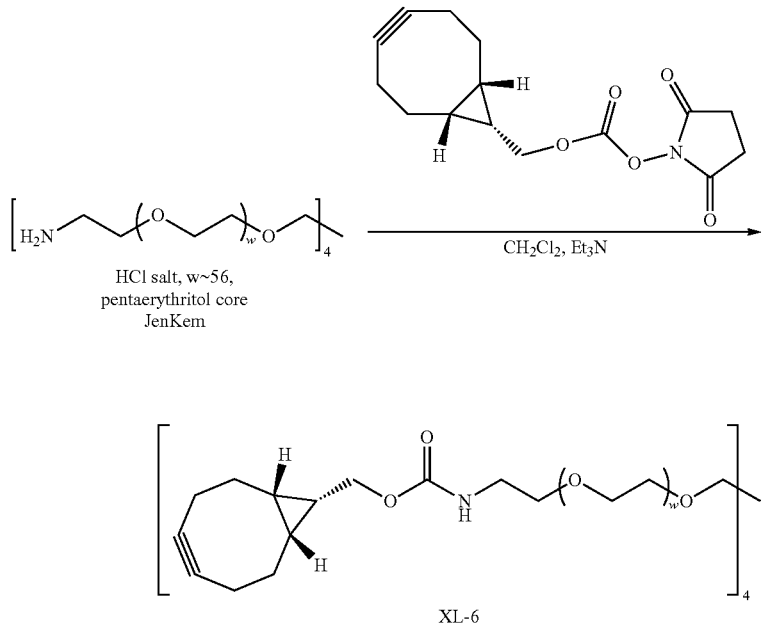

XL-6

$M_n$~10 kDa 4-arm PEG amine hydrochloride (pentaerythritol core, JenKem Technology, 500 mg, 0.05 mmol) was dissolved in dichloromethane (15 mL). Triethylamine (0.554 mL, 4.00 mmol) was added, followed by ((1R,8S,9s)-bicyclo[6.1.0]non-4-yn-9-yl)methyl (2,5-dioxopyrrolidin-1-yl) carbonate (175 mg, 0.600 mmol) and the reaction mixture was stirred at room temperature overnight. The reaction mixture was directly purified by dialysis against methanol using a 2 kDa MWCO Spectra/Por 6 regenerated cellulose dialysis membrane (Spectrum, Inc.). For analysis and utilization in further reactions, XL-6 was isolated by concentration using a roto evaporator. For storage purposes the compound was kept as a methanol solution at room temperature. $^1$H NMR (400 MHz, MeOH-d4) δ 4.14 (m, 8H), 3.63 (br s, 995H), 2.22 (m, 24H), 1.61 (m, 8H), 1.38 (m, 4H), 0.94 (m, 8H). Exchangeable protons are not visible in MeOD.

XL-8.

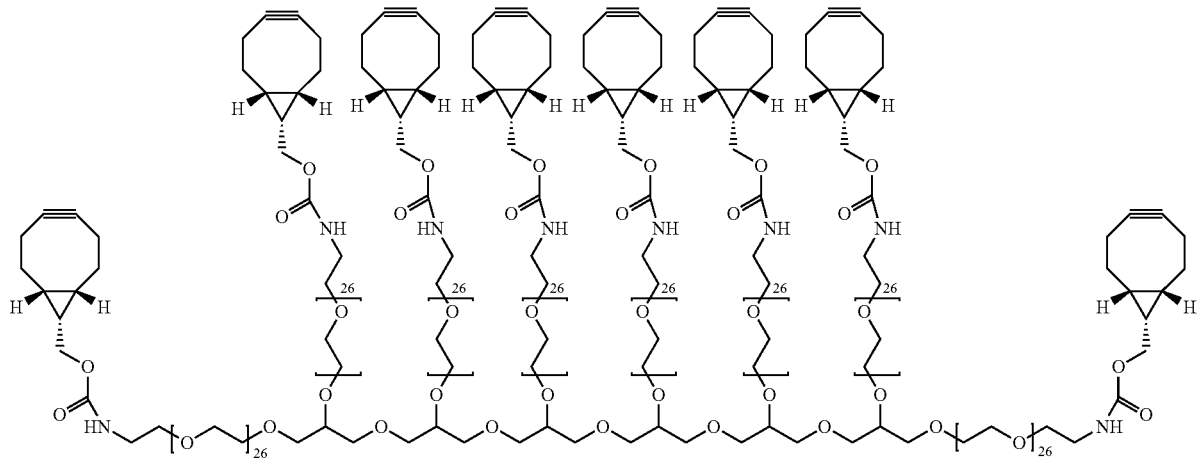

$M_n$~10 kDa 8-arm PEG amine hydrochloride (hexaglycerol core, JenKem Technology, 800 mg, 0.08 mmol) was dissolved in dichloromethane (5 mL). Triethylamine (0.887 mL, 6.40 mmol) was added, followed by ((1R,8S,9s)-bicyclo[6.1.0]non-4-yn-9-yl)methyl (2,5-dioxopyrrolidin-1-yl) carbonate (807 mg, 2.56 mmol) and the reaction mixture was stirred at room temperature for 5 h. The reaction mixture was concentrated using a rotoevaporator, then dissolved in methanol and purified by dialysis against methanol using a 2 kDa MWCO Spectra/Por 6 regenerated cellulose dialysis membrane (Spectrum, Inc.). For analysis and utilization in further reactions, XL-8 was isolated by concentration using rotoevaporator, however for storage purposes XL-8 was kept as a methanol solution at room temperature. $^1$H NMR (400 MHz, MeOH-d$_4$) δ 4.14 (m, 16H), 3.63 (br s, 935H), 2.23 (m, 48H), 1.61 (m, 16H), 1.38 (m, 8H), 0.95 (m, 16H). Exchangeable protons are not visible in MeOD.

XL-12. PEG(4000)-((oxybis(ethane-2,1-diyl))bis(oxy))bis(ethane-2,1-diyl) bis(1-(((((1R,8S)-bicyclo[6.1.0]non-4-yn-9-yl)methoxy)carbonyl)amino)cyclopropane-1-carboxylate)

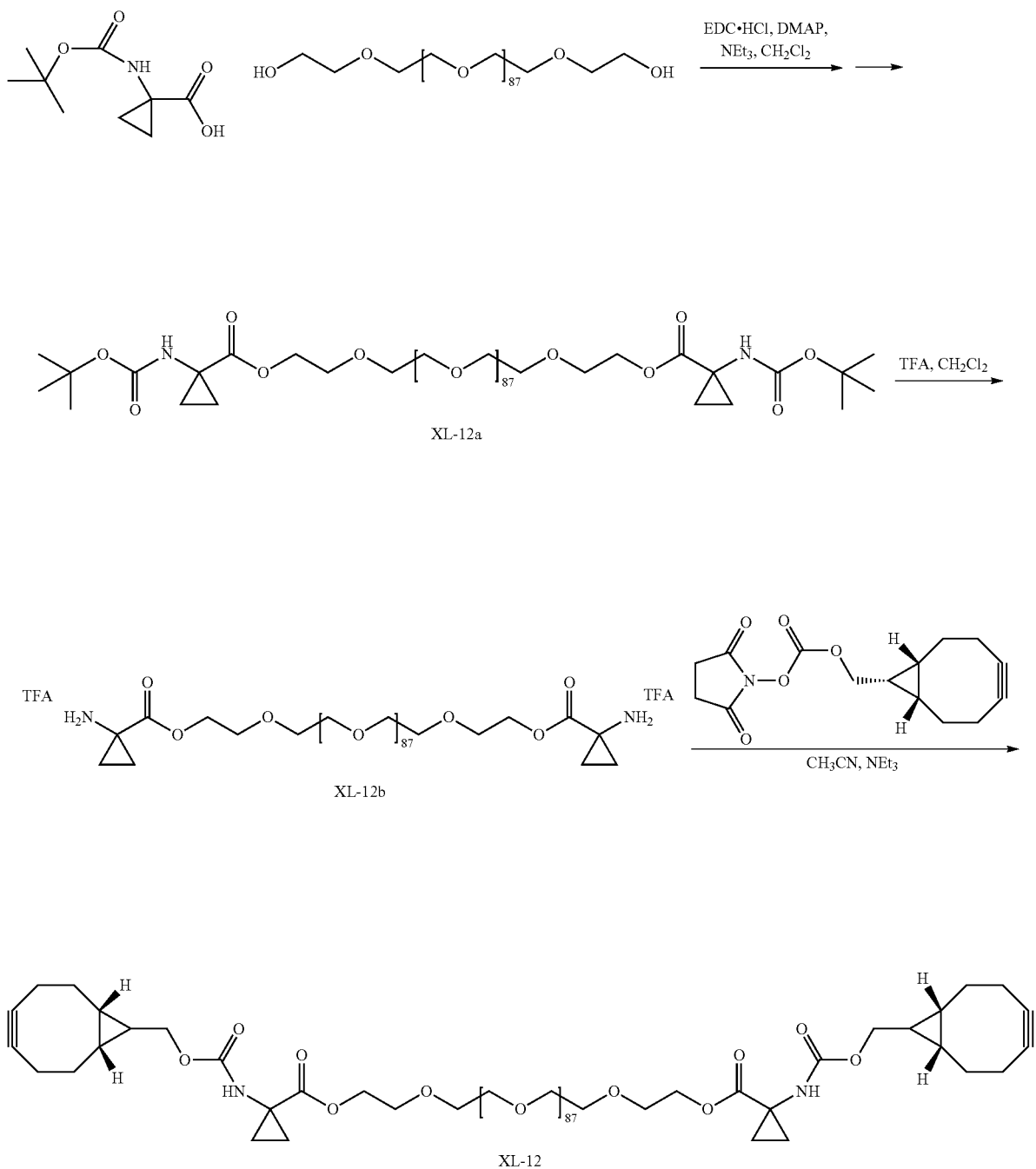

XL-12a. PEG(4000)-((oxybis(ethane-2,1-diyl))bis(oxy))bis(ethane-2,1-diyl), bis(1-((tert-butoxycarbonyl)amino)cyclopropane-1-carboxylate)

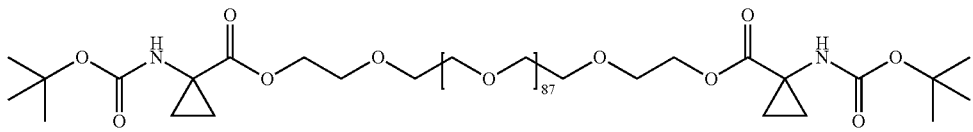

1-((tert-butoxycarbonyl)amino)cyclopropanecarboxylic acid (252 mg, 1.25 mmol) and $M_n$~4 kDa PEG (1 g, 0.25 mmol) were dissolved in 10 mL dichloromethane. Dimethylaminopyridine (15 mg, 0.125 mmol) and EDC-HCl (192 mg, 1.0 mmol) were added and the reaction mixture was stirred at room temperature overnight. The crude product was purified by flash column chromatography (with a ELSD detector) on silica with a 0-100% Heptane:EtOAc, then 0-100% dichloromethane:dichloromethane/methanol (4:2) gradient. The product containing fractions were pooled and concentrated to dryness to provide XL-12a. $^1$H NMR (500 MHz, DMSO-$d_6$) δ 7.53 (s, 2H), 4.09 (t, 4H), 3.51 (s, 446H), 3.38-3.35 (m, 4H), 1.41-1.33 (m, 18H), 1.30 (d, 4H), 1.03-0.97 (m, 4H).

XL-12b. PEG(4000)-((oxybis(ethane-2,1-diyl))bis(oxy))bis(ethane-2,1-diyl) bis(1-aminocyclopropane-1-carboxylate), bis-trifluoroacetic acid

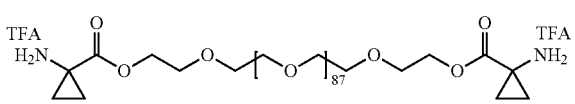

XL-12a (1.03 g, 0.238 mmol) was dissolved in dichloromethane (4 mL). Trifluoroacetic acid was added (4 mL) and the reaction mixture was stirred at room temperature for 2 hours. The solvent was removed under reduced pressure. The crude product was successively triturated with diethyl ether and decanted off. The operation was repeated three times and the resulting solid was dried under vacuum to provide XL-12b. $^1$H NMR (500 MHz, DMSO-$d_6$) δ 8.72 (s, 4H), 4.30-4.20 (m, 4H), 3.67-3.60 (m, 4H), 3.50 (s, 443H), 1.46-1.41 (m, 4H), 1.36-1.31 (m, 4H).

XL-12. PEG(4000)-((oxybis(ethane-2,1-diyl))bis(oxy))bis(ethane-2,1-diyl) bis(1-(((((1R,8S)-bicyclo[6.1.0]non-4-yn-9-yl)methoxy)carbonyl)amino)cyclopropane-1-carboxylate)

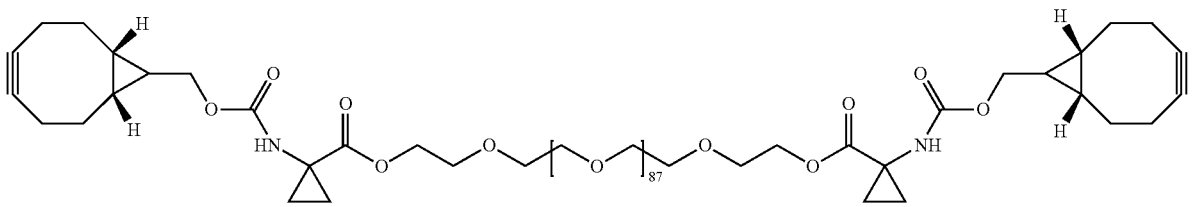

XL-12b (1.04 g, 0.238 mmol) was dissolved in acetonitrile (5 mL). Triethylamine (1.66 mL, 11.89 mmol) was added followed by ((1R,8S,9s)-bicyclo[6.1.0]non-4-yn-9-yl)methyl (2,5-dioxopyrrolidin-1-yl) carbonate (277 mg, 0.952 mmol) and the reaction mixture was stirred at room temperature overnight. The reaction mixture was directly purified by flash column chromatography (with a ELSD detector) on silica with a 0-100% Heptane:EtOAc, then 0-100% dichloromethane:dichloromethane/methanol (4:2) gradient. The product containing fractions were pooled and concentrated to dryness. Then, the solid was dissolved in dichloromethane and washed with deionized water. The organic layer was dried over phase separator to afford XL-12. For storage purposes, XL-12 was kept as a solution in acetonitrile (50 mg/mL) and placed in a freezer. Analytical UPLC (method B, see above): retention time=1.21 min. $^1$H NMR (500 MHz, MeOH-$d_4$) δ 4.25-4.13 (m, 8H), 3.64 (s, 401H), 2.33-2.10 (m, 8H), 1.67-1.56 (m, 4H), 1.52-1.47 (m, 4H), 1.44-1.34 (m, 2H), 1.19-1.11 (m, 4H), 1.00-0.91 (m, 4H). Exchangeable protons are not visible in MeOD.

Example 5
This example describes the synthesis of hydrogels prepared by reacting appropriately functionalized polymers with crosslinkers.
Synthesis of Hyaluronic Acid Hydrogel: H1g
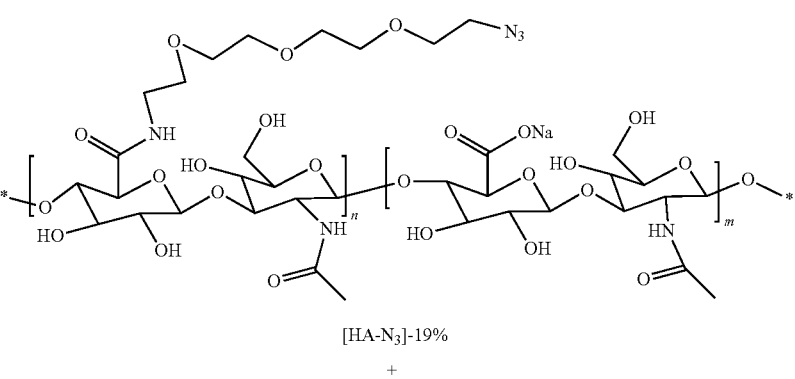
[HA-N₃]-19%
+
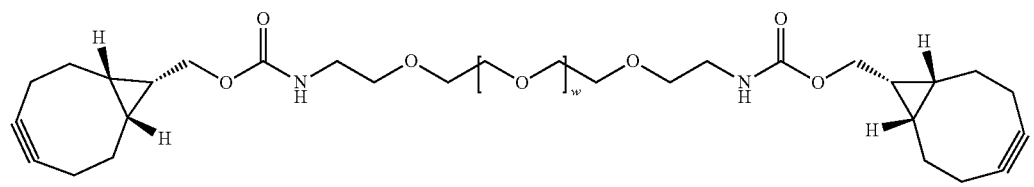
XL-1-1
PBS, 37° C.
PBS, 37° C.

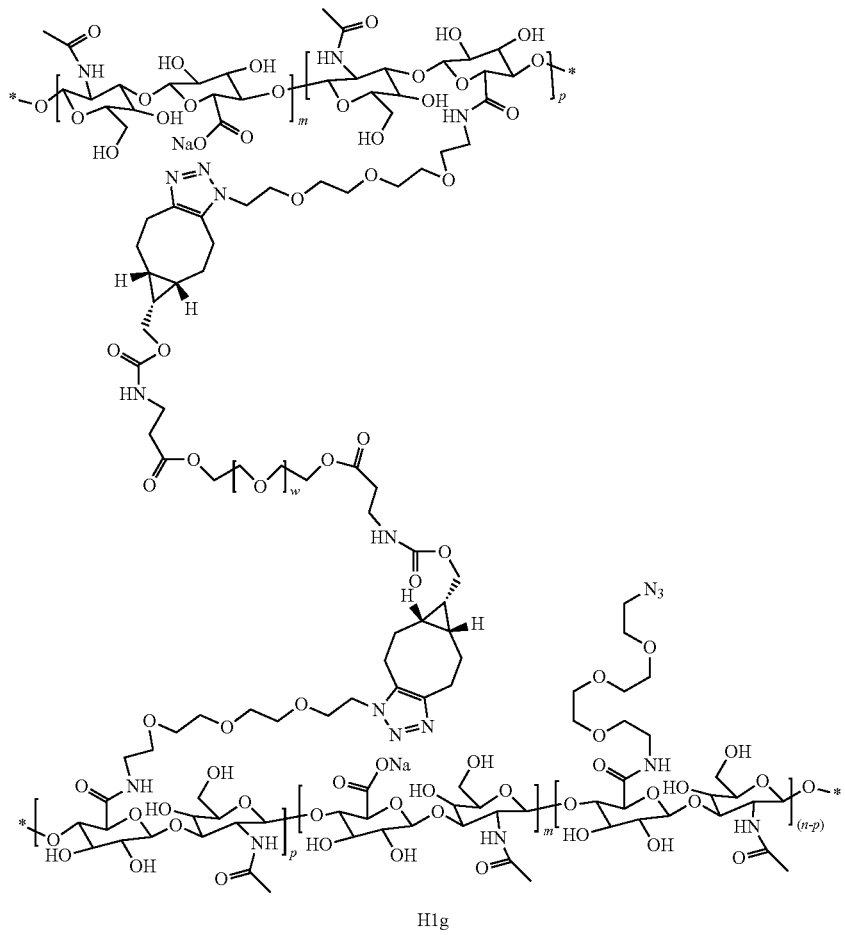

H1g

[HA-N3]-19% (60 mg, 137 μmol, degree of substitution=19%) was dissolved in 4.0 mL sterile 1×PBS buffer, pH 7.4 at room temperature over 1 h in a 15 mL tube. The molecular weight of the unsubstituted carboxylate sodium salt repeat dimer unit is 401.3 Da. The MW of the azidylated repeat dimer unit is 579.6 Da. The average MW of a dimer unit for the sodium salt form of [HA-N3]-19% is 435.2 Da=((401.3×0.81)+(579.6×0.19)). Using the average MW of a sodium salt dimer unit, the total moles of repeat dimer unit is 137 μmol and the number of moles of azidylated repeat dimer unit is 26 μmol.

To this solution was added a 50 mg/mL solution of XL-1-1 (0.205 mL, 4.1 μmol of reagent assuming a MW of 2474 Da, 8.20 μmol of reactive functionality). This resulted in a solution which was 3% w/v with respect to [HA-N3]-19% and where 6% of the [HA-N3]-19% repeat units were predicted to be cross-linked by the XL-1-1] ((8.20 μmol [XL-1-1-reactive functionality]/137 mol [HA-units]× 100=6%).

The mixture was vortexed briefly to mix, then distributed into a 10 mL syringe, which was capped and held at 37° C. overnight to provide H1g. Visual inspection (inversion test) showed successful gelation.

Preparation of Hyaluronic Acid-Based Hydrogel Particles

H1g, 2 mL, was forced through a 100 mesh stainless steel screen disc into a 5 mL syringe, yielding coarse gel particles. To this syringe 1 mL of 1×PBS was added, followed by vortexing to mix. The syringe was held at room temperature for 6 h to allow swelling of the hydrogel. This resulted in a mixture that was 1.5% with respect to [HA-N3]-19%. The swollen, coarse gel particles of H1g were forced 20 times through a 200-mesh stainless steel screen disc, yielding fine gel particles as the final product.

The hyaluronic acid-based hydrogels (and corresponding hydrogel particles) listed in Table 17 were prepared analogously to H1g. A hydrogel is defined by the [HA-N3] component used and its concentration in the crosslinking reaction, as well as by the PEG crosslinker used and the degree with which it is expected to form cross-links to the back bone polymer (% cross-link).

TABLE 17

Exemplary Hyaluronic Acid-based Hydrogels

| Number | [HA-N$_3$]-X % | Conc of [HA-N3] in Hydrogel Reaction | XL-m | % cross-link in hydrogel |
|---|---|---|---|---|
| H1a | [HA-N$_3$]-23% | 1.5% | XL-1-1 | 6.3 |
| H1b | [HA-N$_3$]-23% | 1.0% | XL-1-1 | 4.5 |
| H1c | [HA-N$_3$]-37% | 1.0% | XL-1-1 | 5.3 |
| H1e | [HA-N$_3$]-22% | 1.4% | XL-1-1 | 6.3 |
| H1f | [HA-N$_3$]-23% | 1.0% | XL-1-1 | 5.9 |
| H1g | [HA-N$_3$]-19% | 1.5% | XL-1-1 | 6.0 |
| H2a | [HA-N$_3$]-19% | 1.5% | XL-2-1 | 6.0 |
| H12a | [HA-N$_3$]-19% | 1.5% | XL-12-1 | 6.0 |

Example 6

Synthesis of Hydrogel-Drug Conjugates

This example describes the synthesis of hydrogel-drug conjugates, in which the drug is conjugated to the carrier via a traceless linker.

When preparing samples for in vivo dosing, all manipulations of materials or solutions that were not capped took place in a laminar flow hood under aseptic conditions. All consumables used were previously unopened and were labeled "sterile."

C1-2 (H1g-L2D1)

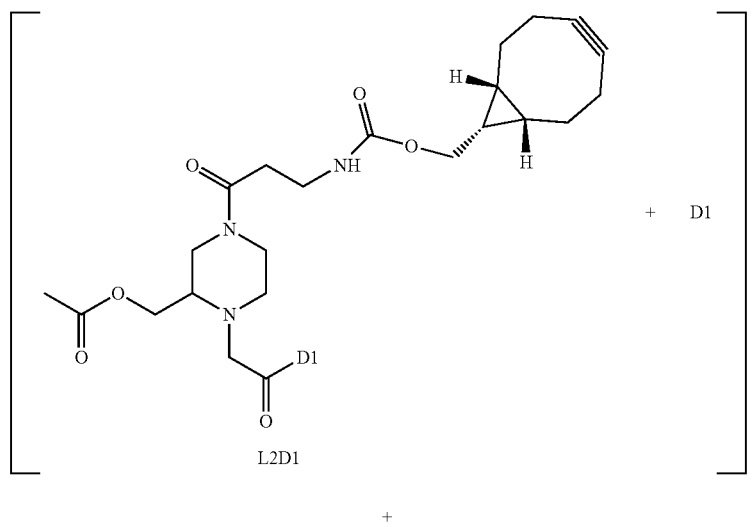

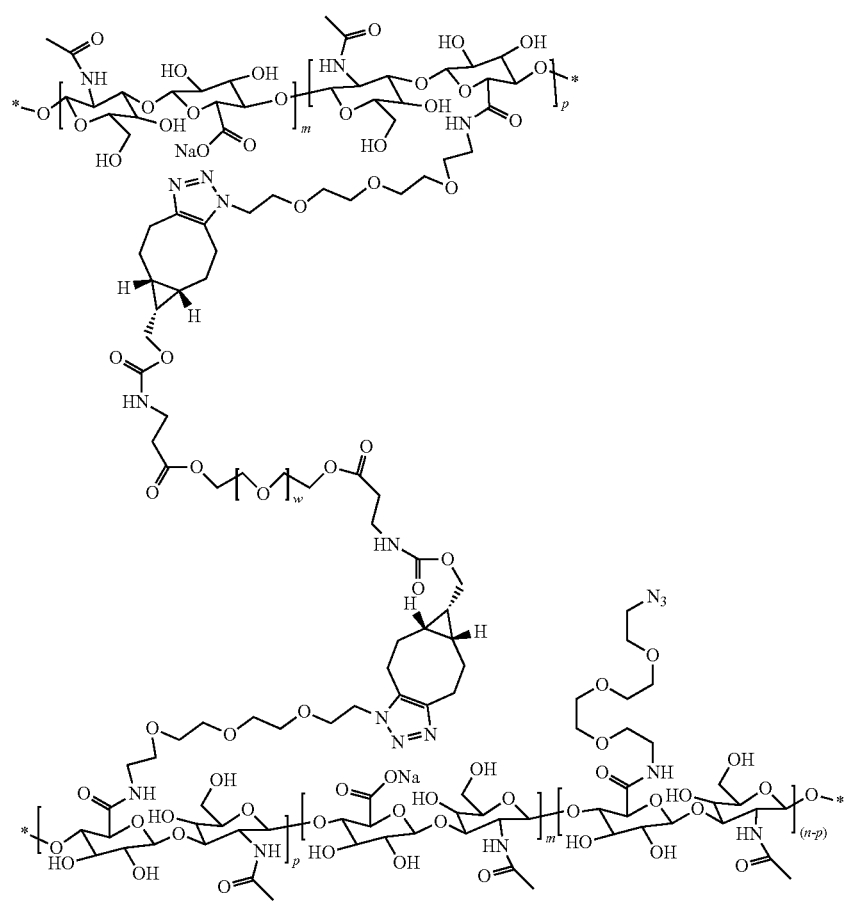
H1g
↓ 30° C.
↓

-continued

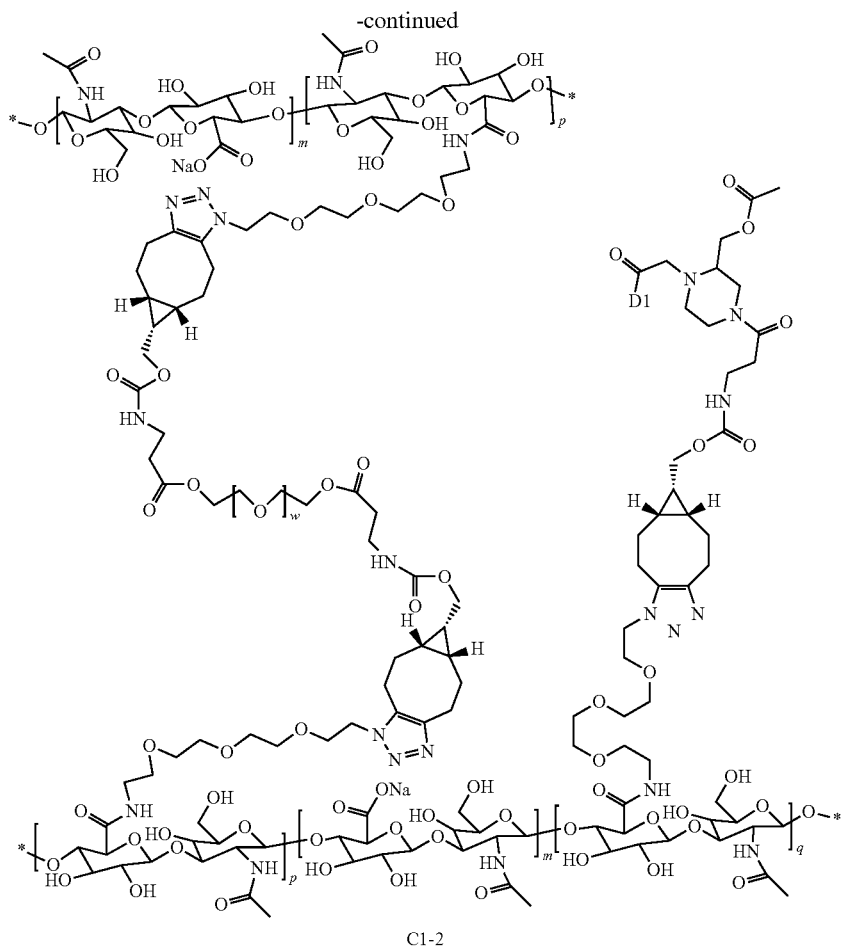

C1-2

Hydrogel particle suspension of H1g (1.08 g, 15 mg/mL, 19 mM total dimer repeat unit) was treated with a solution of L2D1 (7 mL of 13.33 mg/mL solution in 20 mM histidine buffer (pH=5.8)), vortexed and shaken overnight at 30° C. (600 rpm). The reaction tube was centrifuged (1500 rcf, 5 min) and the supernatant was removed from the tube using a needle and syringe. Fresh 1×PBS (10-15 mL) was added to the tube, which was shaken to resuspend the gel. Centrifugation, removal of supernatant, and dilution with fresh buffer was repeated. The washing continued until no D1 was detected in the supernatant. A Nanodrop spectrophotometer used for detection of absorbance at 280 nm.

A key descriptor of hydrogel-drug conjugates is the amount of drug loaded per volume of hydrogel (=drug loading). When the drug is a protein, there are several methods to determine the loading.

Protein loading of the hydrogel was determined by forced release of the conjugated protein from a known volume of hydrogel, followed by quantification of the released protein. In this example: 20.0 mg of [C1-2] was weighed into a reaction tube. The sample was treated with 0.5M NaOH (4 mL, AVS Titrinorm, 31951.290), vortexed and shaken at 37° C. for 30 min. The concentration of released drug, D1 (SEQ ID NO:19) was measured, using a UV spectrophotometer, to be 11.68 mg/mL in this sample, corresponding to 11.68 mg D1/mL of hydrogel in [C1-2]. This analysis was carried out in duplicate. The average determined protein loading for [C1-2] prior to dilution was 12.14 mg of D1/mL of hydrogel.

In another method, 20.8 mg of [C1-2] was weighed into a reaction tube. The sample was treated with 1M Tris-HCl buffer pH=9.5 (4 mL), vortexed and shaken at 37° C. for 24 hours (or until the measured concentration reached a steady state). The concentration of released drug D1 was measured, using a UV spectrophotometer, to be 13.3 mg/mL in this sample, corresponding to 13.3 mg D1/mL of hydrogel in [C1-2]. This analysis was carried out in triplicate. The average determined protein loading for [C1-2] prior to dilution was 12.72 mg of D1/mL of hydrogel.

In another method, 24.5 mg of [C2-2] was weight in a reaction tube and 2800 μL of water was added followed by 58.05 μL of a hyaluronidase solution (from Worthington, LS005475, 8140 U/mg). The reaction mixture was shaken for 3 hr at RT and the absorption was measured, using a UV spectrophotometer, to be 19.68 mg/mL in this sample. This analysis was carried out in triplicate. The average determined protein loading for [C2-2] prior to dilution was 19.49 mg of D1/mL of hydrogel.

An alternate method of determining protein loading relies on difference calculations. In this method, the measured concentration of D1 (using a UV spectrophotometer) recovered in the hydrogel washes is subtracted from the known total added protein at the beginning of the experiment (for example: D1+L2D1). The difference gives the D1 loading based on the volume of total hydrogel.

The hydrogels in Table 18 were prepared using methods analogous to those used in the synthesis of $C_{1-2}$.

TABLE 18

Exemplary Hydrogel-Drug Conjugates

| Number | Study | Linker-drug adduct used | Hydrogel used | Drug loading (mg/mL) | Analytical method |
|---|---|---|---|---|---|
| C1-2 | — | L2D1 | H1g | 12.1 | Forced release (NaOH) |
| C1-2 | — | L2D1 | H1g | 11.8 | Difference |
| C2-1 | — | L1D1 | H2a | 18.5 | Forced release (NaOH) |
| C2-2 | In vitro release Example 8.1 In vivo release Example 9 | L2D1 | H2a | 19.5 | Forced release (Hyaluronidase) |
| C2-2 | In vitro release Example 8.1 In vivo release Example 9 | L2D1 | H2a | 18.9 | Forced release (NaOH) |

TABLE 18-continued

Exemplary Hydrogel-Drug Conjugates

| Number | Study | Linker-drug adduct used | Hydrogel used | Drug loading (mg/mL) | Analytical method |
|---|---|---|---|---|---|
| C2-5 | — | L5D1 | H2a | 18.2 | Difference |
| C12-2 | — | L2D1 | H12a | 18.8 | Forced release (NaOH) |

The hydrogel-drug conjugate may be diluted with 1×PBS to attain the desired final drug concentration for dosing. The amount of 1×PBS to be added can be calculated by the following equation: (PBS diluent (mL))=[(total drug (mg)/desired drug loading (mg/mL)]−(initial volume of conjugate (mL)).

Conjugate $C_{2-2}$ was dispensed for dosing in 0.5 mL insulin syringes with attached 30 G needles, by removing the plunger and backfilling with the desired volume of $C_{2-2}$.

The hydrogel-drug conjugates were stored at RT.

Example 7

In Vitro Drug Release Studies
7-1. Release of D1 (SEQ ID NO:19) from Hydrogel-Drug Conjugates

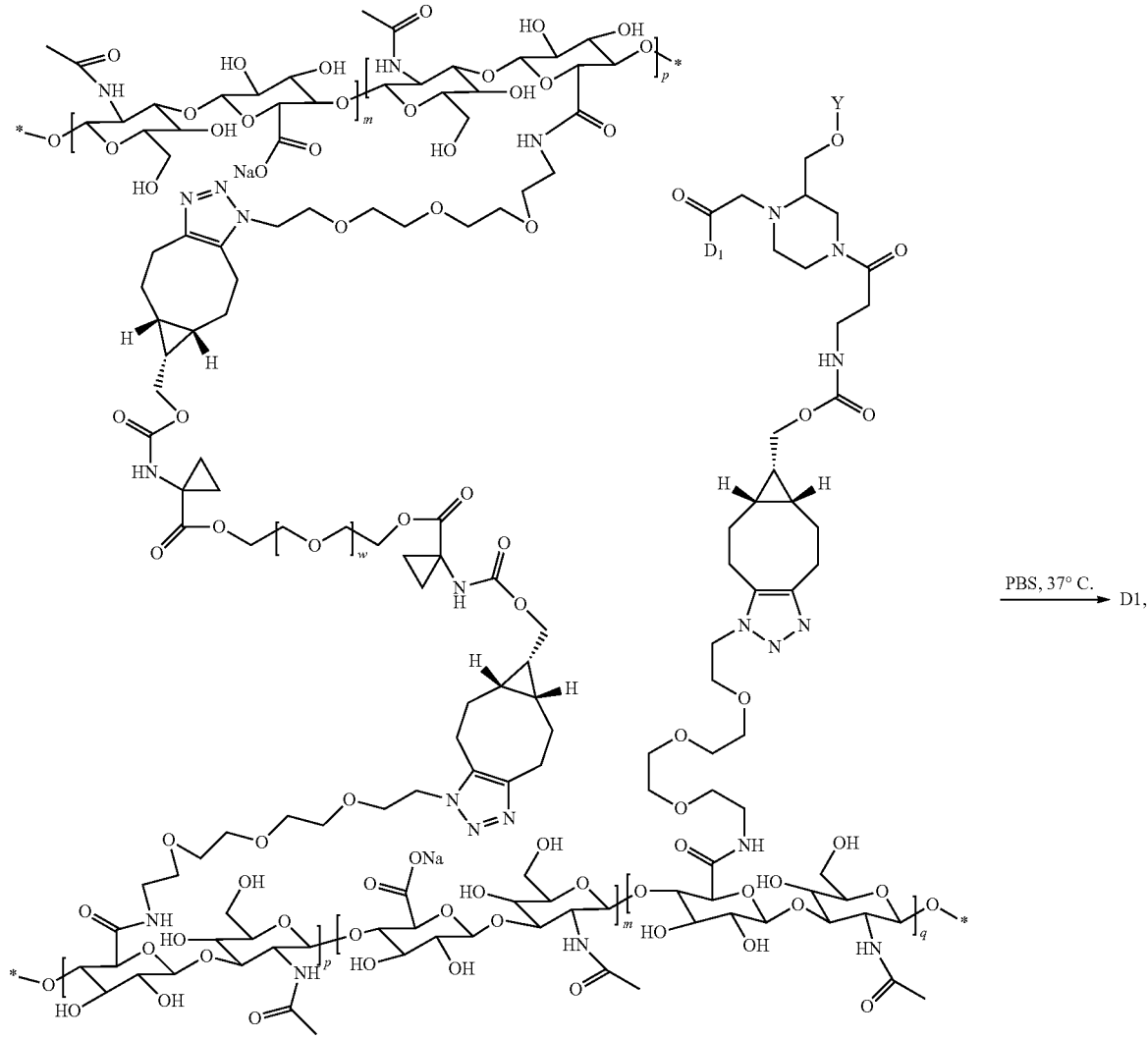

where Y is selected from Table 3, above.

Figure 4A:
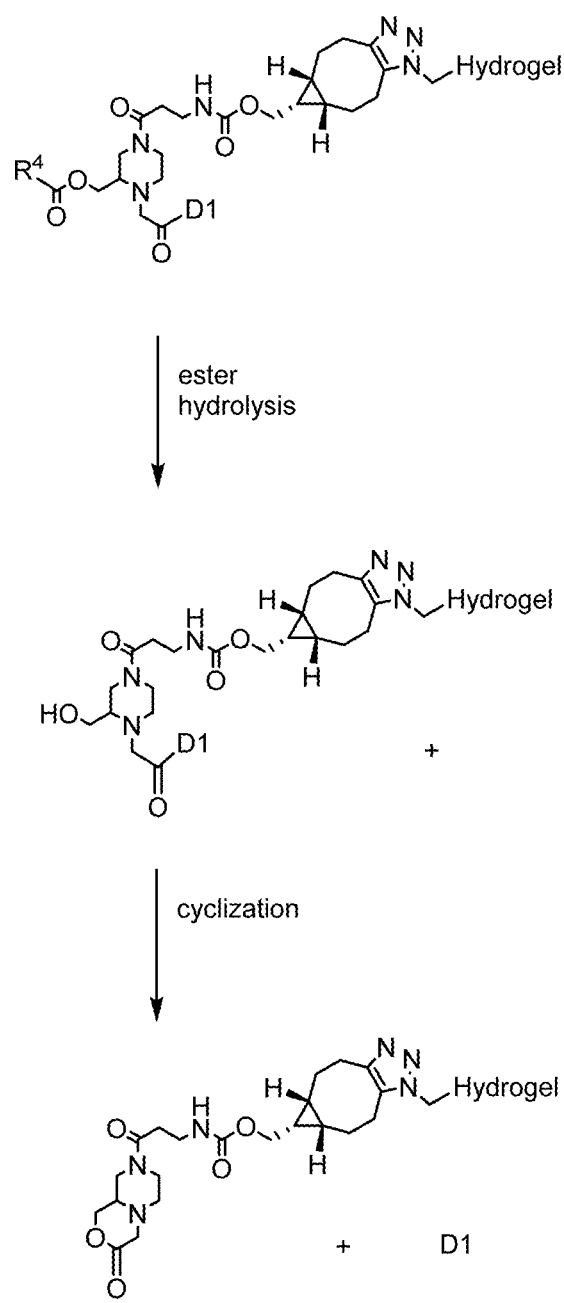
FIG. 4A (illustrating Example 8.1) shows an example of the in vitro release of D1 (SEQ ID NO:19) from a hydrogel conjugate.

Release of D1 (SEQ ID NO:19) from hydrogel conjugates C1-2 and C2-2 occurs as depicted in FIG. 4A. In this study a series of hydrogel-D1-conjugates was held in 1×PBS at 37° C. to assess the release of drug following the traceless linker cleavage reaction. These reactions were sampled at various timepoints and analyzed to determine the concentration of released D1 in the supernatant.

Each hydrogel (approximately 125 μL; exact amount determined by weighing, assumed density of hydrogel=1 g/mL) was added into a Transwell® insert (Corning Inc; 6 well-plate, 24 mm diameter, polycarbonate membrane, 8.0 μm pore size). Wells of the plate were filled with 2.6 mL of PBS+(1%) Penicillin/Streptomycin. (Life Technologies, 10000 IU/g/mL). Then, the hydrogel-containing inserts were placed into the wells and 1.375 mL of PBS+(1%) penicillin/ streptomycin. was added on top of the hydrogel (in the insert). Three wells were prepared for each hydrogel sample. The plate was securely capped and held at 37° C. in a humid environment.

Samples of collection buffer were removed from the wells at various timepoints for up to 28 days. At each timepoint and for each well, the Transwell® insert was removed from the well, drip-dried and transferred to a new plate, in a well containing 3.6 mL of fresh 1×PBS+(1%) penicillin/streptomycin. The replenished plate was returned to the incubator. In the meantime, the entire volume of collection buffer was transferred to a clean tube and weighed, then a timepoint sample was removed from the collection buffer (0.10 mL to be used for analytical purposes) and the rest was stored at −80° C. until assaying.

Other buffers used in this assay are bovine synovial fluid (BSF), 1 M Tris-HCl solution (Teknova, pH 9.5) or Dulbecco's Modified Eagle Medium (Gibco, ref 41965) consisting in 1% fetal bovine serum (Gibco, ref 10270106), 12.5 ug/ml insulin-transferrin-sodium selenite supplement (Roche, ref 11074547001), 50 ug/ml L-ascorbic acid phosphate magnesium salt n-hydrate (Wako, ref 013-12061), 100 units/ml penicilin and 100 ug/ml streptomycin. The penicillin/streptomycin additive could be omitted if the experiment is run at 22° C. instead of 37° C.

For each timepoint samples, the protein concentration (which represents the protein concentration in each well at the timepoint) was determined by size-exclusion chromatography SEC preliminary calibrated with D1 (Instrument: Agilent LC 1260 Infinity; column: Superdex 200 increase 10/300GL (28-9909-44); Column temperature: r.t., flow rate: 0.75 mL/min; injection volume: 10 μL; mobile phase: 1/9 PBS/water preliminary filtered through a 0.10 μm membrane filter; run time: 40 min; detection wavelengths: 214, 280, and 680 nm). Each timepoint sample was analyzed in triplicate and the results were averaged.

Figure 4B:
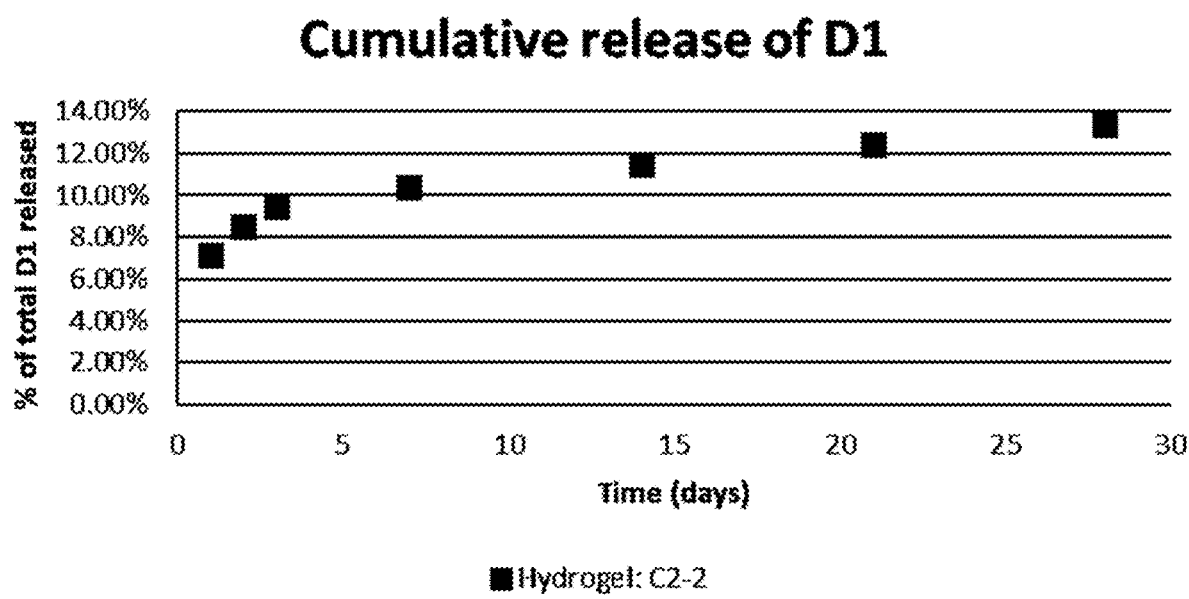
FIG. 4B shows in vitro release of D1 (SEQ ID NO:19) from hydrogel conjugate C2-2.

The total amount of protein in a given well at a given timepoint was calculated by multiplying the protein concentration at the timepoint by the measured volume (assuming density of 1 g/mL). The cumulative D1 released from each hydrogel into each well up to that timepoint was calculated by adding the total amount of D1 in the well at each timepoint. The cumulative percent of protein released from conjugates C2-2 up until a given timepoint is shown in FIG. 4B. The cumulative percent of D1 released is calculated by dividing the cumulative D1 released at a given timepoint by the total D1 present in the initial hydrogel sample and multiplying by 100. As evident from FIG. 4B, release of D1 from the carrier is slow but sustained over a period of one month.

Concentration of protein in a well at timepoint t:

$$[P](t)$$

Total volume in a well at timepoint t:

$$V(t)$$

Total mass of protein in a well at timepoint t:

$$m(P)_{well}(t)=[P](t) \times V(t)$$

Cumulative mass of protein released from hydrogel until timepoint t:

$$m(P)_{cum}(t)=\Sigma_{i=0}^{t} m(P)\text{well}$$

Example 8

Comparative Tissue Tolerability of Hydrogels

This study examined if hydrogels elicit a severe inflammatory response or any other adverse events over a period of 11-weeks after a single intra-articular injection in Lewis rats with knee osteoarthritis. The test articles were H1a, H9a, and Synvisc-One® hyaluronic acid-based injectable solution for treatment of osteoarthritis knee pain (Sanofi).

Preparation of H9a

Hyaluronic acid-based hydrogel particles of H9a were prepared as described for H1a (above, using cross-linker XL-9-1), where a half volume of 1×PBS was added to the particles following the first extrusion. Hydrogel particles of H1a/H9a were dispensed for dosing in 0.5 mL insulin syringes with attached 30 G needles by removing the plunger and backfilling with the desired volume of H1a/H9a. Air bubbles were removed by gentle manipulation of the syringe.

Synvisc-One®

Synvisc-One® was purchased and used as received.

Intra-Articular Injection

Male Lewis rats (LEW/OrlRj Janvier) underwent meniscal tear surgery of one knee. When knee osteoarthritis had developed due to joint stability about 7 days after the surgery, 25 μL of the test article or saline control were injected intra-articular in the operated knee joint under anesthesia (Table 19). One naive (not operated) rat served as control. In-life observations were recorded for 1-2 hours post dosing and at least once daily thereafter for one week. In the following weeks until necropsy, in-life observations were recorded once weekly. Body weights were taken weekly.

TABLE 19

Study design, animal allocation and test article doses

| Group | n | Treatment | Dose (μL) | Necropsy time point |
|---|---|---|---|---|
| 1.1 | 3 | Synvisc-One ® | 25 | 4 weeks post injection |
| 1.2 | 3 | Synvisc-One ® | 25 | 6 weeks post injection |
| 1.3 | 3 | Synvisc-One ® | 25 | 8 weeks post injection |
| 1.4 | 3 | Synvisc-One ® | 25 | 11 weeks post injection |
| 2.1 | 3 | H1a | 25 | 4 weeks post injection |
| 2.2 | 3 | H1a | 25 | 6 weeks post injection |
| 2.3 | 3 | H1a | 25 | 8 weeks post injection |
| 2.4 | 3 | H1a | 25 | 11 weeks post injection |
| 3.1 | 3 | H9a | 25 | 4 weeks post injection |
| 3.2 | 3 | H9a | 25 | 6 weeks post injection |
| 3.3 | 3 | H9a | 25 | 8 weeks post injection |
| 3.4 | 3 | H9a | 25 | 11 weeks post injection |
| 4 | 3 | Saline | 25 | 11 weeks post injection |
| 5 | 1 | — | — | 12 weeks post study start |

Rats were euthanized 4, 6, 8, or 11 weeks post intra-articular injection. Synovial fluid from the injected knee joint was collected by opening the knee joint and lavage with 25 µL saline. Macroscopic abnormalities were recorded during necropsy. The right operated/injected knees were collected from all animals, fixed in 10% neutral-buffered formalin, embedded in paraffin and sectioned. Hematoxylin and eosin and SafraninO/fast green stained knee joint sections were evaluated by a pathologist.

Results and Conclusions

The hydrogels did not cause any adverse events over 11 weeks when injected intra-articular in rat knee joints. The presence of hydrogel in the subsynovial space, blebbing of synovial cells into the joint space and proliferation of synovial and subsynovial cells was transient at early time points and less pronounced for HA hydrogel conjugates than for Synvisc-One®, which is marketed and frequently used for treatment of osteoarthritis knee pain (Sanofi).

Example 9

In Vivo Drug Release Study

This study examined the in vivo release profile of D1 from hydrogel drug conjugate C2-2 after intra-articular injection in rat knee joints.

Preparation of C2-2

Hydrogel drug conjugate C2-2 was prepared as described in Example 6. D1 concentration in C2-2 was 19.0 mg/g, corresponding to a D1 dose of 0.475/joint.

Intra-Articular Injection

Both knee joints of 9 naïve male Lewis rats (LEW/OrlRj Janvier; 9 weeks old) were injected each with 25 µL of C2-2 under anesthesia. Blood/serum was collected at the time points indicated in Table 20. At time points 24, 72 and 168 hours after intraarticular injections, 3 rats each were euthanized. Synovial fluid and articular cartilage were collected from left knee joints, whole joint tissue from right knees.

TABLE 20

| ER Formulation | Dose (mg/animal/ joint) | Animal | Biological matrix collected | Time points post-dose |
| --- | --- | --- | --- | --- |
| C2-2 | 0.25/i.a. | 01-03 | Blood/Serum | 0.5, 1, 3, 6, 24, 72, 168 h |
|  |  | 01-03 | SF; Cart; Knee | 168 h |

TABLE 20-continued

| ER Formulation | Dose (mg/animal/ joint) | Animal | Biological matrix collected | Time points post-dose |
| --- | --- | --- | --- | --- |
|  |  | 04-06 | B/S; SF; Cart; Knee | 24 h |
|  |  | 07-09 | B/S; SF; Cart; Knee | 72 h |

B/S: Blood/Serum;
SF: Synovial fluid;
Cart: Cartilage;
Knee: Whole knee joints

Figure 5:
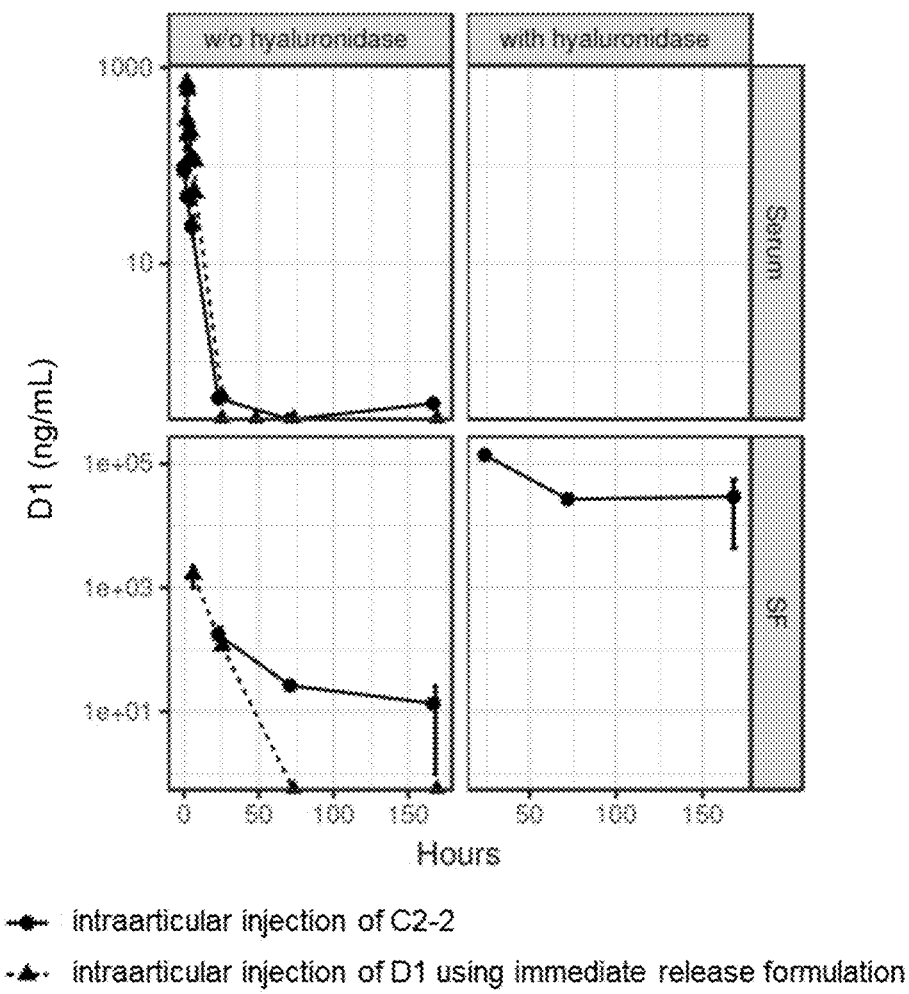
FIG. 5 (illustrating Example 9) shows the in vivo release of D1 (SEQ ID NO:19) from hydrogel conjugate C2-2 administered in rats via intra-articular injection.

Synovial fluid from knee joints was collected by injecting 20 µL saline intra-articularly into the closed knee joint, moving the joint and collecting the fluid directly after opening the knee joint. Afterwards another 20 µL were injected into the open knee joint and collected. The lavage was repeated with another 20 µL saline resulting in a total lavage volume of 60 µL. The pre-weighed vial with the synovial fluid was centrifuged immediately after sampling to ensure that the hydrogel particles are located at the bottom of the tube. Afterwards 5 µL were removed from the pre-weighted vial before storing the main vial at −80° C. The separated 5 µL synovial fluid was kept as back-up sample to allow for analysis without hyaluronidase treatment and was also stored at −80° C. D1 concentrations were quantified in serum and synovial fluid by an ECLIA assay. The method is based on the capture of D1 using an anti-ANGPTL3 monoclonal antibody (Novartis, iProt109046) immobilized on a MSD plate. Captured D1 is detected using a biotinylated anti-ANGPTL3 polyclonal antibody (R&D Systems, BAF3829) followed by the incubation with Streptavidin-SulfoTag. Synovial fluid samples were either pre-treated with hyaluronidase (1500 U/mL) and incubated O/N at 4° C. with shaking at 450 rpm before analysis or kept at −80° C. without hyaluronidase pretreatment Results and Conclusions As shown in FIG. 5, C2-2 hydrogel provided prolonged serum exposure at very low levels for up to 1 week, as compared to the short and high systemic exposure observed with D1 immediate release formulation, which was no longer detectable at 1 week. C2-2 hydrogel intraarticular injection also resulted in high sustained D1 levels for at least one week in synovial fluid, which was hyaluronidase treated to release D1 from residual hydrogel in the synovial fluid. Free D1 levels detected in synovial fluid without hyaluronidase pretreatment were much lower, but also detectable for at least one week.

These results indicate that C2-2 hydrogel prolonged the release of D1 into synovial fluid for at least one week.

What is claimed is:

1. A drug delivery system or pharmaceutically acceptable salt thereof comprising DR, that is represented by Formula (I), where D is an ANGPTL3 polypeptide comprising at least one primary amine; and
R has the formula:

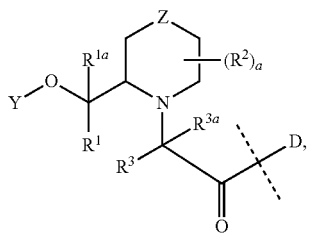

(I)

where the dashed line indicates attachment to the primary amine of D;
$R^1$ is hydrogen or $C_1$-$C_4$alkyl;
$R^{1a}$ is hydrogen or $C_1$-$C_4$alkyl, or $CR^1R^{1a}$, taken in combination form a $C_3$-$C_6$cycloalk-1,1-diyl;
$R^2$ is independently selected at each occurrence from $C_1$-$C_4$alkyl or oxo, or two $R^2$ groups taken in combination with the carbon atom(s) to which they are attached form a fused $C_3$-$C_6$ cycloalkyl or Spiro $C_3$-$C_6$cycloalk-1,1-diyl group;
a is 0, 1, 2, 3 or 4;
$R^3$ is hydrogen or $C_1$-$C_4$alkyl;
$R^{3a}$ is hydrogen, $C_1$-$C_4$alkyl, or $CR^3R^{3a}$, taken in combination form a $C_3$-$C_6$cycloalk-1,1-diyl;
Y is $C(O)R^4$, $C(O)OR^4$, $C(O)NHR^4$, $C(O)NR^5R^6$, $SiR^5R^6R^7$, or $CR^{12}R^{12a}OR^{13}$;

$R^{12}$ is hydrogen or $C_1$-$C_4$alkyl;
$R^{12a}$ is hydrogen or $C_1$-$C_4$alkyl, or $CR^{12}R^{12a}$, taken in combination form a $C_3$-$C_6$cycloalk-1,1-diyl;
$R^{13}$ is $C_1$-$C_4$alkyl; or
$R^{12}$ and $R^{13}$, taken in combination with $C(R^{12a})$ and O form a 5, 6, or 7-member cyclic ether;
$R^4$ is $C_1$-$C_8$alkyl or $C_3$-$C_7$cycloalkyl, wherein cycloalkyl is optionally substituted with 0, 1, or 2 independently selected $C_1$-$C_4$alkyl groups and wherein alkyl is optionally substituted by $C_1$-$C_4$alkoxy;
$R^5$ and $R^6$ are each independently selected from $C_1$-$C_4$alkyl and $C_3$-$C_6$cycloalkyl;
$R^7$ is $C_1$-$C_8$alkyl, $C_3$-$C_7$cycloalkyl, $C_1$-$C_8$alkoxy, $C_3$-$C_7$cycloalkyloxy, heterocycloalkyloxy, or —(OCHR$^3$CH$_2$)$_b$O—$C_1$-$C_4$alkyl, wherein the heterocycloalkyloxy is a 4 to 7 member saturated heterocyclic ring having one ring heteroatom selected from N, O, and S and optionally substituted with 0,1, or 2 independently selected $C_1$-$C_4$alkyl groups;
b is an integer of from 1 to 10;
Z is N-L-A, or N-A, or $NR^9$;
L is an optionally substituted bivalent linker Q-[Sp-Q]h-Q;
Q is independently selected at each occurrence from a bond, O, C(O), N(H), N($C_1$-$C_4$alkyl), C(O)NH, C(O)N($C_1$-$C_4$alkyl), N(H)C(O), N($C_1$-$C_4$alkyl)C(O), N(H)C(O)), N($C_1$-$C_4$alkyl)C(O)O, OC(O)N(H), OC(O)N(C1-$C_4$alkyl), N(H)C(O)N(H), N($C_1$-$C_4$alkyl)C(O)N(H), N(H)C(O)N($C_1$-$C_4$alkyl), N($C_1$-C4alkyl)C(O)N($C_1$-$C_4$alkyl), C(O)O, OC(O), OC(O)O, S, S(O)$_2$, N(H)S(O)$_2$, N($C_1$-$C_4$alkyl)S(O)$_2$, S(O)$_2$N(H), S(O)$_2$N($C_1$-$C_4$alkyl), $C_1$-$C_2$alkyl-C(O)N(H), N(H)C(O)C$_1$-$C_2$alkyl, $C_1$-$C_2$alkyl-C(O)O, OC(O)$C_1$-$C_2$alkyl, 1,2,3-triazole, OP(O)$_2$, P(O)$_2$O, $C_1$-$C_4$alkyl-P(O)$_2$—O, or O—P(O)$_2$-$C_{1-4}$alkyl;

Sp is independently selected at each occurrence from an optionally substituted $C_1$-$C_{20}$alkyl, $C_2$-$C_{20}$alkenyl, $C_2$-$C_{20}$alkynyl, [W—O]$_g$, $C_1$-$C_8$alkyl-[O—W]$_g$, [O—W]$_g$—O—$C_1$-$C_8$alkyl, $C_1$-$C_8$alkyl-[O—W]$_g$—O—$C_1$-$C_8$alkyk, or oligopeptide;

h is an integer of between 1 and 20;

g is a weighted average number of between about 2 and about 50;

$R^9$ is selected from hydrogen, $C_1$-$C_8$alkyl, C(O)—(CH$_2$)$_n$-Q-A, C(O)$C_1$-$C_5$ alkyl, or —C(O)(CH$_2$)$_g$[O—W]$_g$(NHC(O))$_m$(CH$_2$)$_g$[O—W]$_p$-Q-A, wherein the alkyl group is optionally substituted with 0 or 1 Q-A;

W is $C_2$-$C_4$alkyl-1,2-diyl in which a hydrogen methyl, or ethyl side chain may be present on either backbone carbon atom;

A is hydrogen, $C_1$-$C_8$alkyl, C(O)$C_1$-$C_8$alkyl, C(O)N(H)$C_1$-$C_8$alkyl, C(O)O$C_1$-$C_8$alkyl, $R^{10}$, or $R^{11}$, and $R^{11}$ is a carrier.

2. The drug delivery system or pharmaceutically acceptable salt of claim 1, wherein D with is an ANGPTL3 polypeptide having at least 95% identity to any one of SEQ ID NOS: 1 or 3-45.

3. The drug delivery system or pharmaceutically acceptable salt of claim 1, wherein D with is an ANGPTL3 polypeptide comprising amino acid residues 201-460; 207-460; 225-455; 225-455; 225-460; 225-460; 226-455; 226-455; 226-460; 226-460; 228-455; 228-455; 228-460; 228-460; 233-455; 233-455; 233-460; 233-460; 241-455; 241-455; 241-460; 241-460; 242-455; 242-455; 242-460; or 242-460, each in reference to SEQ ID NO:1.

4. The drug delivery system or pharmaceutically acceptable salt of claim 1, wherein D with is an ANGPTL3 polypeptide comprising at least 95% identity to amino acid residues 242-460 in reference to SEQ ID NO:1 and a K423Q substitution.

5. The drug delivery system or pharmaceutically acceptable salt of claim 1 wherein $R^1$ is hydrogen or methyl, $R^{1a}$ is hydrogen or methyl, or $CR^1R^{1a}$, taken in combination form a cyclopropan-1,1-diyl group.

6. The drug delivery system or pharmaceutically acceptable salt of claim 1, wherein the variable a is 0.

7. The drug delivery system or pharmaceutically acceptable salt of claim 1, wherein $R^3$ and Ria are each hydrogen.

8. The drug delivery system or pharmaceutically acceptable salt of claim 1, wherein
Y is C(O)$R^4$ and $R^4$ is $C_1$-$C_6$alkyl, $C_3$-$C_6$cycloalkyl or $C_1$-$C_2$alkoxy$C_1$-$C_2$alkyl, or Y is $SiR^6R^6R^7$;
wherein
$R^5$ and $R^6$ are each methyl, ethyl, propyl or isopropyl; and
$R^7$ is $C_1$-$C_4$ alkyl, ethoxy, propoxy, isopropoxy, butoxy, iso-butoxy, sec-butoxy, 2-ethoxyethoxy, 2-iso-propoxy-ethoxy, tetrahydropyranyloxy, or —(OCHR$^3$CH$_2$)$_b$O—$C_1$-$C_4$alkyl where b is 2,3, or 4.

9. The drug delivery system or pharmaceutically acceptable salt of claim 8, wherein Y is C(O)$R^4$ and $R^4$ is methyl, ethyl, propyl, isopropyl, 1-methyl-cyclopropyl, or methoxymethyl.

10. The drug delivery system or pharmaceutically acceptable salt of claim 1, wherein Z is $NR^9$;
$R^8$ and $R^9$ are each independently selected from hydrogen, $C_1$-$C_8$ alkyl, C(O)—(CH$_2$)$_n$-Q-A, C(O)$C_1$-$C_8$ alkyl, or —C(O)(CH$_2$)$_q$[O—W]$_g$(NHC(O))$_m$(CH$_2$)$_q$[O—W]$_p$-Q-A, wherein the alkyl group is optionally substituted with 0 or 1 Q-A;

q is independently at each occurrence 1, 2, or 3;

g and p each independently have a weighted average length of between about 2 and about 50;

m is 1 or 0;

W is $C_2$-$C_4$alkyl-1,2-diyl in which a hydrogen, methyl, or ethyl side chain may be present on either backbone carbon atom;

Q is a bond, O, N(H) or N($C_1$-$C_4$alkyl);

A is hydrogen, $C_1$-$C_8$alkyl, C(O)$C_1$-$C_8$alkyl, C(O)N(H)$C_1$-$C_8$alkyl, C(O)O$C_1$-$C_8$alkyl, $R^{10}$, or $R^{11}$;
and
$R^{11}$ is a carrier.

11. The drug delivery system or pharmaceutically acceptable salt of claim 1, wherein $R^{11}$ comprises a hydrogel comprising one or more cross-linked polymers.

12. The drug delivery system or pharmaceutically acceptable salt of claim 1, wherein $R^{11}$ comprises a polymer, cross-linked polymer, or hydrogel comprising one or more of hyaluronic acid, polyethylene glycol, polypropylene glycol, polyethylene oxide, polypropylene oxide, polyglutamate, polylysine, polysialic acid, polyvinyl alcohol, polyacrylate, polymethacrylate, polyacrylamide, polymethacrylamide, polyvinyl pyrrolidone, polyoxazoline, polyiminocarbonate, polyamino acid, hydrophilic polyester, polyamide, polyurethane, polyurea, dextran, agarose, xylan, mannan, carrageenan, alginate, gelatin, collagen, albumin, cellulose, methylcellulose, ethylcellulose, hydroxypropylmethylcellulose, hydroxyethyl starch, chitosan, nucleic acids, derivatives thereof, co-polymers thereof, or combinations thereof.

13. The drug delivery system or pharmaceutically acceptable salt of claim 12, wherein $R^{11}$ comprises a hydrogel comprising cross-linked hyaluronic acid, wherein the hyaluronic acid comprises at least one side chain selected from —NH(W1) (O(W1))$_d$—V, wherein W1 is $C_2$-$C_4$alkyl-1,2-diyl in which a hydrogen, methyl, or ethyl side chain may be present on either backbone carbon atom;

d is a number average of 0 to 500; and

V is a suitable functional group comprising azidyl, alkynyl, substituted or unsubstituted $C_7$-$C_{12}$ cycloalkynyl, substituted or unsubstituted $C_7$-$C_{12}$ heterocycloalkynyl, $C_7$-$C_{12}$ cycloalkenyl, norbornyl, vinyl carboxyl, vinyl sulfonyl, $C_2$-$C_8$ alkenyl, amino, thiol, $C_1$-$C_8$ carboxyl, $C_1$-$C_8$ carbonyl, —O—NH2, carbohydrazide, maleimide, alpha-halo carbonyl, furan, substituted or unsubstituted tetrazinyl, lysine, glutamine, cyclodextrin, or adamantanyl.

14. A drug delivery system comprising Formula (III):

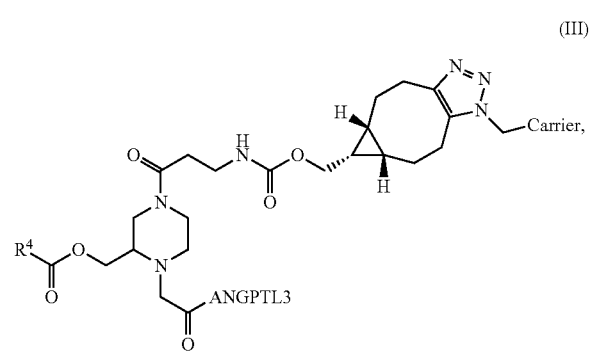

wherein ANGPTL3 comprises an ANGPTL3 polypeptide having at least 95% identity to any one of SEQ ID NO: 1 or 3-45, or combinations thereof.

15. The drug delivery system according to claim 14, wherein ANGPTL3 is a polypeptide comprising amino acid residues 242-460 in reference to SEQ ID NO:1 and a K423Q substitution.
16. The drug delivery system or pharmaceutically acceptable salt thereof according to claim 1, having one of the following formulae:
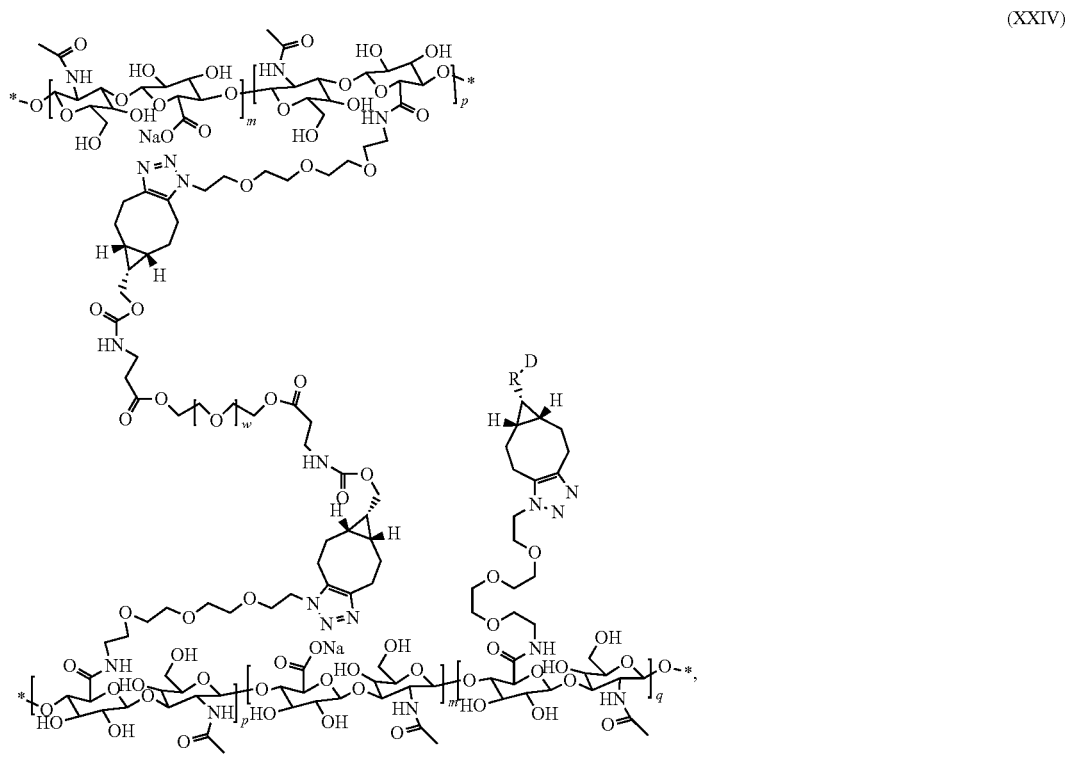
(XXIV)

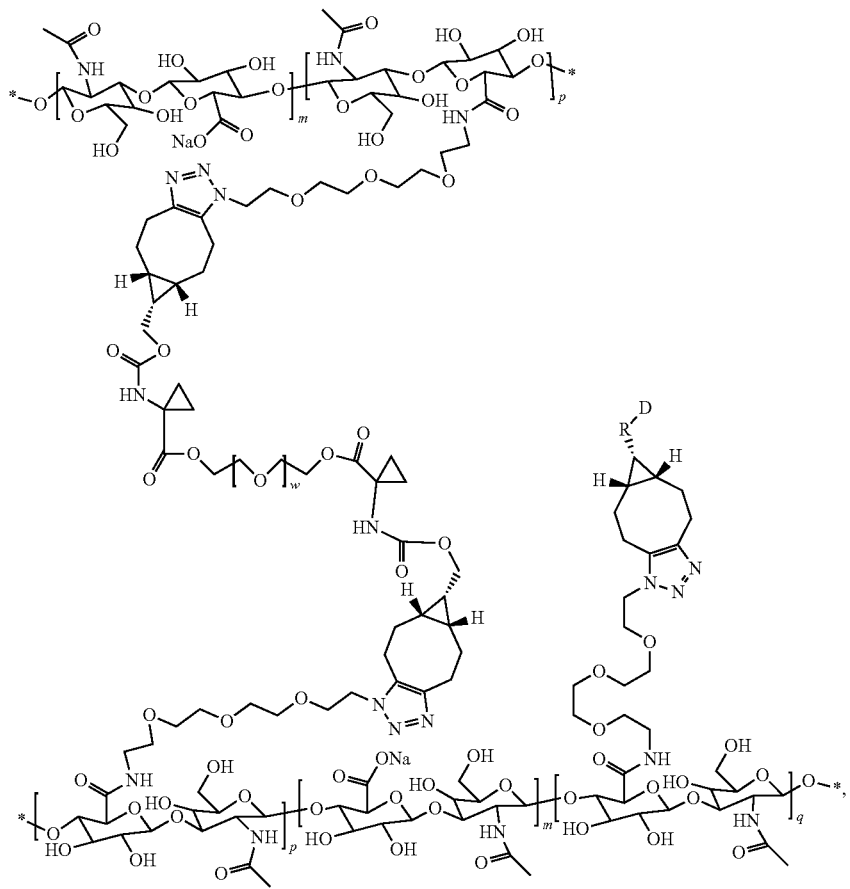
(XXV)

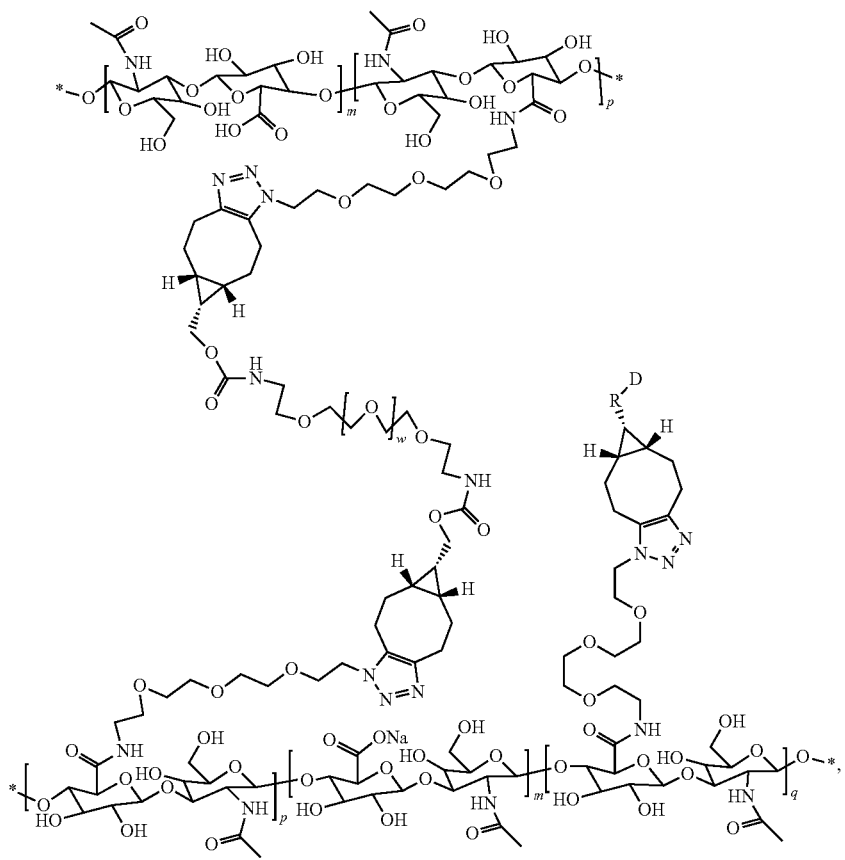
(XXVI)

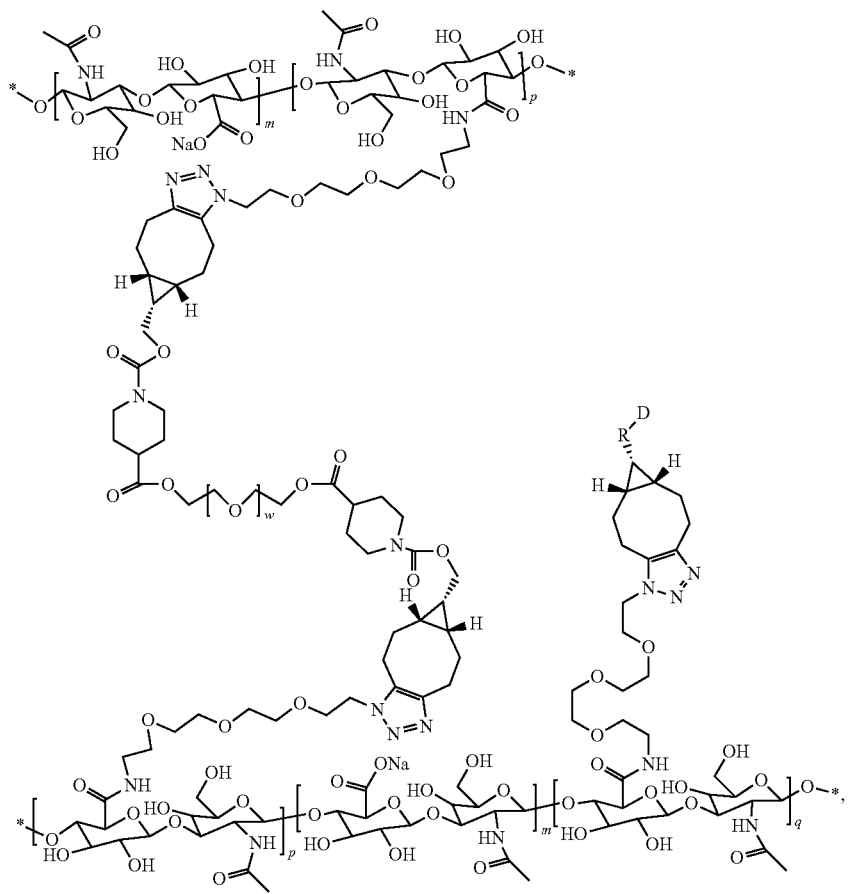
(XXVII)

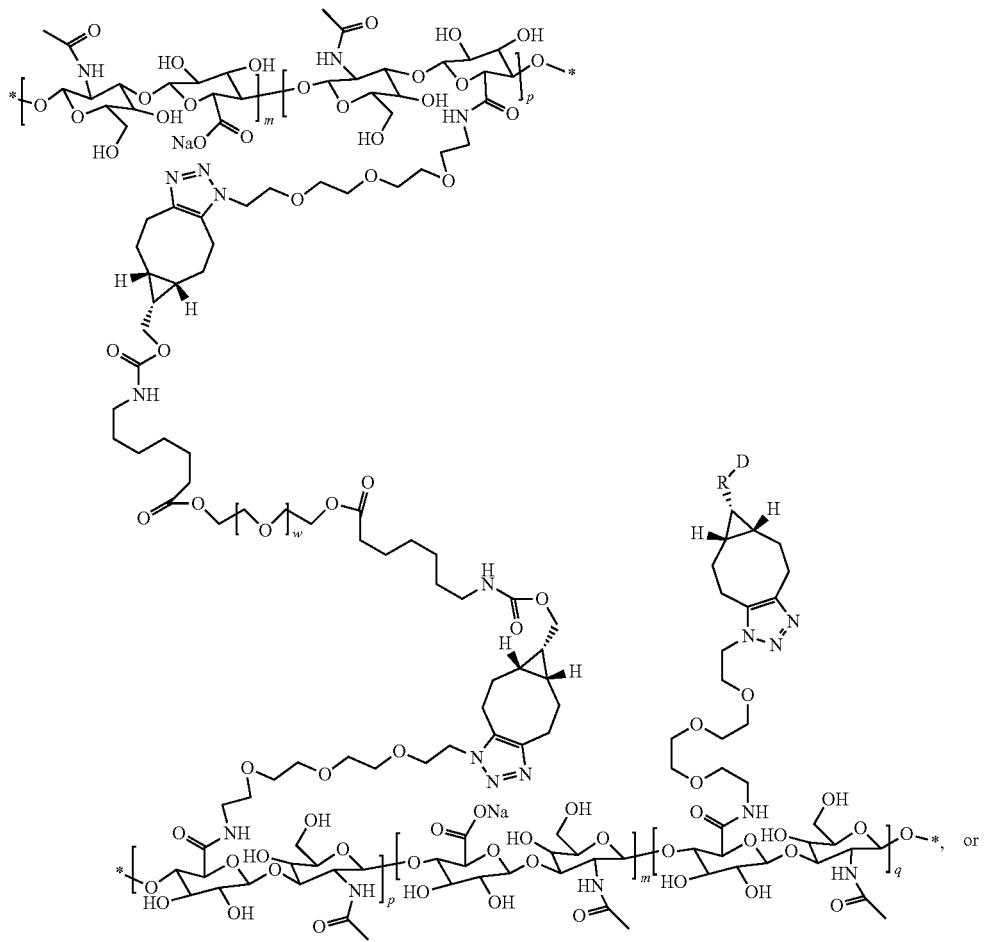
(XXVIII)

(XXIX)

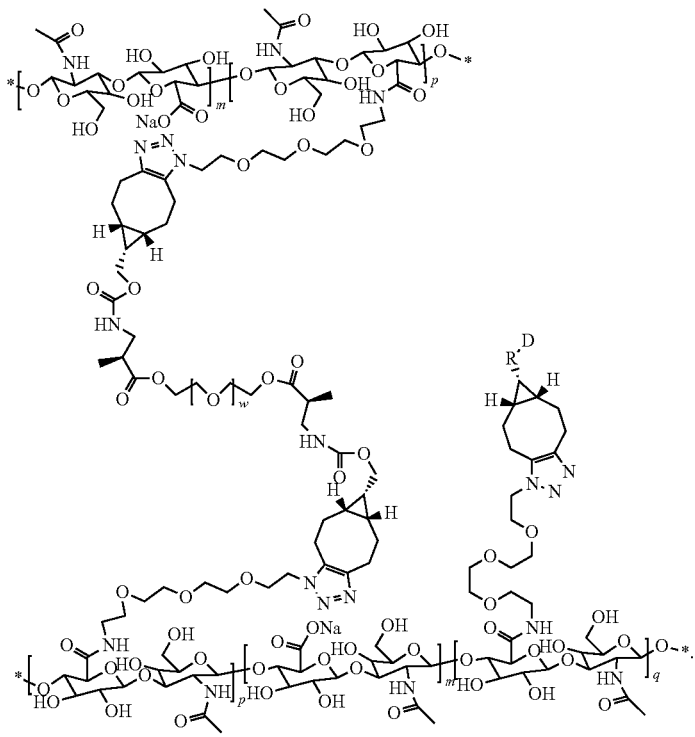

17. The drug delivery system or pharmaceutically acceptable salt thereof according to claim 16, wherein each R has the following formula:

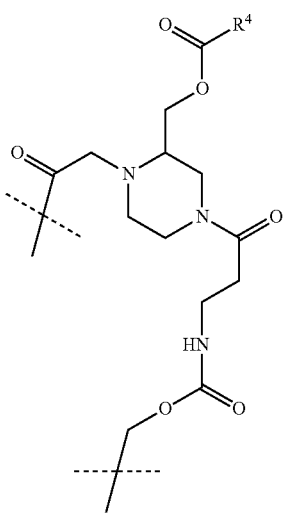

wherein the dashed lines indicate attachment to D and the bicyclo[6.1.0]non-4-yn-9-yl moiety, and $R^4$ is methyl, ethyl, propyl, isopropyl, 1-methyl-cyclopropyl, or methoxymethyl.

18. The drug delivery system or pharmaceutically acceptable salt thereof of claim 1, wherein Y is $C(O)R^4$;

$R^4$ is $C_1$-$C_8$alkyl or $C_3$-$C_7$cycloalkyl, wherein cycloalkyl is optionally substituted with 0, 1, or 2 independently selected $C_1$-$C_4$alkyl groups and wherein alkyl is optionally substituted by $C_1$-$C_4$alkoxy;

Z is N-L-A;

L is $C(O)CH_2CH_2NH$;

A is $R^{11}$; and $R^{11}$ is a hydrogel derived from a cross-linked hyaluronic acid, wherein the hyaluronic acid comprises at least one amide-linked side chain of $N(H)(CH_2CH_2O)_3$ $CH_2CH_2N_3$, and wherein the cross-linker used to form the hydrogel comprises PEG(2000)-bis-[3-(((((1R,8S,9s)-bicyclo[6.1.0]non-4-yn-9-yl)methoxy)carbonyl) amino)propanoate], or $R^{11}$ is a hydrogel derived from a cross-linked hyaluronic acid, wherein the hyaluronic acid comprises at least one amide-linked side chain of $N(H)(CH_2CH_2O)_3$ $CH_2CH_2N_3$, and wherein the cross-linker used to form the hydrogel comprises PEG(2000)-bis-[1-(((((1'R,8'S,9's)-bicyclo[6.1.0]non-4'-yn-9'-yl)methoxy)carbonyl) amino-cyclopropane-1-carboxylic acid ester], or $R^{11}$ is a hydrogel derived from a cross-linked hyaluronic acid, wherein the hyaluronic acid comprises at least one amide-linked side chain of $N(H)(CH_2CH_2O)_3$ $CH_2CH_2N_3$, and wherein the cross-linker used to form the hydrogel comprises PEG(2000)-bis-[1-(((((1R,8'S,9's)-bicyclo[6.1.0]non-4'-yn-9'-yl)methoxy)carbonyl) piperidine-4-carboxylic acid ester], or $R^{11}$ is a hydrogel derived from a cross-linked hyaluronic acid, wherein the hyaluronic acid comprises at least one amide-linked side chain of $N(H)(CH_2CH_2O)3$ $CH_2CH_2N_3$, and wherein the cross-linker used to form the hydrogel comprises PEG(2000)-bis-[7-(((((1'R,8'S,9's)-bicyclo[6.1.0]non-4'-yn-9'-yl)methoxy)carbonyl) amino)heptanoate], or $R^{11}$ is a hydrogel derived from a cross-linked hyaluronic acid, wherein the hyaluronic acid comprises at least one amide-linked side chain of N(H)(CH$_2$CH$_2$O)$_3$CH$_2$CH$_2$N$_3$, and wherein the cross-linker used to form the hydrogel comprises PEG(2000)-bis-[2-methyl-3-(((((1'R,8'S,9's)-bicyclo[6.1.0]non-4'-yn-9'-yl)methoxy)carbonyl)amino)propanoate].

\* \* \* \* \*

SEQUENCE LISTING

```
<160> NUMBER OF SEQ ID NOS: 45

<210> SEQ ID NO 1
<211> LENGTH: 460
<212> TYPE: PRT
<213> ORGANISM: Homo sapiens

<400> SEQUENCE: 1

Met Phe Thr Ile Lys Leu Leu Phe Ile Val Pro Leu Val Ile Ser
1               5                   10                  15

Ser Arg Ile Asp Gln Asp Asn Ser Ser Phe Asp Ser Leu Ser Pro Glu
            20                  25                  30

Pro Lys Ser Arg Phe Ala Met Leu Asp Asp Val Lys Ile Leu Ala Asn
        35                  40                  45
```

```
Gly Leu Leu Gln Leu Gly His Gly Leu Lys Asp Phe Val His Lys Thr
 50                  55                  60
Lys Gly Gln Ile Asn Asp Ile Phe Gln Lys Leu Asn Ile Phe Asp Gln
 65                  70                  75                  80
Ser Phe Tyr Asp Leu Ser Leu Gln Thr Ser Glu Ile Lys Glu Glu
                 85                  90                  95
Lys Glu Leu Arg Arg Thr Thr Tyr Lys Leu Gln Val Lys Asn Glu Glu
                100                 105                 110
Val Lys Asn Met Ser Leu Glu Leu Asn Ser Lys Leu Glu Ser Leu Leu
            115                 120                 125
Glu Glu Lys Ile Leu Leu Gln Gln Lys Val Lys Tyr Leu Glu Glu Gln
        130                 135                 140
Leu Thr Asn Leu Ile Gln Asn Gln Pro Glu Thr Pro Glu His Pro Glu
145                 150                 155                 160
Val Thr Ser Leu Lys Thr Phe Val Glu Lys Gln Asp Asn Ser Ile Lys
                165                 170                 175
Asp Leu Leu Gln Thr Val Glu Asp Gln Tyr Lys Gln Leu Asn Gln Gln
            180                 185                 190
His Ser Gln Ile Lys Glu Ile Glu Asn Gln Leu Arg Arg Thr Ser Ile
        195                 200                 205
Gln Glu Pro Thr Glu Ile Ser Leu Ser Ser Lys Pro Arg Ala Pro Arg
    210                 215                 220
Thr Thr Pro Phe Leu Gln Leu Asn Glu Ile Arg Asn Val Lys His Asp
225                 230                 235                 240
Gly Ile Pro Ala Glu Cys Thr Thr Ile Tyr Asn Arg Gly Glu His Thr
                245                 250                 255
Ser Gly Met Tyr Ala Ile Arg Pro Ser Asn Ser Gln Val Phe His Val
            260                 265                 270
Tyr Cys Asp Val Ile Ser Gly Ser Pro Trp Thr Leu Ile Gln His Arg
        275                 280                 285
Ile Asp Gly Ser Gln Asn Phe Asn Glu Thr Trp Glu Asn Tyr Lys Tyr
    290                 295                 300
Gly Phe Gly Arg Leu Asp Gly Glu Phe Trp Leu Gly Leu Glu Lys Ile
305                 310                 315                 320
Tyr Ser Ile Val Lys Gln Ser Asn Tyr Val Leu Arg Ile Glu Leu Glu
                325                 330                 335
Asp Trp Lys Asp Asn Lys His Tyr Ile Glu Tyr Ser Phe Tyr Leu Gly
            340                 345                 350
Asn His Glu Thr Asn Tyr Thr Leu His Leu Val Ala Ile Thr Gly Asn
        355                 360                 365
Val Pro Asn Ala Ile Pro Glu Asn Lys Asp Leu Val Phe Ser Thr Trp
    370                 375                 380
Asp His Lys Ala Lys Gly His Phe Asn Cys Pro Glu Gly Tyr Ser Gly
385                 390                 395                 400
Gly Trp Trp Trp His Asp Glu Cys Gly Glu Asn Asn Leu Asn Gly Lys
                405                 410                 415
Tyr Asn Lys Pro Arg Ala Lys Ser Lys Pro Glu Arg Arg Gly Leu
            420                 425                 430
Ser Trp Lys Ser Gln Asn Gly Arg Leu Tyr Ser Ile Lys Ser Thr Lys
        435                 440                 445
Met Leu Ile His Pro Thr Asp Ser Glu Ser Phe Glu
450                 455                 460
```

```
<210> SEQ ID NO 2
<211> LENGTH: 2126
<212> TYPE: DNA
<213> ORGANISM: Homo sapiens

<400> SEQUENCE: 2
ttccagaaga aaacagttcc acgttgcttg aaattgaaaa tcaagataaa aatgttcaca      60
attaagctcc ttcttttat tgttcctcta gttatttcct ccagaattga tcaagacaat     120
tcatcatttg attctctatc tccagagcca aaatcaagat ttgctatgtt agacgatgta     180
aaaattttag ccaatggcct ccttcagttg ggacatggtc ttaaagactt tgtccataag     240
acgaagggcc aaattaatga catatttcaa aaactcaaca tatttgatca gtctttttat     300
gatctatcgc tgcaaaccag tgaaatcaaa gaagaagaaa aggaactgag aagaactaca     360
tataaactac aagtcaaaaa tgaagaggta aagaatatgt cacttgaact caactcaaaa     420
cttgaaagcc tcctagaaga aaaaattcta cttcaacaaa aagtgaaata tttagaagag     480
caactaacta acttaattca aaatcaacct gaaactccag aacacccaga agtaacttca     540
cttaaaactt ttgtagaaaa acaagataat agcatcaaag accttctcca gaccgtggaa     600
gaccaatata aacaattaaa ccaacagcat agtcaaataa agaaataga aaatcagctc     660 agaaggacta gtattcaaga acccacagaa atttctctat cttccaagcc aagagcacca     720
agaactactc cctttcttca gttgaatgaa ataagaaatg taaaacatga tggcattcct     780
gctgaatgta ccaccattta taacagaggt gaacatacaa gtggcatgta tgccatcaga     840
cccagcaact ctcaagtttt tcatgtctac tgtgatgtta tcaggtag tccatggaca     900 ttaattcaac atcgaataga tggatcacaa aacttcaatg aaacgtggga gaactacaaa     960
tatggttttg ggaggcttga tggagaattt tggttgggcc tagagaagat atactccata    1020
gtgaagcaat ctaattatgt tttacgaatt gagttggaag actggaaaga caacaaacat    1080
tatattgaat attcttttta cttgggaaat cacgaaacca actatacgct acatctagtt    1140
gcgattactg gcaatgtccc caatgcaatc ccggaaaaca aagatttggt gttttctact    1200
tgggatcaca aagcaaaagg acacttcaac tgtccagagg ttattcagg aggctggtgg    1260 tggcatgatg agtgtggaga aaacaaccta aatggtaaat ataacaaacc aagagcaaaa    1320
tctaagccag agaggagaag aggattatct tggaagtctc aaaatggaag gttatactct    1380
ataaaatcaa ccaaaatgtt gatccatcca acagattcag aaagctttga atgaactgag    1440
gcaaatttaa aaggcaataa tttaaacatt aacctcattc caagttaatg tggtctaata    1500
atctggtatt aaatccttaa gagaaagctt gagaaataga tttttttat cttaaagtca    1560 ctgtctattt aagattaaac atacaatcac ataaccttaa agaataccgt ttacatttct    1620
caatcaaaat tcttataata ctatttgttt taaattttgt gatgtgggaa tcaatttag    1680 atggtcacaa tctagattat aatcaatagg tgaacttatt aaataacttt tctaaataaa    1740
aaatttagag acttttattt taaaaggcat catatgagct aatatcacaa ctttcccagt    1800
ttaaaaaact agtactcttg ttaaaactct aaacttgact aaatacagag gactggtaat    1860
tgtacagttc ttaaatgttg tagtattaat ttcaaaacta aaaatcgtca gcacagagta    1920
tgtgtaaaaa tctgtaatac aaatttttaa actgatgctt cattttgcta caaaataatt    1980
tggagtaaat gtttgatatg atttattat gaaacctaat gaagcagaat taaatactgt    2040
attaaaataa gttcgctgtc tttaaacaaa tggagatgac tactaagtca cattgacttt    2100
aacatgaggt atcactatac cttatt                                        2126
```

-continued

```
<210> SEQ ID NO 3
<211> LENGTH: 460
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ANGPTL3 K423Q

<400> SEQUENCE: 3
```

Met Phe Thr Ile Lys Leu Leu Phe Ile Val Pro Leu Val Ile Ser
1               5                   10                  15

Ser Arg Ile Asp Gln Asp Asn Ser Ser Phe Asp Ser Leu Ser Pro Glu
            20                  25                  30

Pro Lys Ser Arg Phe Ala Met Leu Asp Asp Val Lys Ile Leu Ala Asn
        35                  40                  45

Gly Leu Leu Gln Leu Gly His Gly Leu Lys Asp Phe Val His Lys Thr
    50                  55                  60

Lys Gly Gln Ile Asn Asp Ile Phe Gln Lys Leu Asn Ile Phe Asp Gln
65                  70                  75                  80

Ser Phe Tyr Asp Leu Ser Leu Gln Thr Ser Glu Ile Lys Glu Glu Glu
                85                  90                  95

Lys Glu Leu Arg Arg Thr Thr Tyr Lys Leu Gln Val Lys Asn Glu Glu
            100                 105                 110

Val Lys Asn Met Ser Leu Glu Leu Asn Ser Lys Leu Glu Ser Leu Leu
        115                 120                 125

Glu Glu Lys Ile Leu Leu Gln Gln Lys Val Lys Tyr Leu Glu Glu Gln
    130                 135                 140

Leu Thr Asn Leu Ile Gln Asn Gln Pro Glu Thr Pro Glu His Pro Glu
145                 150                 155                 160

Val Thr Ser Leu Lys Thr Phe Val Glu Lys Gln Asp Asn Ser Ile Lys
                165                 170                 175

Asp Leu Leu Gln Thr Val Glu Asp Gln Tyr Lys Gln Leu Asn Gln Gln
            180                 185                 190

His Ser Gln Ile Lys Glu Ile Glu Asn Gln Leu Arg Arg Thr Ser Ile
        195                 200                 205

Gln Glu Pro Thr Glu Ile Ser Leu Ser Ser Lys Pro Arg Ala Pro Arg
    210                 215                 220

Thr Thr Pro Phe Leu Gln Leu Asn Glu Ile Arg Asn Val Lys His Asp
225                 230                 235                 240

Gly Ile Pro Ala Glu Cys Thr Thr Ile Tyr Asn Arg Gly Glu His Thr
                245                 250                 255

Ser Gly Met Tyr Ala Ile Arg Pro Ser Asn Ser Gln Val Phe His Val
            260                 265                 270

Tyr Cys Asp Val Ile Ser Gly Ser Pro Trp Thr Leu Ile Gln His Arg
        275                 280                 285

Ile Asp Gly Ser Gln Asn Phe Asn Glu Thr Trp Glu Asn Tyr Lys Tyr
    290                 295                 300

Gly Phe Gly Arg Leu Asp Gly Glu Phe Trp Leu Gly Leu Glu Lys Ile
305                 310                 315                 320

Tyr Ser Ile Val Lys Gln Ser Asn Tyr Val Leu Arg Ile Glu Leu Glu
                325                 330                 335

Asp Trp Lys Asp Asn Lys His Tyr Ile Glu Tyr Ser Phe Tyr Leu Gly
            340                 345                 350

```
Asn His Glu Thr Asn Tyr Thr Leu His Leu Val Ala Ile Thr Gly Asn
            355                 360                 365

Val Pro Asn Ala Ile Pro Glu Asn Lys Asp Leu Val Phe Ser Thr Trp
370                 375                 380

Asp His Lys Ala Lys Gly His Phe Asn Cys Pro Glu Gly Tyr Ser Gly
385                 390                 395                 400

Gly Trp Trp Trp His Asp Glu Cys Gly Glu Asn Asn Leu Asn Gly Lys
                405                 410                 415

Tyr Asn Lys Pro Arg Ala Gln Ser Lys Pro Glu Arg Arg Gly Leu
                420                 425                 430

Ser Trp Lys Ser Gln Asn Gly Arg Leu Tyr Ser Ile Lys Ser Thr Lys
    435                 440                 445

Met Leu Ile His Pro Thr Asp Ser Glu Ser Phe Glu
    450                 455                 460

<210> SEQ ID NO 4
<211> LENGTH: 460
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ANGPTL3 K423S

<400> SEQUENCE: 4

Met Phe Thr Ile Lys Leu Leu Phe Ile Val Pro Leu Val Ile Ser
1               5                   10                  15

Ser Arg Ile Asp Gln Asp Asn Ser Ser Phe Asp Ser Leu Ser Pro Glu
                20                  25                  30

Pro Lys Ser Arg Phe Ala Met Leu Asp Asp Val Lys Ile Leu Ala Asn
            35                  40                  45

Gly Leu Leu Gln Leu Gly His Gly Leu Lys Asp Phe Val His Lys Thr
    50                  55                  60

Lys Gly Gln Ile Asn Asp Ile Phe Gln Lys Leu Asn Ile Phe Asp Gln
65                  70                  75                  80

Ser Phe Tyr Asp Leu Ser Leu Gln Thr Ser Glu Ile Lys Glu Glu
                85                  90                  95

Lys Glu Leu Arg Arg Thr Thr Tyr Lys Leu Gln Val Lys Asn Glu Glu
            100                 105                 110

Val Lys Asn Met Ser Leu Glu Leu Asn Ser Lys Leu Glu Ser Leu Leu
        115                 120                 125

Glu Glu Lys Ile Leu Leu Gln Gln Lys Val Lys Tyr Leu Glu Glu Gln
    130                 135                 140

Leu Thr Asn Leu Ile Gln Asn Gln Pro Glu Thr Pro Glu His Pro Glu
145                 150                 155                 160

Val Thr Ser Leu Lys Thr Phe Val Glu Lys Gln Asp Asn Ser Ile Lys
                165                 170                 175

Asp Leu Leu Gln Thr Val Glu Asp Gln Tyr Lys Gln Leu Asn Gln Gln
            180                 185                 190

His Ser Gln Ile Lys Glu Ile Glu Asn Gln Leu Arg Arg Thr Ser Ile
        195                 200                 205

Gln Glu Pro Thr Glu Ile Ser Leu Ser Ser Lys Pro Arg Ala Pro Arg
    210                 215                 220

Thr Thr Pro Phe Leu Gln Leu Asn Glu Ile Arg Asn Val Lys His Asp
225                 230                 235                 240
```

```
Gly Ile Pro Ala Glu Cys Thr Thr Ile Tyr Asn Arg Gly Glu His Thr
                245                 250                 255

Ser Gly Met Tyr Ala Ile Arg Pro Ser Asn Ser Gln Val Phe His Val
            260                 265                 270

Tyr Cys Asp Val Ile Ser Gly Ser Pro Trp Thr Leu Ile Gln His Arg
        275                 280                 285

Ile Asp Gly Ser Gln Asn Phe Asn Glu Thr Trp Glu Asn Tyr Lys Tyr
    290                 295                 300

Gly Phe Gly Arg Leu Asp Gly Glu Phe Trp Leu Gly Leu Glu Lys Ile
305                 310                 315                 320

Tyr Ser Ile Val Lys Gln Ser Asn Tyr Val Leu Arg Ile Glu Leu Glu
                325                 330                 335

Asp Trp Lys Asp Asn Lys His Tyr Ile Glu Tyr Ser Phe Tyr Leu Gly
            340                 345                 350

Asn His Glu Thr Asn Tyr Thr Leu His Leu Val Ala Ile Thr Gly Asn
        355                 360                 365

Val Pro Asn Ala Ile Pro Glu Asn Lys Asp Leu Val Phe Ser Thr Trp
    370                 375                 380

Asp His Lys Ala Lys Gly His Phe Asn Cys Pro Glu Gly Tyr Ser Gly
385                 390                 395                 400

Gly Trp Trp Trp His Asp Glu Cys Gly Glu Asn Asn Leu Asn Gly Lys
                405                 410                 415

Tyr Asn Lys Pro Arg Ala Ser Ser Lys Pro Glu Arg Arg Arg Gly Leu
            420                 425                 430

Ser Trp Lys Ser Gln Asn Gly Arg Leu Tyr Ser Ile Lys Ser Thr Lys
        435                 440                 445

Met Leu Ile His Pro Thr Asp Ser Glu Ser Phe Glu
    450                 455                 460

<210> SEQ ID NO 5
<211> LENGTH: 253
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ANGPTL3 207-460 K423Q

<400> SEQUENCE: 5

Ile Gln Glu Pro Thr Glu Ile Ser Leu Ser Ser Lys Pro Arg Ala Pro
1               5                   10                  15

Arg Thr Thr Pro Phe Leu Gln Leu Asn Glu Ile Arg Asn Val Lys His
            20                  25                  30

Asp Gly Ile Pro Ala Glu Cys Thr Thr Ile Tyr Asn Arg Gly Glu His
        35                  40                  45

Thr Ser Gly Met Tyr Ala Ile Arg Pro Ser Asn Ser Gln Val Phe His
    50                  55                  60

Val Tyr Cys Asp Val Ile Ser Gly Ser Pro Trp Thr Leu Ile Gln His
65                  70                  75                  80

Arg Ile Asp Gly Ser Gln Asn Phe Asn Glu Thr Trp Glu Asn Tyr Lys
                85                  90                  95

Tyr Gly Phe Gly Arg Leu Asp Gly Glu Phe Trp Leu Gly Leu Glu Lys
            100                 105                 110

Ile Tyr Ser Ile Val Lys Gln Ser Asn Tyr Val Leu Arg Ile Glu Leu
        115                 120                 125
```

```
Glu Asp Trp Lys Asp Asn Lys His Tyr Ile Glu Tyr Ser Phe Tyr Leu
            130                 135                 140

Gly Asn His Glu Thr Asn Tyr Thr Leu His Leu Val Ala Ile Thr Gly
145                 150                 155                 160

Asn Val Pro Asn Ala Ile Pro Glu Asn Lys Asp Leu Val Phe Ser Thr
                165                 170                 175

Trp Asp His Lys Ala Lys Gly His Phe Asn Cys Pro Glu Gly Tyr Ser
            180                 185                 190

Gly Gly Trp Trp Trp His Asp Glu Cys Gly Glu Asn Asn Leu Asn Gly
                195                 200                 205

Lys Tyr Asn Lys Pro Arg Ala Gln Ser Lys Pro Glu Arg Arg Arg Gly
210                 215                 220

Leu Ser Trp Lys Ser Gln Asn Gly Arg Leu Tyr Ser Ile Lys Ser Thr
225                 230                 235                 240

Lys Met Leu Ile His Pro Thr Asp Ser Glu Ser Phe Glu
                245                 250
```

<210> SEQ ID NO 6
<211> LENGTH: 253
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: ANGPTL3 207-460 K423S

<400> SEQUENCE: 6

```
Ile Gln Glu Pro Thr Glu Ile Ser Leu Ser Ser Lys Pro Arg Ala Pro
1               5                   10                  15

Arg Thr Thr Pro Phe Leu Gln Leu Asn Glu Ile Arg Asn Val Lys His
                20                  25                  30

Asp Gly Ile Pro Ala Glu Cys Thr Thr Ile Tyr Asn Arg Gly Glu His
            35                  40                  45

Thr Ser Gly Met Tyr Ala Ile Arg Pro Ser Asn Ser Gln Val Phe His
50                  55                  60

Val Tyr Cys Asp Val Ile Ser Gly Ser Pro Trp Thr Leu Ile Gln His
65                  70                  75                  80

Arg Ile Asp Gly Ser Gln Asn Phe Asn Glu Thr Trp Glu Asn Tyr Lys
                85                  90                  95

Tyr Gly Phe Gly Arg Leu Asp Gly Glu Phe Trp Leu Gly Leu Glu Lys
            100                 105                 110

Ile Tyr Ser Ile Val Lys Gln Ser Asn Tyr Val Leu Arg Ile Glu Leu
        115                 120                 125

Glu Asp Trp Lys Asp Asn Lys His Tyr Ile Glu Tyr Ser Phe Tyr Leu
            130                 135                 140

Gly Asn His Glu Thr Asn Tyr Thr Leu His Leu Val Ala Ile Thr Gly
145                 150                 155                 160

Asn Val Pro Asn Ala Ile Pro Glu Asn Lys Asp Leu Val Phe Ser Thr
                165                 170                 175

Trp Asp His Lys Ala Lys Gly His Phe Asn Cys Pro Glu Gly Tyr Ser
            180                 185                 190

Gly Gly Trp Trp Trp His Asp Glu Cys Gly Glu Asn Asn Leu Asn Gly
                195                 200                 205

Lys Tyr Asn Lys Pro Arg Ala Ser Ser Lys Pro Glu Arg Arg Arg Gly
210                 215                 220
```

Leu Ser Trp Lys Ser Gln Asn Gly Arg Leu Tyr Ser Ile Lys Ser Thr
225                 230                 235                 240

Lys Met Leu Ile His Pro Thr Asp Ser Glu Ser Phe Glu
                245                 250

<210> SEQ ID NO 7
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ANGPTL3 225-460 K423Q

<400> SEQUENCE: 7

Thr Thr Pro Phe Leu Gln Leu Asn Glu Ile Arg Asn Val Lys His Asp
1               5                   10                  15

Gly Ile Pro Ala Glu Cys Thr Thr Ile Tyr Asn Arg Gly Glu His Thr
            20                  25                  30

Ser Gly Met Tyr Ala Ile Arg Pro Ser Asn Ser Gln Val Phe His Val
        35                  40                  45

Tyr Cys Asp Val Ile Ser Gly Ser Pro Trp Thr Leu Ile Gln His Arg
50                  55                  60

Ile Asp Gly Ser Gln Asn Phe Asn Glu Thr Trp Glu Asn Tyr Lys Tyr
65                  70                  75                  80

Gly Phe Gly Arg Leu Asp Gly Glu Phe Trp Leu Gly Leu Glu Lys Ile
                85                  90                  95

Tyr Ser Ile Val Lys Gln Ser Asn Tyr Val Leu Arg Ile Glu Leu Glu
            100                 105                 110

Asp Trp Lys Asp Asn Lys His Tyr Ile Glu Tyr Ser Phe Tyr Leu Gly
        115                 120                 125

Asn His Glu Thr Asn Tyr Thr Leu His Leu Val Ala Ile Thr Gly Asn
    130                 135                 140

Val Pro Asn Ala Ile Pro Glu Asn Lys Asp Leu Val Phe Ser Thr Trp
145                 150                 155                 160

Asp His Lys Ala Lys Gly His Phe Asn Cys Pro Glu Gly Tyr Ser Gly
                165                 170                 175

Gly Trp Trp Trp His Asp Glu Cys Gly Glu Asn Asn Leu Asn Gly Lys
            180                 185                 190

Tyr Asn Lys Pro Arg Ala Gln Ser Lys Pro Glu Arg Arg Arg Gly Leu
        195                 200                 205

Ser Trp Lys Ser Gln Asn Gly Arg Leu Tyr Ser Ile Lys Ser Thr Lys
    210                 215                 220

Met Leu Ile His Pro Thr Asp Ser Glu Ser Phe Glu
225                 230                 235

<210> SEQ ID NO 8
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ANGPTL3 225-460 K423S

<400> SEQUENCE: 8

Thr Thr Pro Phe Leu Gln Leu Asn Glu Ile Arg Asn Val Lys His Asp
1               5                   10                  15

Gly Ile Pro Ala Glu Cys Thr Thr Ile Tyr Asn Arg Gly Glu His Thr
            20                  25                  30

Ser Gly Met Tyr Ala Ile Arg Pro Ser Asn Ser Gln Val Phe His Val
        35                  40                  45

Tyr Cys Asp Val Ile Ser Gly Ser Pro Trp Thr Leu Ile Gln His Arg
 50                  55                  60

Ile Asp Gly Ser Gln Asn Phe Asn Glu Thr Trp Glu Asn Tyr Lys Tyr
 65                  70                  75                  80

Gly Phe Gly Arg Leu Asp Gly Glu Phe Trp Leu Gly Leu Glu Lys Ile
                85                  90                  95

Tyr Ser Ile Val Lys Gln Ser Asn Tyr Val Leu Arg Ile Glu Leu Glu
                100                 105                 110

Asp Trp Lys Asp Asn Lys His Tyr Ile Glu Tyr Ser Phe Tyr Leu Gly
            115                 120                 125

Asn His Glu Thr Asn Tyr Thr Leu His Leu Val Ala Ile Thr Gly Asn
130                 135                 140

Val Pro Asn Ala Ile Pro Glu Asn Lys Asp Leu Val Phe Ser Thr Trp
145                 150                 155                 160

Asp His Lys Ala Lys Gly His Phe Asn Cys Pro Glu Gly Tyr Ser Gly
                165                 170                 175

Gly Trp Trp Trp His Asp Glu Cys Gly Glu Asn Asn Leu Asn Gly Lys
            180                 185                 190

Tyr Asn Lys Pro Arg Ala Ser Ser Lys Pro Glu Arg Arg Arg Gly Leu
        195                 200                 205

Ser Trp Lys Ser Gln Asn Gly Arg Leu Tyr Ser Ile Lys Ser Thr Lys
210                 215                 220

Met Leu Ile His Pro Thr Asp Ser Glu Ser Phe Glu
225                 230                 235

<210> SEQ ID NO 9
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ANGPTL3 225-460 S424T

<400> SEQUENCE: 9

Thr Thr Pro Phe Leu Gln Leu Asn Glu Ile Arg Asn Val Lys His Asp
1               5                   10                  15

Gly Ile Pro Ala Glu Cys Thr Thr Ile Tyr Asn Arg Gly Glu His Thr
            20                  25                  30

Ser Gly Met Tyr Ala Ile Arg Pro Ser Asn Ser Gln Val Phe His Val
        35                  40                  45

Tyr Cys Asp Val Ile Ser Gly Ser Pro Trp Thr Leu Ile Gln His Arg
 50                  55                  60

Ile Asp Gly Ser Gln Asn Phe Asn Glu Thr Trp Glu Asn Tyr Lys Tyr
 65                  70                  75                  80

Gly Phe Gly Arg Leu Asp Gly Glu Phe Trp Leu Gly Leu Glu Lys Ile
                85                  90                  95

Tyr Ser Ile Val Lys Gln Ser Asn Tyr Val Leu Arg Ile Glu Leu Glu
                100                 105                 110

Asp Trp Lys Asp Asn Lys His Tyr Ile Glu Tyr Ser Phe Tyr Leu Gly
            115                 120                 125

```
Asn His Glu Thr Asn Tyr Thr Leu His Leu Val Ala Ile Thr Gly Asn
130                 135                 140

Val Pro Asn Ala Ile Pro Glu Asn Lys Asp Leu Val Phe Ser Thr Trp
145                 150                 155                 160

Asp His Lys Ala Lys Gly His Phe Asn Cys Pro Glu Gly Tyr Ser Gly
                165                 170                 175

Gly Trp Trp Trp His Asp Glu Cys Gly Glu Asn Asn Leu Asn Gly Lys
                180                 185                 190

Tyr Asn Lys Pro Arg Ala Lys Thr Lys Pro Glu Arg Arg Arg Gly Leu
            195                 200                 205

Ser Trp Lys Ser Gln Asn Gly Arg Leu Tyr Ser Ile Lys Ser Thr Lys
        210                 215                 220

Met Leu Ile His Pro Thr Asp Ser Glu Ser Phe Glu
225                 230                 235

<210> SEQ ID NO 10
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ANGPTL3 226-460 K423Q

<400> SEQUENCE: 10

Thr Pro Phe Leu Gln Leu Asn Glu Ile Arg Asn Val Lys His Asp Gly
1               5                   10                  15

Ile Pro Ala Glu Cys Thr Thr Ile Tyr Asn Arg Gly Glu His Thr Ser
                20                  25                  30

Gly Met Tyr Ala Ile Arg Pro Ser Asn Ser Gln Val Phe His Val Tyr
            35                  40                  45

Cys Asp Val Ile Ser Gly Ser Pro Trp Thr Leu Ile Gln His Arg Ile
50                  55                  60

Asp Gly Ser Gln Asn Phe Asn Glu Thr Trp Glu Asn Tyr Lys Tyr Gly
65                  70                  75                  80

Phe Gly Arg Leu Asp Gly Glu Phe Trp Leu Gly Leu Glu Lys Ile Tyr
                85                  90                  95

Ser Ile Val Lys Gln Ser Asn Tyr Val Leu Arg Ile Glu Leu Glu Asp
            100                 105                 110

Trp Lys Asp Asn Lys His Tyr Ile Glu Tyr Ser Phe Tyr Leu Gly Asn
        115                 120                 125

His Glu Thr Asn Tyr Thr Leu His Leu Val Ala Ile Thr Gly Asn Val
130                 135                 140

Pro Asn Ala Ile Pro Glu Asn Lys Asp Leu Val Phe Ser Thr Trp Asp
145                 150                 155                 160

His Lys Ala Lys Gly His Phe Asn Cys Pro Glu Gly Tyr Ser Gly Gly
                165                 170                 175

Trp Trp Trp His Asp Glu Cys Gly Glu Asn Asn Leu Asn Gly Lys Tyr
            180                 185                 190

Asn Lys Pro Arg Ala Gln Ser Lys Pro Glu Arg Arg Arg Gly Leu Ser
        195                 200                 205

Trp Lys Ser Gln Asn Gly Arg Leu Tyr Ser Ile Lys Ser Thr Lys Met
210                 215                 220

Leu Ile His Pro Thr Asp Ser Glu Ser Phe Glu
225                 230                 235
```

<210> SEQ ID NO 11
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ANGPTL3 226-460 K423S

<400> SEQUENCE: 11

```
Thr Pro Phe Leu Gln Leu Asn Glu Ile Arg Asn Val Lys His Asp Gly
1               5                   10                  15

Ile Pro Ala Glu Cys Thr Thr Ile Tyr Asn Arg Gly Glu His Thr Ser
            20                  25                  30

Gly Met Tyr Ala Ile Arg Pro Ser Asn Ser Gln Val Phe His Val Tyr
        35                  40                  45

Cys Asp Val Ile Ser Gly Ser Pro Trp Thr Leu Ile Gln His Arg Ile
    50                  55                  60

Asp Gly Ser Gln Asn Phe Asn Glu Thr Trp Glu Asn Tyr Lys Tyr Gly
65                  70                  75                  80

Phe Gly Arg Leu Asp Gly Glu Phe Trp Leu Gly Leu Glu Lys Ile Tyr
                85                  90                  95

Ser Ile Val Lys Gln Ser Asn Tyr Val Leu Arg Ile Glu Leu Glu Asp
            100                 105                 110

Trp Lys Asp Asn Lys His Tyr Ile Glu Tyr Ser Phe Tyr Leu Gly Asn
        115                 120                 125

His Glu Thr Asn Tyr Thr Leu His Leu Val Ala Ile Thr Gly Asn Val
    130                 135                 140

Pro Asn Ala Ile Pro Glu Asn Lys Asp Leu Val Phe Ser Thr Trp Asp
145                 150                 155                 160

His Lys Ala Lys Gly His Phe Asn Cys Pro Glu Gly Tyr Ser Gly Gly
                165                 170                 175

Trp Trp Trp His Asp Glu Cys Gly Glu Asn Asn Leu Asn Gly Lys Tyr
            180                 185                 190

Asn Lys Pro Arg Ala Ser Ser Lys Pro Glu Arg Arg Arg Gly Leu Ser
        195                 200                 205

Trp Lys Ser Gln Asn Gly Arg Leu Tyr Ser Ile Lys Ser Thr Lys Met
    210                 215                 220

Leu Ile His Pro Thr Asp Ser Glu Ser Phe Glu
225                 230                 235
```

<210> SEQ ID NO 12
<211> LENGTH: 233
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ANGPTL3 228-460 K423Q

<400> SEQUENCE: 12

```
Phe Leu Gln Leu Asn Glu Ile Arg Asn Val Lys His Asp Gly Ile Pro
1               5                   10                  15

Ala Glu Cys Thr Thr Ile Tyr Asn Arg Gly Glu His Thr Ser Gly Met
            20                  25                  30
```

```
Tyr Ala Ile Arg Pro Ser Asn Ser Gln Val Phe His Val Tyr Cys Asp
            35                  40                  45

Val Ile Ser Gly Ser Pro Trp Thr Leu Ile Gln His Arg Ile Asp Gly
    50                  55                  60

Ser Gln Asn Phe Asn Glu Thr Trp Glu Asn Tyr Lys Tyr Gly Phe Gly
65                  70                  75                  80

Arg Leu Asp Gly Glu Phe Trp Leu Gly Leu Glu Lys Ile Tyr Ser Ile
                85                  90                  95

Val Lys Gln Ser Asn Tyr Val Leu Arg Ile Glu Leu Glu Asp Trp Lys
            100                 105                 110

Asp Asn Lys His Tyr Ile Glu Tyr Ser Phe Tyr Leu Gly Asn His Glu
            115                 120                 125

Thr Asn Tyr Thr Leu His Leu Val Ala Ile Thr Gly Asn Val Pro Asn
130                 135                 140

Ala Ile Pro Glu Asn Lys Asp Leu Val Phe Ser Thr Trp Asp His Lys
145                 150                 155                 160

Ala Lys Gly His Phe Asn Cys Pro Glu Gly Tyr Ser Gly Gly Trp Trp
                165                 170                 175

Trp His Asp Glu Cys Gly Glu Asn Asn Leu Asn Gly Lys Tyr Asn Lys
            180                 185                 190

Pro Arg Ala Gln Ser Lys Pro Glu Arg Arg Arg Gly Leu Ser Trp Lys
            195                 200                 205

Ser Gln Asn Gly Arg Leu Tyr Ser Ile Lys Ser Thr Lys Met Leu Ile
            210                 215                 220

His Pro Thr Asp Ser Glu Ser Phe Glu
225                 230

<210> SEQ ID NO 13
<211> LENGTH: 233
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ANGPTL3 228-460 K423S

<400> SEQUENCE: 13

Phe Leu Gln Leu Asn Glu Ile Arg Asn Val Lys His Asp Gly Ile Pro
1               5                   10                  15

Ala Glu Cys Thr Thr Ile Tyr Asn Arg Gly Glu His Thr Ser Gly Met
            20                  25                  30

Tyr Ala Ile Arg Pro Ser Asn Ser Gln Val Phe His Val Tyr Cys Asp
            35                  40                  45

Val Ile Ser Gly Ser Pro Trp Thr Leu Ile Gln His Arg Ile Asp Gly
    50                  55                  60

Ser Gln Asn Phe Asn Glu Thr Trp Glu Asn Tyr Lys Tyr Gly Phe Gly
65                  70                  75                  80

Arg Leu Asp Gly Glu Phe Trp Leu Gly Leu Glu Lys Ile Tyr Ser Ile
                85                  90                  95

Val Lys Gln Ser Asn Tyr Val Leu Arg Ile Glu Leu Glu Asp Trp Lys
            100                 105                 110

Asp Asn Lys His Tyr Ile Glu Tyr Ser Phe Tyr Leu Gly Asn His Glu
            115                 120                 125

Thr Asn Tyr Thr Leu His Leu Val Ala Ile Thr Gly Asn Val Pro Asn
130                 135                 140
```

Ala Ile Pro Glu Asn Lys Asp Leu Val Phe Ser Thr Trp Asp His Lys
145                 150                 155                 160

Ala Lys Gly His Phe Asn Cys Pro Glu Gly Tyr Ser Gly Gly Trp Trp
                165                 170                 175

Trp His Asp Glu Cys Gly Glu Asn Asn Leu Asn Gly Lys Tyr Asn Lys
            180                 185                 190

Pro Arg Ala Ser Ser Lys Pro Glu Arg Arg Arg Gly Leu Ser Trp Lys
        195                 200                 205

Ser Gln Asn Gly Arg Leu Tyr Ser Ile Lys Ser Thr Lys Met Leu Ile
    210                 215                 220

His Pro Thr Asp Ser Glu Ser Phe Glu
225                 230

<210> SEQ ID NO 14
<211> LENGTH: 233
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ANGPTL3 228-460 S424T

<400> SEQUENCE: 14

Phe Leu Gln Leu Asn Glu Ile Arg Asn Val Lys His Asp Gly Ile Pro
1               5                   10                  15

Ala Glu Cys Thr Thr Ile Tyr Asn Arg Gly Glu His Thr Ser Gly Met
            20                  25                  30

Tyr Ala Ile Arg Pro Ser Asn Ser Gln Val Phe His Val Tyr Cys Asp
        35                  40                  45

Val Ile Ser Gly Ser Pro Trp Thr Leu Ile Gln His Arg Ile Asp Gly
    50                  55                  60

Ser Gln Asn Phe Asn Glu Thr Trp Glu Asn Tyr Lys Tyr Gly Phe Gly
65                  70                  75                  80

Arg Leu Asp Gly Glu Phe Trp Leu Gly Leu Glu Lys Ile Tyr Ser Ile
                85                  90                  95

Val Lys Gln Ser Asn Tyr Val Leu Arg Ile Glu Leu Glu Asp Trp Lys
            100                 105                 110

Asp Asn Lys His Tyr Ile Glu Tyr Ser Phe Tyr Leu Gly Asn His Glu
        115                 120                 125

Thr Asn Tyr Thr Leu His Leu Val Ala Ile Thr Gly Asn Val Pro Asn
    130                 135                 140

Ala Ile Pro Glu Asn Lys Asp Leu Val Phe Ser Thr Trp Asp His Lys
145                 150                 155                 160

Ala Lys Gly His Phe Asn Cys Pro Glu Gly Tyr Ser Gly Gly Trp Trp
                165                 170                 175

Trp His Asp Glu Cys Gly Glu Asn Asn Leu Asn Gly Lys Tyr Asn Lys
            180                 185                 190

Pro Arg Ala Lys Thr Lys Pro Glu Arg Arg Arg Gly Leu Ser Trp Lys
        195                 200                 205

Ser Gln Asn Gly Arg Leu Tyr Ser Ile Lys Ser Thr Lys Met Leu Ile
    210                 215                 220

His Pro Thr Asp Ser Glu Ser Phe Glu
225                 230

<210> SEQ ID NO 15

```
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ANGPTL3 233-460 K423Q

<400> SEQUENCE: 15

Glu Ile Arg Asn Val Lys His Asp Gly Ile Pro Ala Glu Cys Thr Thr
1               5                   10                  15

Ile Tyr Asn Arg Gly Glu His Thr Ser Gly Met Tyr Ala Ile Arg Pro
            20                  25                  30

Ser Asn Ser Gln Val Phe His Val Tyr Cys Asp Val Ile Ser Gly Ser
        35                  40                  45

Pro Trp Thr Leu Ile Gln His Arg Ile Asp Gly Ser Gln Asn Phe Asn
    50                  55                  60

Glu Thr Trp Glu Asn Tyr Lys Tyr Gly Phe Gly Arg Leu Asp Gly Glu
65                  70                  75                  80

Phe Trp Leu Gly Leu Glu Lys Ile Tyr Ser Ile Val Lys Gln Ser Asn
                85                  90                  95

Tyr Val Leu Arg Ile Glu Leu Glu Asp Trp Lys Asp Asn Lys His Tyr
            100                 105                 110

Ile Glu Tyr Ser Phe Tyr Leu Gly Asn His Glu Thr Asn Tyr Thr Leu
        115                 120                 125

His Leu Val Ala Ile Thr Gly Asn Val Pro Asn Ala Ile Pro Glu Asn
    130                 135                 140

Lys Asp Leu Val Phe Ser Thr Trp Asp His Lys Ala Lys Gly His Phe
145                 150                 155                 160

Asn Cys Pro Glu Gly Tyr Ser Gly Gly Trp Trp Trp His Asp Glu Cys
                165                 170                 175

Gly Glu Asn Asn Leu Asn Gly Lys Tyr Asn Lys Pro Arg Ala Gln Ser
            180                 185                 190

Lys Pro Glu Arg Arg Arg Gly Leu Ser Trp Lys Ser Gln Asn Gly Arg
        195                 200                 205

Leu Tyr Ser Ile Lys Ser Thr Lys Met Leu Ile His Pro Thr Asp Ser
    210                 215                 220

Glu Ser Phe Glu
225

<210> SEQ ID NO 16
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ANGPTL3 233-460 K423S

<400> SEQUENCE: 16

Glu Ile Arg Asn Val Lys His Asp Gly Ile Pro Ala Glu Cys Thr Thr
1               5                   10                  15

Ile Tyr Asn Arg Gly Glu His Thr Ser Gly Met Tyr Ala Ile Arg Pro
            20                  25                  30

Ser Asn Ser Gln Val Phe His Val Tyr Cys Asp Val Ile Ser Gly Ser
        35                  40                  45
```

```
Pro Trp Thr Leu Ile Gln His Arg Ile Asp Gly Ser Gln Asn Phe Asn
            50                   55                  60

Glu Thr Trp Glu Asn Tyr Lys Tyr Gly Phe Gly Arg Leu Asp Gly Glu
 65                  70                  75                  80

Phe Trp Leu Gly Leu Glu Lys Ile Tyr Ser Ile Val Lys Gln Ser Asn
                85                  90                  95

Tyr Val Leu Arg Ile Glu Leu Glu Asp Trp Lys Asp Asn Lys His Tyr
               100                 105                 110

Ile Glu Tyr Ser Phe Tyr Leu Gly Asn His Glu Thr Asn Tyr Thr Leu
               115                 120                 125

His Leu Val Ala Ile Thr Gly Asn Val Pro Asn Ala Ile Pro Glu Asn
               130                 135                 140

Lys Asp Leu Val Phe Ser Thr Trp Asp His Lys Ala Lys Gly His Phe
145                 150                 155                 160

Asn Cys Pro Glu Gly Tyr Ser Gly Gly Trp Trp Trp His Asp Glu Cys
               165                 170                 175

Gly Glu Asn Asn Leu Asn Gly Lys Tyr Asn Lys Pro Arg Ala Ser Ser
               180                 185                 190

Lys Pro Glu Arg Arg Arg Gly Leu Ser Trp Lys Ser Gln Asn Gly Arg
               195                 200                 205

Leu Tyr Ser Ile Lys Ser Thr Lys Met Leu Ile His Pro Thr Asp Ser
               210                 215                 220

Glu Ser Phe Glu
225

<210> SEQ ID NO 17
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ANGPTL3 241-460 K423Q

<400> SEQUENCE: 17

Gly Ile Pro Ala Glu Cys Thr Thr Ile Tyr Asn Arg Gly Glu His Thr
 1               5                  10                  15

Ser Gly Met Tyr Ala Ile Arg Pro Ser Asn Ser Gln Val Phe His Val
                20                  25                  30

Tyr Cys Asp Val Ile Ser Gly Ser Pro Trp Thr Leu Ile Gln His Arg
             35                  40                  45

Ile Asp Gly Ser Gln Asn Phe Asn Glu Thr Trp Glu Asn Tyr Lys Tyr
         50                  55                  60

Gly Phe Gly Arg Leu Asp Gly Glu Phe Trp Leu Gly Leu Glu Lys Ile
 65                  70                  75                  80

Tyr Ser Ile Val Lys Gln Ser Asn Tyr Val Leu Arg Ile Glu Leu Glu
                85                  90                  95

Asp Trp Lys Asp Asn Lys His Tyr Ile Glu Tyr Ser Phe Tyr Leu Gly
            100                 105                 110

Asn His Glu Thr Asn Tyr Thr Leu His Leu Val Ala Ile Thr Gly Asn
            115                 120                 125

Val Pro Asn Ala Ile Pro Glu Asn Lys Asp Leu Val Phe Ser Thr Trp
        130                 135                 140

Asp His Lys Ala Lys Gly His Phe Asn Cys Pro Glu Gly Tyr Ser Gly
145                 150                 155                 160
```

```
Gly Trp Trp Trp His Asp Glu Cys Gly Glu Asn Asn Leu Asn Gly Lys
            165                 170                 175

Tyr Asn Lys Pro Arg Ala Gln Ser Lys Pro Glu Arg Arg Gly Leu
        180                 185                 190

Ser Trp Lys Ser Gln Asn Gly Arg Leu Tyr Ser Ile Lys Ser Thr Lys
        195                 200                 205

Met Leu Ile His Pro Thr Asp Ser Glu Ser Phe Glu
        210                 215                 220

<210> SEQ ID NO 18
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ANGPTL3 241-460 K423S

<400> SEQUENCE: 18

Gly Ile Pro Ala Glu Cys Thr Thr Ile Tyr Asn Arg Gly Glu His Thr
1               5                   10                  15

Ser Gly Met Tyr Ala Ile Arg Pro Ser Asn Ser Gln Val Phe His Val
            20                  25                  30

Tyr Cys Asp Val Ile Ser Gly Ser Pro Trp Thr Leu Ile Gln His Arg
        35                  40                  45

Ile Asp Gly Ser Gln Asn Phe Asn Glu Thr Trp Glu Asn Tyr Lys Tyr
    50                  55                  60

Gly Phe Gly Arg Leu Asp Gly Glu Phe Trp Leu Gly Leu Glu Lys Ile
65                  70                  75                  80

Tyr Ser Ile Val Lys Gln Ser Asn Tyr Val Leu Arg Ile Glu Leu Glu
                85                  90                  95

Asp Trp Lys Asp Asn Lys His Tyr Ile Glu Tyr Ser Phe Tyr Leu Gly
            100                 105                 110

Asn His Glu Thr Asn Tyr Thr Leu His Leu Val Ala Ile Thr Gly Asn
        115                 120                 125

Val Pro Asn Ala Ile Pro Glu Asn Lys Asp Leu Val Phe Ser Thr Trp
    130                 135                 140

Asp His Lys Ala Lys Gly His Phe Asn Cys Pro Glu Gly Tyr Ser Gly
145                 150                 155                 160

Gly Trp Trp Trp His Asp Glu Cys Gly Glu Asn Asn Leu Asn Gly Lys
                165                 170                 175

Tyr Asn Lys Pro Arg Ala Ser Ser Lys Pro Glu Arg Arg Gly Leu
            180                 185                 190

Ser Trp Lys Ser Gln Asn Gly Arg Leu Tyr Ser Ile Lys Ser Thr Lys
        195                 200                 205

Met Leu Ile His Pro Thr Asp Ser Glu Ser Phe Glu
        210                 215                 220

<210> SEQ ID NO 19
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ANGPTL3 242-460 K423Q
```

```
<400> SEQUENCE: 19

Ile Pro Ala Glu Cys Thr Thr Ile Tyr Asn Arg Gly Glu His Thr Ser
1               5                   10                  15

Gly Met Tyr Ala Ile Arg Pro Ser Asn Ser Gln Val Phe His Val Tyr
            20                  25                  30

Cys Asp Val Ile Ser Gly Ser Pro Trp Thr Leu Ile Gln His Arg Ile
            35                  40                  45

Asp Gly Ser Gln Asn Phe Asn Glu Thr Trp Glu Asn Tyr Lys Tyr Gly
        50                  55                  60

Phe Gly Arg Leu Asp Gly Glu Phe Trp Leu Gly Leu Glu Lys Ile Tyr
65                  70                  75                  80

Ser Ile Val Lys Gln Ser Asn Tyr Val Leu Arg Ile Glu Leu Glu Asp
                85                  90                  95

Trp Lys Asp Asn Lys His Tyr Ile Glu Tyr Ser Phe Tyr Leu Gly Asn
            100                 105                 110

His Glu Thr Asn Tyr Thr Leu His Leu Val Ala Ile Thr Gly Asn Val
        115                 120                 125

Pro Asn Ala Ile Pro Glu Asn Lys Asp Leu Val Phe Ser Thr Trp Asp
130                 135                 140

His Lys Ala Lys Gly His Phe Asn Cys Pro Glu Gly Tyr Ser Gly Gly
145                 150                 155                 160

Trp Trp Trp His Asp Glu Cys Gly Glu Asn Asn Leu Asn Gly Lys Tyr
                165                 170                 175

Asn Lys Pro Arg Ala Gln Ser Lys Pro Glu Arg Arg Arg Gly Leu Ser
            180                 185                 190

Trp Lys Ser Gln Asn Gly Arg Leu Tyr Ser Ile Lys Ser Thr Lys Met
        195                 200                 205

Leu Ile His Pro Thr Asp Ser Glu Ser Phe Glu
    210                 215

<210> SEQ ID NO 20
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ANGPTL3 242-460 K423S

<400> SEQUENCE: 20

Ile Pro Ala Glu Cys Thr Thr Ile Tyr Asn Arg Gly Glu His Thr Ser
1               5                   10                  15

Gly Met Tyr Ala Ile Arg Pro Ser Asn Ser Gln Val Phe His Val Tyr
            20                  25                  30

Cys Asp Val Ile Ser Gly Ser Pro Trp Thr Leu Ile Gln His Arg Ile
            35                  40                  45

Asp Gly Ser Gln Asn Phe Asn Glu Thr Trp Glu Asn Tyr Lys Tyr Gly
        50                  55                  60

Phe Gly Arg Leu Asp Gly Glu Phe Trp Leu Gly Leu Glu Lys Ile Tyr
65                  70                  75                  80

Ser Ile Val Lys Gln Ser Asn Tyr Val Leu Arg Ile Glu Leu Glu Asp
                85                  90                  95

Trp Lys Asp Asn Lys His Tyr Ile Glu Tyr Ser Phe Tyr Leu Gly Asn
            100                 105                 110
```

```
His Glu Thr Asn Tyr Thr Leu His Leu Val Ala Ile Thr Gly Asn Val
        115                 120                 125

Pro Asn Ala Ile Pro Glu Asn Lys Asp Leu Val Phe Ser Thr Trp Asp
    130                 135                 140

His Lys Ala Lys Gly His Phe Asn Cys Pro Glu Gly Tyr Ser Gly Gly
145                 150                 155                 160

Trp Trp Trp His Asp Glu Cys Gly Glu Asn Asn Leu Asn Gly Lys Tyr
                165                 170                 175

Asn Lys Pro Arg Ala Ser Ser Lys Pro Glu Arg Arg Gly Leu Ser
                180                 185                 190

Trp Lys Ser Gln Asn Gly Arg Leu Tyr Ser Ile Lys Ser Thr Lys Met
                195                 200                 205

Leu Ile His Pro Thr Asp Ser Glu Ser Phe Glu
            210                 215
```

<210> SEQ ID NO 21
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ANGPTL3 225-455 K423Q

<400> SEQUENCE: 21

```
Thr Thr Pro Phe Leu Gln Leu Asn Glu Ile Arg Asn Val Lys His Asp
1               5                   10                  15

Gly Ile Pro Ala Glu Cys Thr Thr Ile Tyr Asn Arg Gly Glu His Thr
            20                  25                  30

Ser Gly Met Tyr Ala Ile Arg Pro Ser Asn Ser Gln Val Phe His Val
        35                  40                  45

Tyr Cys Asp Val Ile Ser Gly Ser Pro Trp Thr Leu Ile Gln His Arg
    50                  55                  60

Ile Asp Gly Ser Gln Asn Phe Asn Glu Thr Trp Glu Asn Tyr Lys Tyr
65                  70                  75                  80

Gly Phe Gly Arg Leu Asp Gly Glu Phe Trp Leu Gly Leu Glu Lys Ile
                85                  90                  95

Tyr Ser Ile Val Lys Gln Ser Asn Tyr Val Leu Arg Ile Glu Leu Glu
            100                 105                 110

Asp Trp Lys Asp Asn Lys His Tyr Ile Glu Tyr Ser Phe Tyr Leu Gly
        115                 120                 125

Asn His Glu Thr Asn Tyr Thr Leu His Leu Val Ala Ile Thr Gly Asn
    130                 135                 140

Val Pro Asn Ala Ile Pro Glu Asn Lys Asp Leu Val Phe Ser Thr Trp
145                 150                 155                 160

Asp His Lys Ala Lys Gly His Phe Asn Cys Pro Glu Gly Tyr Ser Gly
                165                 170                 175

Gly Trp Trp Trp His Asp Glu Cys Gly Glu Asn Asn Leu Asn Gly Lys
            180                 185                 190

Tyr Asn Lys Pro Arg Ala Gln Ser Lys Pro Glu Arg Arg Gly Leu
        195                 200                 205

Ser Trp Lys Ser Gln Asn Gly Arg Leu Tyr Ser Ile Lys Ser Thr Lys
    210                 215                 220

Met Leu Ile His Pro Thr Asp
225                 230
```

<210> SEQ ID NO 22
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ANGPTL3 225-455 K423S

<400> SEQUENCE: 22

Thr Thr Pro Phe Leu Gln Leu Asn Glu Ile Arg Asn Val Lys His Asp
1               5                   10                  15

Gly Ile Pro Ala Glu Cys Thr Thr Ile Tyr Asn Arg Gly Glu His Thr
            20                  25                  30

Ser Gly Met Tyr Ala Ile Arg Pro Ser Asn Ser Gln Val Phe His Val
        35                  40                  45

Tyr Cys Asp Val Ile Ser Gly Ser Pro Trp Thr Leu Ile Gln His Arg
    50                  55                  60

Ile Asp Gly Ser Gln Asn Phe Asn Glu Thr Trp Glu Asn Tyr Lys Tyr
65                  70                  75                  80

Gly Phe Gly Arg Leu Asp Gly Glu Phe Trp Leu Gly Leu Glu Lys Ile
                85                  90                  95

Tyr Ser Ile Val Lys Gln Ser Asn Tyr Val Leu Arg Ile Glu Leu Glu
            100                 105                 110

Asp Trp Lys Asp Asn Lys His Tyr Ile Glu Tyr Ser Phe Tyr Leu Gly
        115                 120                 125

Asn His Glu Thr Asn Tyr Thr Leu His Leu Val Ala Ile Thr Gly Asn
    130                 135                 140

Val Pro Asn Ala Ile Pro Glu Asn Lys Asp Leu Val Phe Ser Thr Trp
145                 150                 155                 160

Asp His Lys Ala Lys Gly His Phe Asn Cys Pro Glu Gly Tyr Ser Gly
                165                 170                 175

Gly Trp Trp Trp His Asp Glu Cys Gly Glu Asn Asn Leu Asn Gly Lys
            180                 185                 190

Tyr Asn Lys Pro Arg Ala Ser Ser Lys Pro Glu Arg Arg Arg Gly Leu
        195                 200                 205

Ser Trp Lys Ser Gln Asn Gly Arg Leu Tyr Ser Ile Lys Ser Thr Lys
    210                 215                 220

Met Leu Ile His Pro Thr Asp
225                 230

<210> SEQ ID NO 23
<211> LENGTH: 230
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ANGPTL3 226-455 K423Q

<400> SEQUENCE: 23

Thr Pro Phe Leu Gln Leu Asn Glu Ile Arg Asn Val Lys His Asp Gly
1               5                   10                  15

Ile Pro Ala Glu Cys Thr Thr Ile Tyr Asn Arg Gly Glu His Thr Ser
            20                  25                  30

```
Gly Met Tyr Ala Ile Arg Pro Ser Asn Ser Gln Val Phe His Val Tyr
            35                  40                  45

Cys Asp Val Ile Ser Gly Ser Pro Trp Thr Leu Ile Gln His Arg Ile
 50                  55                  60

Asp Gly Ser Gln Asn Phe Asn Glu Thr Trp Glu Asn Tyr Lys Tyr Gly
 65                  70                  75                  80

Phe Gly Arg Leu Asp Gly Glu Phe Trp Leu Gly Leu Glu Lys Ile Tyr
                85                  90                  95

Ser Ile Val Lys Gln Ser Asn Tyr Val Leu Arg Ile Glu Leu Glu Asp
            100                 105                 110

Trp Lys Asp Asn Lys His Tyr Ile Glu Tyr Ser Phe Tyr Leu Gly Asn
            115                 120                 125

His Glu Thr Asn Tyr Thr Leu His Leu Val Ala Ile Thr Gly Asn Val
            130                 135                 140

Pro Asn Ala Ile Pro Glu Asn Lys Asp Leu Val Phe Ser Thr Trp Asp
145                 150                 155                 160

His Lys Ala Lys Gly His Phe Asn Cys Pro Glu Gly Tyr Ser Gly Gly
                165                 170                 175

Trp Trp Trp His Asp Glu Cys Gly Glu Asn Asn Leu Asn Gly Lys Tyr
            180                 185                 190

Asn Lys Pro Arg Ala Gln Ser Lys Pro Glu Arg Arg Arg Gly Leu Ser
            195                 200                 205

Trp Lys Ser Gln Asn Gly Arg Leu Tyr Ser Ile Lys Ser Thr Lys Met
            210                 215                 220

Leu Ile His Pro Thr Asp
225                 230

<210> SEQ ID NO 24
<211> LENGTH: 230
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ANGPTL3 226-455 K423S

<400> SEQUENCE: 24

Thr Pro Phe Leu Gln Leu Asn Glu Ile Arg Asn Val Lys His Asp Gly
1               5                   10                  15

Ile Pro Ala Glu Cys Thr Thr Ile Tyr Asn Arg Gly Glu His Thr Ser
            20                  25                  30

Gly Met Tyr Ala Ile Arg Pro Ser Asn Ser Gln Val Phe His Val Tyr
            35                  40                  45

Cys Asp Val Ile Ser Gly Ser Pro Trp Thr Leu Ile Gln His Arg Ile
 50                  55                  60

Asp Gly Ser Gln Asn Phe Asn Glu Thr Trp Glu Asn Tyr Lys Tyr Gly
 65                  70                  75                  80

Phe Gly Arg Leu Asp Gly Glu Phe Trp Leu Gly Leu Glu Lys Ile Tyr
                85                  90                  95

Ser Ile Val Lys Gln Ser Asn Tyr Val Leu Arg Ile Glu Leu Glu Asp
            100                 105                 110

Trp Lys Asp Asn Lys His Tyr Ile Glu Tyr Ser Phe Tyr Leu Gly Asn
            115                 120                 125

His Glu Thr Asn Tyr Thr Leu His Leu Val Ala Ile Thr Gly Asn Val
            130                 135                 140
```

```
Pro Asn Ala Ile Pro Glu Asn Lys Asp Leu Val Phe Ser Thr Trp Asp
145                 150                 155                 160

His Lys Ala Lys Gly His Phe Asn Cys Pro Glu Gly Tyr Ser Gly Gly
                165                 170                 175

Trp Trp Trp His Asp Glu Cys Gly Glu Asn Asn Leu Asn Gly Lys Tyr
            180                 185                 190

Asn Lys Pro Arg Ala Ser Ser Lys Pro Glu Arg Arg Arg Gly Leu Ser
            195                 200                 205

Trp Lys Ser Gln Asn Gly Arg Leu Tyr Ser Ile Lys Ser Thr Lys Met
210                 215                 220

Leu Ile His Pro Thr Asp
225                 230

<210> SEQ ID NO 25
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ANGPTL3 228-455 K423Q

<400> SEQUENCE: 25

Phe Leu Gln Leu Asn Glu Ile Arg Asn Val Lys His Asp Gly Ile Pro
1               5                   10                  15

Ala Glu Cys Thr Thr Ile Tyr Asn Arg Gly Glu His Thr Ser Gly Met
                20                  25                  30

Tyr Ala Ile Arg Pro Ser Asn Ser Gln Val Phe His Val Tyr Cys Asp
            35                  40                  45

Val Ile Ser Gly Ser Pro Trp Thr Leu Ile Gln His Arg Ile Asp Gly
        50                  55                  60

Ser Gln Asn Phe Asn Glu Thr Trp Glu Asn Tyr Lys Tyr Gly Phe Gly
65                  70                  75                  80

Arg Leu Asp Gly Glu Phe Trp Leu Gly Leu Lys Ile Tyr Ser Ile
                85                  90                  95

Val Lys Gln Ser Asn Tyr Val Leu Arg Ile Glu Leu Glu Asp Trp Lys
                100                 105                 110

Asp Asn Lys His Tyr Ile Glu Tyr Ser Phe Tyr Leu Gly Asn His Glu
            115                 120                 125

Thr Asn Tyr Thr Leu His Leu Val Ala Ile Thr Gly Asn Val Pro Asn
130                 135                 140

Ala Ile Pro Glu Asn Lys Asp Leu Val Phe Ser Thr Trp Asp His Lys
145                 150                 155                 160

Ala Lys Gly His Phe Asn Cys Pro Glu Gly Tyr Ser Gly Gly Trp Trp
                165                 170                 175

Trp His Asp Glu Cys Gly Glu Asn Asn Leu Asn Gly Lys Tyr Asn Lys
            180                 185                 190

Pro Arg Ala Gln Ser Lys Pro Glu Arg Arg Arg Gly Leu Ser Trp Lys
            195                 200                 205

Ser Gln Asn Gly Arg Leu Tyr Ser Ile Lys Ser Thr Lys Met Leu Ile
        210                 215                 220

His Pro Thr Asp
225
```

<210> SEQ ID NO 26
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ANGPTL3 228-455 K423S

<400> SEQUENCE: 26

Phe Leu Gln Leu Asn Glu Ile Arg Asn Val Lys His Asp Gly Ile Pro
1               5                   10                  15

Ala Glu Cys Thr Thr Ile Tyr Asn Arg Gly Glu His Thr Ser Gly Met
            20                  25                  30

Tyr Ala Ile Arg Pro Ser Asn Ser Gln Val Phe His Val Tyr Cys Asp
        35                  40                  45

Val Ile Ser Gly Ser Pro Trp Thr Leu Ile Gln His Arg Ile Asp Gly
    50                  55                  60

Ser Gln Asn Phe Asn Glu Thr Trp Glu Asn Tyr Lys Tyr Gly Phe Gly
65                  70                  75                  80

Arg Leu Asp Gly Glu Phe Trp Leu Gly Leu Glu Lys Ile Tyr Ser Ile
                85                  90                  95

Val Lys Gln Ser Asn Tyr Val Leu Arg Ile Glu Leu Glu Asp Trp Lys
            100                 105                 110

Asp Asn Lys His Tyr Ile Glu Tyr Ser Phe Tyr Leu Gly Asn His Glu
        115                 120                 125

Thr Asn Tyr Thr Leu His Leu Val Ala Ile Thr Gly Asn Val Pro Asn
    130                 135                 140

Ala Ile Pro Glu Asn Lys Asp Leu Val Phe Ser Thr Trp Asp His Lys
145                 150                 155                 160

Ala Lys Gly His Phe Asn Cys Pro Glu Gly Tyr Ser Gly Gly Trp Trp
                165                 170                 175

Trp His Asp Glu Cys Gly Glu Asn Asn Leu Asn Gly Lys Tyr Asn Lys
            180                 185                 190

Pro Arg Ala Ser Ser Lys Pro Glu Arg Arg Arg Gly Leu Ser Trp Lys
        195                 200                 205

Ser Gln Asn Gly Arg Leu Tyr Ser Ile Lys Ser Thr Lys Met Leu Ile
    210                 215                 220

His Pro Thr Asp
225

<210> SEQ ID NO 27
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ANGPTL3 233-455 K423Q

<400> SEQUENCE: 27

Glu Ile Arg Asn Val Lys His Asp Gly Ile Pro Ala Glu Cys Thr Thr
1               5                   10                  15

Ile Tyr Asn Arg Gly Glu His Thr Ser Gly Met Tyr Ala Ile Arg Pro
            20                  25                  30

```
Ser Asn Ser Gln Val Phe His Val Tyr Cys Asp Val Ile Ser Gly Ser
        35                  40                  45

Pro Trp Thr Leu Ile Gln His Arg Ile Asp Gly Ser Gln Asn Phe Asn
 50                  55                  60

Glu Thr Trp Glu Asn Tyr Lys Tyr Gly Phe Gly Arg Leu Asp Gly Glu
 65                  70                  75                  80

Phe Trp Leu Gly Leu Glu Lys Ile Tyr Ser Ile Val Lys Gln Ser Asn
                 85                  90                  95

Tyr Val Leu Arg Ile Glu Leu Glu Asp Trp Lys Asp Asn Lys His Tyr
                100                 105                 110

Ile Glu Tyr Ser Phe Tyr Leu Gly Asn His Glu Thr Asn Tyr Thr Leu
                115                 120                 125

His Leu Val Ala Ile Thr Gly Asn Val Pro Asn Ala Ile Pro Glu Asn
            130                 135                 140

Lys Asp Leu Val Phe Ser Thr Trp Asp His Lys Ala Lys Gly His Phe
145                 150                 155                 160

Asn Cys Pro Glu Gly Tyr Ser Gly Gly Trp Trp His Asp Glu Cys
                165                 170                 175

Gly Glu Asn Asn Leu Asn Gly Lys Tyr Asn Lys Pro Arg Ala Gln Ser
            180                 185                 190

Lys Pro Glu Arg Arg Arg Gly Leu Ser Trp Lys Ser Gln Asn Gly Arg
            195                 200                 205

Leu Tyr Ser Ile Lys Ser Thr Lys Met Leu Ile His Pro Thr Asp
210                 215                 220

<210> SEQ ID NO 28
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ANGPTL3 233-455 K423S

<400> SEQUENCE: 28

Glu Ile Arg Asn Val Lys His Asp Gly Ile Pro Ala Glu Cys Thr Thr
 1               5                  10                  15

Ile Tyr Asn Arg Gly Glu His Thr Ser Gly Met Tyr Ala Ile Arg Pro
                20                  25                  30

Ser Asn Ser Gln Val Phe His Val Tyr Cys Asp Val Ile Ser Gly Ser
        35                  40                  45

Pro Trp Thr Leu Ile Gln His Arg Ile Asp Gly Ser Gln Asn Phe Asn
 50                  55                  60

Glu Thr Trp Glu Asn Tyr Lys Tyr Gly Phe Gly Arg Leu Asp Gly Glu
 65                  70                  75                  80

Phe Trp Leu Gly Leu Glu Lys Ile Tyr Ser Ile Val Lys Gln Ser Asn
                 85                  90                  95

Tyr Val Leu Arg Ile Glu Leu Glu Asp Trp Lys Asp Asn Lys His Tyr
                100                 105                 110

Ile Glu Tyr Ser Phe Tyr Leu Gly Asn His Glu Thr Asn Tyr Thr Leu
                115                 120                 125

His Leu Val Ala Ile Thr Gly Asn Val Pro Asn Ala Ile Pro Glu Asn
            130                 135                 140

Lys Asp Leu Val Phe Ser Thr Trp Asp His Lys Ala Lys Gly His Phe
145                 150                 155                 160
```

```
Asn Cys Pro Glu Gly Tyr Ser Gly Gly Trp Trp His Asp Glu Cys
            165                 170                 175

Gly Glu Asn Asn Leu Asn Gly Lys Tyr Asn Lys Pro Arg Ala Ser Ser
            180                 185                 190

Lys Pro Glu Arg Arg Gly Leu Ser Trp Lys Ser Gln Asn Gly Arg
            195                 200                 205

Leu Tyr Ser Ile Lys Ser Thr Lys Met Leu Ile His Pro Thr Asp
    210                 215                 220
```

<210> SEQ ID NO 29
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ANGPTL3 241-455 K423Q

<400> SEQUENCE: 29

```
Gly Ile Pro Ala Glu Cys Thr Thr Ile Tyr Asn Arg Gly Glu His Thr
1               5                   10                  15

Ser Gly Met Tyr Ala Ile Arg Pro Ser Asn Ser Gln Val Phe His Val
            20                  25                  30

Tyr Cys Asp Val Ile Ser Gly Ser Pro Trp Thr Leu Ile Gln His Arg
        35                  40                  45

Ile Asp Gly Ser Gln Asn Phe Asn Glu Thr Trp Glu Asn Tyr Lys Tyr
    50                  55                  60

Gly Phe Gly Arg Leu Asp Gly Glu Phe Trp Leu Gly Leu Glu Lys Ile
65                  70                  75                  80

Tyr Ser Ile Val Lys Gln Ser Asn Tyr Val Leu Arg Ile Glu Leu Glu
                85                  90                  95

Asp Trp Lys Asp Asn Lys His Tyr Ile Glu Tyr Ser Phe Tyr Leu Gly
            100                 105                 110

Asn His Glu Thr Asn Tyr Thr Leu His Leu Val Ala Ile Thr Gly Asn
        115                 120                 125

Val Pro Asn Ala Ile Pro Glu Asn Lys Asp Leu Val Phe Ser Thr Trp
    130                 135                 140

Asp His Lys Ala Lys Gly His Phe Asn Cys Pro Glu Gly Tyr Ser Gly
145                 150                 155                 160

Gly Trp Trp Trp His Asp Glu Cys Gly Glu Asn Asn Leu Asn Gly Lys
                165                 170                 175

Tyr Asn Lys Pro Arg Ala Gln Ser Lys Pro Glu Arg Arg Gly Leu
            180                 185                 190

Ser Trp Lys Ser Gln Asn Gly Arg Leu Tyr Ser Ile Lys Ser Thr Lys
        195                 200                 205

Met Leu Ile His Pro Thr Asp
    210                 215
```

<210> SEQ ID NO 30
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ANGPTL3 241-455 K423S

<400> SEQUENCE: 30

Gly Ile Pro Ala Glu Cys Thr Thr Ile Tyr Asn Arg Gly Glu His Thr
1               5                   10                  15

Ser Gly Met Tyr Ala Ile Arg Pro Ser Asn Ser Gln Val Phe His Val
            20                  25                  30

Tyr Cys Asp Val Ile Ser Gly Ser Pro Trp Thr Leu Ile Gln His Arg
        35                  40                  45

Ile Asp Gly Ser Gln Asn Phe Asn Glu Thr Trp Glu Asn Tyr Lys Tyr
    50                  55                  60

Gly Phe Gly Arg Leu Asp Gly Glu Phe Trp Leu Gly Leu Glu Lys Ile
65                  70                  75                  80

Tyr Ser Ile Val Lys Gln Ser Asn Tyr Val Leu Arg Ile Glu Leu Glu
                85                  90                  95

Asp Trp Lys Asp Asn Lys His Tyr Ile Glu Tyr Ser Phe Tyr Leu Gly
            100                 105                 110

Asn His Glu Thr Asn Tyr Thr Leu His Leu Val Ala Ile Thr Gly Asn
        115                 120                 125

Val Pro Asn Ala Ile Pro Glu Asn Lys Asp Leu Val Phe Ser Thr Trp
    130                 135                 140

Asp His Lys Ala Lys Gly His Phe Asn Cys Pro Glu Gly Tyr Ser Gly
145                 150                 155                 160

Gly Trp Trp Trp His Asp Glu Cys Gly Glu Asn Asn Leu Asn Gly Lys
                165                 170                 175

Tyr Asn Lys Pro Arg Ala Ser Ser Lys Pro Glu Arg Arg Arg Gly Leu
            180                 185                 190

Ser Trp Lys Ser Gln Asn Gly Arg Leu Tyr Ser Ile Lys Ser Thr Lys
        195                 200                 205

Met Leu Ile His Pro Thr Asp
    210                 215

<210> SEQ ID NO 31
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ANGPTL3 242-455 K423Q

<400> SEQUENCE: 31

Ile Pro Ala Glu Cys Thr Thr Ile Tyr Asn Arg Gly Glu His Thr Ser
1               5                   10                  15

Gly Met Tyr Ala Ile Arg Pro Ser Asn Ser Gln Val Phe His Val Tyr
            20                  25                  30

Cys Asp Val Ile Ser Gly Ser Pro Trp Thr Leu Ile Gln His Arg Ile
        35                  40                  45

Asp Gly Ser Gln Asn Phe Asn Glu Thr Trp Glu Asn Tyr Lys Tyr Gly
    50                  55                  60

Phe Gly Arg Leu Asp Gly Glu Phe Trp Leu Gly Leu Glu Lys Ile Tyr
65                  70                  75                  80

Ser Ile Val Lys Gln Ser Asn Tyr Val Leu Arg Ile Glu Leu Glu Asp
                85                  90                  95

Trp Lys Asp Asn Lys His Tyr Ile Glu Tyr Ser Phe Tyr Leu Gly Asn
            100                 105                 110

His Glu Thr Asn Tyr Thr Leu His Leu Val Ala Ile Thr Gly Asn Val
          115                 120                 125

Pro Asn Ala Ile Pro Glu Asn Lys Asp Leu Val Phe Ser Thr Trp Asp
    130                 135                 140

His Lys Ala Lys Gly His Phe Asn Cys Pro Glu Gly Tyr Ser Gly Gly
145                 150                 155                 160

Trp Trp Trp His Asp Glu Cys Gly Glu Asn Asn Leu Asn Gly Lys Tyr
            165                 170                 175

Asn Lys Pro Arg Ala Gln Ser Lys Pro Glu Arg Arg Arg Gly Leu Ser
                180                 185                 190

Trp Lys Ser Gln Asn Gly Arg Leu Tyr Ser Ile Lys Ser Thr Lys Met
            195                 200                 205

Leu Ile His Pro Thr Asp
        210

<210> SEQ ID NO 32
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ANGPTL3 242-455 K423S

<400> SEQUENCE: 32

Ile Pro Ala Glu Cys Thr Thr Ile Tyr Asn Arg Gly Glu His Thr Ser
1               5                   10                  15

Gly Met Tyr Ala Ile Arg Pro Ser Asn Ser Gln Val Phe His Val Tyr
            20                  25                  30

Cys Asp Val Ile Ser Gly Ser Pro Trp Thr Leu Ile Gln His Arg Ile
            35                  40                  45

Asp Gly Ser Gln Asn Phe Asn Glu Thr Trp Glu Asn Tyr Lys Tyr Gly
        50                  55                  60

Phe Gly Arg Leu Asp Gly Glu Phe Trp Leu Gly Leu Glu Lys Ile Tyr
65                  70                  75                  80

Ser Ile Val Lys Gln Ser Asn Tyr Val Leu Arg Ile Glu Leu Glu Asp
                85                  90                  95

Trp Lys Asp Asn Lys His Tyr Ile Glu Tyr Ser Phe Tyr Leu Gly Asn
            100                 105                 110

His Glu Thr Asn Tyr Thr Leu His Leu Val Ala Ile Thr Gly Asn Val
        115                 120                 125

Pro Asn Ala Ile Pro Glu Asn Lys Asp Leu Val Phe Ser Thr Trp Asp
    130                 135                 140

His Lys Ala Lys Gly His Phe Asn Cys Pro Glu Gly Tyr Ser Gly Gly
145                 150                 155                 160

Trp Trp Trp His Asp Glu Cys Gly Glu Asn Asn Leu Asn Gly Lys Tyr
            165                 170                 175

Asn Lys Pro Arg Ala Ser Ser Lys Pro Glu Arg Arg Arg Gly Leu Ser
                180                 185                 190

Trp Lys Ser Gln Asn Gly Arg Leu Tyr Ser Ile Lys Ser Thr Lys Met
            195                 200                 205

Leu Ile His Pro Thr Asp
        210

<210> SEQ ID NO 33

```
<211> LENGTH: 252
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ANGPTL3 201-460 K423del

<400> SEQUENCE: 33

Ile Gln Glu Pro Thr Glu Ile Ser Leu Ser Ser Lys Pro Arg Ala Pro
1               5                  10                  15

Arg Thr Thr Pro Phe Leu Gln Leu Asn Glu Ile Arg Asn Val Lys His
            20                  25                  30

Asp Gly Ile Pro Ala Glu Cys Thr Thr Ile Tyr Asn Arg Gly Glu His
        35                  40                  45

Thr Ser Gly Met Tyr Ala Ile Arg Pro Ser Asn Ser Gln Val Phe His
    50                  55                  60

Val Tyr Cys Asp Val Ile Ser Gly Ser Pro Trp Thr Leu Ile Gln His
65                  70                  75                  80

Arg Ile Asp Gly Ser Gln Asn Phe Asn Glu Thr Trp Glu Asn Tyr Lys
                85                  90                  95

Tyr Gly Phe Gly Arg Leu Asp Gly Glu Phe Trp Leu Gly Leu Glu Lys
            100                 105                 110

Ile Tyr Ser Ile Val Lys Gln Ser Asn Tyr Val Leu Arg Ile Glu Leu
        115                 120                 125

Glu Asp Trp Lys Asp Asn Lys His Tyr Ile Glu Tyr Ser Phe Tyr Leu
    130                 135                 140

Gly Asn His Glu Thr Asn Tyr Thr Leu His Leu Val Ala Ile Thr Gly
145                 150                 155                 160

Asn Val Pro Asn Ala Ile Pro Glu Asn Lys Asp Leu Val Phe Ser Thr
                165                 170                 175

Trp Asp His Lys Ala Lys Gly His Phe Asn Cys Pro Glu Gly Tyr Ser
            180                 185                 190

Gly Gly Trp Trp Trp His Asp Glu Cys Gly Glu Asn Asn Leu Asn Gly
        195                 200                 205

Lys Tyr Asn Lys Pro Arg Ala Ser Lys Pro Glu Arg Arg Arg Gly Leu
    210                 215                 220

Ser Trp Lys Ser Gln Asn Gly Arg Leu Tyr Ser Ile Lys Ser Thr Lys
225                 230                 235                 240

Met Leu Ile His Pro Thr Asp Ser Glu Ser Phe Glu
                245                 250

<210> SEQ ID NO 34
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ANGPTL3 225-460 K423del

<400> SEQUENCE: 34

Thr Thr Pro Phe Leu Gln Leu Asn Glu Ile Arg Asn Val Lys His Asp
1               5                  10                  15

Gly Ile Pro Ala Glu Cys Thr Thr Ile Tyr Asn Arg Gly Glu His Thr
            20                  25                  30
```

```
Ser Gly Met Tyr Ala Ile Arg Pro Ser Asn Ser Gln Val Phe His Val
        35                  40                  45

Tyr Cys Asp Val Ile Ser Gly Ser Pro Trp Thr Leu Ile Gln His Arg
    50                  55                  60

Ile Asp Gly Ser Gln Asn Phe Asn Glu Thr Trp Glu Asn Tyr Lys Tyr
 65                  70                  75                  80

Gly Phe Gly Arg Leu Asp Gly Glu Phe Trp Leu Gly Leu Glu Lys Ile
                 85                  90                  95

Tyr Ser Ile Val Lys Gln Ser Asn Tyr Val Leu Arg Ile Glu Leu Glu
            100                 105                 110

Asp Trp Lys Asp Asn Lys His Tyr Ile Glu Tyr Ser Phe Tyr Leu Gly
            115                 120                 125

Asn His Glu Thr Asn Tyr Thr Leu His Leu Val Ala Ile Thr Gly Asn
130                 135                 140

Val Pro Asn Ala Ile Pro Glu Asn Lys Asp Leu Val Phe Ser Thr Trp
145                 150                 155                 160

Asp His Lys Ala Lys Gly His Phe Asn Cys Pro Glu Gly Tyr Ser Gly
                165                 170                 175

Gly Trp Trp Trp His Asp Glu Cys Gly Glu Asn Asn Leu Asn Gly Lys
            180                 185                 190

Tyr Asn Lys Pro Arg Ala Ser Lys Pro Glu Arg Arg Arg Gly Leu Ser
            195                 200                 205

Trp Lys Ser Gln Asn Gly Arg Leu Tyr Ser Ile Lys Ser Thr Lys Met
210                 215                 220

Leu Ile His Pro Thr Asp Ser Glu Ser Phe Glu
225                 230                 235

<210> SEQ ID NO 35
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ANGPTL3 226-460 K423del

<400> SEQUENCE: 35

Thr Pro Phe Leu Gln Leu Asn Glu Ile Arg Asn Val Lys His Asp Gly
 1               5                  10                  15

Ile Pro Ala Glu Cys Thr Thr Ile Tyr Asn Arg Gly Glu His Thr Ser
                20                  25                  30

Gly Met Tyr Ala Ile Arg Pro Ser Asn Ser Gln Val Phe His Val Tyr
            35                  40                  45

Cys Asp Val Ile Ser Gly Ser Pro Trp Thr Leu Ile Gln His Arg Ile
 50                  55                  60

Asp Gly Ser Gln Asn Phe Asn Glu Thr Trp Glu Asn Tyr Lys Tyr Gly
 65                  70                  75                  80

Phe Gly Arg Leu Asp Gly Glu Phe Trp Leu Gly Leu Glu Lys Ile Tyr
                 85                  90                  95

Ser Ile Val Lys Gln Ser Asn Tyr Val Leu Arg Ile Glu Leu Glu Asp
            100                 105                 110

Trp Lys Asp Asn Lys His Tyr Ile Glu Tyr Ser Phe Tyr Leu Gly Asn
        115                 120                 125

His Glu Thr Asn Tyr Thr Leu His Leu Val Ala Ile Thr Gly Asn Val
130                 135                 140
```

Pro Asn Ala Ile Pro Glu Asn Lys Asp Leu Val Phe Ser Thr Trp Asp
145                 150                 155                 160

His Lys Ala Lys Gly His Phe Asn Cys Pro Glu Gly Tyr Ser Gly Gly
                165                 170                 175

Trp Trp Trp His Asp Glu Cys Gly Glu Asn Asn Leu Asn Gly Lys Tyr
            180                 185                 190

Asn Lys Pro Arg Ala Ser Lys Pro Glu Arg Arg Gly Leu Ser Trp
        195                 200                 205

Lys Ser Gln Asn Gly Arg Leu Tyr Ser Ile Lys Ser Thr Lys Met Leu
210                 215                 220

Ile His Pro Thr Asp Ser Glu Ser Phe Glu
225                 230

<210> SEQ ID NO 36
<211> LENGTH: 232
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ANGPTL3 228-460 K423del

<400> SEQUENCE: 36

Phe Leu Gln Leu Asn Glu Ile Arg Asn Val Lys His Asp Gly Ile Pro
1               5                   10                  15

Ala Glu Cys Thr Thr Ile Tyr Asn Arg Gly Glu His Thr Ser Gly Met
                20                  25                  30

Tyr Ala Ile Arg Pro Ser Asn Ser Gln Val Phe His Val Tyr Cys Asp
            35                  40                  45

Val Ile Ser Gly Ser Pro Trp Thr Leu Ile Gln His Arg Ile Asp Gly
50                  55                  60

Ser Gln Asn Phe Asn Glu Thr Trp Glu Asn Tyr Lys Tyr Gly Phe Gly
65                  70                  75                  80

Arg Leu Asp Gly Glu Phe Trp Leu Gly Leu Glu Lys Ile Tyr Ser Ile
                85                  90                  95

Val Lys Gln Ser Asn Tyr Val Leu Arg Ile Glu Leu Glu Asp Trp Lys
            100                 105                 110

Asp Asn Lys His Tyr Ile Glu Tyr Ser Phe Tyr Leu Gly Asn His Glu
        115                 120                 125

Thr Asn Tyr Thr Leu His Leu Val Ala Ile Thr Gly Asn Val Pro Asn
130                 135                 140

Ala Ile Pro Glu Asn Lys Asp Leu Val Phe Ser Thr Trp Asp His Lys
145                 150                 155                 160

Ala Lys Gly His Phe Asn Cys Pro Glu Gly Tyr Ser Gly Gly Trp Trp
                165                 170                 175

Trp His Asp Glu Cys Gly Glu Asn Asn Leu Asn Gly Lys Tyr Asn Lys
            180                 185                 190

Pro Arg Ala Ser Lys Pro Glu Arg Arg Gly Leu Ser Trp Lys Ser
        195                 200                 205

Gln Asn Gly Arg Leu Tyr Ser Ile Lys Ser Thr Lys Met Leu Ile His
210                 215                 220

Pro Thr Asp Ser Glu Ser Phe Glu
225                 230

<210> SEQ ID NO 37

<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ANGPTL3 233-460 K423del

<400> SEQUENCE: 37

Glu Ile Arg Asn Val Lys His Asp Gly Ile Pro Ala Glu Cys Thr Thr
1               5                   10                  15

Ile Tyr Asn Arg Gly Glu His Thr Ser Gly Met Tyr Ala Ile Arg Pro
            20                  25                  30

Ser Asn Ser Gln Val Phe His Val Tyr Cys Asp Val Ile Ser Gly Ser
        35                  40                  45

Pro Trp Thr Leu Ile Gln His Arg Ile Asp Gly Ser Gln Asn Phe Asn
    50                  55                  60

Glu Thr Trp Glu Asn Tyr Lys Tyr Gly Phe Gly Arg Leu Asp Gly Glu
65                  70                  75                  80

Phe Trp Leu Gly Leu Glu Lys Ile Tyr Ser Ile Val Lys Gln Ser Asn
                85                  90                  95

Tyr Val Leu Arg Ile Glu Leu Glu Asp Trp Lys Asp Asn Lys His Tyr
            100                 105                 110

Ile Glu Tyr Ser Phe Tyr Leu Gly Asn His Glu Thr Asn Tyr Thr Leu
        115                 120                 125

His Leu Val Ala Ile Thr Gly Asn Val Pro Asn Ala Ile Pro Glu Asn
    130                 135                 140

Lys Asp Leu Val Phe Ser Thr Trp Asp His Lys Ala Lys Gly His Phe
145                 150                 155                 160

Asn Cys Pro Glu Gly Tyr Ser Gly Gly Trp Trp Trp His Asp Glu Cys
                165                 170                 175

Gly Glu Asn Asn Leu Asn Gly Lys Tyr Asn Lys Pro Arg Ala Ser Lys
            180                 185                 190

Pro Glu Arg Arg Arg Gly Leu Ser Trp Lys Ser Gln Asn Gly Arg Leu
        195                 200                 205

Tyr Ser Ile Lys Ser Thr Lys Met Leu Ile His Pro Thr Asp Ser Glu
    210                 215                 220

Ser Phe Glu
225

<210> SEQ ID NO 38
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ANGPTL3 241-460 K423del

<400> SEQUENCE: 38

Gly Ile Pro Ala Glu Cys Thr Thr Ile Tyr Asn Arg Gly Glu His Thr
1               5                   10                  15

Ser Gly Met Tyr Ala Ile Arg Pro Ser Asn Ser Gln Val Phe His Val
            20                  25                  30

Tyr Cys Asp Val Ile Ser Gly Ser Pro Trp Thr Leu Ile Gln His Arg
        35                  40                  45

Ile Asp Gly Ser Gln Asn Phe Asn Glu Thr Trp Glu Asn Tyr Lys Tyr
            50                  55                  60

Gly Phe Gly Arg Leu Asp Gly Glu Phe Trp Leu Gly Leu Glu Lys Ile
 65                  70                  75                  80

Tyr Ser Ile Val Lys Gln Ser Asn Tyr Val Leu Arg Ile Glu Leu Glu
                     85                  90                  95

Asp Trp Lys Asp Asn Lys His Tyr Ile Glu Tyr Ser Phe Tyr Leu Gly
                100                 105                 110

Asn His Glu Thr Asn Tyr Thr Leu His Leu Val Ala Ile Thr Gly Asn
                115                 120                 125

Val Pro Asn Ala Ile Pro Glu Asn Lys Asp Leu Val Phe Ser Thr Trp
130                 135                 140

Asp His Lys Ala Lys Gly His Phe Asn Cys Pro Glu Gly Tyr Ser Gly
145                 150                 155                 160

Gly Trp Trp Trp His Asp Glu Cys Gly Glu Asn Asn Leu Asn Gly Lys
                165                 170                 175

Tyr Asn Lys Pro Arg Ala Ser Lys Pro Glu Arg Arg Arg Gly Leu Ser
                180                 185                 190

Trp Lys Ser Gln Asn Gly Arg Leu Tyr Ser Ile Lys Ser Thr Lys Met
                195                 200                 205

Leu Ile His Pro Thr Asp Ser Glu Ser Phe Glu
                210                 215

<210> SEQ ID NO 39
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ANGPTL3 242-460 K423del

<400> SEQUENCE: 39

Ile Pro Ala Glu Cys Thr Thr Ile Tyr Asn Arg Gly Glu His Thr Ser
 1               5                  10                  15

Gly Met Tyr Ala Ile Arg Pro Ser Asn Ser Gln Val Phe His Val Tyr
                 20                  25                  30

Cys Asp Val Ile Ser Gly Ser Pro Trp Thr Leu Ile Gln His Arg Ile
             35                  40                  45

Asp Gly Ser Gln Asn Phe Asn Glu Thr Trp Glu Asn Tyr Lys Tyr Gly
         50                  55                  60

Phe Gly Arg Leu Asp Gly Glu Phe Trp Leu Gly Leu Glu Lys Ile Tyr
 65                  70                  75                  80

Ser Ile Val Lys Gln Ser Asn Tyr Val Leu Arg Ile Glu Leu Glu Asp
                 85                  90                  95

Trp Lys Asp Asn Lys His Tyr Ile Glu Tyr Ser Phe Tyr Leu Gly Asn
            100                 105                 110

His Glu Thr Asn Tyr Thr Leu His Leu Val Ala Ile Thr Gly Asn Val
        115                 120                 125

Pro Asn Ala Ile Pro Glu Asn Lys Asp Leu Val Phe Ser Thr Trp Asp
130                 135                 140

His Lys Ala Lys Gly His Phe Asn Cys Pro Glu Gly Tyr Ser Gly Gly
145                 150                 155                 160

Trp Trp Trp His Asp Glu Cys Gly Glu Asn Asn Leu Asn Gly Lys Tyr
            165                 170                 175

-continued

```
Asn Lys Pro Arg Ala Ser Lys Pro Glu Arg Arg Gly Leu Ser Trp
        180                 185                 190

Lys Ser Gln Asn Gly Arg Leu Tyr Ser Ile Lys Ser Thr Lys Met Leu
    195                 200                 205

Ile His Pro Thr Asp Ser Glu Ser Phe Glu
    210                 215

<210> SEQ ID NO 40
<211> LENGTH: 230
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ANGPTL3 225-455 K423del

<400> SEQUENCE: 40

Thr Thr Pro Phe Leu Gln Leu Asn Glu Ile Arg Asn Val Lys His Asp
1               5                   10                  15

Gly Ile Pro Ala Glu Cys Thr Thr Ile Tyr Asn Arg Gly Glu His Thr
            20                  25                  30

Ser Gly Met Tyr Ala Ile Arg Pro Ser Asn Ser Gln Val Phe His Val
        35                  40                  45

Tyr Cys Asp Val Ile Ser Gly Ser Pro Trp Thr Leu Ile Gln His Arg
    50                  55                  60

Ile Asp Gly Ser Gln Asn Phe Asn Glu Thr Trp Glu Asn Tyr Lys Tyr
65                  70                  75                  80

Gly Phe Gly Arg Leu Asp Gly Glu Phe Trp Leu Gly Leu Glu Lys Ile
                85                  90                  95

Tyr Ser Ile Val Lys Gln Ser Asn Tyr Val Leu Arg Ile Glu Leu Glu
            100                 105                 110

Asp Trp Lys Asp Asn Lys His Tyr Ile Glu Tyr Ser Phe Tyr Leu Gly
        115                 120                 125

Asn His Glu Thr Asn Tyr Thr Leu His Leu Val Ala Ile Thr Gly Asn
    130                 135                 140

Val Pro Asn Ala Ile Pro Glu Asn Lys Asp Leu Val Phe Ser Thr Trp
145                 150                 155                 160

Asp His Lys Ala Lys Gly His Phe Asn Cys Pro Glu Gly Tyr Ser Gly
                165                 170                 175

Gly Trp Trp Trp His Asp Glu Cys Gly Glu Asn Asn Leu Asn Gly Lys
            180                 185                 190

Tyr Asn Lys Pro Arg Ala Ser Lys Pro Glu Arg Arg Arg Gly Leu Ser
        195                 200                 205

Trp Lys Ser Gln Asn Gly Arg Leu Tyr Ser Ile Lys Ser Thr Lys Met
    210                 215                 220

Leu Ile His Pro Thr Asp
225                 230

<210> SEQ ID NO 41
<211> LENGTH: 229
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ANGPTL3 226-455 K423del
```

<400> SEQUENCE: 41

```
Thr Pro Phe Leu Gln Leu Asn Glu Ile Arg Asn Val Lys His Asp Gly
1               5                   10                  15

Ile Pro Ala Glu Cys Thr Thr Ile Tyr Asn Arg Gly Glu His Thr Ser
            20                  25                  30

Gly Met Tyr Ala Ile Arg Pro Ser Asn Ser Gln Val Phe His Val Tyr
        35                  40                  45

Cys Asp Val Ile Ser Gly Ser Pro Trp Thr Leu Ile Gln His Arg Ile
    50                  55                  60

Asp Gly Ser Gln Asn Phe Asn Glu Thr Trp Glu Asn Tyr Lys Tyr Gly
65                  70                  75                  80

Phe Gly Arg Leu Asp Gly Glu Phe Trp Leu Gly Leu Glu Lys Ile Tyr
                85                  90                  95

Ser Ile Val Lys Gln Ser Asn Tyr Val Leu Arg Ile Glu Leu Glu Asp
            100                 105                 110

Trp Lys Asp Asn Lys His Tyr Ile Glu Tyr Ser Phe Tyr Leu Gly Asn
        115                 120                 125

His Glu Thr Asn Tyr Thr Leu His Leu Val Ala Ile Thr Gly Asn Val
130                 135                 140

Pro Asn Ala Ile Pro Glu Asn Lys Asp Leu Val Phe Ser Thr Trp Asp
145                 150                 155                 160

His Lys Ala Lys Gly His Phe Asn Cys Pro Glu Gly Tyr Ser Gly Gly
                165                 170                 175

Trp Trp Trp His Asp Glu Cys Gly Glu Asn Asn Leu Asn Gly Lys Tyr
            180                 185                 190

Asn Lys Pro Arg Ala Ser Lys Pro Glu Arg Arg Gly Leu Ser Trp
        195                 200                 205

Lys Ser Gln Asn Gly Arg Leu Tyr Ser Ile Lys Ser Thr Lys Met Leu
210                 215                 220

Ile His Pro Thr Asp
225
```

<210> SEQ ID NO 42
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ANGPTL3 228-455 K423del

<400> SEQUENCE: 42

```
Phe Leu Gln Leu Asn Glu Ile Arg Asn Val Lys His Asp Gly Ile Pro
1               5                   10                  15

Ala Glu Cys Thr Thr Ile Tyr Asn Arg Gly Glu His Thr Ser Gly Met
            20                  25                  30

Tyr Ala Ile Arg Pro Ser Asn Ser Gln Val Phe His Val Tyr Cys Asp
        35                  40                  45

Val Ile Ser Gly Ser Pro Trp Thr Leu Ile Gln His Arg Ile Asp Gly
    50                  55                  60

Ser Gln Asn Phe Asn Glu Thr Trp Glu Asn Tyr Lys Tyr Gly Phe Gly
65                  70                  75                  80

Arg Leu Asp Gly Glu Phe Trp Leu Gly Leu Glu Lys Ile Tyr Ser Ile
                85                  90                  95
```

```
Val Lys Gln Ser Asn Tyr Val Leu Arg Ile Glu Leu Glu Asp Trp Lys
            100                 105                 110

Asp Asn Lys His Tyr Ile Glu Tyr Ser Phe Tyr Leu Gly Asn His Glu
            115                 120                 125

Thr Asn Tyr Thr Leu His Leu Val Ala Ile Thr Gly Asn Val Pro Asn
            130                 135                 140

Ala Ile Pro Glu Asn Lys Asp Leu Val Phe Ser Thr Trp Asp His Lys
145                 150                 155                 160

Ala Lys Gly His Phe Asn Cys Pro Glu Gly Tyr Ser Gly Gly Trp Trp
                165                 170                 175

Trp His Asp Glu Cys Gly Glu Asn Asn Leu Asn Gly Lys Tyr Asn Lys
            180                 185                 190

Pro Arg Ala Ser Lys Pro Glu Arg Arg Arg Gly Leu Ser Trp Lys Ser
                195                 200                 205

Gln Asn Gly Arg Leu Tyr Ser Ile Lys Ser Thr Lys Met Leu Ile His
            210                 215                 220

Pro Thr Asp
225

<210> SEQ ID NO 43
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ANGPTL3 233-455 K423del

<400> SEQUENCE: 43

Glu Ile Arg Asn Val Lys His Asp Gly Ile Pro Ala Glu Cys Thr Thr
1               5                   10                  15

Ile Tyr Asn Arg Gly Glu His Thr Ser Gly Met Tyr Ala Ile Arg Pro
            20                  25                  30

Ser Asn Ser Gln Val Phe His Val Tyr Cys Asp Val Ile Ser Gly Ser
        35                  40                  45

Pro Trp Thr Leu Ile Gln His Arg Ile Asp Gly Ser Gln Asn Phe Asn
50                  55                  60

Glu Thr Trp Glu Asn Tyr Lys Tyr Gly Phe Gly Arg Leu Asp Gly Glu
65                  70                  75                  80

Phe Trp Leu Gly Leu Glu Lys Ile Tyr Ser Ile Val Lys Gln Ser Asn
                85                  90                  95

Tyr Val Leu Arg Ile Glu Leu Glu Asp Trp Lys Asp Asn Lys His Tyr
            100                 105                 110

Ile Glu Tyr Ser Phe Tyr Leu Gly Asn His Glu Thr Asn Tyr Thr Leu
            115                 120                 125

His Leu Val Ala Ile Thr Gly Asn Val Pro Asn Ala Ile Pro Glu Asn
            130                 135                 140

Lys Asp Leu Val Phe Ser Thr Trp Asp His Lys Ala Lys Gly His Phe
145                 150                 155                 160

Asn Cys Pro Glu Gly Tyr Ser Gly Gly Trp Trp Trp His Asp Glu Cys
                165                 170                 175

Gly Glu Asn Asn Leu Asn Gly Lys Tyr Asn Lys Pro Arg Ala Ser Lys
            180                 185                 190

Pro Glu Arg Arg Arg Gly Leu Ser Trp Lys Ser Gln Asn Gly Arg Leu
            195                 200                 205
```

Tyr Ser Ile Lys Ser Thr Lys
        210             215

<210> SEQ ID NO 44
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ANGPTL3 241-455 K423del

<400> SEQUENCE: 44

Gly Ile Pro Ala Glu Cys Thr Thr Ile Tyr Asn Arg Gly Glu His Thr
1               5                   10                  15

Ser Gly Met Tyr Ala Ile Arg Pro Ser Asn Ser Gln Val Phe His Val
            20                  25                  30

Tyr Cys Asp Val Ile Ser Gly Ser Pro Trp Thr Leu Ile Gln His Arg
        35                  40                  45

Ile Asp Gly Ser Gln Asn Phe Asn Glu Thr Trp Glu Asn Tyr Lys Tyr
    50                  55                  60

Gly Phe Gly Arg Leu Asp Gly Glu Phe Trp Leu Gly Leu Glu Lys Ile
65                  70                  75                  80

Tyr Ser Ile Val Lys Gln Ser Asn Tyr Val Leu Arg Ile Glu Leu Glu
                85                  90                  95

Asp Trp Lys Asp Asn Lys His Tyr Ile Glu Tyr Ser Phe Tyr Leu Gly
            100                 105                 110

Asn His Glu Thr Asn Tyr Thr Leu His Leu Val Ala Ile Thr Gly Asn
        115                 120                 125

Val Pro Asn Ala Ile Pro Glu Asn Lys Asp Leu Val Phe Ser Thr Trp
    130                 135                 140

Asp His Lys Ala Lys Gly His Phe Asn Cys Pro Glu Gly Tyr Ser Gly
145                 150                 155                 160

Gly Trp Trp Trp His Asp Glu Cys Gly Glu Asn Asn Leu Asn Gly Lys
                165                 170                 175

Tyr Asn Lys Pro Arg Ala Ser Lys Pro Glu Arg Arg Arg Gly Leu Ser
            180                 185                 190

Trp Lys Ser Gln Asn Gly Arg Leu Tyr Ser Ile Lys Ser Thr Lys Met
        195                 200                 205

Leu Ile His Pro Thr Asp
    210

<210> SEQ ID NO 45
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ANGPTL3 242-455 K423del

<400> SEQUENCE: 45

Ile Pro Ala Glu Cys Thr Thr Ile Tyr Asn Arg Gly Glu His Thr Ser
1               5                   10                  15

Gly Met Tyr Ala Ile Arg Pro Ser Asn Ser Gln Val Phe His Val Tyr
            20                  25                  30

-continued

```
Cys Asp Val Ile Ser Gly Ser Pro Trp Thr Leu Ile Gln His Arg Ile
        35              40                  45

Asp Gly Ser Gln Asn Phe Asn Glu Thr Trp Glu Asn Tyr Lys Tyr Gly
    50              55                  60

Phe Gly Arg Leu Asp Gly Glu Phe Trp Leu Gly Leu Glu Lys Ile Tyr
65                  70              75                  80

Ser Ile Val Lys Gln Ser Asn Tyr Val Leu Arg Ile Glu Leu Glu Asp
                85              90                  95

Trp Lys Asp Asn Lys His Tyr Ile Glu Tyr Ser Phe Tyr Leu Gly Asn
            100             105             110

His Glu Thr Asn Tyr Thr Leu His Leu Val Ala Ile Thr Gly Asn Val
        115             120             125

Pro Asn Ala Ile Pro Glu Asn Lys Asp Leu Val Phe Ser Thr Trp Asp
    130             135             140

His Lys Ala Lys Gly His Phe Asn Cys Pro Glu Gly Tyr Ser Gly Gly
145             150             155             160

Trp Trp Trp His Asp Glu Cys Gly Glu Asn Asn Leu Asn Gly Lys Tyr
                165             170             175

Asn Lys Pro Arg Ala Ser Lys Pro Glu Arg Arg Arg Gly Leu Ser Trp
            180             185             190

Lys Ser Gln Asn Gly Arg Leu Tyr Ser Ile Lys Ser Thr Lys Met Leu
        195             200             205

Ile His Pro Thr Asp
        210
```